US010266578B2

(12) United States Patent
Dubowchik et al.

(10) Patent No.: US 10,266,578 B2
(45) Date of Patent: Apr. 23, 2019

(54) MODIFIED RELAXIN POLYPEPTIDES COMPRISING A PHARMACOKINETIC ENHANCER AND USES THEREOF

(71) Applicant: BRISTOL-MYERS SQUIBB COMPANY, Princeton, NJ (US)

(72) Inventors: Gene M. Dubowchik, Middlefield, CT (US); Olafur S. Gudmundsson, West Windsor, NJ (US); Xiaojun Han, Cheshire, CT (US); R. Michael Lawrence, Yardley, PA (US); Dasa Lipovsek, Pepperell, MA (US); Cort S. Madsen, West Windsor, NJ (US); Claudio Mapelli, Linden, NJ (US); Paul E. Morin, Pennington, NJ (US); Michael C. Myers, Newtown, PA (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 15/891,492

(22) Filed: Feb. 8, 2018

(65) Prior Publication Data
US 2018/0222960 A1 Aug. 9, 2018

Related U.S. Application Data

(60) Provisional application No. 62/627,411, filed on Feb. 7, 2018, provisional application No. 62/456,161, filed on Feb. 8, 2017.

(51) Int. Cl.
| | |
|---|---|
| A61K 38/18 | (2006.01) |
| C07K 14/64 | (2006.01) |
| C07K 1/107 | (2006.01) |
| A61K 38/00 | (2006.01) |
| A61K 47/64 | (2017.01) |
| A61P 9/00 | (2006.01) |
| A61K 45/06 | (2006.01) |

(52) U.S. Cl.
CPC ............ *C07K 14/64* (2013.01); *C07K 1/1077* (2013.01); *A61K 38/00* (2013.01); *A61K 45/06* (2013.01); *A61K 47/64* (2017.08); *A61P 9/00* (2018.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. |
| 4,289,872 A | 9/1981 | Denkewalter et al. |
| 4,412,989 A | 11/1983 | Iwashita et al. |
| 4,414,148 A | 11/1983 | Jansen et al. |
| 4,485,045 A | 11/1984 | Regen |
| 4,511,502 A | 4/1985 | Builder et al. |
| 4,511,503 A | 4/1985 | Olson et al. |
| 4,512,922 A | 4/1985 | Jones et al. |
| 4,544,545 A | 10/1985 | Ryan et al. |
| 4,551,433 A | 11/1985 | Deboer |
| 4,569,789 A | 2/1986 | Blattler et al. |
| 4,619,794 A | 10/1986 | Hauser |
| 4,659,839 A | 4/1987 | Nicolotti et al. |
| 4,670,417 A | 6/1987 | Iwasaki et al. |
| 4,671,958 A | 6/1987 | Rodwell et al. |
| 4,680,338 A | 7/1987 | Sundoro |
| 4,689,406 A | 8/1987 | Banks et al. |
| 4,699,784 A | 10/1987 | Shih et al. |
| 4,738,921 A | 4/1988 | Belagaje et al. |
| 4,755,465 A | 7/1988 | Gray et al. |
| 4,837,148 A | 6/1989 | Cregg |
| 4,859,600 A | 8/1989 | Gray et al. |
| 4,876,197 A | 10/1989 | Burke et al. |
| 4,880,734 A | 11/1989 | Burke et al. |
| 4,902,502 A | 2/1990 | Nitecki et al. |
| 4,904,584 A | 2/1990 | Shaw |
| 4,929,555 A | 5/1990 | Cregg et al. |
| 5,021,234 A | 6/1991 | Ehrenfeld |
| 5,089,398 A | 2/1992 | Rosenberg et al. |
| 5,122,614 A | 6/1992 | Zalipsky |
| 5,145,962 A | 9/1992 | Hudson et al. |
| 5,162,601 A | 11/1992 | Slightom |
| 5,219,564 A | 6/1993 | Zalipsky et al. |
| 5,229,490 A | 7/1993 | Tam |
| 5,231,178 A | 7/1993 | Holtz et al. |
| 5,252,714 A | 10/1993 | Harris et al. |

(Continued)

FOREIGN PATENT DOCUMENTS

| | | |
|---|---|---|
| CA | 2300362 | 2/1999 |
| CA | 2707840 | 2/2009 |

(Continued)

OTHER PUBLICATIONS

Ghosh et al.; "Serelaxin in acute heart failure: Most recent update on clinical and preclinical evidence." *Cardiovascular therapeutics* 351 (2017): 55-63.
Hossain et al., "The minimal active structure of human relaxin-2." *Journal of Biological Chemistry* 286.43 (2011): 37555-37565.
Chen et al., "Fusion protein linkers: property, design and functionality." *Advanced drug delivery reviews* 65.10 (2013): 1357-1369.
Zhongming Tang, "Biotechnology Drugs—Introduction and Practical Handbook", Chemical Industry Press, Jan. 2008.

(Continued)

*Primary Examiner* — Christine J Saoud
(74) *Attorney, Agent, or Firm* — Robin L. Teskin; LeClairRyan PLLC

(57) ABSTRACT

The present disclosure generally relates to modified relaxin polypeptides, such as modified human relaxin 2 polypeptides, comprising a non-naturally encoded amino acid which is linked to a pharmacokinetic enhancer, and therapeutic uses of such polypeptides, such as for the treatment of cardiovascular conditions (such as heart failure) and/or conditions relating to fibrosis.

30 Claims, 5 Drawing Sheets
Specification includes a Sequence Listing.

(56) References Cited

U.S. PATENT DOCUMENTS

| | | |
|---|---|---|
| 5,281,698 A | 1/1994 | Nitecki |
| 5,290,686 A | 3/1994 | Kendal et al. |
| 5,324,639 A | 6/1994 | Brierley et al. |
| 5,324,844 A | 6/1994 | Zalipsky |
| 5,382,657 A | 1/1995 | Karasiewicz et al. |
| 5,446,090 A | 8/1995 | Harris |
| 5,468,478 A | 11/1995 | Saifer et al. |
| 5,473,034 A | 12/1995 | Yasui et al. |
| 5,476,653 A | 12/1995 | Pitt et al. |
| 5,516,657 A | 5/1996 | Murphy et al. |
| 5,516,673 A | 5/1996 | Margel et al. |
| 5,532,142 A | 7/1996 | Johnston et al. |
| 5,559,213 A | 9/1996 | Hakimi et al. |
| 5,571,709 A | 11/1996 | Devauchelle et al. |
| 5,580,723 A | 12/1996 | Wells et al. |
| 5,583,023 A | 12/1996 | Cerutti et al. |
| 5,602,034 A | 2/1997 | Tekamp-olson |
| 5,605,827 A | 2/1997 | Jackwood et al. |
| 5,612,460 A | 3/1997 | Zalipsky |
| 5,629,203 A | 5/1997 | Shuster |
| 5,629,384 A | 5/1997 | Veronese et al. |
| 5,643,575 A | 7/1997 | Martinez et al. |
| 5,650,234 A | 7/1997 | Dolence et al. |
| 5,672,662 A | 9/1997 | Harris et al. |
| 5,674,706 A | 10/1997 | Shuster |
| RE35,749 E | 3/1998 | Rosenberg et al. |
| 5,736,625 A | 4/1998 | Callstrom et al. |
| 5,739,208 A | 4/1998 | Harris |
| 5,747,646 A | 5/1998 | Hakimi et al. |
| 5,750,373 A | 5/1998 | Garrard et al. |
| 5,753,220 A | 5/1998 | Suzuki et al. |
| 5,762,939 A | 6/1998 | Smith et al. |
| 5,766,885 A | 6/1998 | Carrington et al. |
| 5,808,096 A | 9/1998 | Zalipsky |
| 5,824,778 A | 10/1998 | Ishikawa et al. |
| 5,824,784 A | 10/1998 | Kinstler et al. |
| 5,834,250 A | 11/1998 | Wells et al. |
| 5,834,594 A | 11/1998 | Hakimi et al. |
| 5,843,733 A | 12/1998 | Estes |
| 5,849,860 A | 12/1998 | Hakimi et al. |
| 5,858,368 A | 1/1999 | Smith et al. |
| 5,861,279 A | 1/1999 | Zhang et al. |
| 5,871,986 A | 2/1999 | Boyce |
| 5,891,676 A | 4/1999 | Estes |
| 5,900,461 A | 5/1999 | Harris |
| 5,911,997 A | 6/1999 | Schwabe et al. |
| 5,932,462 A | 8/1999 | Harris et al. |
| 5,939,285 A | 8/1999 | Devauchelle et al. |
| 5,965,393 A | 10/1999 | Hasnain et al. |
| 5,898,868 A | 11/1999 | Harrison et al. |
| 5,980,948 A | 11/1999 | Goedemoed et al. |
| 5,990,237 A | 11/1999 | Bentley et al. |
| 6,004,573 A | 12/1999 | Rathi et al. |
| 6,013,433 A | 1/2000 | Pellett et al. |
| 6,013,478 A | 1/2000 | Wells et al. |
| 6,017,731 A | 1/2000 | Tekamp-Olson et al. |
| 6,083,723 A | 7/2000 | Tekamp-Olson |
| 6,096,304 A | 8/2000 | McCutchen |
| 6,126,944 A | 10/2000 | Pellett et al. |
| 6,129,912 A | 10/2000 | Hortin et al. |
| 6,168,932 B1 | 1/2001 | Uckun et al. |
| 6,183,985 B1 | 2/2001 | Schuster |
| 6,183,987 B1 | 2/2001 | van de Wiel et al. |
| 6,201,072 B1 | 3/2001 | Rathi et al. |
| 6,214,966 B1 | 4/2001 | Harris |
| 6,225,060 B1 | 5/2001 | Clark et al. |
| 6,245,528 B1 | 6/2001 | Chao |
| 6,261,805 B1 | 7/2001 | Wood |
| RE37,343 E | 8/2001 | Tekamp-Olson |
| 6,281,211 B1 | 8/2001 | Cai et al. |
| 6,306,821 B1 | 10/2001 | Mikos et al. |
| 6,312,923 B1 | 11/2001 | Tekamp-Olson |
| 6,337,191 B1 | 1/2002 | Swartz et al. |
| 6,338,846 B1 | 1/2002 | Kang et al. |
| 6,342,216 B1 | 1/2002 | Fidler et al. |
| 6,361,969 B1 | 3/2002 | Galeotti |
| 6,368,825 B1 | 4/2002 | Chao |
| 6,420,339 B1 | 7/2002 | Gegg et al. |
| 6,423,685 B1 | 7/2002 | Drummond et al. |
| 6,428,954 B1 | 8/2002 | Wells et al. |
| 6,436,386 B1 | 8/2002 | Roberts et al. |
| 6,451,346 B1 | 9/2002 | Shah et al. |
| 6,451,561 B1 | 9/2002 | Wells et al. |
| 6,461,603 B2 | 10/2002 | Bentley et al. |
| 6,515,100 B2 | 2/2003 | Harris |
| 6,521,427 B1 | 2/2003 | Evans |
| 6,552,167 B1 | 4/2003 | Rose |
| 6,586,207 B2 | 7/2003 | Tirrell et al. |
| 6,602,498 B2 | 8/2003 | Shen |
| 6,608,183 B1 | 8/2003 | Cox, III |
| 6,610,281 B2 | 8/2003 | Harris |
| 6,646,110 B2 | 11/2003 | Nissen et al. |
| 6,852,507 B1 | 2/2005 | Cerutti et al. |
| 6,927,042 B2 | 8/2005 | Schultz et al. |
| 7,045,337 B2 | 5/2006 | Schultz et al. |
| 7,083,970 B2 | 8/2006 | Schultz et al. |
| 7,230,068 B2 | 6/2007 | Wilson |
| 7,332,571 B2 | 2/2008 | Miao |
| 7,385,028 B2 | 6/2008 | Miao |
| 7,632,823 B2 | 12/2009 | Tian |
| 7,632,924 B2 | 12/2009 | Cho |
| 7,638,299 B2 | 12/2009 | Cho |
| 7,638,491 B2 | 12/2009 | Miao |
| 7,696,312 B2 | 4/2010 | Miao |
| 7,736,872 B2 | 6/2010 | Paulsel |
| 7,737,226 B2 | 6/2010 | Wilson |
| 7,816,320 B2 | 10/2010 | Hays |
| 7,820,766 B2 | 10/2010 | Wilson |
| 7,829,310 B2 | 11/2010 | Paulsel |
| 7,838,265 B2 | 11/2010 | Paulsel |
| 7,846,689 B2 | 12/2010 | Paulsel |
| 7,858,344 B2 | 12/2010 | Paulsel |
| 7,883,866 B2 | 2/2011 | Paulsel |
| 7,888,533 B2 | 2/2011 | Tian |
| 7,919,591 B2 | 4/2011 | Sheffer |
| 7,928,163 B2 | 4/2011 | Miao |
| 7,939,496 B2 | 5/2011 | Cho |
| 7,947,473 B2 | 5/2011 | Buechler |
| 7,959,926 B2 | 6/2011 | Buechler |
| 8,008,428 B2 | 8/2011 | Wilson |
| 8,008,456 B2 | 8/2011 | Miao |
| 8,012,931 B2 | 9/2011 | Cujec et al. |
| 8,022,186 B2 | 9/2011 | Sheffer |
| 8,048,988 B2 | 11/2011 | Miao |
| 8,053,560 B2 | 11/2011 | Sheffer |
| 8,071,809 B2 | 12/2011 | Tian |
| 8,080,391 B2 | 12/2011 | Buechler |
| 8,093,356 B2 | 1/2012 | Hays |
| 8,097,702 B2 | 1/2012 | Cho |
| 8,114,630 B2 | 2/2012 | Kraynov |
| 8,119,603 B2 | 2/2012 | Cho |
| 8,143,216 B2 | 3/2012 | Cho |
| 8,153,758 B2 | 4/2012 | Miao |
| 8,163,695 B2 | 4/2012 | Hays |
| 8,178,108 B2 | 5/2012 | Buechler |
| 8,178,494 B2 | 5/2012 | Hays |
| 8,232,371 B2 | 7/2012 | Cho |
| 8,263,740 B2 | 9/2012 | Miao |
| 8,278,418 B2 | 10/2012 | Tian |
| 8,329,869 B2 | 12/2012 | Kraynov |
| 8,367,612 B2 | 2/2013 | Miao |
| 8,383,365 B2 | 2/2013 | Cujec |
| 8,399,614 B2 | 3/2013 | Miao |
| 8,420,792 B2 | 4/2013 | Tian |
| 8,476,411 B2 | 7/2013 | Miao |
| 8,557,781 B2 | 10/2013 | Miao |
| 8,569,233 B2 | 10/2013 | Tian |
| 8,618,257 B2 | 12/2013 | Sheffer |
| 8,629,246 B2 * | 1/2014 | Humphreys ............ C07K 16/00 530/387.3 |
| 8,735,539 B2 | 5/2014 | Kraynov et al. |
| 8,778,880 B2 | 7/2014 | Cho |
| 8,791,231 B2 | 7/2014 | Miao |
| 8,809,511 B2 | 8/2014 | Miao |

(56) References Cited

U.S. PATENT DOCUMENTS

| | | |
|---|---|---|
| 9,079,971 B2 | 7/2015 | Cujec et al. |
| 9,452,222 B2 | 9/2016 | Kraynov et al. |
| 9,517,273 B2 | 12/2016 | Cujec et al. |
| 9,567,386 B2 | 2/2017 | Kraynov et al. |
| 2001/0021763 A1 | 9/2001 | Harris |
| 2001/0044526 A1 | 11/2001 | Shen |
| 2001/0056171 A1 | 12/2001 | Kozlowski |
| 2002/0002250 A1 | 1/2002 | Bentley et al. |
| 2002/0037949 A1 | 3/2002 | Harris et al. |
| 2002/0040076 A1 | 4/2002 | Harris et al. |
| 2002/0042097 A1 | 4/2002 | Tirrell et al. |
| 2002/0052009 A1 | 5/2002 | Hornauer et al. |
| 2002/0052430 A1 | 5/2002 | Harris et al. |
| 2002/0055169 A1 | 5/2002 | Tekamp-Olson |
| 2002/0072573 A1 | 6/2002 | Bentley et al. |
| 2002/0081660 A1 | 6/2002 | Swartz et al. |
| 2002/0082345 A1 | 6/2002 | Kozlowski et al. |
| 2002/0086939 A1 | 7/2002 | Kozlowski |
| 2002/0099133 A1 | 7/2002 | Kozlowski |
| 2002/0156047 A1 | 10/2002 | Zhao |
| 2003/0023023 A1 | 1/2003 | Harris et al. |
| 2003/0082575 A1 | 5/2003 | Schultz et al. |
| 2003/0105224 A1 | 6/2003 | Roberts et al. |
| 2003/0105275 A1 | 6/2003 | Bentley et al. |
| 2003/0108885 A1 | 6/2003 | Schultz et al. |
| 2003/0114647 A1 | 6/2003 | Harris et al. |
| 2003/0143596 A1 | 7/2003 | Bentley et al. |
| 2003/0158333 A1 | 8/2003 | Roberts et al. |
| 2003/0162949 A1 | 8/2003 | Cox |
| 2003/0220447 A1 | 11/2003 | Harris |
| 2003/0228274 A1 | 12/2003 | Rose |
| 2004/0001838 A1 | 1/2004 | Zhao et al. |
| 2004/0013637 A1 | 1/2004 | Bentley et al. |
| 2004/0198637 A1 | 10/2004 | Schultz et al. |
| 2005/0009049 A1 | 1/2005 | Chin et al. |
| 2005/0085619 A1 | 4/2005 | Wilson |
| 2005/0170404 A1 | 8/2005 | Cho et al. |
| 2005/0220762 A1 | 10/2005 | Cho et al. |
| 2006/0019347 A1 | 1/2006 | Cho |
| 2006/0135427 A1 | 6/2006 | Hays |
| 2006/0153860 A1 | 7/2006 | Cho |
| 2006/0183198 A1 | 8/2006 | Buechler |
| 2006/0189529 A1 | 8/2006 | Cho |
| 2006/0194256 A1 | 8/2006 | Miao |
| 2006/0217289 A1 | 9/2006 | Miao |
| 2006/0217532 A1 | 9/2006 | Miao |
| 2007/0004619 A1 | 1/2007 | Del Borgo et al. |
| 2007/0123691 A1 | 5/2007 | Wilson |
| 2007/0123693 A1 | 5/2007 | Wilson |
| 2008/0050374 A1 | 2/2008 | Cho |
| 2008/0050777 A1 | 2/2008 | Buechler |
| 2008/0081038 A1 | 4/2008 | Cho |
| 2008/0085277 A1 | 4/2008 | Cho |
| 2008/0085538 A1 | 4/2008 | Buechler |
| 2008/0097083 A1 | 4/2008 | Cho |
| 2008/0102124 A1 | 5/2008 | Cho |
| 2008/0102125 A1 | 5/2008 | Cho |
| 2008/0103293 A1 | 5/2008 | Cho |
| 2008/0103294 A1 | 5/2008 | Cho |
| 2008/0107680 A1 | 5/2008 | Cho |
| 2008/0108791 A1 | 5/2008 | Cho |
| 2008/0108792 A1 | 5/2008 | Hays |
| 2008/0108797 A1 | 5/2008 | Cho |
| 2008/0112943 A1 | 5/2008 | Mariani |
| 2008/0113408 A1 | 5/2008 | Mariani |
| 2008/0113411 A1 | 5/2008 | Sheffer |
| 2008/0113412 A1 | 5/2008 | Sheffer |
| 2008/0113912 A1 | 5/2008 | Hays |
| 2008/0113913 A1 | 5/2008 | Hays |
| 2008/0113914 A1 | 5/2008 | Hays |
| 2008/0114154 A1 | 5/2008 | Cho |
| 2008/0255045 A1 | 10/2008 | Cujec et al. |
| 2008/0268518 A1 | 10/2008 | Miao |
| 2008/0268519 A1 | 10/2008 | Miao |
| 2008/0300163 A1 | 12/2008 | Cho |
| 2008/0317670 A1 | 12/2008 | Miao |
| 2009/0018029 A1 | 1/2009 | Miao |
| 2009/0093405 A1 | 4/2009 | Wallen, III et al. |
| 2009/0111147 A1 | 4/2009 | Miao |
| 2009/0123968 A1 | 5/2009 | Miao |
| 2009/0123971 A1 | 5/2009 | Paulsel |
| 2009/0137736 A1 | 5/2009 | Tian |
| 2009/0163368 A1 | 6/2009 | Liu |
| 2009/0208454 A1 | 8/2009 | Kraynov |
| 2009/0240029 A1 | 9/2009 | Miao |
| 2010/0035812 A1 | 2/2010 | Hay |
| 2010/0048871 A1 | 2/2010 | Cho |
| 2010/0075866 A1 | 3/2010 | Hood et al. |
| 2010/0087677 A1 | 4/2010 | Tian |
| 2010/0093082 A1 | 4/2010 | Tian |
| 2010/0093608 A1 | 4/2010 | Tian |
| 2010/0098630 A1 | 4/2010 | Miao |
| 2010/0120686 A1 | 5/2010 | Miao |
| 2010/0135959 A1 | 6/2010 | Hay |
| 2010/0159585 A1 | 6/2010 | Tian |
| 2011/0172401 A1 | 7/2011 | Cujec et al. |
| 2011/0294161 A1 | 12/2011 | Cho |
| 2012/0041180 A1 | 2/2012 | Sheffer |
| 2012/0046229 A1 | 2/2012 | Kraynov et al. |
| 2012/0142890 A1 | 6/2012 | Mariani |
| 2012/0142896 A1 | 6/2012 | Cho |
| 2012/0149636 A1 | 6/2012 | Kraynov |
| 2012/0190096 A1* | 7/2012 | Siekmann ........ A61K 47/48038 435/188 |
| 2012/0190827 A1 | 7/2012 | Sheffer |
| 2012/0197006 A1 | 8/2012 | Kraynov |
| 2012/0283171 A1 | 11/2012 | Putman |
| 2012/0283172 A1 | 11/2012 | Wallen |
| 2012/0315686 A1 | 12/2012 | Miao |
| 2013/0017995 A1 | 1/2013 | Tian |
| 2013/0030160 A1 | 1/2013 | Miao |
| 2013/0150564 A1 | 7/2013 | Cujec et al. |
| 2013/0237474 A1 | 9/2013 | Mariani |
| 2013/0237481 A1 | 9/2013 | Kraynov et al. |
| 2013/0280301 A1 | 10/2013 | Tian |
| 2013/0323821 A1 | 12/2013 | Tian |
| 2014/0011740 A1 | 1/2014 | Tian |
| 2014/0045259 A1 | 2/2014 | Tian |
| 2014/0100357 A1 | 4/2014 | Miao |
| 2014/0194357 A1 | 7/2014 | Kraynov et al. |
| 2015/0273075 A1 | 10/2015 | Cujec et al. |
| 2016/0030585 A1 | 2/2016 | Barnes et al. |
| 2017/0035897 A1 | 2/2017 | Kraynov et al. |
| 2017/0226178 A1 | 2/2017 | Kraynov et al. |
| 2017/0096463 A1 | 4/2017 | Cujec et al. |

FOREIGN PATENT DOCUMENTS

| | | |
|---|---|---|
| DE | 3218121 | 11/1983 |
| EP | 0 036 676 | 9/1981 |
| EP | 0 036 776 | 9/1981 |
| EP | 0 052 322 | 5/1982 |
| EP | 0 058 481 | 8/1982 |
| EP | 0 073 657 | 3/1983 |
| EP | 0 102 324 | 3/1984 |
| EP | 0 121 775 | 10/1984 |
| EP | 0 127 839 | 12/1984 |
| EP | 0 133 988 | 3/1985 |
| EP | 0 143 949 | 6/1985 |
| EP | 0 154 316 | 9/1985 |
| EP | 0 155 476 | 9/1985 |
| EP | 0 164 556 | 12/1985 |
| EP | 0 183 503 | 6/1986 |
| EP | 0 188 256 | 7/1986 |
| EP | 0 229 108 | 7/1987 |
| EP | 0 244 234 | 11/1987 |
| EP | 0 267 851 | 5/1988 |
| EP | 0 284 044 | 9/1988 |
| EP | 0 324 274 | 7/1989 |
| EP | 0 329 203 | 8/1989 |
| EP | 0 340 986 | 11/1989 |
| EP | 0 400 472 | 12/1990 |
| EP | 0 402 378 | 12/1990 |
| EP | 0 439 508 | 8/1991 |

(56) References Cited

FOREIGN PATENT DOCUMENTS

| | | |
|---|---|---|
| EP | 0 480 480 | 4/1992 |
| EP | 0 510 356 | 10/1992 |
| EP | 0 605 963 | 7/1994 |
| EP | 0 732 403 | 9/1996 |
| EP | 0 809 996 | 12/1997 |
| EP | 0 921 131 | 6/1999 |
| EP | 0 946 736 | 10/1999 |
| JP | 60-007934 | 1/1985 |
| JP | 2010-152800 | 4/2010 |
| WO | WO 88/07082 | 9/1988 |
| WO | WO 89/01037 | 2/1989 |
| WO | WO 89/01038 | 2/1989 |
| WO | WO 90/01556 | 2/1990 |
| WO | WO 90/02186 | 3/1990 |
| WO | WO 90/02566 | 3/1990 |
| WO | WO 90/05785 | 5/1990 |
| WO | WO 90/10078 | 9/1990 |
| WO | WO 90/10277 | 9/1990 |
| WO | WO 90/13540 | 11/1990 |
| WO | WO 90/14428 | 11/1990 |
| WO | WO 91/00357 | 1/1991 |
| WO | WO 92/01801 | 2/1992 |
| WO | WO 92/02628 | 2/1992 |
| WO | WO 92/16555 | 10/1992 |
| WO | WO 92/16619 | 10/1992 |
| WO | WO 93/03173 | 2/1993 |
| WO | WO 93/15189 | 8/1993 |
| WO | WO 93/21259 | 10/1993 |
| WO | WO 94/04193 | 3/1994 |
| WO | WO 94/09027 | 4/1994 |
| WO | WO 94/14758 | 7/1994 |
| WO | WO 94/15625 | 7/1994 |
| WO | WO 94/17039 | 8/1994 |
| WO | WO 94/18247 | 8/1994 |
| WO | WO 94/28024 | 12/1994 |
| WO | WO 95/00162 | 1/1995 |
| WO | WO 95/06058 | 3/1995 |
| WO | WO 95/11924 | 5/1995 |
| WO | WO 95/13090 | 5/1995 |
| WO | WO 95/13312 | 5/1995 |
| WO | WO 95/20672 | 8/1995 |
| WO | WO 95/33490 | 12/1995 |
| WO | WO 96/00080 | 1/1996 |
| WO | WO 96/06161 | 2/1996 |
| WO | WO 96/07670 | 3/1996 |
| WO | WO 96/21469 | 7/1996 |
| WO | WO 96/25496 | 8/1996 |
| WO | WO 96/29400 | 9/1996 |
| WO | WO 96/40791 | 12/1996 |
| WO | WO 96/41813 | 12/1996 |
| WO | WO 97/03106 | 1/1997 |
| WO | WO 97/18832 | 5/1997 |
| WO | WO 97/26332 | 7/1997 |
| WO | WO 97/32607 | 9/1997 |
| WO | WO 98/05363 | 2/1998 |
| WO | WO 98/26080 | 6/1998 |
| WO | WO 98/32466 | 7/1998 |
| WO | WO 98/37208 | 8/1998 |
| WO | WO 98/41562 | 9/1998 |
| WO | WO 98/48837 | 11/1998 |
| WO | WO 99/03887 | 1/1999 |
| WO | WO 99/05297 | 2/1999 |
| WO | WO 99/07862 | 2/1999 |
| WO | WO 99/09193 | 2/1999 |
| WO | WO 99/10515 | 3/1999 |
| WO | WO 99/31257 | 6/1999 |
| WO | WO 99/32134 | 7/1999 |
| WO | WO 99/32139 | 7/1999 |
| WO | WO 99/32140 | 7/1999 |
| WO | WO 99/45130 | 9/1999 |
| WO | WO 99/51721 | 10/1999 |
| WO | WO 99/67291 | 12/1999 |
| WO | WO 00/20032 | 4/2000 |
| WO | WO 00/26354 | 5/2000 |
| WO | WO 00/55345 | 9/2000 |
| WO | WO 00/55353 | 9/2000 |
| WO | WO 01/05956 | 1/2001 |
| WO | WO 01/27301 | 4/2001 |
| WO | WO 01/90390 | 11/2001 |
| WO | WO 02/06305 | 1/2002 |
| WO | WO 02/085923 | 10/2002 |
| WO | WO 02/086075 | 10/2002 |
| WO | WO 03/101972 | 12/2003 |
| WO | WO 04/035605 | 4/2004 |
| WO | WO 04/035743 | 4/2004 |
| WO | WO 04/058946 | 7/2004 |
| WO | WO 04/094593 | 11/2004 |
| WO | WO 05/007624 | 1/2005 |
| WO | WO 05/007870 | 1/2005 |
| WO | WO 05/019415 | 3/2005 |
| WO | WO 05/035727 | 4/2005 |
| WO | WO 05/074524 | 8/2005 |
| WO | WO 05/074546 | 8/2005 |
| WO | WO 05/074650 | 8/2005 |
| WO | WO 06/009901 | 1/2006 |
| WO | WO 06/068802 | 6/2006 |
| WO | WO 2006069220 | 6/2006 |
| WO | WO 2006069246 | 6/2006 |
| WO | WO 2006071840 | 7/2006 |
| WO | WO 2006073846 | 7/2006 |
| WO | WO 2006091231 | 8/2006 |
| WO | WO 2006132969 | 12/2006 |
| WO | WO 2006133088 | 12/2006 |
| WO | WO 2006133089 | 12/2006 |
| WO | WO 2007021297 | 2/2007 |
| WO | WO 2007056083 | 5/2007 |
| WO | WO 2007056448 | 5/2007 |
| WO | WO 2007059312 | 5/2007 |
| WO | WO 2007070659 | 6/2007 |
| WO | WO 2007079130 | 7/2007 |
| WO | WO 2007094916 | 8/2007 |
| WO | WO 2008030558 | 3/2008 |
| WO | WO 2008030612 | 3/2008 |
| WO | WO 2008030613 | 3/2008 |
| WO | WO 2008030614 | 3/2008 |
| WO | WO 08/077079 | 6/2008 |
| WO | WO 2008083346 | 7/2008 |
| WO | WO 2008121563 | 10/2008 |
| WO | WO 2008137471 | 11/2008 |
| WO | WO 2009036460 | 3/2009 |
| WO | WO 2009052435 | 4/2009 |
| WO | WO 09/061369 | 5/2009 |
| WO | WO 2009067636 | 5/2009 |
| WO | WO 2009100255 | 8/2009 |
| WO | WO 2009117622 | 9/2009 |
| WO | WO 09/140659 | 11/2009 |
| WO | WO 2010006214 | 1/2010 |
| WO | WO 2010011735 | 1/2010 |
| WO | WO 2010036964 | 4/2010 |
| WO | WO 2010037062 | 4/2010 |
| WO | WO 2010051056 | 5/2010 |
| WO | WO 2011028195 | 3/2011 |
| WO | WO 2011079293 | 6/2011 |
| WO | WO 2011087808 | 7/2011 |
| WO | WO 2011087810 | 7/2011 |
| WO | WO 2012024452 | 2/2012 |
| WO | WO 2012166559 | 12/2012 |
| WO | WO 2012166560 | 12/2012 |
| WO | WO 2013068874 | 5/2013 |
| WO | WO 2013130676 | 9/2013 |
| WO | WO 2013130814 | 9/2013 |
| WO | WO 2013130913 | 9/2013 |
| WO | WO 2013130917 | 9/2013 |
| WO | WO 2013185117 | 12/2013 |
| WO | WO 2013188740 | 12/2013 |
| WO | WO 2013192360 | 12/2013 |
| WO | WO 2015038938 | 3/2015 |
| WO | WO 2016149501 | 9/2016 |

OTHER PUBLICATIONS

Abuchowski, A et al., "Cancer therapy with chemically modified enzymes. I. Antitumor properties of plyethylene glycol-

(56) References Cited

OTHER PUBLICATIONS asparaginase conjugates," Cancer Biochem Biophys. Jun. 1984;7(2):175-86.
Adams et al., "Molecular cloning of mouse immunoglobulin heavy chain messenger ribonucleic acids coding for mu, alpha, gamma 1, gamma 2a, and gamma 3 chains", Biochemistry (1980) 19(12):2711-2719.
Aebersold et al., "A simplified antigrowth assay based on color change of the medium", Meth. Enzymol. 119:579-582. 1986.
Altschul, SF et al., "Basic local alignment search tool," J Mol Biol. Oct. 5, 1990;215(3):403-10.
Altschul, SF et al., "Gapped BLAST and PSI-BLAST: a new generation of protein database search programs," Nucleic Acids Res. Sep. 1, 1997;25(17):3389-402.
Amann, E et al., "Vectors bearing a hybrid trp-lac promoter useful for regulated expression of cloned genes in *Escherichia coli*," Gene. Nov. 1983;25(2-3):167-78.
Anderson, JC et al., "Exploring the limits of codon and anticodon size," Chem Biol. Feb. 2002;9(2):237-44.
Andresz, H et al., Abstract of "Chemische Synthese verzweigter Polysaccharide, %; Kopplung von Oligosacchariden and Amylose an verschiedene Trager durch Hydrazonbindung," Makromol. Chem. 1978;179:301 Abstract.
Arnold, FH, "Protein engineering for unusual environments," Curr Opin Biotechnol. Aug. 1993;4(4):450-5.
Azoulay, M et al., "Glutamine analogues as Potential Antimalarials," Eur J Med Chem (1991);26(2):201-5.
Bain et al., "Ribosome-mediated incorporation of a non-standard amino acid into a peptide through expansion of the genetic code", Mature (1992) 356(6369):537-9.
Bain, DJ et al., "Biosynthetic site-specific incorporation of a non-natural amino acid into a polypeptide," J Am Chem Soc 1989;111(20):8013-8014.
Balance, DJ et al., "Transformation of Aspergillus nidulans by the orotidine-5'-phosphate decarboxylase gene of Neurospora crassa," Biochem Biophys Res Commun Apr. 15, 1983;112(1):284-9.
Barany, F et al., "Genetic disease detection and DNA amplification using cloned thermostable ligase," Proc Natl Acad Sci USA. Jan. 1, 1991;88(1):189-93.
Barton, DHR et al., "Synthesis of Novel alpha-Amino-Acids and derivatives Using Radical Chemistry: Synthesis of L-and D-alpha-Amino-Adipic Acids, L-alpha-Amino-pimelic Acid and Appropriate Unsaturated Derivatives," Tetrahedron (1987) 43:4297-4308.
Bass, S et al., "Mutant Trp repressors with new DNA-binding specificities," Science (1988) 242:240-245.
Batzer, MA et al., "Enhanced evolutionary PCR using oligonucleotides with inosine at the 3'-terminus," Nucleic Acids Res. Sep. 25, 1991;19(18):5081.
Beach, D et al., "Functionally homologous cell cycle control genes in budding and fission yeast," Nature Dec. 1982;300:706-709.
Beaucage et al., "Deoxynucleoside Phosphoramidites—A New Class of Key Intermediates for Deoxypolynucleotide Synthesis", Tetrahedron Letts. (1981);22(20):1859-1862.
Beauchamp, CO et al., "A new procedure for the synthesis of polyethylene glycol-protein adducts; effects on function, receptor recognition, and clearance of superoxide dismutase, lactoferrin, and alpha 2-macroglobulin," Anal Biochem. May 1983;131(1)25-33.
Behrens et al., "Structure of Human Serum Albumin", Fed. Proc. (1975) Biochemistry 2106:591.
Bernstein, FC et al., "The protein data bank: a computer-based archival file for macromolecular structures," J. Mol. Biol. 1977; 112:535-542.
Boissel, JP et al., "Erythroprotein structure-function relationships. Mutant proteins that test a model of tertiary structure," J Biol Chem Jul. 25, 1993;268(21):15983-93.
Boles, JO et al., "Bio-incorporation of telluromithionine into buried residues of dihydrofolate reductase," nat Struct Biol. May 1994;1(5):283-4.
Botstein, D and D Shortie, "Strategies and applications of in vitro mutagenesis," Science. Sep. 20, 1985;229 (4719):1193-201.

Bowie et al., "A method to identify protein sequences that fold into a known three-dimensional structure", Science (1991) 253(5016):164-170.
Brange, J. J. V., et al., Current Opinion in Structural Biology, 1, 934-940 (1991).
Brems et al., "Altering the association of properties of insulin by amino acid replacement", Protein Engineering, (1992) 5(6):527-533.
Brunner, J, "New photolabeling and crosslinking methods," Annu Rev Biochem. 1993:62:483-514.
Bryant-Greenwood, "Relaxin as a new hormone", Endocrine Reviews, (1982) 3(1):62-90.
Buchner, J et al., "A method for increasing the yield of properly folded recombinant fusion proteins: Single-chain immunotoxins from renaturation of bacterial inclusion bodies," Anal. Biochem. 1992;205(2):263-270.
Buckmann, et al., "Functionalization of Poly(ethylene glycol) and Monomethoxy-Poly(ethylene glycol)," Makromol. Chem. 1981;182:1379-84.
Budisa, N et al., "Bioincorporation of telluromethionine into proteins: a promising new aproach for X-ray structure analysis of proteins," J Mol Biol. Jul. 25, 1997;270(4):616-23.
Budisa, N et al., "High-level biosynthetic substitution of methionine in proteins by its analogs 2-aminohexanoic acid, selenomethionine, telluromethionine and ethionine in *Escherichia coli*," Eur J Biochem. Jun. 1, 1995;230(2):788-96.
Budisa, N et al., "Toward the experimental codon reassignment in vivo: protein building with an expanded amino acid repertoire," FASEB J. Jan. 1999 ;13(1):41-51.
Cai, X-Y et al., "Expression, Purificaiton, and Characterization of an Activated Cytokine-Suppressive Anti-inflammatory Drug-Binding Protein 2 (CSBP2) Kinase from Baculovirus-Infected Insect Cells," Protein Expression and Purificaiton 1997;10(2):263-74.
Caliceti, P and FM Veronese, "Pharmacokinetic and biodistribution properties of poly(ethylene glycol)-protein conjugates," Adv Drug Deliv Rev. Sep. 26, 2003;55(10):1261-77.
Carbonell, LF et al., "Baculovirus-mediated expression of bacterial genes in dipteran and mammalian cells," J Viral Oct. 1985;56(1):153-60.
Carrasco, M and R Brown, "A Versatile Set of Aminooxy Amino Acids for the Synthesis of Neoglycopeptides," J Org Chem (2003); 68(23):8853-8858.
Carter, P et al., "Improved oligonucleotide site-directed mutagenesis using vectors," Nucleic Acids Res. Jun. 25, 1985;13(12):4431-43.
Carter, P, "Improved oligonucleotide-directed mutagenesis using M13 vectors," Methods Enzymol. 1987;154:382-403.
Carter, P, "Site-directed mutagenesis," Biochem J. Jul. 1, 1986;237(1):1-7.
Cate et al., "Isolation of the Bovine and Human Genes for Mullerian Inhibiting Substance and Expression of the Human Gene in Animal Cells", Cell, 45, pp. 685 98 (1986).
Cech, "The Chemistry of Self-Splicing RNA and RNA Enzymes", Science, (1987) 236:1532-1539.
Chaiken, IM, "Semisynthetic peptides and proteins," CRC Grit Rev Biochem. 1981;11(3):255-301.
Chin, JW and PG Schulz, "In vivo photocrosslinking with unnatural amino acid mutagenesis," Chembiochem. Nov. 4, 2002;3(11):1135-7.
Chin, JW et al., "Addition of a photocrosslinking amino acid to the genetic code of *Escherichia coli*," Proc Natl Acad Sci USA. Aug. 20, 2002;99(17):11020-4. Epub Aug. 1, 2002.
Chin, JW et al., "Addition of p-azido-L-phenylalanine to the genetic code of *E. coli*," J Am Chem Soc. Aug. 7, 2002;124(31):9026-7.
Chin, JW et al., "An expanded eukaryotic genetic code," Science. Aug. 15, 2003;301(5635):964-7.
Christie, BD and H Rapoport, "Synthesis of Optically Pure Pipecolates from L-Asparagine. Application to the Total Synthesis of (+)-Apovincamine through Amino Acid Decrbonylation and Iminium Ion Cyclization," J Org Chem 1985;50(8):1239-1246.
Clark, EDB, "Protein refolding for industrial processes," Curr Opin Biotechnol Apr. 2001;12(2):202-7.
Clark, EDB, "Refolding of recombinant protiens," Curr Opin Biotechnol Apr. 1, 1998;9(2):157-63.

(56) References Cited

OTHER PUBLICATIONS

Clark, R et al., "Lon-acting growth hormones produced by conjugation with polyethylene glycol," J Biol Chem. Sep. 6, 1996;271(36):21969-77.
Coloma, "Novel vectors for the expression of antibody molecules using variable regions generated by polymerase chain reaction", J Immunol Methods. (1992) 152(1):89-104.
Corey, DR and PG Schultz, "Generation of a hybrid sequence-specific single-stranded deoxyribonuclease," Science 1987;238(4832):1401-1403.
Cornish, VW et al., "Probing protein Structure and Function with an Expanded Genetic Code," Angew Chem Int Ed Engl, 1995;34(6):621-33.
Cornish, VW et al., "Site-Specific Protein Modification Using a Ketone Handle," J Am Chem Soc 1996: 118(34):8150-8151.
Craig, JC et al., "Absolute Configuration of the Enantiomers of 7-Chloro-4 [[4-(diethylamino)-1-methylbutyl]amino] quinoline (Chloroquine)," J Org Chem. 1988; 53(6):1167-1170.
Cregg, JM et al., "Pichia pastoris as a host system for transformations," Mol Cell Biol. Dec. 1985;5(12):3376-85.
Crick, FHC et al., "General nature of the genetic code of proteins," Nature. Dec. 30, 1961;192:1227-32.
Dahiyat et al., "De novo protein design: fully automated sequence selection", Science (1997) 278(5335):82-7.
Dahiyat et al., "Protein design automation", Protein Sci May 1996;5(5):895-903.
Dale et al., "Oligonucleotide-directed random mutagenesis using the phosphorothioate method," Methods Mol Biol. 1996;57-369-374.
Das, S et al., "Transformation of Kluyveromyces fragilis," J Bacteriol. Jun. 1984;158(3):1165-7.
Davis, GD et al., "New fusion protein systems designed to give soluble expression in *Escherichia coli*," Biotechnol Bioeng Nov. 20, 1999;65(4):382-8.
Dawson, PE and SBH Kent, "Synthesis of native proteins by chemical ligation," Annu Rev Biochem 2000;69:923-60.
De Boer, HA et al., "The tac promoter: a functional hybrid derived from the trp and lac promoters," Proc Natl Acad Sci USA Jan. 1983;80(1):21-5.
De Louvencourt, L et al., "Transformation of Kluyveromyces latis by killer plasmid DNA," J Bacteriol. May 1983;154(2):737-42.
Debinski, W et al., "A wide range of human cancers express interleukin 4 (IL4) receptors that.can be targeted with chimeric toxin composed of IL4 and Pseudomonas exotoxin," J Biol Chem. Jul. 5, 1993;268(19):14065-70.
Deiters, A et al., "Adding Amino Acids with Novel Reactivity to the Genetic Code of *Saccharomyces cerevisiae*," J Am Chem Soc 2003; 125(39):11782-11783.
Deiters, A et al., "Site-specific PEGylation of proteins containing unnatural amino acids," Bioorganic & Medicinal Chemistry Letters 14 (2004) 5743-5745.
Delgado, C et al., "The uses and properties of PEG-linked proteins," Grit Rev Ther Drug Carrier Syst. 1992;9(3-4):249-304.
Dennis, MS et al., "Albumin binding as a general strategy for improving the pharmacokinetics of proteins," J Biol Chem. Sep. 20, 2002;277(38):35035-43. Epub Jul. 15, 2002.
Desjarlais et al., "De novo design of the hydrophobic cores of proteins", Protein Science (1995) 4(10):2006-18.
Dolby et al., "Cloning and partial nucleotide sequence of human immunoglobulin mu chain eDNA from B cells and mouse-human hybridomas", Proc. Natl. Acad. Sci. USA (1980) 77(10):6027-6031.
Dolphin, CT et al., "Missense mutation in flavin-containing monooxygenase 3 gene, FM03, underlies fish-odour syndrome," Nat Genet. Dec. 1997;17(4):491-4.
Doring, V et al., "Enlarging the amino acid set of *Escherichia coli* by infiltration of the valine coding pathway," Science. Apr. 20, 2001;292(5516):501-4.
Dougherty, DA, "Unnatural amino acids as probes of protein structure and function," Curr Opin Chem biol. Dec. 2000;4(6):645-52.
Duewel, H et al., "Incorporation of trifluomethionine into a phage lysozyme: implications and a new marker for use in protein 19F NMR," Biochemistry. Mar. 18, 1997;36(11):3404-16.
Duncan, R, "The dawning era of polymer therapeutics," Nat Rev Drug Discov May 2003;2(5):347-60.
Edwards et al., "A bacterial amber suppressor in *Saccharomyces cerevisiae* is selectively recognized by a bacterial aminoacyl-tRNA synthetase", Mol. Cell. Bioi. (1990) 10(4):1633-1641.
Egel-Mitani et al., "A novel aspartyl protease allowing KEX2-independent MF alpha propheromone processing in yeast", Yeast (1990) 6(2):127-137.
Eghtedarzadeh, MK and S Henikoff, "Use of oligonucleotides to generate large deletions," Nucleic Acids Res. Jun. 25, 1986;14(12):5115.
Elling, L and MR Kula, "Immunoaffinity partitioning: synthesis and use of polyethylene glycol-oxirane for coupling to bovine serum albumin and monoclonal antibodies," Biotechnol Appl Biochem. Jun. 1991;13(3):354-62.
Elliott, S et al., "Yeast-derived recombinant human insulin-like growth factor 1: production, purification, and structural characterization," J Protein Chem.. Feb. 1990;9(1):95-104.
Ellman, JA et al., "Biosynthetic method for introducing unnatural amino acids site-specifically into proteins," Methods in Enz. 1992;202:301-336.
Ellman, JA et al., "Site-specific incorporation of novel backbone structures into proteins," Science. Jan. 10, 1992;255(5041):197-200.
England, PM et al., "Backbone mutations in transmembrane domains of a ligand-gated ion channel: implications for the mechanism of gating," Cell. Jan. 8, 1999;96(1):89-98.
Eppstein et al., "Biological Activity of Liposome-Encapsulated Murine Interferon is Mediated By a Cell Membrane Receptor," Proc Natl Acad Sci USA. (1985);82:3688-3692.
Falkner et al., "Expression of mouse immunoglobulin genes in monkey cells", Nature (1982) 298(5871):286-288.
Familletti et al., "A convenient and rapid cytopathic effect inhibition assay for interferon", Meth. Enzymol. (1981) 78(Pt A):387-394.
Fieschko, JC et al., "Controlled expression and purification of human immune interferon from high-cell-density fermentations of *Saccharomyces cerevisiae*," Biotech Bioeng (1987);29(9):1113-21.
Forster, AC et al., "Programming peptidomimetic syntheses by translating genetic codes designed de novo," Proc Natl Acad Sci USA. May 27, 2003;100(11):6353-7. Epub May 2003.
Frankel, A et al., "Encodamers: unnatural peptide oligomers encoded in RNA," Chem. Biol. Nov. 2003; 10(11):1043-50.
Fraser, MJ et al., "Expression of eucaryotic genes in insect cell cultures," In Vitro Cell Dev Biol. 1989;25:225-235.
Friedman, OM and R Chatterrji, "Synthesis of Derivatives of Glutamine as Model Substrates For Anti-Tumor Agents," J Am Chem Soc 1959; 81(14):3750-3752.
Friesen et al., "The Regulation of Baculovirus Gene Expression", Current Topics in Microbiology and Immunology, (1986) 131:31-49.
Fritz HJ et al., "Oligonucleotide-directed construction of mutations: a gapped duplex DNA procedure without enzymatic reactions in vitro," Nucleic Acids Res Jul. 25, 1988;16(14B):6987-99.
Fromm, M et al., "Expression of Genes Transferred into Mono- and Dicot Plant Cells by Electroporation," Proc Natl Acad Sci USA. (1985) 82:5824-8.
Furter, R, "Expansion of the genetic code: site-directed p-fluoro-phenylalanine incorporation in *Escherichia coli*," Protein Sci. Feb. 1998; 7(2):419-26.
Gaertner, HF and RE Offord, "Site-specific attachment of functionalized poly(ethylene glycol) to the amino terminus of proteins," Bioconjug Chem Jan.-Feb. 1996;7(1):38-44.
Gaertner, HF et al., "Chemo-enzymic backbone engineering of protins. Site-specific incorporation of synthetic peptides that mimic the 64-74 disulfide loop of granulocyte colony-stimulating factor," J Biol Chem. Mar. 11, 1994;269(10):7224-30.
Gaertner, HF et al., "Construction of protein analogues by site-specific condensation of unprotected fragments," Bioconjug Chem. May-Jun. 1992;3(3):262-8.

(56) References Cited

OTHER PUBLICATIONS

Gallivan, JP et al., "Site-specific incorporation of biotinylated amino acids to identify surface-exposed residues in integral membrane proteins," Chem Biol. Oct. 1997;4(10):739-49.
Gellissen, G et al., "Heterologous protien production in yeast," Antonie Van Leeuwenhoek. Aug. 1992; 62(1-2):79-93.
Geoghegan, KF and JG Stroh, "Site-directed conjugation of nonpeptide groups to peptides and proteins via periodate oxidation of a 2-amino alcohol. Application to modification at N-terminal serine," Bioconjug Chem. Mar.-Apr. 1992;3(2):138-46.
Gillam, S and M Smith, "Site-specific mutagenesis using synthetic oligodeoxyribonucleotide primers: I. Optimum conditions and minimum oligodeoxyribonucleotide length," Gene 1979;8(1):81-97.
Gleeson, MA et al., "Transformation of the methylotrophic yeast hansenula polymorphica," J Gen Microbiol (1986) 132:3459-3465.
Goeddel, DV, "Systems for heterologous gene expression," Methods Enzymol 1990;185:3-7.
Goeddel, DV, et al., "Synthesis of human fibroblast interferon by *E. coli*," Nucleic Acids Res. Sep. 25, 1980;8(18):4057-74.
Goodson, RJ and NV Katre, "Site-directed pegylation of recombinant interleukin-2 at its glycosylation site," Biotechnology (NY). Apr. 1990;8(4):343-6.
Gough et al., "Molecular Cloning of Seven Mouse Immunoglobulin k Chain Messenger Ribonucleic Acids", Biochemistry (1980) 19(12):2702-2710.
Graves, SW et al., "Expression, purificaiton, and initial kinetic characterization of the large subunit of the human mitochondrial DNA polymerase," Biochemistry. Apr. 28, 1998;37(17):6050-8.
Griffin, BA et al., "Specific Covalent Labeling of Recombinant Protein Molecules Inside Live Cells," Science (1998) 281:269-272.
Grundstrom, T et al., "Oligonucleotide-directed mutagenesis by microscale 'shot-gun' gene synthesis," Nucleic Acids Res. May 10, 1985; 13(9):3305-16.
Gu, Z et al., "Chromatographic methods for the isolation of, and refolding of proteins from *Escherichia coli* inclusion bodies," Protein Expr Purif. Jun. 2002;25(1):174-9.
Guckian, KM and ET Kool, "Highly Precise Shape Mimicry by a Difluorotoluene Deoxynucleoside, a Replication Competent Substitute for Thymidine," Angew Chem Int Ed Engl (1998) 36(24):2825-8.
Hagenbuchle et al., "Mouse liver and salivary gland alpha-amylase mRNAs differ only in 5'non-translated sequences", Nature (1981) 289(5799):643-646.
Hakola et al., "Recombinant rat follicle-stimulating hormone; production by Chinese hamster ovary cells, purification and functional characterization", Molecular and Cellular Endocrinology, (1997) 127(1):59-69.
Halls, M.L. et al., "Multiple Binding Sites Revealed by Interaction of Relaxin Family Peptides with Native and Chimeric Relaxin Family Peptide Receptors 1 and 2 (LGR7 and LGR8)", J. Pharmacol. Exp. Ther., May 2005; 313(2): 677-687.
Hamano-Takaku, F et al., "A mutant *Escherichia coli* tyrosyl-tRNA synthetase utilizes the unnatural amino acid azatyrosine more efficiently than tyrosine," J Biol Chem. Dec. 22, 2000;275(51):40324-8.
Hang, HC and CR Bertozzi, "Chemoselective approaches to glycoprotein assembly," Acc Chem Res Sep. 2001;34(9):727-36.
Harbury et al., "Repacking protein cores with backbone freedom: structure prediction for coiled cells", PNAS USA (1995) 92(18):8408-12.
Harris, JM et al., "Synthesis and Characterization of Poly(ethylene Glycol) Derivatives," J Polym Sci Chem Ed 1984; 22:341-352.
Harris, JM, "Laboratory Synthesis of Polyethylene Glycol Derivatives," JMS-Rev. Macromol Chem Phys 1985;C25(3):325-373.
Hecht et al., "Chemical Aminoacylation of tRNA's", J. Biol. Chem. (1978) 253(13):4517-4520.
Hecht, "Probing the Synthetic Capabilities of a Center of Biochemical Catalysis", Acc. Chem. Res. (1992) 25(12):545-552.

Heckler et al., "Ribosomal binding and dipeptide formation by misacylated tRNA(Phe),S", Biochemistry (1988) 27(19):7254-7262.
Hellinga et al., "Optimal sequence selection in proteins of known structure by simulated evolution", PNAS USA (1994) 91(13):5803-5807.
Hendrickson, WA et al., "Selenomethionyl proteins produced for analysis by multiwavelength anomalous diffraction (MAD): a vehicle for direct determination of three-dimensional structure," EMBO J. May 1990;9(5):1665-72.
Henikoff, S and JG Henikoff, "Amino Acid Substitution Matrices from Protein Blocks," Proc Natl Acad Sci USA 1992;89:10915-9.
Hess, B et al., "Cooperation of glycolytic enzymes," J Adv Enxyme Reg (1969): 7:149-67.
Hinnen, A et al., "Transformation of yeast," Proc Natl Acad Sci USA. Apr. 1978; 75(4):1929-33.
Hirao, I et al., "An unnatural base pair for incorporating amino acid analogues into proteins," Nat Biotechnol. Feb. 2002;20(2):177-82.
Hitzemann, RA et al., "Isolation and characterization of the yeast 3-phosphoglycerokinase gene (PGK) by an immunological screening technique," J Biol Chem. Dec. 25, 1980;255(24):12073-80.
Hofmann, K and H Bohn, "Studies on polypeptides. XXXVI. The effect of pyrazole-imidazole replacements on the S-protein activating potency of an S-peptide fragment," J Am Chem, (1866);88(24):5914-5919.
Hohsaka, T and M Sisido, "Incorporation of non-natural amino acids into proteins," Curr Opin Chem Biol. Dec. 2002;6(6):809-15.
Hohsaka, T et al., "Efficient Incorporation of Nonnatural Amino Acids with Large Aromatic Groups into Streptavidin in In Vitro Protein Synthesizing Systems," J Am Chem Soc 1999; 121(1):34-40.
Hohsaka, T et al., "Incorporation of Two Different Nonnatural Amino Acids Independently into a Single Protein through Extension of the Genetic Code," J Am Chem Soc 1999; 121(51):12194-12195.
Hokland et al., "Measurements of changes in histocompatibility antigens induced by interferons", Meth. Enzymol. (1986) 119:688-693.
Holland, MJ et al., "The primary structures of two yeast enolase genes. Homology between the 5' noncoding flanking regions of yeast enolase and glyceraldehyde-3-phosphate dehydrogenase genes", J Biol. Chem. Feb. 10, 1981; 256(3):1385-95.
Holland, MJ et JP Holland., "Isolation and identification of yeast messenger ribonucleic acids coding for enolase, glyceraldehyde-3-phosphate dehydrogenase, and phosphoglycerate kinase," Biochemistry. Nov. 14, 1978; 17 (23):4900-7.
Hossain, M.A. et al., "The A-chain of human relaxin family peptides and distinct roles in the binding and activation of the different relaxin family peptide receptors", J. Biol. Chem. Jun. 20, 2008; 283(25): 17287-97.
Hsiao, CL et J Carbon, "High-frequency transformation of yeast by plasmids containing the cloned yeast ARG4 gene," Proc. Natl. Acad. Sci. USA Aug. 1979; 76(8):3829-33.
Hudson et al., "Relaxin gene expression in human ovaries and the predicted structure of a human preprorelaxin by analysis of eDNA clones", The EMBO Journal (1984) 3(10):2333-9.
Hudson et al., "Structure of a genomic clone encoding biologically active human relaxin", Nature (1983) 301(5901):628-31.
Huisgen, R. in 1,3-Dipolar Cycloaddition Chemistry, vol. 1, 1984; Ed. Padwa A.; John Wiley and Sons, New York, p. 1-176.
Hwang, KJ et al., "Hepatic uptake and degradation of unilamellar sphigomyelin/cholesterol liposomes: a kinetic study," Proc. Natl. Acad. Sci. USA Jul. 1980; 77(7):4030-4.
Ibba, M et al., "Substrate specificity is determined by amino acid binding pocket size in *Escherichia coli* phenylalanyl tRNA synthetase," Biochemistry. Jun. 14, 1994; 33(23): 7107-12.
Ibba, M et H Hennecke, "Relaxing the substrate specificity of an aminoacyl-tRNA synthetase allows in vitro and in vivo synthesis of proteins containing unnatural amino acids," FEBS Lett. May 15, 1995; 364(3):272-5.
Illangakekare et al., "Aminoacyl-RNA Synthesis Catalyzed by an RNA", Science (1995) 267(5198):643-647.
Ito, H. et al., "Transformation of intact yeast cells treated with alkali cations," J. Bacteriol. 1983; 153(1):163-8.

(56) References Cited

OTHER PUBLICATIONS

Jackson, DY et al., "A designed peptide ligase for total synthesis of ribonuclease A with unnatural ctalytic residues," Science. Oct. 14, 1994; 266(5183):243-7.

Jakobsson, PJ et al., "Identification and characterization of a novel human microsomal glutathione S-transferase with leukotriene C4 synthase activity and significant sequence identity to 5-lipoxygenase-activating protein and leukotriene C4 synthase," J. Biol. Chem. Sep. 6, 1996;271(36):22203-10.

James et al., "Primary structure of porcine relaxin: homology with insulin and related growth factors", Nature, (1977) 267(5611):544-6.

Jencks, W.P., "Studies on theMechanism of Oxime and Semicarbazone Formation," J. Am. Chem. Soc.; 1959; 81 (2):475-481.

Johnston et al., in Peptides: Structure and Function, Proc. Ninth American Peptide Symposium, Deber, C. M., et al. (eds.) (Pierce Chem. Co. 1985).

Jones, "De novo protein design using pairwise potentials and a genetic algorithm", Protein Science (1994) 3(4):567-74.

Joppich, M. et al., "Peptides Flanked by Two Polymer Chains, 1; Synthesis of Glycl-L-tryptophylglycine Substituted by Poly(ethlene oxide) at both the Carboxy and the Amino End Groups," Markromol. Chem. 1979;180:1381-4.

Kaiser, ET and OS Lawrence, "Chemical mutation of enzyme active sites," Science. Nov. 2, 1984;226(4674):505-11.

Kaiser, ET et al., "The chemical modification of enzymatic specificity," Annu. Rev. Biochem 1985;54:565-95.

Kaiser, ET, "Synthetic approaches to biologically active peptides and proteins including enzymes," Ace Chem Res, (1989); 22(2):47-54.

Karlin, S and SF Altschul "Applications and statistics for multiple high-scoring segments in molecular sequences," Proc Natl Acad Sci USA Jun. 15, 1993;90(12):5873-7.

Kayser, B., et al., "Alkyne bridged alpha-amino acids by palladium mediated coupling of alyknes with N-t-Boc-4-iodo-phenylalanine methyl ester," Tetrahedron (1997); 53(7):2475-2484.

Kelly, JM and MJ Hynes, "Transformation of Aspergillus niger by the amdS gene of Aspergillus nidulans," EMBO J. 1985; 4(2):475-479.

Kiick, KL and DA Tirrell, "Protein Engineering by in Vivo Incorporation of Non-Natural Amino Acids: Control of Incorporation of Methionine Analogues by Methionyl-tRNA Synthetase," Tetrahedron (2000), 56:9487-9493.

Kiick, KL et al., "Incorporation of azides into recombinant proteins for chemoselective modification by the Staudinger ligation," Proc Natl Acad Sci USA Jan. 8, 2002;99(1):19-24. Epub Dec. 18, 2001.

Kim, DM and JR Swartz, "Oxalate improves protein synthesis by enhancing ATP supply in a cell-free system derived form *Escherichia coli*," Biotechnology Letters, 2000: 22:1537-1542.

Kim, DM and JR Swartz, "Prolonging cell-free protein synthesis by selective reagent additions," Biotechnol Prog. May-Jun. 2000;16(3):385-90.

Kim, DM and JR Swartz, "Prolonging cell-free protein synthesis with a novel ATP regeneration system," Biotechnol Bioeng. 1999;66(3):180-8.

Kim, DM and JR Swartz, "Regeneration of adenosine triphosphate from glycolytic intermediates for cell-free protein synthesis," Piotechnol Bioeng. Aug. 20, 2001; 74(4):309-16.

King, FE and Kidd, DA, "A New Synthesis of Glutamine and of gamma-Dipeptides of Glutamic Acid from Phthylated Intermediates," J. Chem. Soc. 1949; 3315-3319.

Kingsman, AJ et al., "Replication in *Saccharomyces cerevisiae* of plasmid pBR313 carrying DNA from the yeast trpl region," Gene. Oct. 1979; 7(2):141-52.

Kitts, PA et al., "Linerarization of baculovirus DNA enhances the recovery of recombinant virus expression vectors," Nucleic Acids Res. Oct. 11, 1990;18(19):5667-72.

Klein, TM et al., "High-velocity microprojectiles for delivering nucleic acids into living cells," Nature 1987; 327(6117):70-73.

Kobayashi, T. et al., "Structural basis for orthogonal tRNA specificities of tyrosyl-tRNA synthases for genetic code expansion," Nature Structural Biology (2003); 10(6):425-432.

Kogan, TP, "The synthesis of substituted methoxy-poly(ethylene glycol) derivatives suitable for selective protein modification," Synthetic Comm. 1992; 22(16):2417-24.

Kono et al., "Energy minimization method using automata network for sequence and side-chain conformaiton prediction from given backbone geometry", Proteins (1994) 19(3):244-255.

Kool, ET, "Synthetically modified DNAs as substrates for polymerases," Curr Opin Chem Biol. Dec. 2000; 4(6):602-8.

Koskinen, AMP and Rapoport, H, "Synthesis of 4-Substituted Prolines as Conformationally Constrained Amino Acid analogues," J. Org. Chem. (1989) 54(8):1859-1866.

Kost, TA et al., "Production of a urokinase plasminogen activator-IgG fusion protein (uPA-IgG) in the baculovirus expression system," Gene Apr. 29, 1997;190(1):139-44.

Kourouklis et al., "Programmable ribozymes for mischarging tRNA with nonnatural amino acids and the applications to translation", Methods (2005) 36:239-244.

Kowal et al., "Exploiting unassigned codons in Micrococcus ltueus for tRNA-based amino acid mutagenesis", Nucl. Acid. Res., (1997) 25(22):4685-4689.

Kowal et al., "Twenty-first aminoacyl syntetase-suppresor tRNA pairs for possible use in site-specific incorporation of amino acid analogues into proteins in eukaryotes and in eubacteria", Proc. Natl. Acad. Sci. U.S.A. (2001) 98(5):2268-2273.

Kramer, B et al., "Different base/base mismatches are corrected with different efficiencies by the methyl-directed DNA mismatch-repair system of *E. coli*," Cell. Oct. 1984; 38(3):879-87.

Kramer, W and HJ Fritz, "Oligonucleotide-directed construction of mutations via gapped duplex DNA," Methods Enzymol. 1987;154:350-67.

Kramer, W et al., "Improved enzymatic in vitro reactions in the gapped duplex DNA aproach to oligonucleotide directed construction of mutations," Nucleic Acids Res. Jul. 25, 1988; 16(14B):7207.

Kramer, W et al., "The gapped duplex DNA approach to oligonucleotide-directed mutation construction," Nucleic Acids Res. Dec. 21, 1984;12(24):9441-56.

Kreitman, RJ and I Pastan, "Purificaiton and characterization of IL6-PE4E, and recombinant fusion of interleukin 6 with Pseudomonas exotoxin," Bioconjug. Chem. Nov.-Dec. 1993;4(6):581-5.

Krieg, UC et al., "Photocrosslinking of the signal sequence of nascent preprolactin to the 54-kilodalton polypeptide of the signal recognition particle," Proc Natl Acad Sci USA. Nov. 1986;83(22):8604-8.

Kunitani, M et al., "Reversed-phase chromatography of interleukin-2 muteins," J Chromatogr May 30, 1986; 359:391-402.

Kunkel, "The efficiency of oligonucleotide directed mutagenesis," in Nucleic Acids & Molecular Biology 1987; Ekstein, F. and Lilley, D.M.J. eds.; Springer Verlag, Berlin; 124-135.

Kunkel, TA et al., "Rapid and efficient site-specific mutagenesisi without phenotypic selection," Methods Enzymol. 1987; 154:367-82.

Kunkel, TA, "Rapid and efficient site-specific mutagenesis without phenotypic selection," Proc Natl Acad Sci USA. Jan. 1985;82(2):488-92.

Kunze, G et al., "Transfomraiton of the industrially important yeasts Candida maltosa and Pichia guillermondii," J. Basic Microbiol. 1985; 25:141-4.

Kurtz et al., "Integrative transformation of Candida albicans, using a clones Candida DE2 gene," Mol Cell Biol. Jan. 1986;6(1):142-9.

Kurtzhals, P et al., "Albumin binding of insulins acylated with fatty acids: characterization of the ligand-protein interactionand correlation between binding affinity and timing of the insulin effect in vivo," Biochem J. Dec. 15, 1995;312 (Pt 3):725-31.

Langer, R et al., "Biocompatibility of polymeric delivery systems for macromolecules," J Biomed Mater Res. Mar. 1981; 15(2):267-77.

Langer, R, "Controlled release of macromolecules," Chem. Tech. 1982; 12:98-105.

(56) References Cited

OTHER PUBLICATIONS

Lawn et al., "The sequence of human serum albumin eDNA and its expression in *E. coli*", Nucleic Acids Research (1981) 9(22):6102-6114.
Liebman, JM et al., "When less is more: enhanced baculovirus production of recombinant proteins at very low multiplicities of infection," Biotechniques. Jan. 1999; 26(1):36-8, 40, 42.
Lilie, H et al., "Advances in refolding of proteins produced in *E. coli*," Curr Opin Biotechnol. Oct. 1998;9(5):497-501.
Ling, MM and BH Robinson, "Approaches to DNA mutagenesis: an overview," Anal Biochem. Dec. 15, 1997;254 (2):157-78.
Liu, DR and Schultz, PG, "Progress toward the evolution of an organism with an expanded genetic code," Proc Natl Acad Sci USA Apr. 27, 1999;96(9):4780-5.
Liu, H et al., "A Method for the Generation of Glycoprotein Mimetics," J Am Chem Soc 2003 125(7):1702-1703.
Lohse et al., "Ribozyme-catalysed amino-acid transfer reactions", Nature (1996) 381:442-444.
Lorimer, IA and I Pastan, "Random recombination of antibody single chain Fv sequences after fragmentation with DnaseI in the presence of Mn2+," Nucleic Acids Res. Aug. 11, 1995;23(15):3067-8.
Lu et al., "Site-specific incorporation of a Phosephotyrosine Mimetic Reveals a Role for Tyrosine Phosphorylation of SHP-2 in Cell Signalling", Mol. Cell. (2001) 8(4):759-69.
Lu, T et al., "Probing ion permeation and gating in a K+ channel with backbone mutations in the selectivity filter," Nature Neurosci. Mar. 2001; 4(3):239-246.
Luckow, VA and MD Summers, "High level expression of nonfused foreign genes with Autographa californica nuclear polyhedrosis virus expression vectors," Virology. May 1989;170(1):31-9.
Ma, C et al., "In vitro protein engineering using synthetic tRNA(Aia) with different anticodons," Biochemistry. Aug. 10, 1993;32(31):7939-45.
Magliery, TJ et al., "Expanding the Genetic Code: Selection of Efficient Suppressors of Four-base Codons and Identification of "Shifty" Four-base Codons with a Library Approach in *Escherichia coli*," J Mol Biol. Mar. 30, 2001; 307(3):755-69.
Mahal, LK et al., "Engineering chemical reactivity on cell surfaces through oligosaccharide biosynthesis," Science. May 16, 1997; 276(5315):1125-8.
Makrides, SC et al., "Extended in vivo half-life of human soluble complement receptor type 1 fused to a serum albumin-binding receptor," J Pharmacol Exp Ther. Apr. 1996; 277(1):534-42.
Mamot, C et al., "Epidermal growth factor receptor (EGFR)-targeted immunoliposomes mediate specidifc and efficient drug deliverty to EGFR- and EGFRvIII-overexpressing tumor cells," Cancer Res. Jun. 15, 2003;63(12):3154-61.
Mandecki, W, "Oligonucleotide-directed double-strand break repair in plasmids of *Escherichia coli*: a method for site-specific mutagenesis," Proc Natl Acad Sci USA. Oct. 1986;83(19):7177-81.
Mann, SG and LA King, "Efficient transfection of insect cells with baculovirus DNA using electroporation," J Gen Virol. Dec. 1989; 70 (Pt12):3501-5.
Matsoukas, JM et al., "Differences in backbone structure between angiotensin II agonists and type I antagonists," J Med Chem. Nov. 10, 1995;38(23):4660-9.
McCorkle et al., "RNA's as Catalysts: A New Class of Enzymes", Concepts Biochem. (1987) 64(3):221-226.
McMinn, DL et al., "Efforts toward Expansion of the Genetic Alphabet: DNA Polymerase Recognition of a Highly Stable, Self-Pairing Hydrophobic Base," J. Am. Chem. Soc. 1999; 121(49):11585-6.
Meggers, E et al., "A Novel Copper-Mediated DNA Base Pair," J. Am. Chem. Soc. 2000; 122(43):10714-10715.
Mehl, RA et al., "Generation of a bacterium with a 21 amino acid genetic code," J Am Chem Soc. Jan. 29, 2003;125(4):935-9.
Mehvar, R, "Modulation of the phamacokinetics and pharmacodynamics of proteins by polyethylene glycol conjugation," J Pharm Pharm Sci. Jan.-Apr. 2000;3(1):125-36.
Meloun et al., "Complete amino acid sequence of human serum albumin", FEBS Letters (1975) 58(1):136-7.
Mendel, D et al., "Site-directed mutagenesis with an expanded genetic code," Annu Rev Biophys Biomol Struct. 1995;24:435-62.
Miller, JC et al., "Flash decaging of tyrosine sidechains in an ion channel," Neuron. Apr. 1998;20(4):619-24.
Miller, LK, "Baculoviruses as gene expression vectors," Ann Rev Microbiol. 1988; 42:177-99.
Miller, LK, "Insect baculoviruses: powerful gene expression vectors," Bioessays. Oct. 1989;11(4):91-5.
Minghetti et al., "Molecular structure of the human albumin gene is revealed by nucleotide sequence within q11-22 of chromosome 4", J Biol Chem. (1986) 261(15):6747-57.
Minks, C et al., "Noninvasive tracing of recombinant proteins with flurophenylalanine-fingers," Anal Biochem. Aug. 15, 2000; 284(1):29-34.
Miyanohara, A et al., "Expression of hepatitis B surface antigen gene in yeast," Proc Natl Acad Sci USA. Jan. 1983; 80(1):1-5.
Moore, B et al., "Quadruplet codons: implications for code expansion and the specification of translation step size," J Mol Biol 2000; 298(2):195-209.
Morrison et al., "Transfer and expression of immunoglobulin genes", Ann. Rev. Immuno. (1984) 2:239-256.
Mosbach, K et al., "Formulation of proinsulin by immobilized Bacillus subtilis," Nature Apr. 1983; 302:543-545.
Nakamaye, KL and Eckstein F, "Inhibition of restriction endonuclease Nci I cleavage by phosphorothioate groups and its application to oligonucleotide-directed mutagenesis," Nucleic Acids Res. Dec. 22, 1986;14(24):9679-98.
Nakatsuka, T et al., "Peptide segment coupling catalyzed by the semisynthetic enzyme thiosubtilisin," J Am Chem Soc 1985; 109(12):3808-3810.
Nambiar, KP et al., "Total synthesis and cloning of a gene coding for the ribonuclease S protein," Science (1984) 223:1299-1301.
Needham-VanDevanter et al., "Characterization of an adduct between CC-1065 and a Defined Oligodeoxynucleotide Duplex", Nucleic Acids Res., (1984) 12(15):6159-6168.
Needleman, SB and CD Wunsch, "A general method applicable to the search for similarities in the amino acid sequence of two proteins," J Mol Biol. Mar. 1970; 48(3):443-53.
Neet, KE et al., "Properties of thiol-subtilisin. The consequences of converting the active serine residue to cysteine in a serine protease," J Biol Chem. Dec. 25, 1968;243(24):6392-401.
Nicol et al., "Amino-acid sequence of human insulin", Nature, (1960) 187:483-5.
Nielsen, UB et al., "Therapeutic efficacy of anti-ErbB2 immunoliposomes targeted by a phage antibody selected for cellular endocytosis," Biochim Biophys Acta. Aug. 19, 2002;1591(13):109-118.
Nomura, T et al., "Purification, cDNA cloning, and Expression of UDP-Gal: Glucosylceramide-1,4-Galactosyltransferase from Rat Brain," J Biol Chem 1998; 273(22):13570-7.
Noren, CJ et al., "A general method for site-specific incorporation of unnatural amino acids into proteins," Science. Apr. 14, 1989;244(4901):182-8.
Nowak, MW et al., "Nicotinic receptor binding site probed with unnatural amino acid incorporation in intact cells," Science. Apr. 21, 1995;268(5209):439-42.
Offord, R.E. "Protein engineering by chemical means?", Protein Eng. 1(3):151-157 (1987).
Ogawa, AK et al., "Efforts toward the Expansion of the Genetic Alphabet: Information Storage and Replication with Unnatural Hydrophobic Base Pairs," J Am Chem Soc. 2000;122(14):3274-3287.
Ogawa, AK et al., "Rational Design of an Unnatural Base Pair with Increased Kinetic Selectivity," J Am Chem Soc 2000;122(36):8803-8804.
Ohno et al., "Co-Expression of Yeast Amber Suppressor tRNATyr and Tyrosyl-tRNA Synthetase in *Escherichia coli*: Possibility to Expand the Genetic Code", J. Biochem. (1998) 124:1065-1068.
Ohtsuka, E et al., "An alternative approach to deoxyoligonucleotides as hybridization probes by insertion of deoxyinosine at ambiguous codon positions," J Biol Chem. Mar. 10, 1985;260(5):2605-8.

(56) References Cited

OTHER PUBLICATIONS

Olson et al., "Preparation and Characterization of Poly(ethylene glycol)yated Human Growth Hormone Antagonist," in Poly-Ethylene glycol) Chemistry & Biological Applications, 1997; Eds. JM Harris & S. Zalipsky; ACS, Washington, D.C., 170-181.
Padwa, A, "Intermolecular 1,3-Dipolar Cycloadditions," in Comprehensive Organic Synthesis, vol. 4, (1991) Ed. Trost, B.M.; Pergamon, Oxford, 1069-1109.
Palva, I et al., "Secretion of interferon by Bacilus subtilis," Gene. May-Jun. 1983;22(2-3):229-35.
Park, JW et al., "Anti-HER2 immunoliposomes: enhanced efficacy attributable to targeted delivery," Clin Cancer Res. Apr. 2002;8(4):1172-81.
Park, JW et al., "Development of anti-p185HER2 immunoliposomes for cancer therapy," Proc Natl Acad Sci USA Feb. 28, 1995;92(5):1327-31.
Pastrnak et al., "A new orthogonal suppressor tRNA/Aminoacyl-tRNA Synthetase Pair for Evolving and Organism with an Expanded Genetic Code", Helv. Chim. Acta (2000) 83:2277-2286.
Patnaik, R and JR Swartz, "E. coli-based in vitro transcription/translation: in vitro-specific.synthesis rates and high yields in a batch system," Biotechniques. May 1998;24(5):862-8.
Pearson et al., "The Importance of Silica Type for Reverse-Phase Protein Separations", Anal Biochem. (1982) 124:217-230.
Pearson, WR and DJ Lipman, " Improved tools for biological sequence comparison," Proc Natl Acad Sci USA Apr. 1988;85(8):2444-8.
Peng et al., "Rapid Purification of Recombinant Caculovirus Using Fluorescence-Activated Cell Sorting", BioTechniques (1993) 14(2):274-277.
Pepinsky, RB et al., "Improved pharmacokinetic properties of a polyethylene glycol-modified form of interferonbeta-1a with preserved in vitro bioactivity," J Pharmacol Exp Ther. Jun. 2001;297(3):1059-66.
Piccirilli, JA et al., "Enzymatic incorporation of a new base pair into DNA and RNA extends the genetic alphabet," Nature 1990; 343:33-37.
Pintar, A et al., "CX, an algorithm that identifies protruding atoms in proteins," Bioinformatics. Jul. 2002;18(7):980-4.
Pitha, J et al., "Detergents linked to polysaccharides: preparation and effects on membranes and cells," Eur J Biochem. Feb. 15, 1979;94(1):11-18.
Polgar, L and ML Bender, "A new enzyme containing a synthetically formed active site. Thiol-subtilisin.," J Am Chem Soc. 1966; 88(13): 3153-3154.
Pollack, SJ et al., "Introduction of nucleophiles and spectroscopic probes into antibody combining sites," Science Nov. 18, 1988;242(4881):1038-40.
Preneta, AZ, "Separation on the basis of size: gel permeation chromatography," in Protein Purification Methods, a practical approach, 1989; Eds. Harris & Angal; IRL Press, Oxford; 293-306.
Raibaud, O and M Schwartz, "Positive control of transcription initiation in bacteria," Annu Rev Genet. 1984;18:173-206.
Reverey, H et al., "Differential Fatty Acid Selection during Biosynthetic S-Acylation of a Transmembrande protein (HEF) and Other Proteins in Insect Cells (Sf9) and in Mammalian Cells (CV1)," J Biol Chem 1996; 271(39):23607-10.
Rice et al., "Regulated Expression of an immunoglobulin kappa gene introduced into a mouse lyphoid cell line", Proc. Natl. Acad. Sci. USA (1982) 79(24):7862-7862.
Rivier, J and R McClintock, "Reversed-phase high-performance liquid chromatography of insulins from different species," J Chromatogr. Sep. 23, 1983;268(1):112-9.
Roberts et al., "Generation of an antibody with enhanced affinity and specificity for its antigen by protein engineering," Nature 1987;328:731-734.
Roberts, RW and JW Szostak, "RNA-peptide fusions for the in vitro selection of prptides and proteins," Proc Natl Acad Sci USA. Nov. 11, 1997;94(23):12297-302.

Robertson et al., "A General and Efficient Route for Chemical Aminoacylation of Transfer RNAs", J. Am. Chem. Soc. (1991) 113:2722-2729.
Roggenkamp, R et al., "Transformation of the methylotrophic yeast Hansenula polymorpha by autonomous replication and integration vectors," Mol Genetics and Genomics 1986;202(2):302-8.
Romani et al., "Synthesis of unsymmetrical cystine peptides: directed disulfide pairing with the sulfenohydrazide method," in Chemistry of Peptides and Proteins 1984; eds. Voeller, W.et al.; Walter de Gruyter et al., Berlin; vol. 2:29-33.
Romanos, MA et al., "Foreign gene expression in yeast: a review," Yeast. Jun. 1992;8(6):423-88.
Rosenthal, GA, "L-canaline: a potent antimetabolite and anti-cancer agent from leguminous plants," Life Sci. 1997;60(19):1635-41.
Rossolini, GM et al., "Use of deoxyinosine-containing primers vs degenerate primers for polymerase chain reaction based on ambiguous sequence information," Mol Cell Probes 1994; 8:91-98.
Rostovtsev, VV et al., "A stepwise huisgen cycloaddition process: copper(I)-catalyzed regioselective "ligation" of azides and terminal alkynes," Angew Chem in Jul. 15, 2002;41(14):2596-9.
Rowles, J et al., "Cloning and characterization of PDK4 on 7q21.3 encoding a fourth pyruvate dehydrogenase kinase isoenzyme in human," J biol Chem. Sep. 13, 1996;271(37):22376-82.
Sakamoto et al., "Site-specific incorporation of unnatural amino acid into proteins in mammalian cells", Nucleic Acids Res. (2002) 30(21):4692-4699.
Sakmar, TP and HG Khorana, "Total synthesis and expression of a gene for the alpha-subunit of bovine rod outer segment guanine nucleotide-binding protein (transducin)" Nucleic Acids Res. Jul. 25, 1988;16(14A):6361-72.
Saks et al., "An Engineered Tetrahymena tRNAGln for in Vivo Incorporation of Unnatural Amino Acids into Protein by Nonsense Suppression", J. Biol. Chem. (1996) 271(38):23169-23175.
Samuel, C.S., "Relaxin: Antifibrotic Properties and Effects in Models of Disease", Clinical Medicine & Research, 2005; 3(4): 241-249.
Sandler and Karo, "Polyoxyalkylation of hydroxyl compounds," in Polymer Synthesis, vol. 3, 1980; Academic Press, New York, 138-161.
Santoro, SW et al., "An efficient system for the evolution of an aminoacyl-tRNA synthetase specificity," Nat Biotechnol. Oct. 2002;20(10):1044-8. Epub Sep. 16, 2002.
Sartore, L et al., "Enzyme modificaiton by MPEG with an amino acid or peptide as spacer arms," Appl Biochem Biotechnol Jan. 1991;27(1):45-54.
Sawhney, AS et al., "Bioerodible Hydrogels Based on Photopolymerized Poly(ethylene glycol)-co-poly(alpha-hydroxy acid) Diacrylate Macromers," Macromolecules 1993; 26(4):581-7.
Saxon, E and C Bertozzi, "Cell Surface Engineering by a Modified Staudinger Reaction," Science (2000); 287(5460):2007-2010.
Sayers, JR et al., "5'-3' exonucleases in phosphorothioate-based oligonucleotide-directed mutagenesis," Nucleic Acids Res. Feb. 11, 1988;16(3):791-802.
Sayers, JR et al., "Strand specific cleavage of phosphorothioate-containing DNA by reaction with restriction endonucleases in the presence of ethidium bromide," Nucleic Acids Res. Feb. 11, 1988;16(3):803-14.
Schanbacher, FL et al., "Galactosyltransferase Acceptor Specificity of the Lactose Synthetase A Protein," J Biol Chem 1970; 245(19):5057-5061.
Schmidt, M et al., "Baculovirus-mediated large-scale expression and purification of a polyhistidine-tagged rubella virus capsid protein," Protein Expr Purif. Apr. 1998;12(3):323-30.
Schneider, E et al., "Functional Purificaiton of a Bacterial ATP-Binding Cassette Transporter Protein (MaiK) form the Cytoplasmic Fraction of an Overproducing Strain," Protein Expr. Purif. 1995; 6(1):10-14.
Schnolzer, M. and SBH Kent, "Constructing proteins by dovetailing unprotected synthetic peptides: backbone engineered HIV protease," Science. Apr. 10, 1992; 256(5054):221-5.
Schwabe et al., "Primary structure of the B-chain of porcine relaxin", Biochem. Biophys. Res. Comm. (1977) 75(2):503-570.
Scouten, WH, "A survey of enzyme coupling techniques," Methods Enzymol. 1987;135:30-65.

(56) References Cited

OTHER PUBLICATIONS

Shao, J and JP Tam, "Unprotected Peptides as Building Blocks for the Synthesis of Peptide Dendrimers with Oxime, Hydrazone, and Thiazolidine Linkages," J Am Chem Soc 1995:117(14):3893-3899.
Sharma, N et al., "Efficient introduction of aryl bromide funcitonality into proteins in vivo,". FEBS Lett. Feb. 4, 2000;467(1):37-40.
Sherwood, The Physiology of Reproduction, Chapter 16, "Relaxin", Knobil, E. and Neill, J., et. al. (eds.), (Raven Press Ltd., New York), pp. 585-673 (1988).
Shimatake, H and M Rosenberg,"Purified gamma regulatory protein ell positively activates promoters for lysogenic development," Nature Jul. 1981;292:128-132.
Shine, J and L Dalgarno, "Determinant of cistron specificity in bacterial ribosomes," Nature. Mar. 6, 1975;254(5495):34-8.
Sidman, KR et al., "Controlled release of macromolecules and pharmaceuticals from synthetic polypeptides based on glutamic acid," Biopolymers. Jan. 1983;22(1):547-56.
Sieber, V. et al., "Libraries of hybrid proteins from distantly related sequences," Nature Biotechnology. May 2001; 19:456-460.
Siffert, W et al., "Association of a human G-protein beta3 subunit variant with hypertension," Nat Genet. Jan. 1998; 18(1):45-8.
Sikorski, RS et al., "A System of Shuttle Vectors and Yeast Host Strains Designed for Efficient Manipulation of DNA in *Saccharomyces cerevisiae*," Genetics (1989) 122:19-27.
Sisk, WP et al., "High-level expression and purification of secreted forms of herpes simplex virus type 1 glycoprotein gD synthesized by baculovirus-infected insect cells," J Virol. Feb. 1994:68(2):766-75.
Sjolander, A et al., "The serum albumin-binding region of streptococcal protein G: a bacterial fusion partner with carrier-related properties," J Immunol Methods. Feb. 14, 1997: 201(1):115-23.
Smith, GE et al., "Production of human beta interferon in insect cells infected with a baculovirus expression vector," Mol Cell Biol. Dec. 1983;3(12):2156-65.
Smith, M, "In vitro mutagenesis" Ann. Rev. Genet. 1985; 19: 423-462.
Stanley, SL et al., "The serine-rich Entamoeba hislolytica protein is a phosphorylated membrane protein containing O-linked terminal N-acetylglucosamine residues," J Biol Chem. Feb. 24, 1995;270(8):4121-6.
Steitz, JA et al., "Genetic signals and nucleotide sequences in messenger RNA," in Biological Regulation and Development: Gene Expression 1979; ed. R. F. Goldberger; Plenum Press, New York; 349-399.
Stemmer, WP, "DNA shuffling by random fragmentation and reassembly: In vitro recombination for molecular evolution," Proc Natl Acad Sci USA. Oct. 25, 1994;91(22):10747-51.
Stemmer, WPC, "Rapid evolution of a protein in vitro by DNA shuffling," Nature 1994;.370(4):389-391.
Stephan, "Give Your Protein a Tune-Up", Scientists (Oct. 2005) 30-33 (9 pages, webpage printout).
Strausberg, R.L. et al., Database GeneBank[online], Accession No. AAI26416, <http://ncbi.nlm.nih.gov/protein/116497221?sat=15&satkey=6070787>, Mar. 10, 2010 uploaded, Jul. 24, 2015 retrieved, Definition: Relaxin 2 [*Homo sapiens*].
Studier, FW and BA Moffatt, "Use of bacteriophage T7 RNA polymerase to direct selective high-level expression of cloned genes," J. Mol. Biol. May 5, 1986;189(1):113-30.
Subasinghe, N et al., "Quisqualic acid analogues: synthesis of beta-heterocyclic 2-aminopropanoic acid derivatives and their activity at a novel quisqualate-sensitized site," J Med Chem. Nov. 27, 1992;35(24):4602-7.
Switzer, C et al., "Enzymatic incorporation of a new base pair into DNA and RNA," J Am Chem Soc 1989; 111(21):8322-8323.
Tabor, S and CC Richardson, "A bacteriophage T7 RNA polymerase/promoter system for controlled exclusive expression of specific genes," Proc Natl Acad Sci USA Feb. 1985;82(4):1074-8.
Tae, EL et al., "Efforts toward Expansion of the Genetic Alphabet: Replication of DNA iwht Three Base Pairs," J Am Chem Soc 2001; 123(30):7439-7440.

Tang, Y et al., "Fluorinated Coiled-Coil Proteins Prepared in Vivo Display Enhanced Thermal and Chemical Stability," Angew Chem Int Ed Engl. Apr. 17, 2001;40(8):1494-1496.
Taylor, JW et al., "The rapid generation of oligonucleotide-directed mutations at high frequency using phosphorothioate-modified DNA," Nucleic Acids Res. Dec. 20, 1985;13(24):8765-85.
Taylor, JW et al., "The use of phosphorothioate-modified DNA in restriction enzyme reactions to prepare nicked DNA," Nucleic Acids Res. Dec. 20, 1985;13(24):8749-64.
Taylor, MD et al., Annual Reports in Med. Chem. 22, 85-94 (1987).
Teichman, S.L. et al., "Relaxin: Review of Biology and Potential Role in Treating Heart Failure", Curr. Heart Fail. Rep., 2010. 7:75-82.
Tijssen, P, "Overview of principles of hybridization and the strategy of nucleic acid assays," in Laboratory Techniques in Biochemistry and Molecular Biology—Hybridization with Nucleic Probes, Part I, 1993; Elsevier Science Publishers, Amsterdam, 19-78.
Tilburn, J et al., "Transformation by integration in Aspergillus nidulans," Gene. Dec. 1983; 26(2-3):205-21.
Tondelli, L et al., "Poly(ethylene glycol) Imidazolyl Formates as Oligomeric Drug-Binding Matrices," J. Controlled Release 1985; 1(4):251-7.
Tornoe, CW et al., "Peptidotriazoles on solid phase: [1,2,3]-triazoles by regiospecific copper(i)-catalyzed 1,3-dipolar cycloadditions of terminal alkynes to azides," J Org Chem. May 3, 2002;67(9):3057-64.
Trotter, KM and HA Wood, "Transfection techniques for producing recombinant baculoviruses," in Methods in Molecular Biology-Baculovirus Expression Protocols, vol. 39 (1995); Ed. C.D. Richardson, 97-107.
Tschumper, G et al., "Sequence of a yeast DNA fragment containing a chromosomal replicator and the TRP1 gene," Gene. 1980;10(2):157-66.
Tsumoto, K et al., "Practical considerations in refolding proteins from inclusion bodies," Protein Expr Purif. Mar. 2003;18(1):1-8.
Turcatti, G et al., "Probing the structure and function of the tachykinin neurokinin-2 receptor through biosynthetic incorporation of fluorescent amino acids at specific sites," J Biol Chem. Aug. 16, 1996;271(33):19991-8.
Valls et al., "Protein smting in yeast: the localization determinant of yeast vacuolar carboxypeptidase Y resides in the propeptide", Cell (1987) 48(5):887-897.
Van Den Berg, JA et al., "Kiuyveromyces as a host for heterologous gene expression: expression and secretion of prochymosin," Biotechnology (NY). Feb. 1990;8(2):135-9.
Van Hest, JC et a., "Efficient Incorporation of Unsaturated Methionine Analogues into Proteins in Vivo," J Am Chem Soc 2000;122(7):1282-1288.
Van Hest, JC and DA Tirrell, "Efficient introduciton of alkene funcitonality into proteins in vivo," FEBS Lett. May 22, 1998;428(1-2):68-70.
Van Solingen, P and JB van der Plaal, "Fusion of yeast spheroplasts," J Bacteriol. May 1977; 130(2):946-7.
Veronese, FM et al., "Surface modification of proteins. Activation of monomethoxy-polyethylene glycols by phenylchloroformates and modification of ribonuclease and superoxide dismutase," Appl Biochem Biotechnol. Apr. 1985;11(2):141-52.
Vlak, JM et al., "Functional studies on the p10 gene of Autographa californica nuclear polyhedrosis virus using a recombinant expressing a p10-beta-galactosidase fusion gene," J Gen Virol. Apr. 1988;69(P14):765-76.
Wang, L and PG Schulz, "Expanding the genetic code," Chem Commun (Camb). Jan. 7, 2002;1:1-11.
Wang, L et al., "Addition of the keto funcitonal group to the genetic code of *Escherichia coli*," Proc Natl Acad Sci. (2003);100(1):56-61.
Wang, L et al., "Expanding the genetic code of *Escherichia coli*," Science. Apr. 20, 2001;292(5516):498-500.
Wang, Q, et al., "Bioconjugation by Copper(I)-Catalyzed Azide-Aikyne [3 + 2] Cycloaddition," J Am Chem Soc 2003;125(11):3192-3193.
Wang, W, "Instability, stabilization, and formulation of liquid protein pharmaceuticals," Intl Pharm. Aug. 20, 1999;185(2):129-88.
Weiss, "Relaxin", Ann. Rev. Physiol., (1984) 46:43-52.

(56) References Cited

OTHER PUBLICATIONS

Weissman, C, "The cloning of interferon and other mistakes," in Interferon 3 1981; ed. I. Gresser; Academic Press, London, 101-134.
Weitkamp et al., "Additional Data on the Population Distribution of Human Serum Albumin Genes; Three New Variants", Ann. Hum. Genet. (1973) 37:219-26.
Wells, JA et al., "Cassette mutagenesis: an efficient method for generation of multiple mutations at defined sites," Gene. 1985;34(2-3):315-23.
Wells, JA et al., "Importance of hydrogen-bond formation in stabilizing the transition state of subtilisin," Phil Trans R Soc Lond A 1986; 317:415-423.
Woghiren, C et al., "Protected thiol-polythylene glycol: a new activated polymer for reversible protein modification," Bioconjug Chem. Sep.-Oct. 1993; 4(5):314-8.
Wong, SS and LJ Wong, "Chemical crosslinking and the stabilization of proteins and enzymes," Enxyme Microb Technol. Nov. 1992; 14(11):866-74.
Wright, K, "Biotechnology: Insect virus as super-vector?," Nature (1986) 321(6072):718.
Wu, et al., "Enzymatic Phosphorylation of Unnatural Nucleosides", J. Am. Chem. Soc. (2002) 124(49):14626-14630.
Yelton, MM et al., "Transformation of Aspergillus nidulans by using a trpC plasmid," Proc Natl Acad Sci USA. Mar. 1984;81(5):1470-4.
Yelverton, E et al., "Bacterial synthesis of a novel human leukocyte interferon," Nucleic Acids Res. Feb. 11, 1981;9(3):731-41.
Zalipsky, S et al., "Attachment of drugs to polyethylene glycols," Eur Polymer Journal. 1983;19(12):1177-83.
Zalipsky, S et al., "Functionalized Poly(ethylene glycol) for preparation of biologically relevant conjugates," Bioconjug Chem. Mar.-Apr. 1995;6(2):150-65.
Zalipsky, S., et al., "Use of Functionalized Poly(Ethylene Glycols) for Modification of Polypeptides" in Polyethylene Glycol Chemistry: Biotechnical and Biomedical Applications, Harris, ed., Plenum Publishing Corporation, New York (1992), Chapter 21, pp. 347-370.
Zhang, Z et al., "A new strategy for the site-specific modificaiton of proteins in vivo," Biochemistry. Jun. 10, 2003;42(22):6735-46.
Zoller, MJ & M. Smith, "Oligonucleotide-directed mutagenesis of DNA fragments cloned into M13 vectors", Methods Enzymol. 1983; 100: 468-500.
Zoller, MJ and M Smith, "Oligonucleotide-directed mutagenesis using M13-derived vectors: an efficient and general procedure for the produciton of point mutations in any fragment of DNA" Nucleic Acids Res. Oct. 25, 1982; 10(20):6487-500.
Zoller, MJ and M Smith, "Oligonucleotide-directed mutagenesis: a simple method using two oligonucleotide primers and a single-stranded DNA template," Methods Enzymol. 1987; 154:329-50.
Büllesbach EE, et al. "Functional importance of the A chain loop in relaxin and insulin," J Biol Chem. May 6, 1994;269(18):13124-8.
Feng S, et al. "Relaxin promotes prostate cancer progression," Clin Cancer Res. Mar. 15, 2007;13(6):1695-702.
Roy SS, et al. "A new cell secreting insulin," Endocrinology. Apr. 2003;144(4):1585-93.
Sudo S, et al. "H3 relaxin is a specific ligand for LGR7 and activates the receptor by interacting with both the ectodomain and the exoloop 2," J Biol Chem. Mar. 7, 2003;278(10):7855-62.
Teerlink JR, et al. "Relaxin for the treatment of patients with acute heart failure (Pre-RELAX-AHF): a multicentre, randomised, placebo-controlled, parallel-group, dose-finding phase IIb study," Lancet. Apr. 25, 2009;373(9673):1429-39.

\* cited by examiner

FIG. 1
WT-RLX   A-chain   QLYSALANKCCHVGCTKRSLARFC
         B-chain   ASWMEEVIKLCGRELVRAQIAICGMSTWS FIG. 2
RLX-AQ1  A-chain   (pAcF)LYSALANKCCHVGCTKRSLARFC
         B-chain   ASWMEEVIKLCGRELVRAQIAICGMSTWS FIG. 3
RLX-BM25/AN1  A-chain   NLYSALANKCCHVGCTKRSLARFC FIG. 5
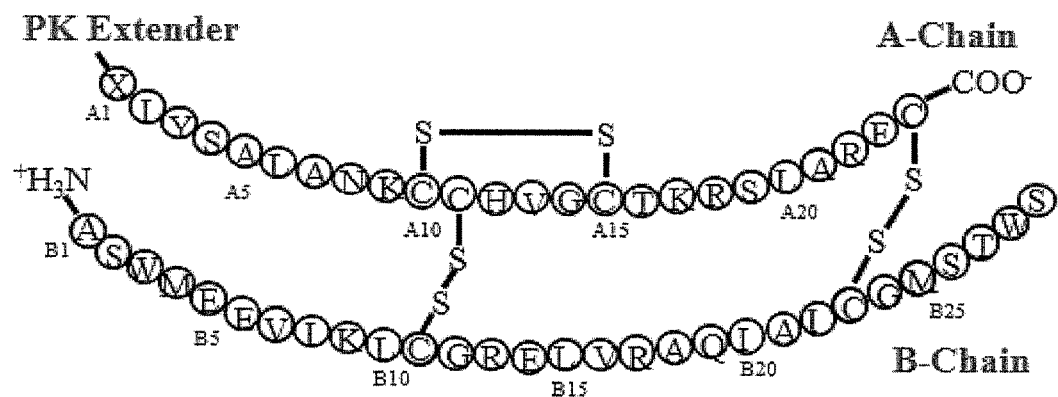
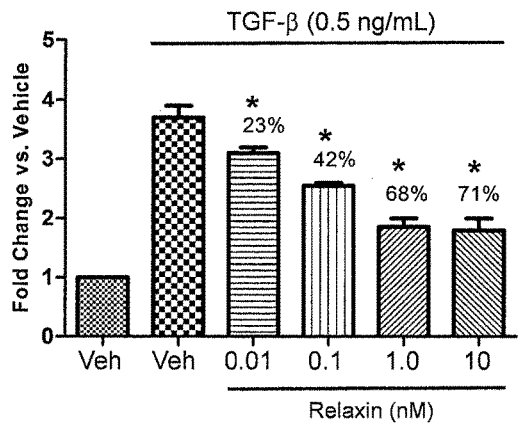
FIG. 6A
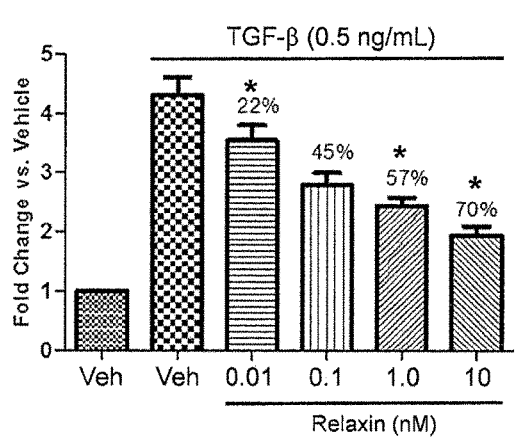
FIG. 6B

SEQUENCE LISTING

<160> NUMBER OF SEQ ID NOS: 279

<210> SEQ ID NO 1
<211> LENGTH: 53
<212> TYPE: PRT
<213> ORGANISM: Homo sapiens

<400> SEQUENCE: 1

Gln Leu Tyr Ser Ala Leu Ala Asn Lys Cys Cys His Val Gly Cys Thr
1               5                   10                  15

Lys Arg Ser Leu Ala Arg Phe Cys Asp Ser Trp Met Glu Glu Val Ile
            20                  25                  30

Lys Leu Cys Gly Arg Glu Leu Val Arg Ala Gln Ile Ala Ile Cys Gly
        35                  40                  45

Met Ser Thr Trp Ser
    50

<210> SEQ ID NO 2
<211> LENGTH: 53
<212> TYPE: PRT
<213> ORGANISM: Homo sapiens

<400> SEQUENCE: 2

Gln Leu Tyr Ser Ala Leu Ala Asn Lys Cys Cys His Val Gly Cys Thr
1               5                   10                  15

Lys Arg Ser Leu Ala Arg Phe Cys Ala Ser Trp Met Glu Glu Val Ile
            20                  25                  30

Lys Leu Cys Gly Arg Glu Leu Val Arg Ala Gln Ile Ala Ile Cys Gly
        35                  40                  45

Met Ser Thr Trp Ser
    50

<210> SEQ ID NO 3
<211> LENGTH: 88
<212> TYPE: PRT
<213> ORGANISM: Homo sapiens

<400> SEQUENCE: 3

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser Arg Arg Glu
            20                  25                  30

Ala Glu Asp Leu Gln Val Gly Gln Val Glu Leu Gly Gly Gly Pro Gly
            35                  40                  45

Ala Gly Ser Leu Gln Pro Leu Ala Leu Glu Gly Ser Leu Gln Lys Arg
        50                  55                  60

Gln Leu Tyr Ser Ala Leu Ala Asn Lys Cys Cys His Val Gly Cys Thr
65                  70                  75                  80

Lys Arg Ser Leu Ala Arg Phe Cys
                85

<210> SEQ ID NO 4
<211> LENGTH: 24
<212> TYPE: PRT
<213> ORGANISM: Homo sapiens

<400> SEQUENCE: 4

Gln Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 5
<211> LENGTH: 29
<212> TYPE: PRT
<213> ORGANISM: Homo sapiens

<400> SEQUENCE: 5

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser
            20                  25

<210> SEQ ID NO 6
<211> LENGTH: 29
<212> TYPE: PRT
<213> ORGANISM: Homo sapiens

<400> SEQUENCE: 6

Ala Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser
            20                  25

<210> SEQ ID NO 7
<211> LENGTH: 35
<212> TYPE: PRT
<213> ORGANISM: Homo sapiens

<400> SEQUENCE: 7

Arg Arg Glu Ala Glu Asp Leu Gln Val Gly Gln Val Glu Leu Gly Gly
1               5                   10                  15

Gly Pro Gly Ala Gly Ser Leu Gln Pro Leu Ala Leu Glu Gly Ser Leu
            20                  25                  30

Gln Lys Arg
        35

<210> SEQ ID NO 8
<211> LENGTH: 11
<212> TYPE: PRT
<213> ORGANISM: Homo sapiens

<400> SEQUENCE: 8

Met Lys Lys Asn Ile Ala Phe Leu Leu Lys Arg
1               5                   10

<210> SEQ ID NO 9
<211> LENGTH: 6
<212> TYPE: PRT
<213> ORGANISM: Homo sapiens

<400> SEQUENCE: 9

Met Ile Glu Gly Gly Arg
1               5

<210> SEQ ID NO 10
<211> LENGTH: 72
<212> TYPE: DNA
<213> ORGANISM: Homo sapiens

<400> SEQUENCE: 10
caactctaca gtgcattggc taataaatgt tgccatgttg gttgtaccaa aagatctctt      60

```
gctagatttt gc                                                             72

<210> SEQ ID NO 11
<211> LENGTH: 87
<212> TYPE: DNA
<213> ORGANISM: Homo sapiens

<400> SEQUENCE: 11
gactcatgga tggaggaagt tattaaatta tgcggccgcg aattagttcg cgcgcagatt         60
gccatttgcg gcatgagcac ctggagc                                             87

<210> SEQ ID NO 12
<211> LENGTH: 159
<212> TYPE: DNA
<213> ORGANISM: Homo sapiens

<400> SEQUENCE: 12
caactctaca gtgcattggc taataaatgt tgccatgttg ttgtaccaa aagatctctt          60 gctagatttt gcgactcatg gatggaggaa gttattaaat tatgcggccg cgaattagtt        120
cgcgcgcaga ttgccatttg cggcatgagc acctggagc                               159

<210> SEQ ID NO 13
<211> LENGTH: 33
<212> TYPE: DNA
<213> ORGANISM: Homo sapiens

<400> SEQUENCE: 13
atgaaaaaga atatcgcatt tcttcttaaa cgg                                      33

<210> SEQ ID NO 14
<211> LENGTH: 18
<212> TYPE: DNA
<213> ORGANISM: Homo sapiens

<400> SEQUENCE: 14
atgattgaag gtggtcgt                                                       18

<210> SEQ ID NO 15
<211> LENGTH: 94
<212> TYPE: PRT
<213> ORGANISM: Homo sapiens

<400> SEQUENCE: 15

Met Ile Glu Gly Gly Arg Asp Ser Trp Met Glu Glu Val Ile Lys Leu
1               5                   10                  15

Cys Gly Arg Glu Leu Val Arg Ala Gln Ile Ala Ile Cys Gly Met Ser
            20                  25                  30

Thr Trp Ser Arg Arg Glu Ala Glu Asp Leu Gln Val Gly Gln Val Glu
        35                  40                  45

Leu Gly Gly Gly Pro Gly Ala Gly Ser Leu Gln Pro Leu Ala Leu Glu
    50                  55                  60

Gly Ser Leu Gln Lys Arg Gln Leu Tyr Ser Ala Leu Ala Asn Lys Cys
65                  70                  75                  80

Cys His Val Gly Cys Thr Lys Arg Ser Leu Ala Arg Phe Cys
                85                  90

<210> SEQ ID NO 16
<211> LENGTH: 306
<212> TYPE: PRT
```

<213> ORGANISM: Artificial
<220> FEATURE:
<223> OTHER INFORMATION: Mutant synthetase derived from Methanococcus
      jannaschii synthetase

<400> SEQUENCE: 16

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Val
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Tyr Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu His Gly Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Gly Ile His
145                 150                 155                 160

Tyr Glu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305
```

<210> SEQ ID NO 17
<211> LENGTH: 77
<212> TYPE: DNA
<213> ORGANISM: Artificial
<220> FEATURE:
<223> OTHER INFORMATION: Mutant tRNA derived from Methanococcus
      jannaschii tRNA

<400> SEQUENCE: 17
ccggcggtag ttcagcaggg cagaacggcg gactctaaat ccgcatggcg ctggttcaaa     60

-continued tccagcccgc cggacca    77

<210> SEQ ID NO 18
<211> LENGTH: 77
<212> TYPE: DNA
<213> ORGANISM: Methanococcus jannaschii

<400> SEQUENCE: 18
ccggcggtag ttcagcaggg cagaacggcg gactctaaat ccgcatggcg ctggttcaaa    60
tccggcccgc cggacca    77

<210> SEQ ID NO 19
<211> LENGTH: 88
<212> TYPE: DNA
<213> ORGANISM: Artificial
<220> FEATURE:
<223> OTHER INFORMATION: An optimized amber supressor tRNA

<400> SEQUENCE: 19
cccagggtag ccaagctcgg ccaacggcga cggactctaa atccgttctc gtaggagttc    60
gagggttcga tcccttccc tgggacca    88

<210> SEQ ID NO 20
<211> LENGTH: 89
<212> TYPE: DNA
<213> ORGANISM: Artificial
<220> FEATURE:
<223> OTHER INFORMATION: An optimized AGGA frameshift supressor tRNA

<400> SEQUENCE: 20
gcgagggtag ccaagctcgg ccaacggcga cggacttcct aatccgttct cgtaggagtt    60
cgagggttcg aatccctccc ctcgcacca    89

<210> SEQ ID NO 21
<211> LENGTH: 306
<212> TYPE: PRT
<213> ORGANISM: Artificial
<220> FEATURE:
<223> OTHER INFORMATION: Aminoacyl tRNA synthetase for the incorporation
      of p-azido-L-phenylalanine

<400> SEQUENCE: 21

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro

```
                    130                 135                 140
Lys Val Ala Glu Val Ile Tyr Pro Ile Met Gln Val Asn Thr Tyr Tyr
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
        290                 295                 300

Arg Leu
305

<210> SEQ ID NO 22
<211> LENGTH: 306
<212> TYPE: PRT
<213> ORGANISM: Artificial
<220> FEATURE:
<223> OTHER INFORMATION: Aminoacyl tRNA synthetase for the incorporation
      of p-benzoyl-L-phenylalanine

<400> SEQUENCE: 22

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Thr Ser His
145                 150                 155                 160

Tyr Leu Gly Val Asp Val Ala Val Gly Gly Met Glu Gln Arg Lys Ile
                165                 170                 175
```

```
His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 23
<211> LENGTH: 305
<212> TYPE: PRT
<213> ORGANISM: Artificial
<220> FEATURE:
<223> OTHER INFORMATION: Aminoacyl tRNA synthetase for the incorporation
      of propargyl-phenylalanine

<400> SEQUENCE: 23

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ala Ile Tyr
145                 150                 155                 160

Leu Ala Val Asp Val Ala Val Gly Gly Met Glu Gln Arg Lys Ile His
                165                 170                 175

Met Leu Ala Arg Glu Leu Leu Pro Lys Lys Val Val Cys Ile His Asn
            180                 185                 190

Pro Val Leu Thr Gly Leu Asp Gly Glu Gly Lys Met Ser Ser Ser Lys
        195                 200                 205

Gly Asn Phe Ile Ala Val Asp Asp Ser Pro Glu Glu Ile Arg Ala Lys
    210                 215                 220
```

```
Ile Lys Lys Ala Tyr Cys Pro Ala Gly Val Val Glu Gly Asn Pro Ile
225                 230                 235                 240

Met Glu Ile Ala Lys Tyr Phe Leu Glu Tyr Pro Leu Thr Ile Lys Arg
                245                 250                 255

Pro Glu Lys Phe Gly Gly Asp Leu Thr Val Asn Ser Tyr Glu Glu Leu
            260                 265                 270

Glu Ser Leu Phe Lys Asn Lys Glu Leu His Pro Met Asp Leu Lys Asn
        275                 280                 285

Ala Val Ala Glu Glu Leu Ile Lys Ile Leu Glu Pro Ile Arg Lys Arg
    290                 295                 300

Leu
305

<210> SEQ ID NO 24
<211> LENGTH: 305
<212> TYPE: PRT
<213> ORGANISM: Artificial
<220> FEATURE:
<223> OTHER INFORMATION: Aminoacyl tRNA synthetase for the incorporation
      of propargyl-phenylalanine

<400> SEQUENCE: 24

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Ile Pro Tyr
145                 150                 155                 160

Leu Pro Val Asp Val Ala Val Gly Gly Met Glu Gln Arg Lys Ile His
                165                 170                 175

Met Leu Ala Arg Glu Leu Leu Pro Lys Lys Val Val Cys Ile His Asn
            180                 185                 190

Pro Val Leu Thr Gly Leu Asp Gly Glu Gly Lys Met Ser Ser Ser Lys
        195                 200                 205

Gly Asn Phe Ile Ala Val Asp Asp Ser Pro Glu Glu Ile Arg Ala Lys
210                 215                 220

Ile Lys Lys Ala Tyr Cys Pro Ala Gly Val Val Glu Gly Asn Pro Ile
225                 230                 235                 240

Met Glu Ile Ala Lys Tyr Phe Leu Glu Tyr Pro Leu Thr Ile Lys Arg
                245                 250                 255

Pro Glu Lys Phe Gly Gly Asp Leu Thr Val Asn Ser Tyr Glu Glu Leu
```

```
                260                 265                 270
Glu Ser Leu Phe Lys Asn Lys Glu Leu His Pro Met Asp Leu Lys Asn
            275                 280                 285

Ala Val Ala Glu Glu Leu Ile Lys Ile Leu Glu Pro Ile Arg Lys Arg
            290                 295                 300

Leu
305

<210> SEQ ID NO 25
<211> LENGTH: 305
<212> TYPE: PRT
<213> ORGANISM: Artificial
<220> FEATURE:
<223> OTHER INFORMATION: Aminoacyl tRNA synthetase for the incorporation
      of propargyl-phenylalanine

<400> SEQUENCE: 25

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Lys Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Ala Ile Tyr
145                 150                 155                 160

Leu Ala Val Asp Val Ala Val Gly Gly Met Glu Gln Arg Lys Ile His
                165                 170                 175

Met Leu Ala Arg Glu Leu Leu Pro Lys Lys Val Val Cys Ile His Asn
            180                 185                 190

Pro Val Leu Thr Gly Leu Asp Gly Glu Gly Lys Met Ser Ser Ser Lys
        195                 200                 205

Gly Asn Phe Ile Ala Val Asp Asp Ser Pro Glu Glu Ile Arg Ala Lys
210                 215                 220

Ile Lys Lys Ala Tyr Cys Pro Ala Gly Val Val Glu Gly Asn Pro Ile
225                 230                 235                 240

Met Glu Ile Ala Lys Tyr Phe Leu Glu Tyr Pro Leu Thr Ile Lys Arg
                245                 250                 255

Pro Glu Lys Phe Gly Gly Asp Leu Thr Val Asn Ser Tyr Glu Glu Leu
            260                 265                 270

Glu Ser Leu Phe Lys Asn Lys Glu Leu His Pro Met Asp Leu Lys Asn
        275                 280                 285

Ala Val Ala Glu Glu Leu Ile Lys Ile Leu Glu Pro Ile Arg Lys Arg
        290                 295                 300
```

Leu
305

<210> SEQ ID NO 26
<211> LENGTH: 306
<212> TYPE: PRT
<213> ORGANISM: Artificial
<220> FEATURE:
<223> OTHER INFORMATION: Aminoacyl tRNA synthetase for the incorporation of p-azido-phenylalanine

<400> SEQUENCE: 26

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Asn Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Leu His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 27
<211> LENGTH: 306
<212> TYPE: PRT
<213> ORGANISM: Artificial

<220> FEATURE:
<223> OTHER INFORMATION: Aminoacyl tRNA synthetase for the
    incorporation of p-azido-phenylalanine

<400> SEQUENCE: 27

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Leu His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 28
<211> LENGTH: 306
<212> TYPE: PRT
<213> ORGANISM: Artificial
<220> FEATURE:
<223> OTHER INFORMATION: Aminoacyl tRNA synthetase for the incorporation
    of p-azido-phenylalanine

<400> SEQUENCE: 28

Met Asp Glu Phe Glu Met Ile Lys Arg Asn Thr Ser Glu Ile Ile Ser
1               5                   10                  15

```
Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
 50                  55                  60

Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                 85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Pro Val His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 29
<211> LENGTH: 306
<212> TYPE: PRT
<213> ORGANISM: Artificial
<220> FEATURE:
<223> OTHER INFORMATION: Aminoacyl tRNA synthetase for the
      incorporation of p-azido-phenylalanine

<400> SEQUENCE: 29

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
```

```
            50                  55                  60
Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                 85                  90                  95

Gly Leu Lys Ala Lys Tyr Val Tyr Gly Ser Ser Phe Gln Leu Asp Lys
                100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
        130                 135                 140

Lys Val Ala Glu Val Ile Tyr Pro Ile Met Gln Val Asn Pro Ser His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
                180                 185                 190

Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
        210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
        290                 295                 300

Arg Leu
305

<210> SEQ ID NO 30
<211> LENGTH: 306
<212> TYPE: PRT
<213> ORGANISM: Artificial
<220> FEATURE:
<223> OTHER INFORMATION: Aminoacyl tRNA synthetase for the
      incorporation of p-acetyl-phenylalanine

<400> SEQUENCE: 30

Met Asp Glu Phe Glu Met Ile Lys Arg Asn Thr Ser Glu Ile Ile Ser
 1               5                  10                  15

Glu Glu Glu Leu Arg Glu Val Leu Lys Lys Asp Glu Lys Ser Ala Leu
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                 85                  90                  95
```

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Gly Cys His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 31
<211> LENGTH: 306
<212> TYPE: PRT
<213> ORGANISM: Artificial
<220> FEATURE:
<223> OTHER INFORMATION: Aminoacyl tRNA synthetase for the
      incorporation of p-acetyl-phenylalanine

<400> SEQUENCE: 31

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

```
Lys Val Ala Glu Val Ile Tyr Pro Ile Met Gln Val Asn Gly Thr His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
                275                 280                 285

Asn Ala Val Ala Glu Glu Leu Ile Lys Ile Leu Glu Pro Ile Arg Lys
        290                 295                 300

Arg Leu
305

<210> SEQ ID NO 32
<211> LENGTH: 306
<212> TYPE: PRT
<213> ORGANISM: Artificial
<220> FEATURE:
<223> OTHER INFORMATION: Aminoacyl tRNA synthetase for the
      incorporation of p-acetyl-phenylalanine

<400> SEQUENCE: 32

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Gly Gly His
145                 150                 155                 160

Tyr Leu Gly Val Asp Val Ile Val Gly Gly Met Glu Gln Arg Lys Ile
                165                 170                 175

His Met Leu Ala Arg Glu Leu Leu Pro Lys Lys Val Val Cys Ile His
```

```
                180                 185                 190
Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
        210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 33
<211> LENGTH: 306
<212> TYPE: PRT
<213> ORGANISM: Artificial
<220> FEATURE:
<223> OTHER INFORMATION: Aminoacyl tRNA synthetase for the
      incorporation of p-azido-phenylalanine

<400> SEQUENCE: 33

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Arg Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Val Ile His
145                 150                 155                 160

Tyr Asp Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220
```

```
Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Leu Ile Lys Ile Leu Glu Pro Ile Arg Lys
290                 295                 300

Arg Leu
305

<210> SEQ ID NO 34
<211> LENGTH: 306
<212> TYPE: PRT
<213> ORGANISM: Artificial
<220> FEATURE:
<223> OTHER INFORMATION: Aminoacyl tRNA synthetase for the
      incorporation of p-azido-phenylalanine

<400> SEQUENCE: 34

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Thr Tyr Tyr
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270
```

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
        290                 295                 300

Arg Leu
305

<210> SEQ ID NO 35
<211> LENGTH: 24
<212> TYPE: PRT
<213> ORGANISM: ARTIFICIAL
<220> FEATURE:
<223> OTHER INFORMATION: Modified relaxin polypeptide A chain
<220> FEATURE:
<221> NAME/KEY: misc_feature
<222> LOCATION: (1)..(1)
<223> OTHER INFORMATION: Xaa is a non-naturally encoded amino acid such
      as para-acetyl-L-phenylalanine

<400> SEQUENCE: 35

Xaa Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 36
<211> LENGTH: 24
<212> TYPE: PRT
<213> ORGANISM: ARTIFICIAL
<220> FEATURE:
<223> OTHER INFORMATION: Modified relaxin polypeptide A chain

<400> SEQUENCE: 36

Asn Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 37
<211> LENGTH: 29
<212> TYPE: PRT
<213> ORGANISM: ARTIFICIAL
<220> FEATURE:
<223> OTHER INFORMATION: Modified relaxin polypeptide B chain
<220> FEATURE:
<221> NAME/KEY: misc_feature
<222> LOCATION: (25)..(25)
<223> OTHER INFORMATION: Xaa is a non-naturally encoded amino acid such
      as para-acetyl-L-phenylalanine

<400> SEQUENCE: 37

Ala Ser Trp Met Glu Glu Val Ile Lys Leu Cys Gly Arg Glu Leu Val
1               5                   10                  15

Arg Ala Gln Ile Ala Ile Cys Gly Xaa Ser Thr Trp Ser
            20                  25

<210> SEQ ID NO 38
<211> LENGTH: 94
<212> TYPE: PRT
<213> ORGANISM: ARTIFICIAL
<220> FEATURE:
<223> OTHER INFORMATION: Modified relaxin polypeptide (prepro sequence)
<220> FEATURE:
<221> NAME/KEY: misc_feature
<222> LOCATION: (71)..(71)
<223> OTHER INFORMATION: Xaa is a non-naturally encoded amino acid such as para-acetyl-L-phenylalanine

<400> SEQUENCE: 38

Met Ile Glu Glu Gly Arg Ala Ser Trp Met Glu Val Ile Lys Leu
1               5                   10                  15
Cys Gly Arg Glu Leu Val Arg Ala Gln Ile Ala Ile Cys Gly Met Ser
            20                  25                  30
Thr Trp Ser Arg Arg Glu Ala Glu Asp Leu Gln Val Gly Gln Val Glu
        35                  40                  45
Leu Gly Gly Gly Pro Gly Ala Gly Ser Leu Gln Pro Leu Ala Leu Glu
    50                  55                  60
Gly Ser Leu Gln Gly Arg Xaa Leu Tyr Ser Ala Leu Ala Asn Lys Cys
65                  70                  75                  80
Cys His Val Gly Cys Thr Lys Arg Ser Leu Ala Arg Phe Cys
                85                  90

<210> SEQ ID NO 39
<211> LENGTH: 6
<212> TYPE: PRT
<213> ORGANISM: ARTIFICIAL
<220> FEATURE:
<223> OTHER INFORMATION: Exemplary insulin leader amino acid sequence

<400> SEQUENCE: 39

Met Ile Glu Glu Gly Arg
1               5

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51
<211> LENGTH: 27
<212> TYPE: DNA
<213> ORGANISM: ARTIFICIAL
<220> FEATURE:
<223> OTHER INFORMATION: PCR Primer

<400> SEQUENCE: 51
aaatactctg tctggatcgg tggctcc                27

<210> SEQ ID NO 52
<211> LENGTH: 30
<212> TYPE: DNA
<213> ORGANISM: ARTIFICIAL
<220> FEATURE:
<223> OTHER INFORMATION: PCR Primer

<400> SEQUENCE: 52
cacataggta acgagtcaga gctttggcta                30

<210> SEQ ID NO 53
<211> LENGTH: 22
<212> TYPE: DNA
<213> ORGANISM: ARTIFICIAL
<220> FEATURE:
<223> OTHER INFORMATION: PCR Primer

<400> SEQUENCE: 53
gctggagtcg atcaactcta gg                22

<210> SEQ ID NO 54
<211> LENGTH: 21
<212> TYPE: DNA
<213> ORGANISM: ARTIFICIAL
<220> FEATURE:
<223> OTHER INFORMATION: PCR Primer

<400> SEQUENCE: 54
ccaatttcgc tttgccttgt c                    21

<210> SEQ ID NO 55
<211> LENGTH: 9
<212> TYPE: PRT
<213> ORGANISM: ARTIFICIAL
<220> FEATURE:
<223> OTHER INFORMATION: Polyhistidine purification tag

<400> SEQUENCE: 55

His His His His His His Ser Gly Gly
1               5

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: gamma carbon optionally linked to a half-life
      extending moiety such as C13-COOH

<400> SEQUENCE: 101

Gly Gly Gly Gly Ser Glu
1               5

<210> SEQ ID NO 102
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: optionally linked to a half-life extending
      moiety such as C13-COOH

<400> SEQUENCE: 102

Asp Arg Asp Asp Arg Asp
1               5

<210> SEQ ID NO 103
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: gamma carbon optionally linked to a half-life extending moiety such as C13-COOH

<400> SEQUENCE: 103

Lys Lys Lys Lys Lys Lys Glu
1               5

<210> SEQ ID NO 104
<211> LENGTH: 13
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 13
<223> OTHER INFORMATION: gamma carbon optionally linked to a half-life
      extending moiety such as C13-COOH

<400> SEQUENCE: 104

Arg Gly Gly Glu Glu Lys Lys Lys Glu Lys Glu Lys Glu
1               5                   10

<210> SEQ ID NO 105
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: gamma carbon optionally linked to a half-life
      extending moiety such as C13-COOH

<400> SEQUENCE: 105

Gly Gly Gly Glu Glu Glu Glu
1               5

<210> SEQ ID NO 106
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: gamma carbon optionally linked to a half-life
      extending moiety such as C13-COOH

<400> SEQUENCE: 106

Glu Glu Glu Gly Gly Gly Glu
1               5

```
<210> SEQ ID NO 107
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: gamma carbon optionally linked to a half-life
      extending moiety such as C13-COOH

<400> SEQUENCE: 107

Lys Lys Lys Gly Gly Gly Glu
1               5

<210> SEQ ID NO 108
<211> LENGTH: 11
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 11
<223> OTHER INFORMATION: gamma carbon optionally linked to a half-life
      extending moiety such as C13-COOH

<400> SEQUENCE: 108

Gly Glu Thr Gly Ser Ser Gly Glu Gly Thr Glu
1               5                   10

<210> SEQ ID NO 109
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: gamma carbon optionally linked to a half-life
      extending moiety such as C13-COOH

<400> SEQUENCE: 109

Gly Gly Gly Lys Lys Lys Glu
1               5

<210> SEQ ID NO 110
<211> LENGTH: 10
<212> TYPE: PRT
<213> ORGANISM: ARTIFICIAL
<220> FEATURE:
<223> OTHER INFORMATION: Synthetic linker
```

```
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 10
<223> OTHER INFORMATION: gamma carbon optionally linked to a half-life
      extending moiety such as C13-COOH

<400> SEQUENCE: 110

Gly Ser His His His His His Gly Ser Glu
1               5                   10

<210> SEQ ID NO 111
<211> LENGTH: 10
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 1..4
<223> OTHER INFORMATION: Sarcosine (N-methyl glycine)
<220> FEATURE:
<221> NAME/KEY: MOD_RES
<222> LOCATION: 6..9
<223> OTHER INFORMATION: Sarcosine (N-methyl glycine)
<220> FEATURE:
<221> NAME/KEY: MOD_RES
<222> LOCATION: 10
<223> OTHER INFORMATION: gamma carbon optionally linked to a half-life
      extending moiety such as C13-COOH

<400> SEQUENCE: 111

Xaa Xaa Xaa Xaa Ser Xaa Xaa Xaa Xaa Glu
1               5                   10

<210> SEQ ID NO 112
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 1..4
<223> OTHER INFORMATION: Sarcosine (N-methyl glycine)
<220> FEATURE:
<221> NAME/KEY: MOD_RES
<222> LOCATION: 6
<223> OTHER INFORMATION: gamma carbon optionally linked to a half-life
      extending moiety such as C13-COOH

<400> SEQUENCE: 112

Xaa Xaa Xaa Xaa Ser Glu
1               5

<210> SEQ ID NO 113
```

```
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 1..3
<223> OTHER INFORMATION: Sarcosine (N-methyl glycine)
<220> FEATURE:
<221> NAME/KEY: MOD_RES
<222> LOCATION: 6
<223> OTHER INFORMATION: gamma carbon optionally linked to a half-life
      extending moiety such as C13-COOH

<400> SEQUENCE: 113

Xaa Xaa Xaa Glu Glu Glu
1               5

<210> SEQ ID NO 114
<211> LENGTH: 9
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 9
<223> OTHER INFORMATION: gamma carbon optionally linked to a half-life
      extending moiety such as C13-COOH

<400> SEQUENCE: 114

Lys Lys Ser Gly Gly Ser Gly Gly Glu
1               5

<210> SEQ ID NO 115
<211> LENGTH: 9
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 9
<223> OTHER INFORMATION: alpha carbon optionally linked to a half-life
      extending moiety such as C13-COOH

<400> SEQUENCE: 115

Lys Lys Ser Gly Gly Ser Gly Gly Glu
1               5

<210> SEQ ID NO 116
<211> LENGTH: 9
<212> TYPE: PRT
<213> ORGANISM: ARTIFICIAL
```

```
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 9
<223> OTHER INFORMATION: gamma carbon optionally linked to a half-life
      extending moiety such as C13-COOH

<400> SEQUENCE: 116

Lys Lys Ser Ala Gly Ser Ala Gly Glu
1               5

<210> SEQ ID NO 117
<211> LENGTH: 8
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 8
<223> OTHER INFORMATION: gamma carbon optionally linked to a half-life
      extending moiety such as C13-COOH

<400> SEQUENCE: 117

Lys Ser Gly Gly Ser Gly Gly Glu
1               5

<210> SEQ ID NO 118
<211> LENGTH: 10
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 10
<223> OTHER INFORMATION: gamma carbon optionally linked to a half-life
      extending moiety such as C13-COOH

<400> SEQUENCE: 118

Lys Lys Lys Ser Gly Gly Ser Gly Gly Glu
1               5                   10

<210> SEQ ID NO 119
<211> LENGTH: 11
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
```

```
            polypeptide
<220> FEATURE:
<221> NAME/KEY: MOD_RES
<222> LOCATION: 11
<223> OTHER INFORMATION: gamma carbon optionally linked to a half-life
      extending moiety such as C13-COOH

<400> SEQUENCE: 119

Lys Lys Ser Gly Gly Ser Gly Gly Glu Glu Glu
1               5                   10

<210> SEQ ID NO 120
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 1..6
<223> OTHER INFORMATION: D-amino acid(s)
<220> FEATURE:
<221> NAME/KEY: MOD_RES
<222> LOCATION: 7
<223> OTHER INFORMATION: gamma carbon optionally linked to a half-life
      extending moiety such as C13-COOH

<400> SEQUENCE: 120

Lys Lys Lys Lys Lys Lys Glu
1               5

<210> SEQ ID NO 121
<211> LENGTH: 9
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 9
<223> OTHER INFORMATION: gamma carbon optionally linked to a half-life
      extending moiety such as C13-COOH

<400> SEQUENCE: 121

Glu Glu Ser Gly Gly Ser Gly Gly Glu
1               5

<210> SEQ ID NO 122
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
```

```
<222> LOCATION: 6
<223> OTHER INFORMATION: gamma carbon optionally linked to a half-life
      extending moiety such as C15-COOH

<400> SEQUENCE: 122

Gly Gly Gly Gly Ser Glu
1               5

<210> SEQ ID NO 123
<211> LENGTH: 9
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 9
<223> OTHER INFORMATION: gamma carbon optionally linked to a half-life
      extending moiety such as C15-COOH

<400> SEQUENCE: 123

Gly Ser Gly Ser Gly Ser Gly Ser Glu
1               5

<210> SEQ ID NO 124
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: gamma carbon optionally linked to a half-life
      extending moiety such as C15-COOH

<400> SEQUENCE: 124

Glu Glu Glu Gly Gly Gly Glu
1               5

<210> SEQ ID NO 125
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: gamma carbon optionally linked to a half-life
      extending moiety such as C17-COOH

<400> SEQUENCE: 125

Glu Glu Glu Gly Gly Gly Glu
```

```
<210> SEQ ID NO 126
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: gamma carbon optionally linked to a half-life
      extending moiety such as C13-CH3

<400> SEQUENCE: 126

Glu Glu Glu Gly Gly Gly Glu
1               5

<210> SEQ ID NO 127
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: gamma carbon optionally linked to a half-life
      extending moiety such as C15-CH3

<400> SEQUENCE: 127

Glu Glu Glu Gly Gly Gly Glu
1               5

<210> SEQ ID NO 128
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: D-amino acid(s)
<220> FEATURE:
<221> NAME/KEY: MOD_RES
<222> LOCATION: 7
<223> OTHER INFORMATION: gamma carbon optionally linked to a half-life
      extending moiety such as C13-COOH

<400> SEQUENCE: 128

Glu Glu Glu Gly Gly Gly Glu
1               5
```

```
<210> SEQ ID NO 129
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: gamma carbon optionally linked to a half-life
      extending moiety such as C14-COOH

<400> SEQUENCE: 129

Glu Glu Glu Gly Gly Gly Glu
1               5

<210> SEQ ID NO 130
<211> LENGTH: 8
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 8
<223> OTHER INFORMATION: gamma carbon optionally linked to a half-life
      extending moiety such as C13-COOH

<400> SEQUENCE: 130

Glu Gly Gly Gly Gly Ser Lys Glu
1               5

<210> SEQ ID NO 131
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: gamma carbon optionally linked to a half-life
      extending moiety such as C15-COOH

<400> SEQUENCE: 131

Glu Glu Glu Glu Glu Glu Glu
1               5

<210> SEQ ID NO 132

<400> SEQUENCE: 132

000
```

```
<210> SEQ ID NO 133
<211> LENGTH: 20
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 20
<223> OTHER INFORMATION: gamma carbon optionally linked to a half-life
      extending moiety such as C14-CH3

<400> SEQUENCE: 133

Glu Glu Glu Glu Pro Glu Glu Glu Glu Pro Glu Glu Glu Glu Pro Glu
1               5                   10                  15

Glu Glu Glu Glu
            20

<210> SEQ ID NO 134
<211> LENGTH: 20
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 20
<223> OTHER INFORMATION: gamma carbon optionally linked to a half-life
      extending moiety such as C15-CH3

<400> SEQUENCE: 134

Glu Glu Glu Glu Pro Glu Glu Glu Glu Pro Glu Glu Glu Glu Pro Glu
1               5                   10                  15

Glu Glu Glu Glu
            20

<210> SEQ ID NO 135
<211> LENGTH: 20
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 20
<223> OTHER INFORMATION: optionally linked to a half-life extending
      moiety such as C14-CH3

<400> SEQUENCE: 135

Glu Glu Glu Glu Pro Glu Glu Glu Glu Pro Glu Glu Glu Glu Pro Glu
1               5                   10                  15

Glu Gly Gly Gly
            20
```

```
<210> SEQ ID NO 136
<211> LENGTH: 20
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 20
<223> OTHER INFORMATION: gamma carbon optionally linked to a half-life
      extending moiety such as C14-CH3

<400> SEQUENCE: 136

Glu Glu Glu Glu Gly Glu Glu Glu Gly Glu Glu Glu Glu Gly Glu
1               5                   10                  15

Glu Glu Glu Glu
            20

<210> SEQ ID NO 137
<211> LENGTH: 27
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 27
<223> OTHER INFORMATION: gamma carbon optionally linked to a half-life
      extending moiety such as C15-COOH

<400> SEQUENCE: 137

Lys Gly Gly Glu Glu Lys Lys Lys Glu Lys Glu Lys Glu Pro Lys Gly
1               5                   10                  15

Gly Glu Glu Lys Lys Lys Glu Lys Glu Lys Glu
            20                  25

<210> SEQ ID NO 138
<211> LENGTH: 22
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 22
<223> OTHER INFORMATION: gamma carbon optionally linked to a half-life
      extending moiety such as C15-COOH

<400> SEQUENCE: 138

Glu Ala Gln Lys Ala Gln Ala Glu Ala Gln Lys Ala Gln Ala Glu Ala
1               5                   10                  15
```

Gln Lys Ala Gln Ala Glu
            20

<210> SEQ ID NO 139
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: gamma carbon optionally linked to a half-life
      extending moiety such as C14-COOH

<400> SEQUENCE: 139

Gly Gly Gly Gly Ser Glu
1               5

<210> SEQ ID NO 140
<211> LENGTH: 3
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 3
<223> OTHER INFORMATION: gamma carbon optionally linked to a half-life
      extending moiety such as C13-COOH

<400> SEQUENCE: 140

Lys Lys Glu
1

<210> SEQ ID NO 141
<211> LENGTH: 3
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 3
<223> OTHER INFORMATION: gamma carbon optionally linked to a half-life
      extending moiety such as C14-COOH

<400> SEQUENCE: 141

Lys Lys Glu
1

<210> SEQ ID NO 142
<211> LENGTH: 3
<212> TYPE: PRT

```
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 3
<223> OTHER INFORMATION: gamma carbon optionally linked to a half-life
      extending moiety such as C15-COOH

<400> SEQUENCE: 142

Lys Lys Glu
1

<210> SEQ ID NO 143
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: gamma carbon optionally linked to a half-life
      extending moiety such as C14-CH3

<400> SEQUENCE: 143

Glu Glu Glu Glu Glu Glu Glu
1               5

<210> SEQ ID NO 144
<211> LENGTH: 3
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 3
<223> OTHER INFORMATION: gamma carbon optionally linked to a half-life
      extending moiety such as C14-CH3

<400> SEQUENCE: 144

Lys Lys Glu
1

<210> SEQ ID NO 145
<211> LENGTH: 4
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
``` of a para-acetyl-phenylalanine residue of a modified relaxin
      polypeptide
<220> FEATURE:
<221> NAME/KEY: MOD_RES
<222> LOCATION: 4
<223> OTHER INFORMATION: gamma carbon optionally linked to a half-life
      extending moiety such as C14-COOH

<400> SEQUENCE: 145

Lys Gly Pro Glu
1

<210> SEQ ID NO 146
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: gamma carbon optionally linked to a half-life
      extending moiety such as C14-COOH

<400> SEQUENCE: 146

Lys Gly Pro Lys Gly Pro Glu
1               5

<210> SEQ ID NO 147
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: gamma carbon optionally linked to a half-life
      extending moiety such as C14-COOH

<400> SEQUENCE: 147

Ser Gly Gly Gly Ser Glu
1               5

<210> SEQ ID NO 148
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: gamma carbon optionally linked to a half-life
      extending moiety such as C14-COOH

<400> SEQUENCE: 148

Lys Gly Gly Gly Ser Glu
1               5

<210> SEQ ID NO 149
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: gamma carbon optionally linked to a half-life
      extending moiety such as C14-COOH

<400> SEQUENCE: 149

Lys Gly Gly Gly Ser Glu Glu
1               5

<210> SEQ ID NO 150
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: gamma carbon optionally linked to a half-life
      extending moiety such as C14-COOH

<400> SEQUENCE: 150

Gly Ser Pro Gly Ser Pro Glu
1               5

<210> SEQ ID NO 151
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: gamma carbon optionally linked to a half-life
      extending moiety such as C14-COOH

<400> SEQUENCE: 151

Gly Gly Gly Gly Pro Glu
1               5

```
<210> SEQ ID NO 152
<211> LENGTH: 5
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 5
<223> OTHER INFORMATION: gamma carbon optionally linked to a half-life
      extending moiety such as C14-COOH

<400> SEQUENCE: 152

Glu Gly Gly Ser Glu
1               5

<210> SEQ ID NO 153
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: gamma carbon optionally linked to a half-life
      extending moiety such as C14-COOH

<400> SEQUENCE: 153

Glu Gly Gly Gly Pro Glu
1               5

<210> SEQ ID NO 154
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: gamma carbon optionally linked to a half-life
      extending moiety such as C14-COOH

<400> SEQUENCE: 154

Lys Gly Pro Gly Ser Glu Glu
1               5

<210> SEQ ID NO 155

<400> SEQUENCE: 155

000
```

```
<210> SEQ ID NO 156
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: gamma carbon optionally linked to a half-life
      extending moiety such as C15-COOH

<400> SEQUENCE: 156

Lys Lys Gly Gly Ser Glu
1               5

<210> SEQ ID NO 157
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 1..4
<223> OTHER INFORMATION: Sarcosine (N-methyl glycine)
<220> FEATURE:
<221> NAME/KEY: MOD_RES
<222> LOCATION: 6
<223> OTHER INFORMATION: gamma carbon optionally linked to a half-life
      extending moiety such as C13-COOH

<400> SEQUENCE: 157

Xaa Xaa Xaa Xaa Ser Glu
1               5

<210> SEQ ID NO 158
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 1..3
<223> OTHER INFORMATION: Sarcosine (N-methyl glycine)
<220> FEATURE:
<221> NAME/KEY: MOD_RES
<222> LOCATION: 6
<223> OTHER INFORMATION: gamma carbon optionally linked to a half-life
      extending moiety such as C13-COOH

<400> SEQUENCE: 158

Xaa Xaa Xaa Glu Glu Glu
1               5
```

```
<210> SEQ ID NO 159
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: Glu-gamma, (D)-Glu-gamma, Asp-alpha, Asp-beta,
      (D)-Asp-alpha, or (D)-Asp-beta

<400> SEQUENCE: 159

Ala Ala Ala Ala Ala Ser Xaa
1               5

<210> SEQ ID NO 160
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or
      C15-COOH

<400> SEQUENCE: 160

Ala Ala Ala Ala Ser Xaa
1               5

<210> SEQ ID NO 161
<211> LENGTH: 5
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 5
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 5
<223> OTHER INFORMATION: optionally linked to a half-life extending
      moiety such as a fatty acid, such as C13-COOH, C14-COOH, or
      C15-COOH
```

```
<400> SEQUENCE: 161

Ala Ala Ala Ser Xaa
1               5

<210> SEQ ID NO 162
<211> LENGTH: 12
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 12
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 12
<223> OTHER INFORMATION: optionally linked to a half-life extending
      moiety such as a fatty acid, such as C13-COOH, C14-COOH, or
      C15-COOH

<400> SEQUENCE: 162

Ala Ala Ser Ala Ala Ser Ala Ala Ser Ala Ala Xaa
1               5                   10

<210> SEQ ID NO 163
<211> LENGTH: 10
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 10
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 10
<223> OTHER INFORMATION: optionally linked to a half-life extending
      moiety such as a fatty acid, such as C13-COOH, C14-COOH, or
      C15-COOH

<400> SEQUENCE: 163

Ala Ala Ser Ala Ala Ser Ala Ala Ser Xaa
1               5                   10

<210> SEQ ID NO 164
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
```

```
<221> NAME/KEY: MOD_RES
<222> LOCATION: 7
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 7
<223> OTHER INFORMATION: optionally linked to a half-life extending
      moiety such as a fatty acid, such as C13-COOH, C14-COOH, or
      C15-COOH

<400> SEQUENCE: 164

Ala Ala Ser Ala Ala Ser Xaa
1               5

<210> SEQ ID NO 165
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or
      C15-COOH

<400> SEQUENCE: 165

Ala Ala Ser Ser Ala Xaa
1               5

<210> SEQ ID NO 166
<211> LENGTH: 4
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 4
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 4
<223> OTHER INFORMATION: optionally linked to a half-life extending
      moiety such as a fatty acid, such as C13-COOH, C14-COOH, or
      C15-COOH

<400> SEQUENCE: 166

Ala Ala Ser Xaa
1

<210> SEQ ID NO 167
<211> LENGTH: 6
```

```
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or
      C15-COOH

<400> SEQUENCE: 167

Ala Gly Ala Gly Ser Xaa
1               5

<210> SEQ ID NO 168
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or
      C15-COOH

<400> SEQUENCE: 168

Ala Gly Ala Gly Ser Xaa
1               5

<210> SEQ ID NO 169
<211> LENGTH: 5
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 5
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 5
<223> OTHER INFORMATION: optionally linked to a half-life extending
```

```
      moiety such as a fatty acid, such as C13-COOH, C14-COOH, or
      C15-COOH

<400> SEQUENCE: 169

Ala Gly Ala Ser Xaa
1               5

<210> SEQ ID NO 170
<211> LENGTH: 5
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 5
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 5
<223> OTHER INFORMATION: optionally linked to a half-life extending
      moiety such as a fatty acid, such as C13-COOH, C14-COOH, or
      C15-COOH

<400> SEQUENCE: 170

Ala Gly Ala Ser Xaa
1               5

<210> SEQ ID NO 171
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or
      C15-COOH

<400> SEQUENCE: 171

Ala Gly Gly Ala Ser Xaa
1               5

<210> SEQ ID NO 172
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
```

```
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or
      C15-COOH

<400> SEQUENCE: 172

Ala Gly Gly Ala Ser Xaa
1               5

<210> SEQ ID NO 173
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or
      C15-COOH

<400> SEQUENCE: 173

Ala Gly Gly Gly Ser Xaa
1               5

<210> SEQ ID NO 174
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or
      C15-COOH

<400> SEQUENCE: 174

Ala Gly Gly Gly Ser Xaa
1               5
```

```
<210> SEQ ID NO 175
<211> LENGTH: 3
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 3
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 3
<223> OTHER INFORMATION: optionally linked to a half-life extending
      moiety such as a fatty acid, such as C13-COOH, C14-COOH, or
      C15-COOH

<400> SEQUENCE: 175

Ala Ser Xaa
1

<210> SEQ ID NO 176
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MISC_FEATURE
<222> LOCATION: 1..5
<223> OTHER INFORMATION: joined by beta linkages
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or
      C15-COOH

<400> SEQUENCE: 176

Ala Ala Ala Ala Ser Xaa
1               5

<210> SEQ ID NO 177
<211> LENGTH: 5
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MISC_FEATURE
```

```
<222> LOCATION: 1..4
<223> OTHER INFORMATION: joined by beta linkages
<220> FEATURE:
<221> NAME/KEY: MOD_RES
<222> LOCATION: 5
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 5
<223> OTHER INFORMATION: optionally linked to a half-life extending
      moiety such as a fatty acid, such as C13-COOH, C14-COOH, or
      C15-COOH

<400> SEQUENCE: 177

Ala Ala Ala Ser Xaa
1               5

<210> SEQ ID NO 178
<211> LENGTH: 4
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MISC_FEATURE
<222> LOCATION: 1..3
<223> OTHER INFORMATION: joined by beta linkages
<220> FEATURE:
<221> NAME/KEY: MOD_RES
<222> LOCATION: 4
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 4
<223> OTHER INFORMATION: optionally linked to a half-life extending
      moiety such as a fatty acid, such as C13-COOH, C14-COOH, or
      C15-COOH

<400> SEQUENCE: 178

Ala Ala Ser Xaa
1

<210> SEQ ID NO 179
<211> LENGTH: 3
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MISC_FEATURE
<222> LOCATION: 1..2
<223> OTHER INFORMATION: joined by beta linkage
<220> FEATURE:
<221> NAME/KEY: MOD_RES
<222> LOCATION: 3
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 3
<223> OTHER INFORMATION: optionally linked to a half-life extending
``` moiety such as a fatty acid, such as C13-COOH, C14-COOH, or
C15-COOH

<400> SEQUENCE: 179

Ala Ser Xaa
1

<210> SEQ ID NO 180
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: (D)-Glu-gamma, Asp-alpha, Asp-beta, (D)-Asp-
      alpha, or (D)-Asp-beta
<220> FEATURE:
<221> NAME/KEY: MOD_RES
<222> LOCATION: 7
<223> OTHER INFORMATION: optionally linked to a half-life extending
      moiety such as a fatty acid, such as C13-COOH, C14-COOH, or
      C15-COOH

<400> SEQUENCE: 180

Glu Gly Gly Glu Gly Gly Xaa
1               5

<210> SEQ ID NO 181
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: (D)-Glu-gamma, Asp-alpha, Asp-beta, (D)-Asp-
      alpha, or (D)-Asp-beta
<220> FEATURE:
<221> NAME/KEY: MOD_RES
<222> LOCATION: 7
<223> OTHER INFORMATION: optionally linked to a half-life extending
      moiety such as a fatty acid, such as C13-COOH, C14-COOH, or
      C15-COOH

<400> SEQUENCE: 181

Glu Gly Gly Glu Gly Pro Xaa
1               5

<210> SEQ ID NO 182
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group

```
      of a para-acetyl-phenylalanine residue of a modified relaxin
      polypeptide
<220> FEATURE:
<221> NAME/KEY: MOD_RES
<222> LOCATION: 7
<223> OTHER INFORMATION: (D)-Glu-gamma, Asp-alpha, Asp-beta, (D)-Asp-
      alpha, or (D)-Asp-beta
<220> FEATURE:
<221> NAME/KEY: MOD_RES
<222> LOCATION: 7
<223> OTHER INFORMATION: optionally linked to a half-life extending
      moiety such as a fatty acid, such as C13-COOH, C14-COOH, or C15-
      COOH

<400> SEQUENCE: 182

Glu Gly Pro Glu Gly Pro Xaa
1               5

<210> SEQ ID NO 183
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or C15-
      COOH

<400> SEQUENCE: 183

Gly Gly Ala Ala Ser Xaa
1               5

<210> SEQ ID NO 184
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or
      C15-COOH

<400> SEQUENCE: 184

Gly Gly Ala Ala Ser Xaa
1               5
```

```
<210> SEQ ID NO 185
<211> LENGTH: 5
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 5
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 5
<223> OTHER INFORMATION: optionally linked to a half-life extending
      moiety such as a fatty acid, such as C13-COOH, C14-COOH, or
      C15-COOH

<400> SEQUENCE: 185

Gly Gly Ala Ser Xaa
1               5

<210> SEQ ID NO 186
<211> LENGTH: 5
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 5
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 5
<223> OTHER INFORMATION: optionally linked to a half-life extending
      moiety such as a fatty acid, such as C13-COOH, C14-COOH, or C15-
      COOH

<400> SEQUENCE: 186

Gly Gly Ala Ser Xaa
1               5

<210> SEQ ID NO 187
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
```

```
<221> NAME/KEY: MOD_RES
<222> LOCATION: 6
<223> OTHER INFORMATION: optionally linked to a half-life extending
      moiety such as a fatty acid, such as C13-COOH, C14-COOH, or C15-
      COOH

<400> SEQUENCE: 187

Gly Gly Gly Ala Ser Xaa
1               5

<210> SEQ ID NO 188
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or C15-
      COOH

<400> SEQUENCE: 188

Gly Gly Gly Ala Ser Xaa
1               5

<210> SEQ ID NO 189
<211> LENGTH: 8
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 8
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 8
<223> OTHER INFORMATION: optionally linked to a half-life extending
      moiety such as a fatty acid, such as C13-COOH, C14-COOH, or
      C15-COOH

<400> SEQUENCE: 189

Gly Gly Gly Gly Gly Gly Ser Xaa
1               5

<210> SEQ ID NO 190
<211> LENGTH: 7
<212> TYPE: PRT
<213> ORGANISM: ARTIFICIAL
<220> FEATURE:
<223> OTHER INFORMATION: Synthetic linker
<220> FEATURE:
```

```
<221> NAME/KEY: MOD_RES
<222> LOCATION: 1
<223> OTHER INFORMATION: optionally linked to side-chain carbonyl
      group of a para-acetyl-phenylalanine residue of a modified
      relaxin polypeptide
<220> FEATURE:
<221> NAME/KEY: MOD_RES
<222> LOCATION: 7
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 7
<223> OTHER INFORMATION: optionally linked to a half-life extending
      moiety such as a fatty acid, such as C13-COOH, C14-COOH, or C15-
      COOH

<400> SEQUENCE: 190

Gly Gly Gly Gly Gly Ser Xaa
1               5

<210> SEQ ID NO 191
<211> LENGTH: 5
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 5
<223> OTHER INFORMATION: optionally linked to a half-life extending
      moiety such as a fatty acid, such as C13-COOH, C14-COOH, or C15-
      COOH

<400> SEQUENCE: 191

Gly Gly Gly Gly Ser
1               5

<210> SEQ ID NO 192
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MISC_FEATURE
<222> LOCATION: 5..6
<223> OTHER INFORMATION: joined by -PEG2-PEG2- linkage
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or
      C15-COOH

<400> SEQUENCE: 192

Gly Gly Gly Gly Ser Xaa
```

<210> SEQ ID NO 193
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as C14-COOH

<400> SEQUENCE: 193

Gly Gly Gly Gly Ser Xaa
1               5

<210> SEQ ID NO 194
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or C15-
      COOH having malonic acid tail

<400> SEQUENCE: 194

Gly Gly Gly Gly Ser Xaa
1               5

<210> SEQ ID NO 195
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta

```
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or C15-
      COOH having a succinic acid tail

<400> SEQUENCE: 195

Gly Gly Gly Gly Ser Xaa
1               5

<210> SEQ ID NO 196
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: (D)-Glu-gamma, Asp-alpha, Asp-beta, (D)-Asp-
      alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or C15-
      COOH

<400> SEQUENCE: 196

Gly Gly Gly Gly Ser Xaa
1               5

<210> SEQ ID NO 197
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: (D)-Glu-gamma, Asp-alpha, Asp-beta, (D)-Asp-
      alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or
      C15-COOH

<400> SEQUENCE: 197

Gly Gly Gly Gly Ser Xaa
1               5

<210> SEQ ID NO 198
<211> LENGTH: 5
<212> TYPE: PRT
<213> ORGANISM: ARTIFICIAL
<220> FEATURE:
<223> OTHER INFORMATION: Synthetic linker
```

```
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 5
<223> OTHER INFORMATION: optionally linked to a half-life extending
      moiety such as a fatty acid, such as C13-COOH, C14-COOH, or C15-
      COOH

<400> SEQUENCE: 198

Gly Gly Gly Gly Thr
1               5

<210> SEQ ID NO 199
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or C15-
      COOH

<400> SEQUENCE: 199

Gly Gly Gly Ser Gly Xaa
1               5

<210> SEQ ID NO 200
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 7
<223> OTHER INFORMATION: optionally linked to a half-life extending
      moiety such as a fatty acid, such as C13-COOH, C14-COOH, or C15-
      COOH

<400> SEQUENCE: 200

Gly Gly Gly Ser Ser Ser Xaa
1               5
```

-continued

```
<210> SEQ ID NO 201
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or C15-
      COOH

<400> SEQUENCE: 201

Gly Gly Gly Ser Ser Xaa
1               5

<210> SEQ ID NO 202
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or C15-
      COOH

<400> SEQUENCE: 202

Gly Gly Gly Ser Ser Xaa
1               5

<210> SEQ ID NO 203
<211> LENGTH: 5
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 5
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
```

<222> LOCATION: 5
<223> OTHER INFORMATION: optionally linked to a half-life extending
      moiety such as a fatty acid, such as C13-COOH, C14-COOH, or C15-
      COOH

<400> SEQUENCE: 203

Gly Gly Gly Ser Xaa
1               5

<210> SEQ ID NO 204
<211> LENGTH: 8
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 8
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 8
<223> OTHER INFORMATION: optionally linked to a half-life extending
      moiety such as a fatty acid, such as C13-COOH, C14-COOH, or C15-
      COOH

<400> SEQUENCE: 204

Gly Gly Gly Thr Thr Thr Thr Xaa
1               5

<210> SEQ ID NO 205
<211> LENGTH: 9
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 9
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 9
<223> OTHER INFORMATION: optionally linked to a half-life extending
      moiety such as a fatty acid, such as C13-COOH, C14-COOH, or C15-
      COOH

<400> SEQUENCE: 205

Gly Gly Ser Gly Gly Gly Gly Gly Xaa
1               5

<210> SEQ ID NO 206
<211> LENGTH: 12
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES

```
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 12
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 12
<223> OTHER INFORMATION: optionally linked to a half-life extending
      moiety such as a fatty acid, such as C13-COOH, C14-COOH, or C15-
      COOH

<400> SEQUENCE: 206

Gly Gly Ser Gly Gly Ser Gly Gly Ser Gly Gly Xaa
1               5                   10

<210> SEQ ID NO 207
<211> LENGTH: 10
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 10
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 10
<223> OTHER INFORMATION: optionally linked to a half-life extending
      moiety such as a fatty acid, such as C13-COOH, C14-COOH, or C15-
      COOH

<400> SEQUENCE: 207

Gly Gly Ser Gly Gly Ser Gly Gly Ser Xaa
1               5                   10

<210> SEQ ID NO 208
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 7
<223> OTHER INFORMATION: optionally linked to a half-life extending
      moiety such as a fatty acid, such as C13-COOH, C14-COOH, or C15-
      COOH

<400> SEQUENCE: 208

Gly Gly Ser Gly Gly Ser Xaa
```

```
<210> SEQ ID NO 209
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or C15-
      COOH

<400> SEQUENCE: 209

Gly Gly Ser Gly Gly Xaa
1               5

<210> SEQ ID NO 210
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or C15-
      COOH

<400> SEQUENCE: 210

Gly Gly Ser Gly Ser Xaa
1               5

<210> SEQ ID NO 211
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
```

(D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or C15-
      COOH

<400> SEQUENCE: 211

Gly Gly Ser Ser Gly Xaa
1               5

<210> SEQ ID NO 212
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 7
<223> OTHER INFORMATION: optionally linked to a half-life extending
      moiety such as a fatty acid, such as C13-COOH, C14-COOH, or C15-
      COOH

<400> SEQUENCE: 212

Gly Gly Ser Ser Ser Ser Xaa
1               5

<210> SEQ ID NO 213
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or C15-
      COOH

<400> SEQUENCE: 213

Gly Gly Ser Ser Ser Xaa
1               5

<210> SEQ ID NO 214
<211> LENGTH: 5
<212> TYPE: PRT
<213> ORGANISM: ARTIFICIAL
<220> FEATURE:

```
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 5
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 5
<223> OTHER INFORMATION: optionally linked to a half-life extending
      moiety such as a fatty acid, such as C13-COOH, C14-COOH, or C15-
      COOH

<400> SEQUENCE: 214

Gly Gly Ser Ser Xaa
1               5

<210> SEQ ID NO 215
<211> LENGTH: 5
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 5
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 5
<223> OTHER INFORMATION: optionally linked to a half-life extending
      moiety such as a fatty acid, such as C13-COOH, C14-COOH, or C15-
      COOH

<400> SEQUENCE: 215

Gly Gly Ser Ser Xaa
1               5

<210> SEQ ID NO 216
<211> LENGTH: 5
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 5
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 5
<223> OTHER INFORMATION: optionally linked to a half-life extending
      moiety such as a fatty acid, such as C13-COOH, C14-COOH, or C15-
      COOH
```

```
<400> SEQUENCE: 216

Gly Gly Ser Ser Xaa
1               5

<210> SEQ ID NO 217
<211> LENGTH: 4
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 4
<223> OTHER INFORMATION: (D)-Glu-gamma, Asp-alpha, Asp-beta, (D)-Asp-
      alpha, or (D)-Asp-beta
<220> FEATURE:
<221> NAME/KEY: MOD_RES
<222> LOCATION: 4
<223> OTHER INFORMATION: optionally linked to a half-life extending
      moiety such as a fatty acid, such as C13-COOH, C14-COOH, or C15-
      COOH

<400> SEQUENCE: 217

Gly Gly Ser Xaa
1

<210> SEQ ID NO 218
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 7
<223> OTHER INFORMATION: optionally linked to a half-life extending
      moiety such as a fatty acid, such as C13-COOH, C14-COOH, or C15-
      COOH

<400> SEQUENCE: 218

Gly Gly Thr Thr Thr Thr Xaa
1               5

<210> SEQ ID NO 219
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
```

```
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or C15-
      COOH

<400> SEQUENCE: 219

Gly Gly Thr Thr Thr Xaa
1               5

<210> SEQ ID NO 220
<211> LENGTH: 5
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 5
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 5
<223> OTHER INFORMATION: optionally linked to a half-life extending
      moiety such as a fatty acid, such as C13-COOH, C14-COOH, or C15-
      COOH

<400> SEQUENCE: 220

Gly Gly Thr Thr Xaa
1               5

<210> SEQ ID NO 221
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or C15-
      COOH

<400> SEQUENCE: 221

Gly Ser Gly Gly Gly Xaa
1               5

<210> SEQ ID NO 222
<211> LENGTH: 6
```

```
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or C15-
      COOH

<400> SEQUENCE: 222

Gly Ser Gly Gly Ser Xaa
1               5

<210> SEQ ID NO 223
<211> LENGTH: 11
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 11
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 11
<223> OTHER INFORMATION: optionally linked to a half-life extending
      moiety such as a fatty acid, such as C13-COOH, C14-COOH, or C15-
      COOH

<400> SEQUENCE: 223

Gly Ser Gly Ser Gly Ser Gly Ser Gly Ser Xaa
1               5                   10

<210> SEQ ID NO 224
<211> LENGTH: 9
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 9
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 9
<223> OTHER INFORMATION: optionally linked to a half-life extending
``` moiety such as a fatty acid, such as C13-COOH, C14-COOH, or C15-
      COOH

<400> SEQUENCE: 224

Gly Ser Gly Ser Gly Ser Gly Ser Xaa
1               5

<210> SEQ ID NO 225
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 7
<223> OTHER INFORMATION: optionally linked to a half-life extending
      moiety such as a fatty acid, such as C13-COOH, C14-COOH, or C15-
      COOH

<400> SEQUENCE: 225

Gly Ser Gly Ser Gly Ser Xaa
1               5

<210> SEQ ID NO 226
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or C15-
      COOH

<400> SEQUENCE: 226

Gly Ser Gly Ser Gly Xaa
1               5

<210> SEQ ID NO 227
<211> LENGTH: 5
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group

```
      of a para-acetyl-phenylalanine residue of a modified relaxin
      polypeptide
<220> FEATURE:
<221> NAME/KEY: MOD_RES
<222> LOCATION: 5
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 5
<223> OTHER INFORMATION: optionally linked to a half-life extending
      moiety such as a fatty acid, such as C13-COOH, C14-COOH, or C15-
      COOH

<400> SEQUENCE: 227

Gly Ser Gly Ser Xaa
1               5

<210> SEQ ID NO 228
<211> LENGTH: 4
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 4
<223> OTHER INFORMATION: (D)-Glu-gamma, Asp-alpha, Asp-beta, (D)-Asp-
      alpha, or (D)-Asp-beta
<220> FEATURE:
<221> NAME/KEY: MOD_RES
<222> LOCATION: 4
<223> OTHER INFORMATION: optionally linked to a half-life extending
      moiety such as a fatty acid, such as C13-COOH, C14-COOH, or C15-
      COOH

<400> SEQUENCE: 228

Gly Ser Pro Xaa
1

<210> SEQ ID NO 229
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or C15-
      COOH

<400> SEQUENCE: 229

Gly Ser Ser Ser Ser Xaa
1               5
```

<210> SEQ ID NO 230
<211> LENGTH: 5
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 5
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 5
<223> OTHER INFORMATION: optionally linked to a half-life extending
      moiety such as a fatty acid, such as C13-COOH, C14-COOH, or C15-
      COOH

<400> SEQUENCE: 230

Gly Ser Ser Ser Xaa
1               5

<210> SEQ ID NO 231
<211> LENGTH: 4
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 4
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 4
<223> OTHER INFORMATION: optionally linked to a half-life extending
      moiety such as a fatty acid, such as C13-COOH, C14-COOH, or C15-
      COOH

<400> SEQUENCE: 231

Gly Ser Ser Xaa
1

<210> SEQ ID NO 232
<211> LENGTH: 3
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 3
<223> OTHER INFORMATION: (D)-Glu-gamma, Asp-alpha, Asp-beta, (D)-Asp-
      alpha, or (D)-Asp-beta
<220> FEATURE:

```
<221> NAME/KEY: MOD_RES
<222> LOCATION: 3
<223> OTHER INFORMATION: optionally linked to a half-life extending
      moiety such as a fatty acid, such as C13-COOH, C14-COOH, or C15-
      COOH

<400> SEQUENCE: 232

Gly Ser Xaa
1

<210> SEQ ID NO 233
<211> LENGTH: 5
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 5
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 5
<223> OTHER INFORMATION: optionally linked to a half-life extending
      moiety such as a fatty acid, such as C13-COOH, C14-COOH, or C15-
      COOH

<400> SEQUENCE: 233

Gly Thr Thr Thr Xaa
1               5

<210> SEQ ID NO 234
<211> LENGTH: 4
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 4
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 4
<223> OTHER INFORMATION: optionally linked to a half-life extending
      moiety such as a fatty acid, such as C13-COOH, C14-COOH, or C15-
      COOH

<400> SEQUENCE: 234

Gly Thr Thr Xaa
1

<210> SEQ ID NO 235
<211> LENGTH: 6
<212> TYPE: PRT
<213> ORGANISM: ARTIFICIAL
<220> FEATURE:
<223> OTHER INFORMATION: Synthetic linker
<220> FEATURE:
```

```
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: (D)-Glu-gamma, Asp-alpha, Asp-beta, (D)-Asp-
      alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or C15-
      COOH

<400> SEQUENCE: 235

Lys Gly Gly Gly Ser Xaa
1               5

<210> SEQ ID NO 236
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: (D)-Glu-gamma, Asp-alpha, Asp-beta, (D)-Asp-
      alpha, or (D)-Asp-beta
<220> FEATURE:
<221> NAME/KEY: MOD_RES
<222> LOCATION: 7
<223> OTHER INFORMATION: optionally linked to a half-life extending
      moiety such as a fatty acid, such as C13-COOH, C14-COOH, or C15-
      COOH

<400> SEQUENCE: 236

Lys Gly Gly Lys Gly Gly Xaa
1               5

<210> SEQ ID NO 237
<211> LENGTH: 3
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MISC_FEATURE
<222> LOCATION: 2..3
<223> OTHER INFORMATION: joined by -PEG2-PEG2- linkage
<220> FEATURE:
<221> NAME/KEY: MOD_RES
<222> LOCATION: 3
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 3
<223> OTHER INFORMATION: optionally linked to a half-life extending
      moiety such as a fatty acid, such as C13-COOH, C14-COOH, or C15-
```

COOH

<400> SEQUENCE: 237

Lys Lys Xaa
1

<210> SEQ ID NO 238
<211> LENGTH: 3
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 3
<223> OTHER INFORMATION: optionally linked to a half-life extending
      moiety such as a fatty acid, such as C13-COOH, C14-COOH, or C15-
      COOH

<400> SEQUENCE: 238

Lys Lys Ser
1

<210> SEQ ID NO 239
<211> LENGTH: 4
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 4
<223> OTHER INFORMATION: (D)-Glu-gamma, Asp-alpha, Asp-beta, (D)-Asp-
      alpha, or (D)-Asp-beta
<220> FEATURE:
<221> NAME/KEY: MOD_RES
<222> LOCATION: 4
<223> OTHER INFORMATION: optionally linked to a half-life extending
      moiety such as a fatty acid, such as C13-COOH, C14-COOH, or C15-
      COOH

<400> SEQUENCE: 239

Lys Lys Ser Xaa
1

<210> SEQ ID NO 240
<211> LENGTH: 3
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 3
<223> OTHER INFORMATION: optionally linked to a half-life extending

```
       moiety such as a fatty acid, such as C13-COOH, C14-COOH, or C15-
       COOH

<400> SEQUENCE: 240

Lys Lys Thr
1

<210> SEQ ID NO 241
<211> LENGTH: 4
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
       of a para-acetyl-phenylalanine residue of a modified relaxin
       polypeptide
<220> FEATURE:
<221> NAME/KEY: MOD_RES
<222> LOCATION: 4
<223> OTHER INFORMATION: (D)-Glu-gamma, Asp-alpha, Asp-beta, (D)-Asp-
       alpha, or (D)-Asp-beta
<220> FEATURE:
<221> NAME/KEY: MOD_RES
<222> LOCATION: 4
<223> OTHER INFORMATION: optionally linked to a half-life extending
       moiety such as a fatty acid, such as C13-COOH, C14-COOH, or C15-
       COOH

<400> SEQUENCE: 241

Lys Lys Thr Xaa
1

<210> SEQ ID NO 242
<211> LENGTH: 3
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
       of a para-acetyl-phenylalanine residue of a modified relaxin
       polypeptide
<220> FEATURE:
<221> NAME/KEY: MOD_RES
<222> LOCATION: 3
<223> OTHER INFORMATION: Glu-gamma, (D)-Glu-gamma, Asp-alpha, Asp-beta,
       (D)-Asp-alpha, or (D)-Asp-beta
<220> FEATURE:
<221> NAME/KEY: MOD_RES
<222> LOCATION: 3
<223> OTHER INFORMATION: optionally linked to a half-life extending
       moiety such as a malonic acid tail

<400> SEQUENCE: 242

Lys Lys Xaa
1

<210> SEQ ID NO 243
<211> LENGTH: 3
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
       of a para-acetyl-phenylalanine residue of a modified relaxin
```

```
        polypeptide
<220> FEATURE:
<221> NAME/KEY: MOD_RES
<222> LOCATION: 3
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 3
<223> OTHER INFORMATION: optionally linked to a half-life extending
      moiety such as a succinic acid tail

<400> SEQUENCE: 243

Lys Lys Xaa
1

<210> SEQ ID NO 244
<211> LENGTH: 3
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 3
<223> OTHER INFORMATION: (D)-Glu-gamma, Asp-alpha, Asp-beta, (D)-Asp-
      alpha, or (D)-Asp-beta
<220> FEATURE:
<221> NAME/KEY: MOD_RES
<222> LOCATION: 3
<223> OTHER INFORMATION: optionally linked to a half-life extending
      moiety such as a fatty acid, such as C13-COOH, C14-COOH, or C15-
      COOH

<400> SEQUENCE: 244

Lys Lys Xaa
1

<210> SEQ ID NO 245
<211> LENGTH: 5
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 5
<223> OTHER INFORMATION: (D)-Glu-gamma, Asp-alpha, Asp-beta, (D)-Asp-
      alpha, or (D)-Asp-beta
<220> FEATURE:
<221> NAME/KEY: MOD_RES
<222> LOCATION: 5
<223> OTHER INFORMATION: optionally linked to a half-life extending
      moiety such as a fatty acid, such as C13-COOH, C14-COOH, or C15-
      COOH

<400> SEQUENCE: 245

Lys Pro Lys Ser Xaa
1               5

<210> SEQ ID NO 246
```

```
<211> LENGTH: 8
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 8
<223> OTHER INFORMATION: (D)-Glu-gamma, Asp-alpha, Asp-beta, (D)-Asp-
      alpha, or (D)-Asp-beta
<220> FEATURE:
<221> NAME/KEY: MOD_RES
<222> LOCATION: 8
<223> OTHER INFORMATION: optionally linked to a half-life extending
      moiety such as a fatty acid, such as C13-COOH, C14-COOH, or C15-
      COOH

<400> SEQUENCE: 246

Lys Ser Gly Gly Gly Ser Lys Xaa
1               5

<210> SEQ ID NO 247
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: (D)-Glu-gamma, Asp-alpha, Asp-beta, (D)-Asp-
      alpha, or (D)-Asp-beta
<220> FEATURE:
<221> NAME/KEY: MOD_RES
<222> LOCATION: 7
<223> OTHER INFORMATION: optionally linked to a half-life extending
      moiety such as a fatty acid, such as C13-COOH, C14-COOH, or C15-
      COOH

<400> SEQUENCE: 247

Lys Ser Gly Lys Ser Gly Xaa
1               5

<210> SEQ ID NO 248
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 7
```

```
<223> OTHER INFORMATION: optionally linked to a half-life extending
      moiety such as a fatty acid, such as C13-COOH, C14-COOH, or C15-
      COOH

<400> SEQUENCE: 248

Ser Gly Gly Gly Gly Gly Xaa
1               5

<210> SEQ ID NO 249
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or C15-
      COOH

<400> SEQUENCE: 249

Ser Gly Gly Gly Gly Xaa
1               5

<210> SEQ ID NO 250
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or C15-
      COOH

<400> SEQUENCE: 250

Ser Gly Gly Gly Gly Xaa
1               5

<210> SEQ ID NO 251
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
```

```
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 6
<223> OTHER INFORMATION: optionally linked to a half-life extending
      moiety such as a fatty acid, such as C13-COOH, C14-COOH, or C15-
      COOH

<400> SEQUENCE: 251

Ser Gly Gly Gly Ser Xaa
1               5

<210> SEQ ID NO 252
<211> LENGTH: 5
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 5
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 5
<223> OTHER INFORMATION: optionally linked to a half-life extending
      moiety such as a fatty acid, such as C13-COOH, C14-COOH, or C15-
      COOH

<400> SEQUENCE: 252

Ser Gly Gly Gly Xaa
1               5

<210> SEQ ID NO 253
<211> LENGTH: 4
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 4
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 4
<223> OTHER INFORMATION: optionally linked to a half-life extending
      moiety such as a fatty acid, such as C13-COOH, C14-COOH, or C15-
      COOH

<400> SEQUENCE: 253

Ser Gly Gly Xaa
1
```

```
<210> SEQ ID NO 254
<211> LENGTH: 3
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 3
<223> OTHER INFORMATION: Glu-gamma, (D)-Glu-gamma, Asp-alpha, Asp-beta,
      (D)-Asp-alpha, or (D)-Asp-beta
<220> FEATURE:
<221> NAME/KEY: MOD_RES
<222> LOCATION: 3
<223> OTHER INFORMATION: optionally linked to a half-life extending
      moiety such as a fatty acid, such as C13-COOH, C14-COOH, or C15-
      COOH

<400> SEQUENCE: 254

Ser Gly Xaa
1

<210> SEQ ID NO 255
<211> LENGTH: 3
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 3
<223> OTHER INFORMATION: gamma carbon optionally linked to a half-life
      extending moiety such as C14-COOH

<400> SEQUENCE: 255

Gly Ser Glu
1

<210> SEQ ID NO 256
<211> LENGTH: 4
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 4
<223> OTHER INFORMATION: gamma carbon optionally linked to a half-life
      extending moiety such as C14-COOH

<400> SEQUENCE: 256

Gly Gly Ser Glu
1
```

```
<210> SEQ ID NO 257
<211> LENGTH: 4
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 4
<223> OTHER INFORMATION: gamma carbon optionally linked to a half-life
      extending moiety such as C14-COOH

<400> SEQUENCE: 257

Gly Ser Pro Glu
1

<210> SEQ ID NO 258
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: gamma carbon optionally linked to a half-life
      extending moiety such as C14-COOH

<400> SEQUENCE: 258

Glu Gly Gly Glu Gly Gly Glu
1               5

<210> SEQ ID NO 259
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MISC_FEATURE
<222> LOCATION: 1..2
<223> OTHER INFORMATION: joined by gamma linkage
<220> FEATURE:
<221> NAME/KEY: MOD_RES
<222> LOCATION: 7
<223> OTHER INFORMATION: gamma carbon optionally linked to a half-life
      extending moiety such as C14-COOH

<400> SEQUENCE: 259

Glu Gly Gly Gly Gly Ser Glu
1               5

<210> SEQ ID NO 260
<211> LENGTH: 7
```

```
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: gamma carbon optionally linked to a half-life
      extending moiety such as C14-COOH

<400> SEQUENCE: 260

Glu Gly Gly Glu Gly Pro Glu
1               5

<210> SEQ ID NO 261
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: gamma carbon optionally linked to a half-life
      extending moiety such as C14-COOH

<400> SEQUENCE: 261

Glu Gly Pro Glu Gly Pro Glu
1               5

<210> SEQ ID NO 262
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: gamma carbon optionally linked to a half-life
      extending moiety such as C15-COOH

<400> SEQUENCE: 262

Lys Gly Gly Gly Ser Glu
1               5

<210> SEQ ID NO 263
<211> LENGTH: 8
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
```

```
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 8
<223> OTHER INFORMATION: gamma carbon optionally linked to a half-life
      extending moiety such as C15-COOH

<400> SEQUENCE: 263

Lys Ser Gly Gly Gly Ser Lys Glu
1               5

<210> SEQ ID NO 264
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: gamma carbon optionally linked to a half-life
      extending moiety such as C15-COOH

<400> SEQUENCE: 264

Lys Ser Gly Lys Ser Gly Glu
1               5

<210> SEQ ID NO 265
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: gamma carbon optionally linked to a half-life
      extending moiety such as C15-COOH

<400> SEQUENCE: 265

Lys Gly Gly Lys Gly Gly Glu
1               5

<210> SEQ ID NO 266
<211> LENGTH: 5
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 5
<223> OTHER INFORMATION: gamma carbon optionally linked to a half-life
``` extending moiety such as C15-COOH

<400> SEQUENCE: 266

Lys Pro Lys Ser Glu
1               5

<210> SEQ ID NO 267
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 1..6
<223> OTHER INFORMATION: D-amino acid(s)
<220> FEATURE:
<221> NAME/KEY: MOD_RES
<222> LOCATION: 7
<223> OTHER INFORMATION: gamma carbon optionally linked to a half-life
      extending moiety such as C13-COOH

<400> SEQUENCE: 267

Lys Lys Lys Lys Lys Lys Glu
1               5

<210> SEQ ID NO 268
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 1..6
<223> OTHER INFORMATION: 2,3-diaminopropionic acid
<220> FEATURE:
<221> NAME/KEY: MOD_RES
<222> LOCATION: 7
<223> OTHER INFORMATION: gamma carbon optionally linked to a half-life
      extending moiety such as C13-COOH

<400> SEQUENCE: 268

Xaa Xaa Xaa Xaa Xaa Xaa Glu
1               5

<210> SEQ ID NO 269
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 1..6

```
<223> OTHER INFORMATION: 6-N-methyllysine
<220> FEATURE:
<221> NAME/KEY: MOD_RES
<222> LOCATION: 7
<223> OTHER INFORMATION: gamma carbon optionally linked to a half-life
      extending moiety such as C13-COOH

<400> SEQUENCE: 269

Xaa Xaa Xaa Xaa Xaa Xaa Glu
1               5

<210> SEQ ID NO 270
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 1..3
<223> OTHER INFORMATION: D-amino acid(s)
<220> FEATURE:
<221> NAME/KEY: MOD_RES
<222> LOCATION: 7
<223> OTHER INFORMATION: gamma carbon optionally linked to a half-life
      extending moiety such as C13-COOH

<400> SEQUENCE: 270

Lys Lys Lys Gly Gly Gly Glu
1               5

<210> SEQ ID NO 271
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: gamma carbon optionally linked to a half-life
      extending moiety such as C15-COOH

<400> SEQUENCE: 271

Gly Gly Gly Glu Glu Glu Glu
1               5

<210> SEQ ID NO 272
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
```

```
<222> LOCATION: 7
<223> OTHER INFORMATION: gamma carbon optionally linked to a half-life
      extending moiety such as C17-COOH

<400> SEQUENCE: 272

Gly Gly Gly Glu Glu Glu Glu
1               5

<210> SEQ ID NO 273
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: gamma carbon optionally linked to a half-life
      extending moiety such as C13-COOH

<400> SEQUENCE: 273

Lys Lys Lys Lys Pro Glu
1               5

<210> SEQ ID NO 274
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: optionally linked to a half-life extending
      moiety such as C13-COOH

<400> SEQUENCE: 274

Lys Lys Lys Lys Lys Lys
1               5

<210> SEQ ID NO 275
<211> LENGTH: 8
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 8
<223> OTHER INFORMATION: gamma carbon optionally linked to a half-life
      extending moiety such as C13-COOH

<400> SEQUENCE: 275

Lys Ala Gln Lys Ala Gln Ala Glu
```

```
<210> SEQ ID NO 276
<211> LENGTH: 10
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 10
<223> OTHER INFORMATION: gamma carbon optionally linked to a half-life
      extending moiety such as C13-COOH

<400> SEQUENCE: 276

Lys Lys Lys Lys Pro Lys Lys Lys Lys Glu
1               5                   10

<210> SEQ ID NO 277
<211> LENGTH: 10
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 10
<223> OTHER INFORMATION: gamma carbon optionally linked to a half-life
      extending moiety such as C13-COOH

<400> SEQUENCE: 277

Lys Lys Lys Lys Lys Lys Gly Gly Gly Glu
1               5                   10

<210> SEQ ID NO 278
<211> LENGTH: 7
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 7
<223> OTHER INFORMATION: D-amino acid(s)
<220> FEATURE:
<221> NAME/KEY: MOD_RES
<222> LOCATION: 7
<223> OTHER INFORMATION: gamma carbon optionally linked to a half-life
      extending moiety such as C13-CH3

<400> SEQUENCE: 278

Glu Glu Glu Gly Gly Gly Glu
1               5
```

```
<210> SEQ ID NO 279
<211> LENGTH: 6
<212> TYPE: PRT
<213> ORGANISM: ARTIFICIAL
<220> FEATURE:
<223> OTHER INFORMATION: Synthetic linker
<220> FEATURE:
<221> NAME/KEY: MOD_RES
<222> LOCATION: 1
<223> OTHER INFORMATION: optionally linked to side-chain carbonyl group
      of a para-acetyl-phenylalanine residue of a modified relaxin
      polypeptide
<220> FEATURE:
<221> NAME/KEY: MOD_RES
<222> LOCATION: 6
<223> OTHER INFORMATION: gamma carbon optionally linked to a half-life
      extending moiety such as C13-CH3

<400> SEQUENCE: 279

Gly Gly Gly Gly Ser Glu
1               5
```

MODIFIED RELAXIN POLYPEPTIDES COMPRISING A PHARMACOKINETIC ENHANCER AND USES THEREOF

RELATED APPLICATION DISCLOSURES

This application claims the benefit of U.S. Provisional Application 62/627,411, filed Feb. 7, 2018 and U.S. Provisional Application No. 62/456,161, filed Feb. 8, 2017, the disclosure of all of which listed above are herein incorporated by reference in their entirety.

SEQUENCE DISCLOSURE

This application includes as part of its disclosure a biological sequence listing, contained in a file named "46561o2401.txt" having a size of 150,746 bytes, which was created on Feb. 8, 2018, which is hereby incorporated by reference in its entirety.

BACKGROUND OF THE DISCLOSURE

The present disclosure generally relates to modified relaxin polypeptides, such as modified human relaxin 2 polypeptides, comprising a pharmacokinetic enhancer, and therapeutic uses of such polypeptides, such as for the treatment of cardiovascular conditions (such as heart failure) and/or conditions relating to fibrosis. In exemplary embodiments, the pharmacokinetic enhancer is linked to a non-naturally encoded amino acid, which may be ribosomally incorporated into the relaxin polypeptide.

Heart failure (HF) represents a tremendous burden on today's health care system with an estimated United States prevalence of 5.8 million and greater than 23 million worldwide (Roger et al., 2012. *Circulation*, 125(1): e2-e220). The symptoms of HF are the result of inadequate cardiac output and can be debilitating depending upon the advanced stage of the disease. Major symptoms and signs of HF include: 1) dyspnea (difficulty in breathing) resulting from pulmonary edema due to ineffective forward flow from the left ventricle and increased pressure in the pulmonary capillary bed; 2) lower extremity edema occurs when the right ventricle is unable to accommodate systemic venous return; and 3) fatigue due to the failing heart's inability to sustain sufficient cardiac output to meet the body's metabolic needs (Kemp & Conte, 2012. *Cardiovascular Pathology*, 21:365-371).

Many contributory diseases, risk factors, and pathological changes may ultimately lead to heart failure (Jessup & Brozena, 2003. *N Engl J Med*, 348(20): 2007-2018). Injurious events thought to be involved in the pathophysiology of HF range from the very acute such as myocardial infarction to a more chronic insult such as life-long hypertension. The death rate remains high with ~50% of people with HF dying within 5 years of diagnosis (Roger et al., 2012. *Circulation*, 125(1): e2-e220; Roger et al., 2004. *Jama*, 292(3): 344-50). Heart failure clearly presents a significant unmet medical need.

The human relaxin 2 hormone (also called H2 relaxin) is a 6-kDa peptide composed of 53 amino acids which was known to be responsible for remodeling the reproductive tract before parturition, thus facilitating the birth process. While predominantly a hormone of pregnancy, relaxin has also been detected in the non-pregnant female as well as in the male. Human relaxin is a member of the insulin peptide family which includes insulin, a number of insulin like peptides (INSL3-6), and the insulin-like growth factors (IGFI and IGFII) (Van Der Westhuizen et al., 2007. *Curr Drug Targets*, 8(1): 91-104). These heterodimeric peptides are all structurally related with each comprised of two peptide chains (A & B) that are connected by two disulfide bonds, and with the A-chain containing a single intramolecular disulfide bond. The receptor for relaxin 2 (H2), called the Relaxin Family Peptide Receptor 1 (RXFP1), is conserved between mouse and human with 85% amino acid identity and is essentially ubiquitously expressed in humans and in other species (Halls et al., 2007. *Br J Pharmacol*, 150(6): 677-91).

During human gestation, in order to meet the nutritional demands imposed upon it by the fetus, the female body undergoes a significant ~30% decrease in systemic vascular resistance (SVR) and a concomitant ~50% increase in cardiac output (Jeyabalan, 2010: *Renal and Electrolyte Disorders*. Lippincott Williams & Wilkins. 462-518; Clapp and Capeless, 1997. *Am J Cardiol*, 80(11): 1469-73). Additional vascular adaptations include an ~30% increase in global arterial compliance that is important for maintaining efficient ventricular-arterial coupling, as well as an ~50% increase in both renal blood flow (RBF) and glomerular filtration rate (GFR), important for metabolic waste elimination (Jeyabalan, 2010: *Renal and Electrolyte Disorders*. Lippincott Williams & Wilkins. 462-518; Poppas et al., 1997. *Circulation*, 95(10): p. 2407-15). Both pre-clinical studies in rodents as well as clinical studies performed in a variety of patient settings provide evidence that relaxin is involved, at least to some extent, in mediating these adaptive physiological changes (Conrad, 2011. *Am J Physiol Regul Integr Comp Physiol*, 301(2), R267-275; Teichman et al., 2009. *Heart Fail Rev*, 14(4), 321-329.). Many of these adaptive responses would likely be of benefit to HF patients in that excessive fibrosis, poor arterial compliance, and poor renal function are all characteristics common to heart failure patients (Mohammed et al., 2015. *Circulation*, 131(6), 550-559), (Wohlfahrt et al., 2015. *Eur J Heart Fail*, 17(1), 27-34; Dammon et al., 2011. *Prog Cardiovasc Dis*, 54(2), 144-153). As an estimated 30% of patients with HF suffer from moderate to severe renal impairment (Triposkiadis and Skoularigis, 2012. *Curr Heart Fail Rep*, (4):354-62), an agent such as relaxin by improving both vascular flow and electrolyte handling, may be of particular benefit to HF patients.

The relaxin peptide has a short pharmacokinetic half-life: Serelaxin, a recombinant human relaxin peptide, which was developed for the treatment of HF, has a short first-phase pharmacokinetic half-life of 5-15 minutes, and necessitated 48 hours continuous intravenous infusion for therapeutic utility (REASANZ (serelaxin) Briefing Document Prepared by Novartis for FDA Cardiovascular and Renal Drugs Advisory Committee Meeting. Feb. 26, 2014). For chronic diseases like heart failure, a relaxin molecule with an improved pharmacokinetic profile provides the opportunity for alternate routes of drug administration, beyond continuous intravenous infusion, likely to be more amenable as a therapeutic for patients suffering from chronic diseases.

SUMMARY OF THE DISCLOSURE

Provided herein are modified relaxin polypeptides comprising a non-naturally encoded amino acid, wherein (a) the relaxin polypeptide comprises the relaxin A chain polypeptide of SEQ ID NO: 4 and the relaxin B chain polypeptide of SEQ ID NO: 5 or SEQ ID NO: 6, substituted with a non-naturally encoded amino acid at a position selected from the group consisting of: A chain residue 1, A chain residue 2, A chain residue 5, A chain residue 13, A chain residue 18, B chain residue 5, B chain residue 7, and B chain residue 25, and optionally having up to two additional amino-acid substitutions, insertions and/or deletions in said relaxin A chain and/or said relaxin B chain; (b) said non-naturally encoded amino acid has the structure:

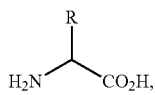

wherein the R group is any substituent other than the side chain found in alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine; and (c) said non-naturally encoded amino acid is linked to a pharmacokinetic enhancer comprising a peptide component between 2 and 30 amino acids and a half-life extending moiety.

Also provided herein is a modified relaxin polypeptide comprising AQ1-GGGGS-Glu$^\gamma$ (SEQ ID NO: 139)-C14-COOH which has the structure:

In another aspect, provided herein is a method of treating a cardiovascular disease comprising administering an effective amount of a modified relaxin polypeptide or composition comprising a modified relaxin polypeptide as described herein to a patient in need thereof.

In another aspect, provided herein is a method of treating or alleviating a symptom of heart failure comprising administering an effective amount of a modified relaxin polypeptide or composition comprising a modified relaxin polypeptide as described herein to a patient in need thereof.

In another aspect, provided herein is a method of treating a disease associated with fibrosis, comprising administering a therapeutically effective amount of a modified relaxin polypeptide or composition comprising a modified relaxin polypeptide as described herein to a patient in need thereof.

In another aspect, provided herein is a method of treating or preventing kidney failure, comprising administering a therapeutically effective amount of a modified relaxin polypeptide or composition comprising a modified relaxin polypeptide as described herein to a patient in need thereof.

In another aspect, provided herein is a method of improving, stabilizing or restoring renal function in a patient in need thereof, comprising administering a therapeutically (Formula III)

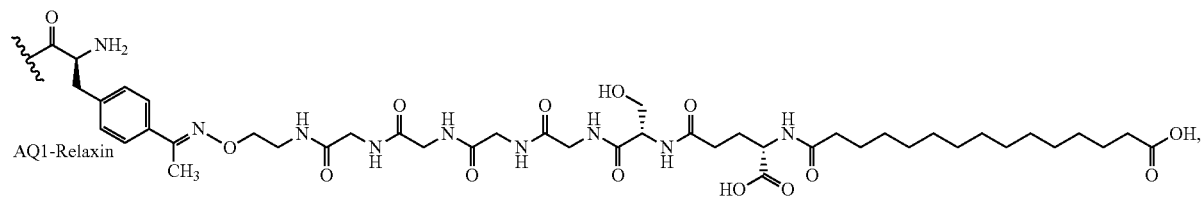

wherein said AQ1-Relaxin comprises a relaxin A chain polypeptide having at least 90% amino acid sequence identity to SEQ ID NO: 35 and a relaxin B chain polypeptide having at least 90% amino sequence identity to SEQ ID NO: 5 or SEQ ID NO: 6, wherein the modified para-acetyl-phenylalanine depicted in Formula III is located at the N-terminus of said relaxin A chain polypeptide.

Also provided herein is a modified relaxin polypeptide comprising AQ1-Relaxin-GGGGS-Glu$^\gamma$ (SEQ ID NO: 139)-C14-COOH, which has the structure of Formula III described herein, wherein AQ1-Relaxin comprises a relaxin A chain polypeptide of SEQ ID NO: 35 and a relaxin B chain polypeptide of SEQ ID NO: 6, wherein the modified para-acetyl-phenylalanine depicted in Formula III is located at the N-terminus of said relaxin A chain polypeptide.

Also provided herein is a modified relaxin polypeptide comprising the structure shown in FIG. 8.

Also provided herein is a modified relaxin polypeptide comprising the structure shown in FIG. 9.

In another aspect, provided herein is a pharmaceutical composition comprising a modified relaxin polypeptide as described herein and a pharmaceutically acceptable carrier.

In another aspect, provided herein is a pharmaceutical composition comprising an effective amount of a modified relaxin polypeptide as described herein for the treatment of a relaxin-associated disorder and a pharmaceutically acceptable carrier.

In another aspect, provided herein is a method of treating a disease associated with relaxin comprising administering an effective amount of a modified relaxin polypeptide or composition comprising a modified relaxin polypeptide as described herein.

effective amount of a modified relaxin polypeptide or composition comprising a modified relaxin polypeptide as described herein to the patient.

In another aspect, provided herein is a method of manufacturing a modified relaxin polypeptide as described herein, comprising: (a) providing a polypeptide comprising said relaxin A chain and said relaxin B chain, wherein said polypeptide comprises said non-naturally encoded amino acid; and (b) linking said non-naturally encoded amino acid to said pharmacokinetic enhancer.

BRIEF DESCRIPTION OF THE SEVERAL VIEWS OF THE DRAWING

FIG. 1. Sequence of a human relaxin 2 polypeptide without a non-naturally encoded amino acid. The A chain (SEQ ID NO: 4) and B chain (SEQ ID NO: 6) polypeptides are linked by disulfide bonds as depicted in FIG. 5. Position 1 in the B chain is modified relative to the human relaxin 2 polypeptide B chain (SEQ ID NO: 5) (underlined position, aspartic acid substituted with alanine as shown), which has been observed to improve manufacturing without significantly adversely affecting potency. In the working examples herein this polypeptide is referred to as "wild-type" or WT-RLX.

FIG. 2. Sequence of RLX-AQ1 ("AQ1"), a human relaxin 2 polypeptide with a non-naturally encoded amino acid, para-acetyl-phenylalanine (pAcF, underlined) substituted for A chain position 1. The A chain (SEQ ID NO: 35) and B chain (SEQ ID NO: 6) are linked by disulfide bonds at the positions depicted in FIG. 5.

FIG. 3. Sequence of RLX-BM25/AN1 ("BM25/AN1"), a human relaxin 2 polypeptide with a non-naturally encoded amino acid, para-acetyl-phenylalanine (pAcF, underlined) substituted for B chain position 25, and further A chain position 1 contains the substitution of asparagine for glutamine (underlined). The A chain (SEQ ID NO: 36) and B chain (SEQ ID NO: 37) are linked by disulfide bonds at the positions depicted in FIG. 5.

FIG. 4. Schematic of a prepro-relaxin polypeptide for expression of RLX-AQ1. A prepro-relaxin polypeptide (SEQ ID NO: 38) is expressed in E. coli or another expression system. A non-naturally encoded amino acid such as pAcF can be ribosomally incorporated into the prepro-relaxin polypeptide sequence, facilitating subsequent linkage to a pharmacokinetic enhancer ("PK extender"). The leader sequence specific for E. coli expression is indicated by grey circles. The C-peptide (connecting peptide), derived from proinsulin with added peptide cleavage sites and a Lys to Gly substitution, is indicated by black circles. The leader sequence and C-peptide are removed by enzymatic cleavage (cleavage sites indicated by unlabeled arrows). The Alanine substitution at B chain residue 1 ("B1") (present in SEQ ID NO: 6) aids leader sequence removal. The pAcF residue for site specific PK enhancer attachment is indicated. The A and B chains align with the HUGO named RLN2 and are derived from the relaxin2 transcript variant 1 cDNA (refseq NM_134441).

FIG. 5. Structural depiction of mature RLX-AQ1 comprising an A chain (SEQ ID NO: 36) and B chain (SEQ ID NO: 6), which is linked through a non-naturally encoded amino acid at A chain position 1 to a pharmacokinetic enhancer ("PK extender").

FIGS. 6A-6B. WT-RLX (FIG. 6A) and AQ1-GGGGS-Glu$^\gamma$ (SEQ ID NO: 139)-C14-COOH (FIG. 6B) effects on changes in smooth muscle alpha-actin gene expression in TGF-beta treated human cardiac fibroblasts using qRT-PCR to measure mRNA concentrations. Numbers above bars indicate percent reduction vs. TGF-beta only with vehicle set as baseline. Means±SEM; *P<0.05. Veh=vehicle. nM=nanomolar.

FIG. 7A: Vehicle (150 mM Arg in 10 mM citrate buffer pH 5.5) SQ for 10 days. FIG. 7B: AQ1-PEG36-Glu-C13-COOH (1.5 kD PEG) SQ at 40 mg/kg/day for 7 days. FIG. 7C: AQ1-20-kDa-PEG (20 kD PEG) SQ at 15 mg/kg/day for 10 days. FIG. 7D: AQ1-GGGGS-Glu$^\gamma$ (SEQ ID NO: 139)-C14-COOH SQ at 40 mg/kg for 7 days. Magnification 40×, H&E.

DETAILED DESCRIPTION

Definitions

Figure 7A:
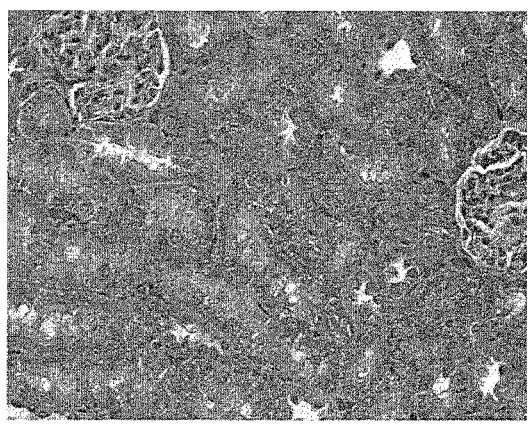
FIGS. 7A-7D. PEG-related renal cortical tubule epithelial vacuolation in female Sprague Dawley rats. Kidney from rats treated subcutaneously (SQ) once a day with vehicle or relaxin analogs. PEG containing relaxin analogs (FIGS. 7B and 7C) show marked cortical tubular vacuolation characterized by the presence of large coalescing vacuoles. Vacuoles are not observed in vehicle (FIG. 7A) or non-pegylated relaxin (FIG. 7D) treated animals.

As used herein and in the appended claims, the singular forms "a," "an," and "the" include plural reference unless the context clearly indicates otherwise. Thus, for example, reference to a "relaxin," "relaxin polypeptide," or "modified relaxin polypeptide" is a reference to one or more such proteins and includes equivalents thereof known to those of ordinary skill in the art, and so forth.

Unless defined otherwise, all technical and scientific terms used herein have the same meaning as commonly understood to one of ordinary skill in the art to which this invention belongs.

The terms "pharmacokinetic extender," "pharmacokinetic enhancer," "PK extender," and "PK enhancer" are used interchangeably and each refer to a pharmaceutically acceptable moiety, domain, or molecule covalently linked ("conjugated" or "fused") to the modified relaxin polypeptide described herein, optionally via a non-naturally encoded amino acid, that prevents, delays or mitigates in vivo proteolytic degradation or other activity-diminishing chemical modification of the modified relaxin polypeptide, increases half-life (serum half-life and/or therapeutic half-life), and/or improves or alters other pharmacokinetic or biophysical properties including but not limited to increasing the rate of absorption, reducing toxicity, improving solubility, reducing aggregation, increasing biological activity and/or target selectivity of the modified relaxin polypeptide, and/or reducing immunogenicity of the modified relaxin polypeptide, compared to a comparator such as an unconjugated form of the modified relaxin polypeptide or wild-type relaxin polypeptide. The PK enhancer described herein may comprise a peptide component, comprising one or more amino acids, and a half-life extending moiety.

The term "half-life extending moiety" refers to a pharmaceutically acceptable moiety, domain, or molecule covalently linked ("conjugated" or "fused") to the modified relaxin polypeptide described herein, e.g., as a component of a PK extender, optionally via a non-naturally encoded amino acid, directly or via a linker (e.g. a peptide component or PEG), that increases half-life (serum half-life and/or therapeutic half-life), and/or improves or alters other pharmacokinetic or biophysical properties including but not limited to increasing the rate of absorption, reducing toxicity, improving solubility, reducing aggregation, increasing biological activity and/or target selectivity of the modified relaxin polypeptide, increasing manufacturability, and/or reducing immunogenicity of the modified relaxin polypeptide, compared to a comparator such as an unconjugated form of the modified relaxin polypeptide or wild-type relaxin polypeptide. The term half-life extending moiety includes, but is not limited to, non-proteinaceous, half-life extending moieties, such as a fatty acid or derivative thereof, a water soluble polymer such as polyethylene glycol (PEG) or discrete PEG, hydroxyethyl starch (HES), a lipid, a branched or unbranched acyl group, a branched or unbranched C8-C30 acyl group, a branched or unbranched alkyl group, and a branched or unbranched C8-C30 alkyl group; and proteinaceous half-life extending moieties, such as serum albumin, transferrin, adnectin (e.g., albumin-binding or pharmacokinetics extending (PKE) adnectin), Fc domain, and unstructured polypeptide, such as XTEN and PAS polypeptide (e.g. conformationally disordered polypeptide sequences composed of the amino acids Pro, Ala, and/or Ser), and a fragment of any of the foregoing. The term "linker" or "spacer" may be any component that links a half-life extending moiety to the modified relaxin polypeptide. Exemplary linkers include but are not limited to, small organic compounds, water soluble polymers of a variety of lengths such as poly(ethylene glycol) or polydextran, and peptides or polypeptides, e.g., of up to 50, 40, 30, 25, 20, 15, 10 or up to 6 amino acids in length.

The term "peptide component" refers to a component of a PK extender and comprises a peptide of up to 50 amino acids in length. Exemplary peptide components include but are not limited to peptides of up to 40, 30, 25, 20, 15, 10, 9, 8, 7, 6, 5, 4, 3, 2, or 1 amino acids in length. Such a peptide component may covalently link a half-life extending moiety to the modified relaxin polypeptide described herein. In some embodiments, the peptide component may comprise 2-50 amino acids. In some embodiments, the peptide component may comprise 2-30 amino acids. In some embodiments, the peptide component may comprise 3-20 amino acids. In some embodiments, the peptide component may comprise 5-10 amino acids.

The term "stability" or "thermal stability" refers to the ability of a polypeptide to resist unfolding when heated. Generally the higher the thermal stability of a molecule, the greater the temperature that is required for the polypeptide to become unfolded. Exemplary methods of determining the thermal stability of a polypeptide are the differential scanning calorimetry (DSC) and thermal scanning fluorescence methods. Thermal stability may be determined with respect to a comparator compound, e.g., to identify a polypeptide having increased thermal stability.

The term "aggregation" refers to the tendency of a polypeptide to form non-covalently linked complexes with other molecules (such as other molecules of the same polypeptide) thereby forming high molecular weight complexes. Exemplary methods of measuring the formation of aggregates include analytical size exclusion chromatography. Relative amounts of aggregation may be determined with respect to a comparator compound, e.g., to identify a polypeptide having reduced aggregation.

The term "deamidation" refers to the tendency of amino acid residues within a polypeptide to spontaneously undergo a deamidation reaction, thereby changing the chemical structure of the amino acid, and potentially affecting the function of the polypeptide. Exemplary methods of measuring deamidation include imaged capillary isoelectric focusing (icIEF). The relative amount of deamidation may be determined with respect to a comparator compound, e.g., to identify a polypeptide having decreased deamidation.

The term "in vivo proteolysis" refers to the cleavage of a polypeptide when introduced into a living system (e.g., when injected into an organism) which may result from proteases occurring in said organism. Proteolysis can potentially affect the biological activity or half-life of a polypeptide. For example, wild-type relaxin may undergo cleavage, resulting in a truncated, inactive polypeptide. An exemplary method of measuring in vivo proteolysis of relaxin is the Meso Scale Discovery (MSD)-based electrochemiluminescent immunosorbent assay (ECLIA). The relative amount of in vivo proteolysis may be determined with respect to a comparator compound, e.g., to identify a polypeptide having decreased in vivo proteolysis.

The term "solubility" refers to the amount of a substance that can dissolve in another substance, e.g., the amount of an unmodified or modified relaxin polypeptide that can dissolve in an aqueous solution. An exemplary method of measuring the solubility of an unmodified or modified relaxin polypeptide is the plug flow solubility test. Relative solubility may be determined with respect to a comparator compound, e.g., to identify a polypeptide having increased solubility.

The term "biological activity" or "bioactivity" refers to the ability of a molecule to affect any physical or biochemical properties of a biological system, pathway, molecule, or interaction relating to an organism, including but not limited to, viruses, bacteria, bacteriophage, transposon, prion, insects, fungi, plants, animals, and humans. For example, in the context of an unmodified or modified relaxin, biological activity includes any of the functions performed by relaxin. For example, a "biologically active" modified relaxin polypeptide may exhibit one or more of the biological activities of wild-type relaxin, including but without limitation thereto: activation of a relaxin 2 receptor RXFP1 including human and non-human RXFP1 orthologs, activation of another relaxin receptor such as RXFP2 including human and non-human orthologs, anti-fibrotic activity in vitro or in vivo, efficacy in treatment of heart failure or a fibrotic disease whether in a human, non-human animal, and/or model system, and other biological activities as disclosed herein, for example, decreasing systemic vascular resistance (SVR), increasing cardiac output, increasing global arterial compliance, increasing renal blood flow (RBF) and/or glomerular filtration rate (GFR). Exemplary methods of determining whether a molecule possesses at least one biological activity of wild-type relaxin (such as the wild-type relaxin polypeptide of SEQ ID NOs: 4 and SEQ ID NO: 5) may include in vitro activity assays or receptor-binding assays, for example, intracellular cAMP accumulation assay. The relative level of biological activity may be determined with respect to a comparator compound, e.g., to identify a polypeptide having biological activity or having sufficiently high biological activity for an intended therapeutic use, e.g., having an EC50 less than 5-fold, 10-fold, less than 20-fold, less than 50-fold, or less than 100-fold higher than the EC50 of a comparator, in an in vitro or in vivo activity assay.

The comparator compound described herein may be another sequence lacking a modification, such as a modification described herein. For example, the comparator compound may be the same modified relaxin polypeptide sequence without linkage to a PK extender. Exemplary comparator compounds include without limitation thereto the wild-type relaxin polypeptide of SEQ ID NO: 4 and SEQ ID NO: 5, a modified relaxin polypeptide of SEQ ID NO: 4 and SEQ ID NO: 6, a modified relaxin polypeptide of SEQ ID NO: 36 and SEQ ID NO: 6, a modified relaxin polypeptide of SEQ ID NO: 35 and SEQ ID NO: 6, or another comparator compound. In some embodiments, the comparator compound may contain at least one non-naturally encoded amino acid, which may be linked to a linker, polymer, biologically active molecule, peptide, polypeptide, or half-life extending moiety described herein (e.g. PEG, or fatty acid). In some embodiments, a comparator compound may contain at least one non-naturally encoded amino acid, which may or may not be linked to a linker, polymer, biologically active molecule, peptide, polypeptide, or half-life extending moiety described herein. In some embodiments, a comparator compound may contain additional amino acid substitutions, deletions, and/or insertions. In some embodiments, the comparison may be performed with an acylated or non-acylated form of the polypeptide; in the former instance, the comparison may be performed with a polypeptide comprising or not comprising a non-naturally encoded amino acid.

The term "corresponding" refers to a position ("position corresponding" or "corresponding position") or region ("region corresponding" or "corresponding region") within a polypeptide or polynucleotide sequence that is identified by comparison to a reference sequence. The reference sequence may be a wild-type or unmodified sequence, such as the wild-type relaxin polypeptide of SEQ ID NO: 4 and SEQ ID NO: 5. A corresponding position or region may be identified by alignment of the sequence with a reference sequence. For example, the "position corresponding to amino acid 1 in the relaxin A chain" refers to the position in the sequence that is in the same alignment column as amino acid 1 in SEQ ID NO: 4 when that sequence is aligned with SEQ ID NO: 4. In the alignment, the amino acid or nucleotide may or may not match the amino acid or nucleotide in the corresponding position in the reference sequence.

The alignment used to identify a corresponding position or corresponding region may be obtained using a conventional alignment algorithm such as Blast (Altschul et al., J Mol Biol. 1990 Oct. 5; 215(3):403-10), Smith-Waterman (Smith and Waterman, J Mol Biol. 1981 Mar. 25; 147(1): 195-7), or Needleman-Wunsch (Needleman and Wunsch, J Mol Biol. 1970 March; 48(3):443-53). The Needleman-Wunsch algorithm may be used in order to obtain the highest-scoring global alignment (i.e., an alignment containing every residue in both sequences, though an alignment may start and/or end in gaps). Whether Blast, Smith-Waterman, or Needleman-Wunsch is utilized, the highest scoring alignment may be identified using "default" parameters, such as use of the BLOSUM62 scoring matrix, a gap open penalty of 11, and a gap extend penalty of 1, and (when using Blast for pairwise alignment) a word size of 3.

The term "disease associated with fibrosis" includes diseases, disorders, and conditions in which fibrosis has been observed to occur or in which fibrosis is known or thought to be associated with or contribute to disease etiology, progression, or symptoms, or in which fibrosis is known or thought to occur as the disease progresses. The fibrosis may affect an organ or tissue such as the pancreas, lung, heart, kidney, liver, eyes, nervous system, bone marrow, lymph nodes, endomyocardium, or retroperitoneum. Exemplary diseases associated with fibrosis include, but are not limited to nonalcoholic steatohepatitis (NASH), liver fibrosis, pre-cirrhosis, cirrhosis, diffuse parenchymal lung disease, cystic fibrosis, lung or pulmonary fibrosis, progressive massive fibrosis, idiopathic pulmonary fibrosis, injection fibrosis, kidney or renal fibrosis, chronic kidney disease, diabetic kidney disease, focal segmental glomerulosclerosis, membranous nephropathy, IgA nephropathy, myelofibrosis, heart failure, metabolic heart failure, cardiac fibrosis, cataract fibrosis, cataract, ocular scarring, pancreatic fibrosis, skin fibrosis, intestinal fibrosis, intestinal strictures, endomyocardial fibrosis, atrial fibrosis, mediastinal fibrosis, Crohn's disease, retroperitoneal fibrosis, keloid, nephrogenic systemic fibrosis, scleroderma, systemic sclerosis, arthrofibrosis, Peyronie's syndrome, Dupuytren's contracture, diabetic neuropathy, adhesive capsulitis, alcoholic liver disease, hepatosteatosis, viral hepatitis, biliary disease, primary hemochromatosis, drug-related cirrhosis, cryptogenic cirrhosis, Wilson's disease, alpha 1-antitrypsin deficiency, interstitial lung disease (ILD), human fibrotic lung disease, macular degeneration, retinal retinopathy, vitreal retinopathy, myocardial fibrosis, Grave's ophthalmopathy, drug induced ergotism, cardiovascular disease, atherosclerosis/restenosis, hypertrophic scars, primary or idiopathic myelofibrosis, and inflammatory bowel disease (including, but not limited to, collagenous colitis). In some embodiments, the disease associated with fibrosis may include liver fibrosis, kidney or renal fibrosis, lung or pulmonary fibrosis, and heart or cardiac fibrosis. In some embodiments, the disease associated with fibrosis may be liver fibrosis. In some embodiments, the disease associated with fibrosis may be NASH.

The term "substantially purified" refers to an unmodified or modified relaxin polypeptide that may be substantially or essentially free of components that normally accompany or interact with the protein as found in its naturally occurring environment, i.e. a native cell, or host cell in the case of recombinantly produced unmodified or modified relaxin polypeptides. Unmodified or modified relaxin polypeptide that may be substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry or wet weight) of contaminating protein. Thus, "substantially purified" unmodified or modified relaxin polypeptide as produced by the methods of the present disclosure may have a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

As used herein, the tetra "eukaryote" refers to organisms belonging to the phylogenetic domain Eucarya such as animals (including but not limited to, mammals, insects, reptiles, birds, etc.), ciliates, plants (including but not limited to, monocots, dicots, algae, etc.), fungi, yeasts, *flagellates*, microsporidia, protists, etc.

As used herein, the term "non-eukaryote" refers to non-eukaryotic organisms or prokayrotic organisms. For example, a non-eukaryotic organism can belong to the Eubacteria (including but not limited to, *Escherichia coli, Thermus thermophilus, Bacillus stearothermophilus, Pseudomonas fluorescens, Pseudomonas aeruginosa, Pseudomonas putida*, etc.) phylogenetic domain, or the Archaea (including but not limited to, *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix*, etc.) phylogenetic domain.

As used herein, the term "medium" or "media" includes any culture medium, solution, solid, semi-solid, or rigid support that may support or contain any host cell, including bacterial host cells, yeast host cells, insect host cells, plant host cells, eukaryotic host cells, mammalian host cells, CHO cells, prokaryotic host cells, *E. coli*, or *Pseudomonas* host cells, and cell contents. Thus, the term may encompass medium in which the host cell has been grown, e.g., medium into which the unmodified or modified relaxin polypeptide has been secreted, including medium either before or after a proliferation step. The term also may encompass buffers or reagents that contain host cell lysates, such as in the case where the unmodified or modified relaxin polypeptide is produced intracellularly and the host cells are lysed or disrupted to release the unmodified or modified relaxin polypeptide.

The term "relaxin" as used herein, refers to human relaxin, specifically human relaxin 2 (also known as H2 relaxin or RLN2) unless the context indicates otherwise, whose amino acid sequence and spatial structure are well-known. Human relaxin is comprised of a twenty-four amino acid A-chain and a twenty-nine amino acid B-chain which are cross-linked by disulfide bonds (see FIG. 5). A properly cross-linked wild-type relaxin contains three disulfide bridges: one between position 11 of the A-chain and position 11 of the B-chain, a second between position 24 of the A-chain and position 23 of the B-chain, and a third between positions 10 and 15 of the A-chain.

As used herein, "modified relaxin polypeptide" or "modified relaxin" are used interchangeably and shall include those polypeptides and proteins that differ from wild-type relaxin (e.g., wild-type human relaxin of SEQ ID NO:4 and SEQ ID NO:5) and typically have at least one biological activity of a relaxin 2, as well as relaxin analogs, relaxin isoforms, relaxin mimetics, polymorphisms (e.g., naturally occurring relaxin sequence variants), relaxin fragments, hybrid relaxin proteins, fusion proteins, oligomers and multimers, homologues, glycosylation pattern variants, variants, splice variants, and muteins, thereof. The term "modified relaxin polypeptide" and "modified relaxin" encompass relaxin polypeptides comprising one or more amino acid substitutions, additions or deletions.

Substitutions in a wide variety of amino acid positions in naturally-occurring relaxin may be incorporated into a modified relaxin polypeptide. Substitutions including but not limited to, those that modulate solubility or stability, increase agonist activity, increase in vivo or in vitro half-life, increase protease resistance, reduce immunogenicity or toxicity, facilitate purification or manufacturability, etc. and are encompassed by the term "modified relaxin polypeptide" or "modified relaxin." In some embodiments, the non-naturally encoded amino acid substitution(s) described herein may be combined with other additions, substitutions or deletions within the modified relaxin polypeptide to affect biological traits of the modified relaxin polypeptide relative to another relaxin polypeptide (e.g., the wild-type relaxin polypeptide of SEQ ID NO: 4 and SEQ ID NO: 5, or another relaxin polypeptide such as the same relaxin polypeptide without said addition, substitution, or deletion, or another unmodified or modified relaxin unmodified or modified polypeptide). In some embodiments, the other additions, substitutions or deletions may increase the stability (including but not limited to, resistance to proteolytic degradation) of the modified relaxin polypeptide or increase affinity of the modified relaxin polypeptide for its receptor. In some cases, the other additions, substitutions or deletions may increase the pharmaceutical stability of the modified relaxin polypeptide. In some embodiments, the other additions, substitutions or deletions may increase the solubility (including but not limited to, when expressed in E. coli or other host cells), increase the manufacturability, or decrease the aggregation of the modified relaxin polypeptide. In some embodiments, the additions, substitutions or deletions may increase the polypeptide solubility following expression in E. coli or other recombinant host cells. In some embodiments, site(s) may be selected for substitution with a naturally encoded or non-natural amino acid in addition to another site for incorporation of a non-natural amino acid that results in increasing the solubility of a polypeptide following expression in E. coli or other recombinant host cells.

In some embodiments, the modified relaxin polypeptides further comprise an additional insertion, substitution or deletion that modulates biological activity of the modified relaxin polypeptide. For example, the additions, substitutions or deletions may modulate one or more properties or activities of modified relaxin. For example, the additions, substitutions or deletions may modulate affinity for the relaxin polypeptide receptor, binding proteins, or associated ligand, modulate signal transduction after binding to the relaxin receptor, modulate in vivo or circulating half-life, modulate therapeutic half-life, modulate stability of the polypeptide, modulate cleavage by proteases, modulate dose, modulate release or bio-availability, facilitate purification, decrease deamidation, decrease aggregation, improve shelf-life or in vitro half life, or improve or alter a particular route of administration. Similarly, modified relaxin polypeptides may comprise protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification or other traits of the polypeptide.

The term "modified relaxin polypeptide" also includes biologically-active fragments, biologically active variants and stereoisomers of the naturally-occurring relaxin as well as agonist, mimetic, and antagonist variants of the naturally-occurring relaxin and polypeptide fusions thereof. Fusions comprising additional amino acids at the amino terminus, carboxyl terminus, or both, are encompassed by the term "modified relaxin polypeptide." Exemplary fusions include, but are not limited to, e.g., methionyl relaxin in which a methionine is linked to the N-terminus of a relaxin A chain and/or B chain resulting from the recombinant expression of the mature form of relaxin lacking the leader or signal peptide or portion thereof (for example, a methionine is linked to the N-terminus of a relaxin A chain and/or B chain resulting from the recombinant expression, e.g. in E. coli), fusions for the purpose of purification (including, but not limited to, to poly-histidine or affinity epitopes), fusions with serum albumin binding peptides such as PKE adnectin and fusions with serum proteins such as serum albumin, and fusion proteins comprising relaxin and one or more other molecules ("fusion partner"), including but not limited to, serum albumin, Fc domain, immunoglobulin constant region, unstructured polypeptide, and adnectin, and a fragment thereof. Any such fragments can be prepared from the proteins by standard biochemical methods, or by expressing a polynucleotide encoding the fragment.

Except where indicated otherwise, in general the terms "relaxin polypeptide" and "relaxin" as used herein encompasses both unmodified (i.e., wild-type) relaxin and modified relaxin polypeptides.

The term "modified relaxin polypeptide" includes polypeptides conjugated to a polymer such as PEG or PK extender and may optionally comprise one or more derivitizations of cysteine, lysine, or other residues. In some embodiments, the modified relaxin polypeptide may comprise a linker, polymer, or PK extender, wherein the amino acid to which the linker, polymer or PK extender is conjugated may be a non-natural amino acid according to the present disclosure, or a naturally encoded amino acid (e.g. lysine or cysteine) utilizing techniques known in the art such as coupling to lysine or cysteine.

The term "modified relaxin polypeptide" also includes relaxin polypeptides conjugated or linked to the PK extender described herein via a naturally-encoded amino acid, for example, cysteine or lysine, in the relaxin polypeptide. In some embodiments, the naturally-encoded amino acid may be a substitution or insertion in the relaxin polypeptide.

The term "modified relaxin polypeptide" also includes glycosylated modified relaxin, such as but not limited to, polypeptides glycosylated at any amino acid position, N-linked or O-linked glycosylated forms of the polypeptide. In addition, splice variants are also included.

All references to amino acid positions in unmodified or modified relaxin described herein are based on the corresponding position in the A chain of SEQ ID NO: 4 or B chain of SEQ ID NO:5, unless otherwise specified. Those of skill in the art will appreciate that amino acid positions corresponding to positions in SEQ ID NO: 4 or 5 or another relaxin sequence can be readily identified in any other relaxin molecule such as relaxin fusions, variants, fragments, etc. For example, sequence alignment programs such as BLAST can be used to align and identify a particular position in a protein that corresponds with a position in SEQ ID NO: 4 or 5 or other relaxin sequence. Substitutions, deletions or additions of amino acids described herein in reference to SEQ ID NO: 4 or 5, or other relaxin sequence are intended to also refer to substitutions, deletions or additions in corresponding positions in relaxin fusions, variants, fragments, etc. described herein or known in the art and are expressly encompassed by the present disclosure.

The term "modified relaxin polypeptide" also encompasses homodimers, heterodimers, homomultimers, and heteromultimers that are formed via fusion partners, such as Fc domains, or that are linked, including but not limited to those linked directly via non-naturally encoded amino acid side chains, either to the same or different non-naturally encoded amino acid side chains, to naturally-encoded amino acid side chains, or indirectly via a linker. Exemplary linkers including but are not limited to, small organic compounds, water soluble polymers of a variety of lengths such as poly (ethylene glycol) or polydextran, or peptides or polypeptides, e.g., of up to 50, 40, 30, 25, 20, 15, 10, 9, 8, 7, 6, 5, 4, 3, 2, or up to 1 amino acids in length.

The term "modified," as used herein refers to any changes made to a given polypeptide, such as changes to the length of the polypeptide, the amino acid sequence, chemical structure, co-translational modification, or post-translational modification of a polypeptide. The term "post-translationally modified" refers to any modification of a natural or non-natural amino acid that occurs to such an amino acid after it has been incorporated into a polypeptide chain. The term encompasses, by way of example only, co-translational in vivo modifications, co-translational in vitro modifications (such as in a cell-free translation system), post-translational in vivo modifications, and post-translational in vitro modifications.

A "non-naturally encoded amino acid" refers to an amino acid that is not one of the 20 common amino acids or pyrrolysine or selenocysteine. Other terms that may be used synonymously with the term "non-naturally encoded amino acid" are "non-natural amino acid," "unnatural amino acid," "non-naturally occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrrolysine and selenocysteine) but are not themselves naturally incorporated into a growing polypeptide chain by the translation complex. Examples of such non-naturally encoded amino acids include, but are not limited to, N-acetylglucosaminyl-L-serine, N-acetylglucosaminyl-L-threonine, and O-phosphotyrosine.

In the context of a modified relaxin polypeptide, as used herein the terms "para-acetyl-phenylalanine" and "para-acetyl-L-phenylalanine" (including the abbreviations pAcF and pAF) also embrace the products of chemical reactions wherein the acetyl group in the para position is absent and a linkage to another molecule is present in its place. Thus, for example, in a modified relaxin polypeptide that comprises a para-acetyl-phenylalanine (such as para-acetyl-L-phenylalanine), the para-acetyl-phenylalanine may comprise an oxime, triazole, amide, or other linkage at the para-position, e.g., having an oxime linkage that results from the reaction of the carbonyl group of para-acetyl-L-phenylalanine with an aminooxy group, and lacking a carbonyl carbon, at the para position. Such a para-acetyl-phenylalanine may be referred to as a "modified para-acetyl-phenylalanine", e.g., "modified para-acetyl-L-phenylalanine."

An exemplary non-naturally encoded amino acid is para-acetyl phenylalanine (pACF). It may be synthesized using the previously described procedure in Zhang, Z., Smith, B. A. C., Wang, L., Brock, A., Cho, C. & Schultz, P. G., Biochemistry, (2003) 42, 6735-6746, which is hereby incorporated by reference in its entirety.

An "amino terminus modification group" refers to any molecule that can be attached to the amino terminus of a polypeptide. Similarly, a "carboxy terminus modification group" refers to any molecule that can be attached to the carboxy terminus of a polypeptide. Terminus modification groups include, but are not limited to, various water soluble polymers, methionine, peptides, or proteins such as serum albumin, Fc domain, immunoglobulin constant region, unstructured polypeptide, adnectin, or a fragment thereof, fatty acids or derivatives thereof, or other moieties that increase serum (in vivo) half-life of polypeptides.

The terms "functional group", "active moiety", "activating group", "leaving group", "reactive site", "chemically reactive group" and "chemically reactive moiety" are used in the art and herein to refer to distinct definable portions or units of a molecule. The terms are somewhat synonymous in the chemical arts and are used herein to indicate the portions of molecules that perform some function or activity and are reactive with other molecules.

The term "linkage" is used herein to refer to groups or bonds that normally are formed as the result of a chemical reaction and typically are covalent linkages. Hydrolytically stable linkages means that the linkages are substantially stable in water and do not react with water at useful pH values, including but not limited to, under physiological conditions for an extended period of time, perhaps even indefinitely. Hydrolytically unstable or degradable linkages mean that the linkages are degradable in water or in aqueous solutions, including for example, blood. Enzymatically unstable or degradable linkages mean that the linkage can be degraded by one or more enzymes. As understood in the art, PEG, fatty acids, and other polymers may include degradable linkages in the polymer backbone or in the linker group between the polymer backbone and one or more of the terminal functional groups of the polymer molecule. For example, ester linkages that can be formed by the reaction of carboxylic acids or activated carboxylic acids with alcohol groups on a biologically active agent generally hydrolyze under physiological conditions to release the agent. Other hydrolytically degradable linkages include, but are not limited to, carbonate linkages; imine linkages that can result from reaction of an amine and an aldehyde; phosphate ester linkages that can be formed by reacting an alcohol with a phosphate group; hydrazone linkages which can be reaction product of a hydrazide and an aldehyde; acetal linkages that can be the reaction product of an aldehyde and an alcohol; orthoester linkages that can be the reaction product of a formate and an alcohol; peptide linkages that can be formed by an amine group, including but not limited to, at an end of a polymer, and a carboxyl group of a peptide; oxime, or semicarbazone linkages that can be the reaction product of a carbonyl functionality and a hydroxylamine-, or semicarbazide-containing reagent; and oligonucleotide linkages that can be formed by a phosphoramidite group, including but not limited to, at the end of a polymer, and a 5' hydroxyl group of an oligonucleotide.

Where substituent groups are specified by their conventional chemical formulas, written from left to right, they equally encompass the chemically identical substituents that would result from writing the structure from right to left, for example, the structure CH2O is equivalent to the structure —OCH2. Compositions presented herein may include isotopically-labelled compounds with one or more atoms replaced by an atom having an atomic mass or mass number different from the atomic mass or mass number usually found in nature. Compositions presented herein may include isomers, including but not limited to diastereomers, enantiomers, and mixtures thereof, e.g., L-amino acids and/or D-amino acids (such as para-acetyl-D-phenylalanine and/or para-acetyl-L-phenylalanine).

The term "substituents" includes but is not limited to "non-interfering substituents". "Non-interfering substituents" are those groups that yield stable compounds. Suitable non-interfering substituents or radicals include, but are not limited to, halo, C1-C10 alkyl, C2-C10 alkenyl, C2-C10 alkynyl, C1-C10 alkoxy, C1-C12 aralkyl, C1-C12 alkaryl, C3-C12 cycloalkyl, C3-C12 cycloalkenyl, phenyl, substituted phenyl, toluoyl, xylenyl, biphenyl, C2-C12 alkoxyalkyl, C2-C12 alkoxyaryl, C7-C12 aryloxyalkyl, C7-C12 oxyaryl, C1-C6 alkylsulfinyl, C1-C10 alkylsulfonyl, —(CH2)m-O—(C1-C10 alkyl) wherein m is from 1 to 8, aryl, substituted aryl, substituted alkoxy, fluoroalkyl, heterocyclic radical, substituted heterocyclic radical, nitroalkyl, —NO2, —CN, —NRC(O)—(C1-C10 alkyl), —C(O)—(C1-C10 alkyl), C2-C10 alkyl thioalkyl, —C(O)O—(C1-C10 alkyl), —OH, —SO2, =S, —COOH, —NR2, carbonyl, —C(O)—(C1-C10 alkyl)-CF3, —C(O)—CF3, —C(O)NR2, —(C1-C10 aryl)-S—(C6-C10 aryl), —C(O)—(C1-C10 aryl), —(CH2)m-O—(—(CH2)m-O—(C1-C10 alkyl) wherein each m is from 1 to 8, —C(O)NR2, —C(S)NR2, —SO2NR2, —NRC(O)NR2, —NRC(S)NR2, salts thereof, and the like. Each R as used herein is H, alkyl or substituted alkyl, aryl or substituted aryl, aralkyl, or alkaryl.

The term "halogen" includes fluorine, chlorine, iodine, and bromine.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. C1-C10 means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups which are limited to hydrocarbon groups are termed "homoalkyl".

The term "alkylene" by itself or as part of another substituent means a divalent radical derived from an alkane, as exemplified, but not limited, by the structures —CH2CH2- and —CH2CH2CH2CH2-, and further includes those groups described below as "heteroalkylene." Typically, an alkyl (or alkylene) group will have from 1 to 24 carbon atoms, with those groups having 10 or fewer carbon atoms being a particular embodiment of the methods and compositions described herein. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH2-CH2-O—CH3, —CH2-CH2-NH—CH3, —CH2-CH2-N(CH3)-CH3, —CH2-S—CH2-CH3, —CH2-CH2, —S(O)—CH3, —CH2-CH2-S(O)2-CH3, —CH=CH—O—CH3, —Si(CH3)3, —CH2-CH=N—OCH3, and —CH=CH—N(CH3)-CH3. Up to two heteroatoms may be consecutive, such as, for example, —CH2-NH—OCH3 and —CH2-O—Si(CH3)3. Similarly, the term "heteroalkylene" by itself or as part of another substituent means a divalent radical derived from heteroalkyl, as exemplified, but not limited by, —CH2-CH2-S—CH2 CH2- and —CH2-S—CH2-CH2-NH—CH2-. For heteroalkylene groups, the same or different heteroatoms can also occupy either or both of the chain termini (including but not limited to, alkyleneoxy, alkylenedioxy, alkyleneamino, alkylenediamino, aminooxyalkylene, and the like). Still further, for alkylene and heteroalkylene linking groups, no orientation of the linking group is implied by the direction in which the formula of the linking group is written. For example, the formula —C(O)2R' represents both —C(O)2R' and —R'C(O)2.

The terms "cycloalkyl" and "heterocycloalkyl", by themselves or in combination with other terms, represent, unless otherwise stated, cyclic versions of "alkyl" and "heteroalkyl", respectively. Thus, a cycloalkyl or heterocycloalkyl include saturated, partially unsaturated and fully unsaturated ring linkages. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. Additionally, the term encompasses bicyclic and tricyclic ring structures. Similarly, the term "heterocycloalkylene" by itself or as part of another substituent means a divalent radical derived from heterocycloalkyl, and the term "cycloalkylene" by itself or as part of another substituent means a divalent radical derived from cycloalkyl.

The term "aryl" means, unless otherwise stated, a polyunsaturated, aromatic, hydrocarbon substituent which can be a single ring or multiple rings (including but not limited to, from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (including but not limited to, aryloxy, arylthioxy, arylalkyl) includes both aryl and heteroaryl rings as defined above. Thus, the term "arylalkyl" is meant to include those radicals in which an aryl group is attached to an alkyl group (including but not limited to, benzyl, phenethyl, pyridylmethyl and the like) including those alkyl groups in which a carbon atom (including but not limited to, a methylene group) has been replaced by, for example, an oxygen atom (including but not limited to, phenoxymethyl, 2-pyridyloxymethyl, 3-(1-naphthyloxy)propyl, and the like).

Each of the above terms (including but not limited to, "alkyl," "heteroalkyl," "aryl" and "heteroaryl") are meant to include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', OC(O)R', —C(O)R', —CO2R', —CONR'R", —OC(O)NR'R", —NR"C(O)R', NR' C(O) NR"R''', —NR"C(O)2R', —NR—C(NR'R"R''')=NR", NRC(NR'R")=NR''', —S(O)R', —S(O)2R', —S(O) 2NR'R", NRSO2R', —CN and —NO2 in a number ranging from zero to (2m'+1), where m' is the total number of carbon atoms in such a radical. R', R", R''' and R'''' each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —CF3 and —CH2CF3) and acyl (including but not limited to, —C(O)CH3, —C(O)CF3, —C(O) CH2OCH3, and the like).

Similar to the substituents described for the alkyl radical, substituents for the aryl and heteroaryl groups are varied and are selected from, but are not limited to: halogen, OR', =O, =NR', =N—OR', —NR'R", —SR', -halogen, -SiR'R"R''', OC(O)R', —C(O)R', CO2R', —CONR'R", —OC(O)NR'R", —NR"C(O)R', NR' C(O)NR"R''', —NR"C(O)2R', NR—C (NR'R"R''')=NR"", NR C(NR'R")=NR''', —S(O)R', —S(O)2R', —S(O)2NR'R", NRSO2R', —CN and —NO2, —R', —N3, —CH(Ph)2, fluoro(C1-C4)alkoxy, and fluoro (C1-C4)alkyl, in a number ranging from zero to the total number of open valences on the aromatic ring system; and where R', R", R''' and R'''' are independently selected from hydrogen, alkyl, heteroalkyl, aryl and heteroaryl. When a compound of the invention includes more than one R group, for example, each of the R groups is independently selected as are each R', R", R''' and R'''' groups when more than one of these groups is present.

The term "fatty acid" refers to a saturated or unsaturated acyl chain having from 6 to 20 carbon atoms or derivative thereof. In some embodiments, the fatty acid may be linked to a peptide component of the PK enhancer described herein and terminate in a carboxylic acid or a methyl group. In some embodiments, the fatty acid linked to the peptide component of the PK enhancer may terminate in a carboxylic acid. In some embodiments, the fatty acid may be linked to the peptide component through an amide bond. In some embodiments, the fatty acid may have between 10 and 18 carbon atoms. In some embodiments, the fatty acid may have between 12 and 17 carbon atoms. In some embodiments, the fatty acid may have 14, 15, or 16 carbon atoms. In some embodiments, the fatty acid may have 15 carbon atoms.

As used herein, the term "water soluble polymer" refers to any polymer that is soluble in aqueous solvents. Linkage of water soluble polymers to modified relaxin polypeptides can result in changes including, but not limited to, increased or modulated serum (in vivo) half-life, or increased or modulated therapeutic half-life relative to the unmodified form, reduced or modulated immunogenicity or toxicity, modulated physical association characteristics such as decreased aggregation and multimer formation, altered receptor binding, altered binding to one or more binding partners, and altered receptor dimerization or multimerization. The water soluble polymer may or may not have its own biological activity, and may be utilized as a linker for attaching modified relaxin to other substances, including but not limited to one or more unmodified or modified relaxin polypeptides, or one or more biologically active molecules. Suitable polymers include, but are not limited to, polyethylene glycol, polyethylene glycol propionaldehyde, mono C1-C10 alkoxy or aryloxy derivatives thereof (described in U.S. Pat. No. 5,252,714 which is incorporated by reference herein), monomethoxy-polyethylene glycol, discrete PEG, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, starch and starch derivatives, polypeptides of two or more amino acids, polyalkylene glycol and derivatives thereof, copolymers of polyalkylene glycols and derivatives thereof, polyvinyl ethyl ethers, and alpha-beta-poly[(2-hydroxyethyl)-DL-aspartamide, and the like, or mixtures thereof. Examples of such water soluble polymers include, but are not limited to, polyethylene glycol and serum albumin.

As used herein, the term "polyalkylene glycol" (PEG) or "poly(alkene glycol)" refers to polyethylene glycol (poly (ethylene glycol)), polypropylene glycol, polybutylene glycol, and derivatives thereof. The term "polyalkylene glycol" encompasses both linear and branched polymers and average molecular weights of between 0.1 kDa and 100 kDa. Other exemplary embodiments are listed, for example, in commercial supplier catalogs, such as Shearwater Corporation's catalog "Polyethylene Glycol and Derivatives for Biomedical Applications" (2001).

As used herein, the terms "modulated serum half-life" or "modulated in vivo half-life" and similar terms refer to the positive or negative change in circulating half-life of a modified relaxin relative to a comparator such as its non-modified form or the wild-type relaxin. Serum half-life can be measured by taking blood samples at various time points after administration of a modified relaxin, and determining the concentration of that molecule in each sample. Correlation of the serum concentration with time allows calculation of the serum half-life. Increased serum (in vivo) half-life desirably may be at least about two-fold, but a smaller increase may be useful, for example where it enables a satisfactory dosing regimen or avoids a toxic effect. In some embodiments, the increase may be at least about three-fold, at least about five-fold, at least about ten-fold, at least about twenty-fold, or at least about fifty-fold.

The term "modulated therapeutic half-life" as used herein means the positive or negative change in the serum or in vivo half-life of the therapeutically effective amount of the modified relaxin polypeptide described herein, relative to a comparator such as its non-modified form or the wild-type relaxin. Therapeutic half-life is measured by measuring pharmacokinetic and/or pharmacodynamic properties of the molecule at various time points after administration. Increased therapeutic half-life desirably enables a particular beneficial dosing regimen, a particular beneficial total dose, or avoids an undesired effect. In some embodiments, the increased therapeutic half-life results from increased potency, increased or decreased binding of the modified molecule to its target, increased or decreased breakdown of the molecule by enzymes such as proteases, or an increase or decrease in another parameter or mechanism of action of the non-modified molecule or an increase or decrease in receptor-mediated clearance of the molecule. In some embodiments, the increase in therapeutic half-life may be at least about two-fold, at least about three-fold, at least about five-fold, at least about ten-fold, at least about twenty-fold, or at least about fifty-fold.

The term "isolated," when applied to a nucleic acid or protein, denotes that the nucleic acid or protein is free of at least some of the cellular components with which it is associated in the natural state, or that the nucleic acid or protein has been concentrated to a level greater than the concentration of its in vivo or in vitro production. It can be in a homogeneous state. Isolated substances can be in either a dry or semi-dry state, or in solution, including but not limited to, an aqueous solution. It can be a component of a pharmaceutical composition that comprises additional pharmaceutically acceptable carriers and/or excipients. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to substantially one band in an electrophoretic gel. Particularly, it may mean that the nucleic acid or protein is at least 85% pure, at least 90% pure, at least 95% pure, at least 99% or greater pure.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally encoded amino acid. As used herein, the terms encompass amino acid chains of any length, including full length proteins, wherein the amino acid residues are linked by covalent peptide bonds.

"Conservatively modified variants" refers to amino acid sequences containing conservative substitutions. Exemplary conservatively modified variants include substitutions, deletions or insertions to a nucleic acid, peptide, polypeptide, or protein sequence which alters, adds or deletes a single amino acid or a small percentage of amino acids in the polypeptide sequence or encoded polypeptide sequence, e.g., up to 1, 2, 3, 4, or 5 amino acids, or up to 0.5%, 1%, 1.5%, 2%, 2.5%, or 3.5% of the amino acids in the polypeptide sequence or encoded polypeptide sequence, which optionally may be or may include substitution of amino acid(s) with chemically similar amino acid(s). Conservative substitution tables providing functionally similar amino acids are known to those of ordinary skill in the art. Such conservatively modified variants are in addition to and do not exclude polymorphic variants, interspecies homologs, and alleles of the disclosed modified relaxin polypeptides.

Conservative substitution tables providing functionally similar amino acids are known to those of ordinary skill in the art. The following eight groups each contain amino acids that are conservative substitutions for one another:

1) Alanine (A or Ala), Glycine (G or Gly);
2) Aspartic acid (D or Asp), Glutamic acid (E or Glu);
3) Asparagine (N or Asn), Glutamine (Q or Gln);
4) Arginine (R or Arg), Lysine (K or Lys), Histidine (H or His);
5) Isoleucine (I or Ile), Leucine (L or Leu), Methionine (M or Met), Valine (V or Val);

6) Phenylalanine (F or Phe), Tyrosine (Y or Tyr), Tryptophan (W or Trp);
7) Serine (S or Ser), Threonine (T or Thr); and
8) Cysteine (C or Cys), Methionine (M or Met)
(see, e.g., Creighton, *Proteins: Structures and Molecular Properties* (W H Freeman & Co.; 2nd edition (December 1993))

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 60% identity, about 65%, about 70%, about 75%, about 80%, about 85%, about 90%, about 95%, about 96%, about 97%, about 98%, about 99%, identity over a specified region), when compared and aligned for maximum correspondence over a comparison window, or designated region as measured using one of the following sequence comparison algorithms (or other algorithms available to persons of ordinary skill in the art) or by manual alignment and visual inspection. The identity may exist over a region or comparison window that is at least about 20 amino acids or nucleotides in length, or over a region that is at least about 25 amino acids or nucleotides in length, or, where not specified, across the entire sequence of a polynucleotide or polypeptide. A "comparison window", as used herein, includes reference to any segment of contiguous positions, for example, at least or about 10, 15, 20, 25, or 30 amino acids, in which a sequence may be compared to a reference sequence of the same number of contiguous positions after the two sequences are optimally aligned. Examples of algorithms that may be suitable for determining percent sequence identity and sequence similarity are the BLAST and BLAST 2.0 algorithms, which are described in Altschul et al. (1997) *Nuc. Acids Res.* 25:3389-3402, and Altschul et al. (1990) *J. Mol. Biol.* 215:403-410, respectively, as well as the Smith-Waterman (Smith and Waterman, J Mol Biol. 1981 Mar. 25; 147(1):195-7), or Needleman-Wunsch (Needleman and Wunsch, J Mol Biol. 1970 March; 48(3): 443-53) algorithms, which may be run with the default parameters, e.g., as described in those respective publications.

The term "subject" as used herein, refers to an animal, in some embodiments a mammal, and in other embodiments a human, who is the object of treatment, observation or experiment. An animal may be a companion animal (e.g., dogs, cats, and the like), farm animal (e.g., cows, sheep, pigs, horses, and the like) or a laboratory animal (e.g., rats, mice, guinea pigs, and the like).

The term "effective amount" as used herein refers to that amount of the compound (e.g., a modified relaxin polypeptide described herein) being administered which may prevent, cure, relieve, alleviate, delay the onset, decrease the severity, or reduce to some extent one or more of the symptoms of the disease, condition or disorder being treated. Compositions containing the modified relaxin polypeptide described herein can be administered for prophylactic, enhancing, and/or therapeutic treatments.

The terms "enhance" or "enhancing" means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system.

In prophylactic applications, compositions containing the modified relaxin polypeptide are administered to a patient susceptible to or otherwise at risk of a particular disease, disorder or condition. Such an amount is defined to be a "prophylactically effective amount."

In therapeutic applications, compositions comprising the modified non-natural amino acid polypeptide are administered to a patient already suffering from a disease, condition or disorder, in an amount sufficient to cure or at least partially arrest or alleviate the symptoms of the disease, disorder or condition. Such an amount is defined to be a "therapeutically effective amount," and may depend on the severity and course of the disease, disorder or condition, previous therapy, the patient's health status and response to the drugs, and the judgment of the treating physician. It is considered well within the skill of the art for one to determine such therapeutically effective amounts by routine experimentation (e.g., a dose escalation clinical trial).

The term "treating" is used to refer to prophylactic and/or therapeutic treatments.

"Reducing agent," as used herein with respect to protein refolding, is defined as any compound or material which maintains sulfhydryl groups in the reduced state and reduces intra- or intermolecular disulfide bonds. Suitable reducing agents include, but are not limited to, dithiothreitol (DTT), 2-mercaptoethanol, cysteine, cysteamine (2-aminoethanethiol), and reduced glutathione. It is readily apparent to those of ordinary skill in the art that a wide variety of reducing agents are suitable for use in the methods and compositions of the present invention.

"Oxidizing agent," as used herein with respect to protein refolding, is defined as any compound or material which is capable of removing an electron from a compound being oxidized. Suitable oxidizing agents include, but are not limited to, oxidized glutathione, cystine, cystamine, oxidized dithiothreitol, oxidized erythreitol, and oxygen. It is readily apparent to those of ordinary skill in the art that a wide variety of oxidizing agents are suitable for use in the methods of the present invention.

"Denaturing agent" or "denaturant," as used herein, is defined as any compound or material which will cause a reversible unfolding of a protein. The strength of a denaturing agent or denaturant will be determined both by the properties and the concentration of the particular denaturing agent or denaturant. Suitable denaturing agents or denaturants may be chaotropes, detergents, organic solvents, water miscible solvents, phospholipids, or a combination of two or more such agents. Suitable chaotropes include, but are not limited to, urea, guanidine, and sodium thiocyanate. Useful detergents may include, but are not limited to, strong detergents such as sodium dodecyl sulfate, or polyoxyethylene ethers (e.g. Tween or Triton detergents), Sarkosyl, mild non-ionic detergents (e.g., digitonin), mild cationic detergents such as N→2,3-(Dioleyoxy)-propyl-N,N,N-trimethylammonium, mild ionic detergents (e.g. sodium cholate or sodium deoxycholate) or zwitterionic detergents including, but not limited to, sulfobetaines (Zwittergent), 3-(3-chlolamidopropyl)dimethylammonio-1-propane sulfate (CHAPS), and 3-(3-chlolamidopropyl)dimethylammonio-2-hydroxy-1-propane sulfonate (CHAPSO). Organic, water miscible solvents such as acetonitrile, lower alkanols (especially C2-C4 alkanols such as ethanol or isopropanol), or lower alkandiols (especially C2-C4 alkandiols such as ethylene-glycol) may be used as denaturants. Phospholipids useful in the present invention may be naturally occurring phospholipids such as phosphatidylethanolamine, phosphatidylcholine, phosphatidylserine, and phosphatidylinositol or synthetic phospholipid derivatives or variants such as dihexanoylphosphatidylcholine or diheptanoylphosphatidylcholine.

"Refolding," as used herein describes any process, reaction or method which transforms disulfide bond containing polypeptides from an improperly folded or unfolded state to a native or properly folded conformation with respect to disulfide bonds.

"Co-folding," as used herein, refers specifically to refolding processes, reactions, or methods which employ at least two polypeptides which interact with each other and result in the transformation of unfolded or improperly folded polypeptides to native, properly folded polypeptides.

The term "protected" refers to the presence of a "protecting group" or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in or with the methods and compositions described herein, including photolabile groups such as Nvoc and MeNvoc. Other protecting groups known in the art may also be used in or with the methods and compositions described herein.

By way of example only, blocking/protecting groups may be selected from:

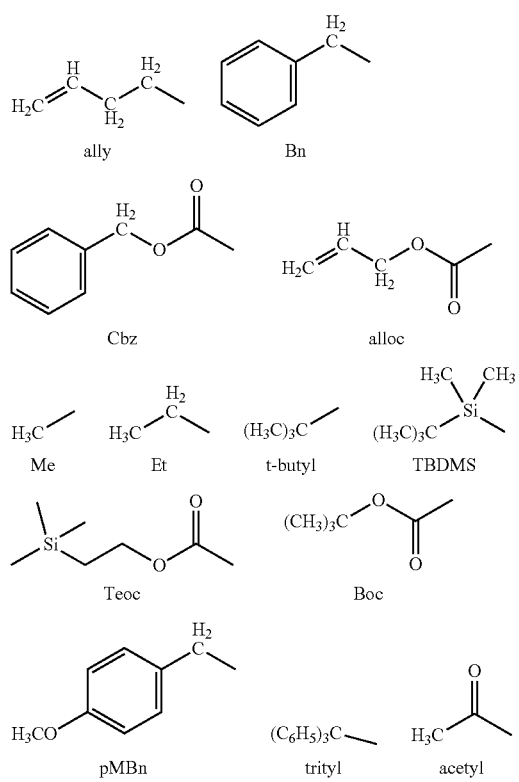

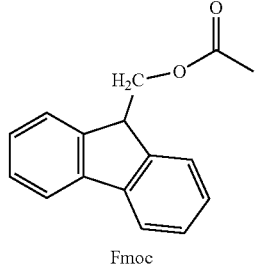

Fmoc

Other protecting groups are described in Greene and Wuts, Protective Groups in Organic Synthesis, 3rd Ed., John Wiley & Sons, New York, N.Y., 1999, which is incorporated herein by reference in its entirety.

The terms "disorders of the cardiovascular system" or "cardiovascular disorders" include for example the following disorders: hypertension (high blood pressure), peripheral and cardiac vascular disorders, coronary heart disease, stable and unstable angina pectoris, heart attack, myocardial insufficiency, abnormal heart rhythms (or arrhythmias), persistent ischemic dysfunction ("hibernating myocardium"), temporary postischemic dysfunction ("stunned myocardium"), heart failure, disturbances of peripheral blood flow, acute coronary syndrome, heart failure, heart muscle disease (cardiomyopathy), myocardial infarction and vascular disease (blood vessel disease).

The term "heart failure" includes both acute and chronic manifestations of heart failure, as well as more specific or related types of disease, such as advanced heart failure, post-acute heart failure, cardio-renal syndrome, heart failure with impaired kidney function, chronic heart failure, chronic heart failure with mid-range ejection fraction (HFmEF), compensated heart failure, decompensated heart failure, right heart failure, left heart failure, global failure, ischemic cardiomyopathy, dilated cardiomyopathy, heart failure associated with congenital heart defects, heart valve defects, heart failure associated with heart valve defects, mitral stenosis, mitral insufficiency, aortic stenosis, aortic insufficiency, tricuspid stenosis, tricuspid insufficiency, pulmonary stenosis, pulmonary valve insufficiency, heart failure associated with combined heart valve defects, myocardial inflammation (myocarditis), chronic myocarditis, acute myocarditis, viral myocarditis, diabetic heart failure, alcoholic cardiomyopathy, heart failure associated with cardiac storage disorders, diastolic heart failure, systolic heart failure, acute phases of worsening heart failure, heart failure with preserved ejection fraction (HFpEF), heart failure with reduced ejection fraction (HFrEF), chronic heart failure with reduced ejection fraction (HFrEF), chronic heart failure with preserved ejection fraction (HFpEF), post myocardial remodeling, angina, hypertension, pulmonary hypertension and pulmonary artery hypertension.

The term "fibrotic disorders" encompasses diseases and disorders characterized by fibrosis, including among others the following diseases and disorders: liver or hepatic fibrosis, cirrhosis of the liver, NASH, pulmonary fibrosis or lung fibrosis, cardiac fibrosis, endomyocardial fibrosis, nephropathy, glomerulonephritis, interstitial renal fibrosis, fibrotic damage resulting from diabetes, bone marrow fibrosis and similar fibrotic disorders, scleroderma, morphea, keloids, hypertrophic scarring (also following surgical procedures), naevi, diabetic retinopathy, proliferative vitreoretinopathy and disorders of the connective tissue (for example sarcoidosis).

The terms "relaxin-associated disorder" and "disease associated with relaxin" encompasse diseases and disorders that may be prevented, treated, alleviated or otherwise affected by modulation of the relaxin level in the body such as increasing serum relaxin protein level. Relaxin-associated disorders include but are not limited to disorders of the cardiovascular system and fibrotic disorders described herein.

Polypeptide comprising non-naturally encoded amino acids presented herein may include isotopically-labelled compounds with one or more atoms replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as 2H, 3H, 13C, 14C, 15N, 18O, 17O, 35S, 18F, 36Cl, respectively. Certain isotopically-labelled compounds described herein, for example those into which radioactive isotopes such as 3H and 14C are incorporated, may be useful in drug and/or substrate tissue distribution assays. Further, substitution with isotopes such as deuterium, i.e., 2H, can afford certain therapeutic advantages resulting from greater metabolic stability, for example increased in vivo half-life or reduced dosage requirements.

I. Overview

Modified relaxin molecules linked to a PK enhancer are provided in the disclosure. Exemplary embodiments are demonstrated to exhibit at least one advantageous property selected from increased in vivo half-life, decreased kidney vacuole formation, increased renal blood flow, higher solubility, decreased aggregation, lower viscosity, increased manufacturability, compared to other modified or wild-type relaxin polypeptides.

In one aspect, the present disclosure provides a modified relaxin polypeptide comprising a non-naturally encoded amino acid, wherein:

(a) the modified relaxin polypeptide comprises the relaxin A chain polypeptide of SEQ ID NO: 4 and the relaxin B chain polypeptide of SEQ ID NO: 5 or SEQ ID NO: 6, substituted with a non-naturally encoded amino acid at a position selected from the group consisting of: A chain residue 1, A chain residue 2, A chain residue 5, A chain residue 13, A chain residue 18, B chain residue 5, B chain residue 7, and B chain residue 25, and optionally having up to two additional amino-acid substitutions, insertions and/or deletions in said relaxin A chain and/or said relaxin B chain;

(b) said non-naturally encoded amino acid has the structure:

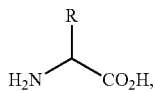

wherein the R group is any substituent other than the side chain found in alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine;

(c) said non-naturally encoded amino acid is linked to a pharmacokinetic enhancer comprising a peptide component of between 2 and 30 amino acids and a half-life extending moiety.

In some embodiments, said relaxin A chain polypeptide may comprise SEQ ID NO: 4 substituted with said non-naturally encoded amino acid at residue 1 and optionally having up to two additional amino acid substitutions, insertions and/or deletions. Said relaxin A chain polypeptide may comprise SEQ ID NO: 4 substituted with said non-naturally encoded amino acid at residue 1 and optionally having one additional amino acid substitution, insertion or deletion. Said relaxin B chain polypeptide may comprise SEQ ID NO: 5 or SEQ ID NO: 6 optionally having up to two additional amino acid substitution, insertion or deletion. Said relaxin B chain polypeptide may comprise SEQ ID NO: 5 or SEQ ID NO: 6 optionally having one additional amino acid substitution, insertion or deletion. Said relaxin A chain polypeptide may comprise SEQ ID NO: 4 substituted with said non-naturally encoded amino acid at residue 1 and said relaxin B chain polypeptide may comprise SEQ ID NO: 5 or SEQ ID NO: 6.

In some embodiments, said at least one non-naturally encoded amino acid may comprise a carbonyl group, an aminooxy group, a hydrazide group, a hydrazine group, a semicarbazide group, an azide group, or an alkyne group. Said non-naturally encoded amino acid may comprise a phenylalanine derivative. Said non-naturally encoded amino acid may be selected from a para-substituted, ortho-substituted, or meta-substituted phenylalanine. Said non-naturally encoded amino acid may be selected from a para-substituted, ortho-substituted, or meta-substituted phenylalanine comprising a carbonyl group, an aminooxy group, a hydrazide group, a hydrazine group, a semicarbazide group, an azide group, or an alkyne group. Said non-naturally encoded amino acid may comprise para-acetyl-L-phenylalanine. Said non-naturally encoded amino acid may be linked to said pharmacokinetic enhancer. For example, said non-naturally encoded amino acid may be linked to said pharmacokinetic enhancer through an oxime linkage or triazole linkage, e.g., an oxime linkage.

In some embodiments, said relaxin A chain polypeptide may comprise SEQ ID NO: 35, and said relaxin B chain polypeptide may comprise SEQ ID NO: 5 or SEQ ID NO: 6, and wherein said relaxin A chain or B chain optionally may have up to two additional amino acid substitution, insertion or deletion. Said modified relaxin polypeptide may comprise a relaxin A chain polypeptide having at least 90% amino acid sequence identity to SEQ ID NO: 35 and a relaxin B chain polypeptide having at least 90% amino sequence identity to SEQ ID NO: 5 or SEQ ID NO: 6. Said relaxin A chain polypeptide may have at least 95% amino acid sequence identity to SEQ ID NO: 35. Said relaxin B chain polypeptide may have at least 95% amino acid sequence identity to SEQ ID NO: 5 or SEQ ID NO: 6. Said relaxin A chain polypeptide may comprise SEQ ID NO: 35 and the relaxin B chain polypeptide may comprise SEQ ID NO: 5 or SEQ ID NO: 6. In some embodiments, said relaxin A chain polypeptide may comprise SEQ ID NO: 35 and the relaxin B chain polypeptide may comprise SEQ ID NO: 6.

In some embodiments, said peptide component may comprise between 1 and 25 amino acids, e.g., between 2 and 20 amino acids, between 3 and 10 amino acids, or between 4 and 8 amino acids. Said peptide component may comprise Glu, Glu$^y$, GGGGS-Glu$^y$ (SEQ ID NO: 139), DRDDRD (SEQ ID NO: 102), KKKKKK-Glu$^y$ (SEQ ID NO: 103), RGGEEKKKEKEK-Glu$^y$ (SEQ ID NO: 104), GGGEEE-Glu$^y$ (SEQ ID NO: 105), EEEGGG-Glu$^y$ (SEQ ID NO: 106), KKKGGG-Glu$^y$ (SEQ ID NO: 107), GETGSSGEGT-Glu$^y$ (SEQ ID NO: 108), GGGKKK-Glu$^y$ (SEQ ID NO: 109), GSHHHHHGS-Glu$^y$ (SEQ ID NO: 110), Sar-Sar-Sar-Sar-Ser-Sar-Sar-Sar-Sar-Glu$^y$ (SEQ ID NO: 111), Sar-Sar-Sar-Sar-Ser-Glu$^y$ (SEQ ID NO: 112), Sar-Sar-Sar-Glu-Glu-Glu$^y$ (SEQ ID NO: 113), KKKSGGSGG-Glu$^y$ (SEQ ID NO: 118), KKSGGSGG-Glu$^y$ (SEQ ID NO: 114), KKSGGSGG-Glu$^y$ (SEQ ID NO: 115), KKSAGSAG-Glu$^y$ (SEQ ID NO: 116), KSGGSGG-Glu$^y$ (SEQ ID NO: 117), KKSGGSGGEE-Glu$^y$ (SEQ ID NO: 119), dKdKdKdKdKdK-Glu$^y$ (SEQ ID NO: 120), EESGGSGG-Glu$^y$ (SEQ ID NO: 121), GSGSGSGS-Glu$^y$ (SEQ ID NO: 123), EEEGGG-dGlu$^y$ (SEQ ID NO:

128), EGGGGSK-Glu$^\gamma$ (SEQ ID NO: 130), EEEEEE-Glu$^\gamma$ (SEQ ID NO: 131), EEEEPEEEEPEEEEPEEEE-Glu$^\gamma$ (SEQ ID NO: 133), EEEEPEEEEPEEEEPEEGGG (SEQ ID NO: 135), EEEEGEEEEGEEEEGEEEE-Glu$^\gamma$ (SEQ ID NO: 136), KGGEEKKKEKEKEPKGGEEKKKEKEK-Glu$^\gamma$ (SEQ ID NO: 137), EAQKAQAEAQKAQAEAQKAQA-Glu$^\gamma$ (SEQ ID NO: 138), KK-Glu$^\gamma$ (SEQ ID NO: 140), Glu$^\gamma$, KGPKGP-Glu$^\gamma$ (SEQ ID NO: 146), SGGGS-Glu$^\gamma$ (SEQ ID NO: 147), KGGGS-Glu$^\gamma$ (SEQ ID NO: 148), KGGGSE-Glu$^\gamma$ (SEQ ID NO: 149), GSPGSP-Glu$^\gamma$ (SEQ ID NO: 150), GGGGP-Glu$^\gamma$ (SEQ ID NO: 151), EGGS-Glu$^\gamma$ (SEQ ID NO: 152), EGGGP-Glu$^\gamma$ (SEQ ID NO: 153), KGPGSE-Glu$^\gamma$ (SEQ ID NO: 154), Spermine-Glu$^\gamma$, or KKGGS-Glu$^\gamma$ (SEQ ID NO: 156).

Said peptide component may comprise GGGGS-Glu$^\gamma$ (SEQ ID NO: 139), DRDDRD (SEQ ID NO: 102), KKK-KKK-Glu$^\gamma$ (SEQ ID NO: 103), RGGEEKKKEKEK-Glu$^\gamma$ (SEQ ID NO: 104), GGGEEE-Glu$^\gamma$ (SEQ ID NO: 105), EEEGGG-Glu$^\gamma$ (SEQ ID NO: 106), KKKGGG-Glu$^\gamma$ (SEQ ID NO: 107), GGGKKK-Glu$^\gamma$ (SEQ ID NO: 109), GSHH-HHHGS-Glu$^\gamma$ (SEQ ID NO: 110), Sar-Sar-Sar-Ser-Ser-Glu$^\gamma$ (SEQ ID NO: 112), Sar-Sar-Sar-Glu-Glu-Glu$^\gamma$ (SEQ ID NO: 113), or KSGGSGG-Glu$^\gamma$ (SEQ ID NO: 117).

Said peptide component may comprise Glu$^\gamma$. For example, said peptide component may comprise GGGGS-Glu$^\gamma$ (SEQ ID NO: 139).

In exemplary embodiments, said modified relaxin polypeptide may comprise the relaxin A chain polypeptide of SEQ ID NO: 4 and the relaxin B chain polypeptide of SEQ ID NO: 5 or SEQ ID NO: 6, substituted with a non-naturally encoded amino acid at A chain residue 1, wherein said non-naturally encoded amino acid is linked to said pharmacokinetic enhancer and said pharmacokinetic enhancer comprises the peptide component GGGGS-Glu$^\gamma$ (SEQ ID NO: 139). In some embodiments, the peptide component may be covalently linked to said non-naturally encoded amino acid, e.g. via an oxime linkage.

In exemplary embodiments, said half-life extending moiety may comprise a fatty acid or derivative thereof, wherein the fatty acid or derivative thereof may be covalently linked to the peptide component. Said half-life extending moiety may comprise a saturated fatty acid or derivative thereof. Said half-life extending moiety may comprise a fatty acid terminated with a carboxylic acid. Said half-life extending moiety may comprise a fatty acid of Formula I: —Cn-COOH (Formula I), wherein n may be between 10 and 18, such as between 12 and 17, or 13, 14, 15, or 16. In some embodiments, —Cn— of Formula I may comprise a first carbonyl carbon and —(CH$_2$)$_{n-1}$—. For example, —C13— may be —(C=O)—(CH$_2$)$_{12}$—; —C14— may be —(C=O)—(CH$_2$)$_{13}$—; —C15— may be —(C=O)—(CH$_2$)$_{14}$—. In some embodiments, the first carbonyl carbon of the fatty acid may be bonded to a (gamma) Glu residue, optionally via an amide bond. In some embodiments, the first carbonyl carbon of the fatty acid may be bonded to a gamma Glu residue via an amide bond.

In further exemplary embodiments, said half-life extending moiety may comprise —C14-COOH.

In further exemplary embodiments, said pharmacokinetic enhancer may comprise the structure:

(Formula II)

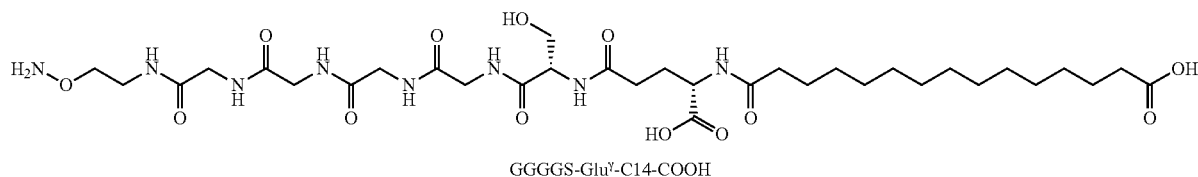

GGGGS-Glu$^\gamma$-C14-COOH wherein the aminooxy group of Formula II is linked to the non-natural amino acid in said modified relaxin polypeptide, e.g., via an oxime linkage.

In further exemplary embodiments, said half-life extending moiety may be conjugated to said peptide component through an amide bond.

In further exemplary embodiments, said relaxin polypeptide may comprise the relaxin A chain polypeptide of SEQ ID NO: 4 and the relaxin B chain polypeptide of SEQ ID NO: 5 or SEQ ID NO: 6, substituted with a non-naturally encoded amino acid at A chain residue 1; wherein said non-naturally encoded amino acid comprises para-acetyl-L-phenylalanine; wherein said non-naturally encoded amino acid is linked to said pharmacokinetic enhancer which comprises a peptide component comprising GGGGS-Glu$^\gamma$ (SEQ ID NO: 139); and a half-life extending moiety comprising —C14-COOH, such as —(C=O)—(CH$_2$)$_{13}$—COOH.

In a further embodiment, the disclosure provides a modified relaxin polypeptide comprising the structure:

(Formula III)

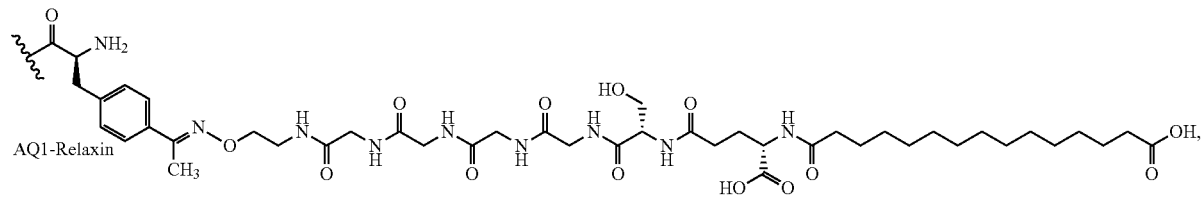

wherein said AQ1-Relaxin comprises a relaxin A chain polypeptide having at least 90% amino acid sequence identity to SEQ ID NO: 35 and a relaxin B chain polypeptide having at least 90% amino sequence identity to SEQ ID NO: 5 or SEQ ID NO: 6, wherein the para-acetyl-L-phenylalanine depicted in Formula III is located at the N-terminus of said relaxin A chain polypeptide. Said relaxin A chain polypeptide may have at least 95% amino acid sequence identity to SEQ ID NO: 35. Said relaxin B chain polypeptide may have at least 95% amino acid sequence identity to SEQ ID NO: 5 or SEQ ID NO: 6. Said AQ1-Relaxin may comprise a relaxin A chain polypeptide of SEQ ID NO: 35 and a relaxin B chain polypeptide of SEQ ID NO: 5 or SEQ ID NO: 6.

In a further embodiment, the disclosure provides a modified relaxin polypeptide comprising Relaxin Conjugate "AQ1-GGGGS-Glu$^\gamma$ (SEQ ID NO: 139) -C14-COOH" which comprises a relaxin A chain polypeptide of SEQ ID NO: 35 and a relaxin B chain polypeptide of SEQ ID NO: 6, wherein the para-acetyl-L-phenylalanine located at the N-terminus of said relaxin A chain polypeptide may be linked to PK enhancer GGGGS-Glu$^\gamma$ (SEQ ID NO: 139)-C14-COOH, as depicted in Formula III:

(Formula III)

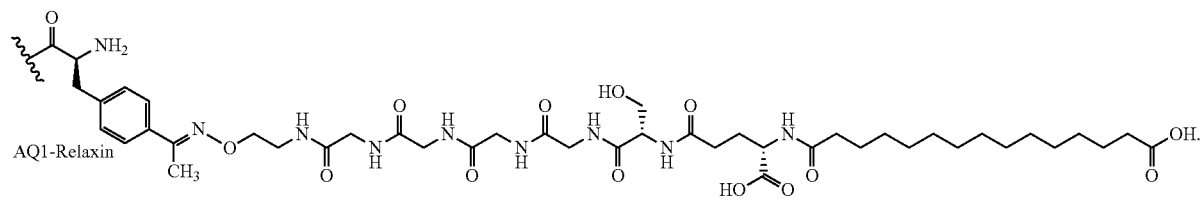

Figure 8:
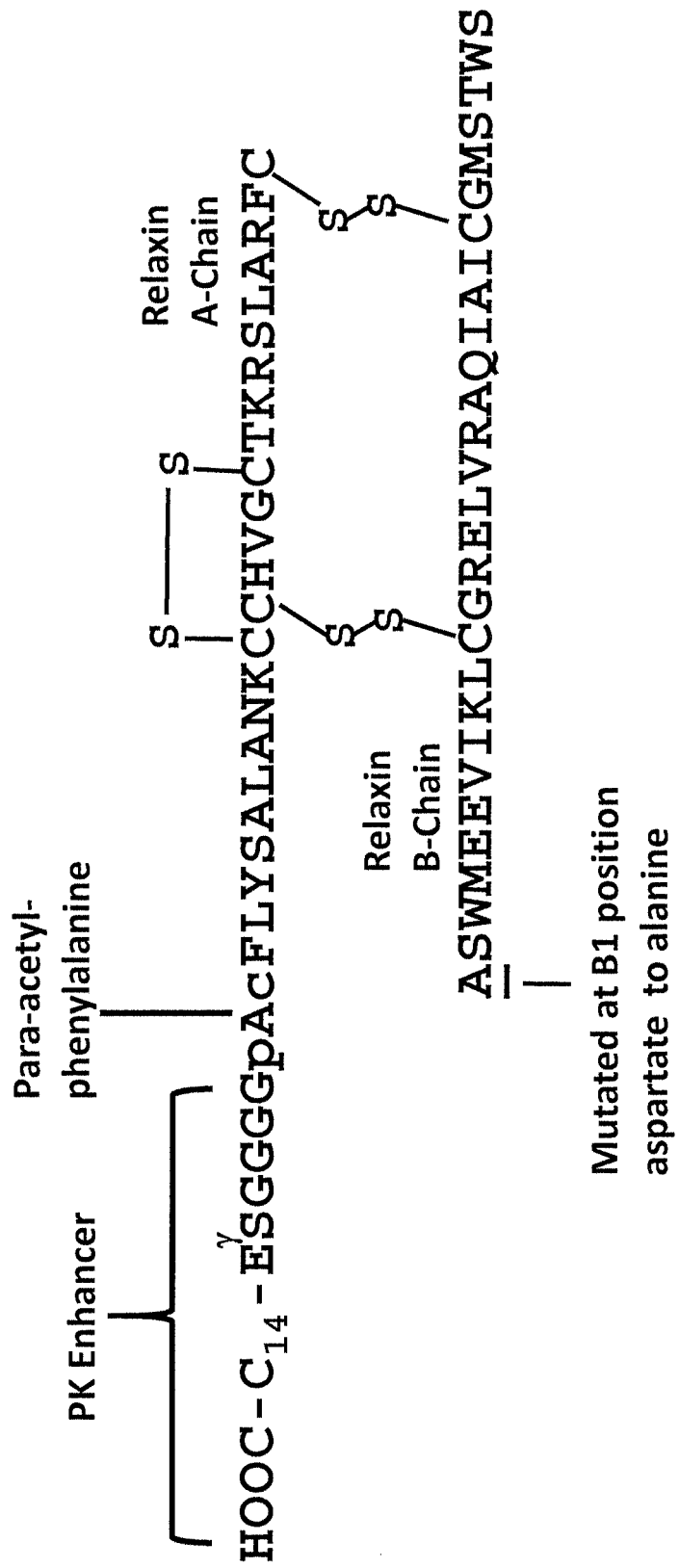
FIG. 8. Structure of AQ1-GGGGS-Glu$^\gamma$ (SEQ ID NO: 139)-C14-COOH depicted in Formula III.

In a further embodiment, the modified relaxin polypeptide comprises the structure shown in FIG. 8.

Figure 9:
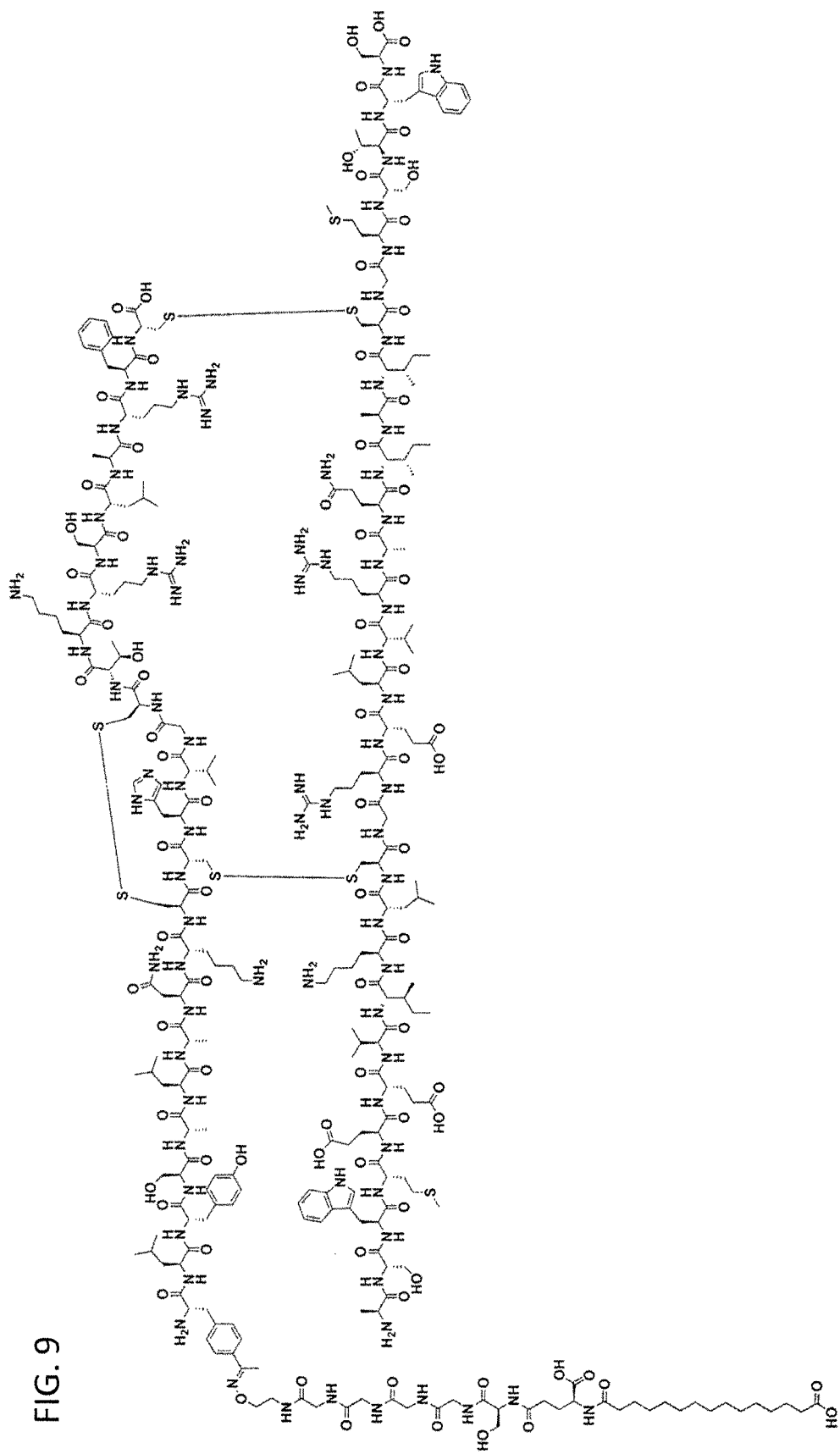
FIG. 9. Structure of AQ1-GGGGS-Glu$^\gamma$ (SEQ ID NO: 139)-C14-COOH depicted in Formula III.

In a further embodiment, the modified relaxin polypeptide comprises the structure shown in FIG. 9.

In exemplary embodiments, said modified relaxin polypeptide may be biologically active. Said modified relaxin polypeptide may be therapeutically effective for the treatment of one or more diseases or conditions associated with relaxin. Said modified relaxin polypeptide may exhibit decreased renal vacuole formation, as compared to a comparator compound, such as AQ1-20 kDa PEG (AQ1 relaxin conjugated to PEG with an average MW of 20 kDa). Said modified relaxin polypeptide may exhibit no or decreased impairment of renal function, as compared to a comparator compound, such as AQ1-20 kDa PEG. Said renal function may be measured by determining one or more of estimated glomerular filtration rate, creatine clearance, insulin glomerular filtration rate, or isotopic glomerular filtration rate.

In exemplary embodiments, said modified relaxin polypeptide does not exhibit decreased renal blood flow, and/or may be capable of increasing renal blood flow, after administration. Renal blood flow may be measured by determining para-aminohippurate clearance.

Said modified relaxin polypeptide may exhibit an increased in vivo half-life, e.g., increased by at least 5-fold, at least 10-fold, at least 20-fold, at least 30-fold, or at least 50-fold, as compared to a comparator compound, such as wild-type relaxin.

In another aspect, the disclosure provides a pharmaceutical composition comprising a modified relaxin polypeptide as described herein and a pharmaceutically acceptable carrier.

In another aspect, the disclosure provides a pharmaceutical composition comprising an effective amount of a modified relaxin polypeptide as described herein for the treatment or prevention of a relaxin-associated disorder and a pharmaceutically acceptable carrier.

In another aspect, the disclosure provides a method of treating or preventing a disease associated with relaxin comprising administering an effective amount of a modified relaxin polypeptide or composition comprising a modified relaxin polypeptide as described herein to a patient in need thereof.

In another aspect, the disclosure provides a method of treating or preventing a cardiovascular disease comprising administering an effective amount of a modified relaxin polypeptide or composition comprising a modified relaxin polypeptide as described herein to a patient in need thereof. Said cardiovascular disease may be selected from coronary artery disease, heart attack, arrhythmia, heart failure, cardiomyopathy, and vascular disease.

In another aspect, the disclosure provides a method of treating, preventing, or alleviating a symptom of heart failure comprising administering an effective amount of a modified relaxin polypeptide or composition comprising a modified relaxin polypeptide as described herein to a patient in need thereof. Said heart failure may be selected from advanced heart failure, cardio-renal syndrome, heart failure with impaired kidney function, chronic heart failure, chronic heart failure with mid-range ejection fraction (HFmEF), acute heart failure, post-acute heart failure, compensated heart failure, decompensated heart failure, right heart failure, left heart failure, global heart failure, ischemic cardiomyopathy, dilated cardiomyopathy, heart failure associated with congenital heart defects, heart failure associated with heart valve defects, heart failure associated with combined heart valve defects, diabetic heart failure, alcoholic cardiomyopathy, heart failure associated with cardiac storage disorders, diastolic heart failure, systolic heart failure, post myocardial remodeling, heart failure with preserved ejection fraction (HFpEF), heart failure with reduced ejection fraction (HFrEF), angina, hypertension, pulmonary hypertension, and pulmonary artery hypertension.

In some embodiments, said heart failure may be selected from chronic heart failure, acute heart failure, post-acute heart failure, chronic heart failure with reduced ejection fraction (HFrEF), chronic heart failure with preserved ejection fraction (HFpEF), chronic heart failure with mid-range ejection fraction (HFmEF), diastolic heart failure, systolic heart failure, post myocardial remodeling, angina, hypertension, pulmonary hypertension and pulmonary artery hypertension.

In some embodiments, said heart failure may be selected from post-acute heart failure, advanced heart failure, cardio-renal syndrome, and heart failure with impaired kidney function.

Said methods of treatment may further comprise administering, in combination, concurrently or sequentially, with said modified relaxin polypeptide, at least one additional therapeutic agent selected from ACE inhibitors, β-blockers, diuretics, mineralocorticoid receptor antagonists, ryanodine receptor modulators, SERCA2a activators, renin inhibitors, calcium channel blockers, adenosine A1 receptor agonists, partial adenosine A1 receptor, dopamine β-hydroxylase inhibitors, angiotensin II receptor antagonists, angiotensin II receptor antagonists with biased agonism for select cell signaling pathways, combinations of angiotensin II receptor antagonists and neprilysin enzyme inhibitors, neprilysin enzyme inhibitors, soluble guanylate cyclase activators, myosin ATPase activators, rho-kinase 1 inhibitors, rho-kinase 2 inhibitors, apelin receptor agonists, nitroxyl donating compounds, calcium-dependent kinase II inhibitors, antifibrotic agents, galectin-3 inhibitors, vasopressin receptor antagonists, FPR2 receptor modulators, natriuretic peptide receptor agonists, transient receptor potential vanilloid-4 channel blockers, anti-arrhythmic agents, $I_f$ "funny current" channel blockers, nitrates, *digitalis* compounds, inotropic agents and β-receptor agonists, cell membrane resealing agents for example Poloxamer 188, anti-hyperlipidemic agents, plasma HDL-raising agents, anti-hypercholesterolemic agents, cholesterol biosynthesis inhibitors (such as HMG CoA reductase inhibitors), LXR agonist, FXR agonist, probucol, raloxifene, nicotinic acid, niacinamide, cholesterol absorption inhibitors, bile acid sequestrants, anion exchange resins, quaternary amines, cholestyramine, colestipol, low density lipoprotein receptor inducers, clofibrate, fenofibrate, bezafibrate, ciprofibrate, gemfibrizol, vitamin B6, vitamin B12, anti-oxidant vitamins, anti-diabetes agents, platelet aggregation inhibitors, fibrinogen receptor antagonists, aspirin and fibric acid derivatives, PCSK9 inhibitors, aspirin, and P2Y12 Inhibitors such as Clopidogrel.

In another aspect, the disclosure provides a method of treating, preventing, or alleviating a symptom of a disease associated with fibrosis, comprising administering a therapeutically effective amount of a modified relaxin polypeptide or composition comprising modified relaxin polypeptide as described herein to a patient in need thereof. Said disease associated with fibrosis may comprise fibrosis of the heart, lung, kidney, bone marrow, or liver, dermatological fibrosis, or a fibrotic eye disorder. Said disease associated with fibrosis may be selected from liver fibrosis, nonalcoholic steatohepatitis (NASH), cirrhosis, pre-cirrhosis, diffuse parenchymal lung disease, cystic fibrosis, pulmonary fibrosis, progressive massive fibrosis, idiopathic pulmonary fibrosis, injection fibrosis, renal fibrosis, chronic kidney disease, diabetic kidney disease, focal segmental glomerulosclerosis, membranous nephropathy, IgA nephropathy, myelofibrosis, heart failure, metabolic heart failure, cardiac fibrosis, cataract fibrosis, cataract, ocular scarring, pancreatic fibrosis, skin fibrosis, intestinal fibrosis, intestinal strictures, endomyocardial fibrosis, atrial fibrosis, mediastinal fibrosis, Crohn's disease, retroperitoneal fibrosis, keloid, nephrogenic systemic fibrosis, scleroderma, systemic sclerosis, arthrofibrosis, Peyronie's syndrome, Dupuytren's contracture, diabetic neuropathy, adhesive capsulitis, alcoholic liver disease, hepatosteatosis, viral hepatitis, biliary disease, primary hemochromatosis, drug-related cirrhosis, cryptogenic cirrhosis, Wilson's disease, alpha 1-antitrypsin deficiency, interstitial lung disease (ILD), human fibrotic lung disease, macular degeneration, retinal retinopathy, vitreal retinopathy, myocardial fibrosis, Grave's ophthalmopathy, drug induced ergotism, cardiovascular disease, atherosclerosis/restenosis, hypertrophic scars, primary or idiopathic myelofibrosis, inflammatory bowel disease, and collagenous colitis.

Said method of treating a disease associated with fibrosis may further comprise administering, in combination, concurrently or sequentially, with said modified relaxin polypeptide, at least one anti-fibrosis agent to said patient. Said anti-fibrosis agent may be selected from nintedanib, Pirfenidone, LPA1 antagonists, LPA1 receptor antagonists, GLP1 analogs, tralokinumab (IL-13, AstraZeneca), vismodegib (hedgehog antagonist, Roche), PRM-151 (pentraxin-2, TGF beta-1, Promedior), SAR-156597 (bispecific Mab IL-4&IL-13, Sanofi), simtuzumab ((anti-lysyl oxidase-like 2 (anti-LOXL2) antibody, Gilead), CKD-942, PTL-202 (PDE inh./pentoxifylline/NAC oral control. release, Pacific Ther.), omipalisib (oral PI3K/mTOR inhibitor, GSK), IW-001 (oral sol. bovine type V collagen mod., ImmuneWorks), STX-100 (integrin alpha V/beta-6 ant, Stromedix/Biogen), Actimmune (IFN gamma), PC-SOD (midismase; inhaled, LTT Bio-Pharma/CKD Pharm), lebrikizumab (anti-IL-13 SC humanized mAb, Roche), AQX-1125 (SHIP1 activator, Aquinox), CC-539 (JNK inhibitor, Celgene), FG-3019 (FibroGen), SAR-100842 (Sanofi), and obeticholic acid (OCA or INT-747, Intercept).

In another aspect, the disclosure provides a method of treating or preventing kidney failure, comprising administering a therapeutically effective amount of a modified relaxin polypeptide or composition comprising a modified relaxin polypeptide as described herein to a patient in need thereof.

In another aspect, the disclosure provides a method of improving, stabilizing or restoring renal function in a patient in need thereof, comprising administering a therapeutically effective amount of a modified relaxin polypeptide or composition comprising a modified relaxin polypeptide as described herein to said patient.

In another aspect, the disclosure provides a method of manufacturing a modified relaxin polypeptide as described herein, comprising: (a) providing a polypeptide comprising a relaxin A chain and a relaxin B chain, wherein said polypeptide comprises a non-naturally encoded amino acid; and (b) linking said non-naturally encoded amino acid to said pharmacokinetic enhancer. Said non-naturally encoded amino acid may be linked to said pharmacokinetic enhancer by an oxime linkage, e.g., that links said non-naturally encoded amino acid to a peptide component of the pharmacokinetic enhancer. Said oxime linkage may be formed by the reaction of a carbonyl group and an aminooxy group. Said carbonyl group may be a substituent of said non-naturally encoded amino acid, and said aminooxy group may be a constituent of said pharmacokinetic enhancer. Said aminooxy group may be a substituent of said non-naturally encoded amino acid, and said carbonyl group may be a constituent of said pharmacokinetic enhancer, e.g., a constituent of a peptide component of said pharmacokinetic enhancer. Said non-naturally encoded amino acid may be ribosomally incorporated into said polypeptide.

II. General Recombinant Nucleic Acids and Methods for Use with the Disclosed Modified relaxin Polypeptides In embodiments of the present disclosure, nucleic acids encoding a modified relaxin polypeptide of interest may be isolated, cloned and often altered using recombinant methods. Such embodiments may be used, including but not limited to, for protein expression or during the generation of variants, derivatives, or other sequences derived from a modified relaxin polypeptide. In some embodiments, the sequences encoding the modified relaxin polypeptides of the disclosure are operably linked to a heterologous promoter. In some embodiments DNA codon usage in the polynucleotide sequences encoding the modified relaxin polypeptide may be optimized for *E. coli* or a mammalian cell (e.g. CHO) expression using techniques that are well known in the art.

Exemplary polynucleotides encoding a Relaxin A chain (SEQ ID NO: 10), Relaxin B chain (SEQ ID NO: 11), Relaxin A and B chains (SEQ ID NO: 12), and leader sequences (SEQ ID NO: 13-14) are provided herein.

A nucleotide sequence encoding a modified relaxin polypeptide described herein may be synthesized on the basis of the amino acid sequence of the parent polypeptide, including but not limited to, having the amino acid sequence shown in SEQ ID NO: 4, 5, 6, 35, 36, or 37 and then changing the nucleotide sequence so as to effect introduction (i.e., incorporation or substitution) or removal (i.e., deletion or substitution) of the relevant amino acid residue(s). The nucleotide sequence may be conveniently modified by site-directed mutagenesis in accordance with conventional methods. Alternatively, the nucleotide sequence may be prepared by chemical synthesis, including but not limited to, by using an oligonucleotide synthesizer, wherein oligonucleotides are designed based on the amino acid sequence of the desired polypeptide, and preferably selecting those codons that are favored in the host cell in which the recombinant polypeptide is to be produced.

Additionally, a selector codon encoding a non-naturally encoded amino acid may be incorporated into the polynucleotide sequence, as further described herein.

The disclosure also relates to eukaryotic host cells, non-eukaryotic host cells, and organisms for the in vivo incorporation of an unnatural amino acid via orthogonal tRNA/RS pairs. Host cells are genetically engineered (including but not limited to, transformed, transduced or transfected) with the polynucleotides of the disclosure or constructs which include a polynucleotide of the disclosure, including but not limited to, a vector of the disclosure, which can be, for example, a cloning vector or an expression vector. For example, the coding regions for the orthogonal tRNA, the orthogonal tRNA synthetase, and the protein to be derivatized are operably linked to gene expression control elements that are functional in the desired host cell. The vector can be, for example, in the form of a plasmid, a cosmid, a phage, a bacterium, a virus, a naked polynucleotide, or a conjugated polynucleotide. The vectors may be introduced into cells and/or microorganisms by standard methods.

III. Selector Codons

Selector codons of the disclosure expand the genetic codon framework of protein biosynthetic machinery. For example, a selector codon includes, but is not limited to, a unique three base codon, a nonsense codon, such as a stop codon, including but not limited to, an amber codon (UAG), an ochre codon, or an opal codon (UGA), an unnatural codon, a four or more base codon, a rare codon, or the like. It is readily apparent to those of ordinary skill in the art that there is a wide range in the number of selector codons that can be introduced into a desired gene or polynucleotide, including but not limited to, one or more, two or more, three or more, 4, 5, 6, 7, 8, 9, 10 or more in a single polynucleotide encoding at least a portion of the modified relaxin polypeptide.

In one embodiment, the methods involve the use of a selector codon that is a stop codon for the incorporation of one or more unnatural (i.e., non-naturally encoded) amino acids in vivo. For example, an O-tRNA is produced that recognizes the stop codon, including but not limited to, UAG, and is aminoacylated by an O—RS with a desired unnatural amino acid. This O-tRNA is not recognized by the naturally occurring host's aminoacyl-tRNA synthetases. Conventional site-directed mutagenesis can be used to introduce the stop codon, including but not limited to, TAG, at the site of interest in a polypeptide of interest. See, e.g., Sayers, J. R., et al. (1988), *Nucleic Acids Res,* 16:791-802. When the O—RS, O-tRNA and the nucleic acid that encodes the polypeptide of interest are combined in vivo, the unnatural amino acid is incorporated in response to the UAG codon to give a polypeptide containing the unnatural amino acid at the specified position.

The incorporation of unnatural amino acids in vivo can be done without significant perturbation of the eukaryotic host cell. For example, because the suppression efficiency for the UAG codon depends upon the competition between the O-tRNA, including but not limited to, the amber suppressor tRNA, and a eukaryotic release factor (including but not limited to, eRF) (which binds to a stop codon and initiates release of the growing peptide from the ribosome), the suppression efficiency can be modulated by, including but not limited to, increasing the expression level of O-tRNA, and/or the suppressor tRNA.

Unnatural amino acids can also be encoded with rare codons. For example, when the arginine concentration in an in vitro protein synthesis reaction is reduced, the rare arginine codon, AGG, has proven to be efficient for insertion of Ala by a synthetic tRNA acylated with alanine. See, e.g., Ma et al., *Biochemistry,* 32:7939 (1993). In this case, the synthetic tRNA competes with the naturally occurring tRNAArg, which exists as a minor species in *Escherichia coli.*

Selector codons also comprise extended codons, including but not limited to, four or more base codons, such as, four, five, six or more base codons. Examples of four base codons include, but are not limited to, AGGA, CUAG, UAGA, CCCU and the like. Examples of five base codons include, but are not limited to, AGGAC, CCCCU, CCCUC, CUAGA, CUACU, UAGGC and the like.

In one embodiment, extended codons based on rare codons or nonsense codons can be used in the present disclosure, which can reduce missense readthrough and frameshift suppression at other unwanted sites.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Genes coding for proteins or polypeptides of interest such as a modified relaxin polypeptide can be mutagenized using methods known to one of ordinary skill in the art and described herein to include, for example, one or more selector codon for the incorporation of an unnatural amino acid. For example, a nucleic acid for a protein of interest is mutagenized to include one or more selector codon, providing for the incorporation of one or more unnatural amino acids. The disclosure includes any such variant, including but not limited to, mutant, versions of any protein, for example, including at least one unnatural amino acid.

Nucleic acid molecules encoding a protein of interest such as a modified relaxin polypeptide may be readily mutated to introduce a cysteine at any desired position of the polypeptide. Cysteine is widely used to introduce reactive molecules, water soluble polymers, proteins, or a wide variety of other molecules, onto a protein of interest.

IV. Non-Naturally Encoded Amino Acids

A very wide variety of non-naturally encoded amino acids are suitable for use in the present disclosure. Any number of non-naturally encoded amino acids can be introduced into a modified relaxin polypeptide. In general, the introduced non-naturally encoded amino acids are substantially chemically inert toward the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). In some embodiments, the non-naturally encoded amino acids include side chain functional groups that react efficiently and selectively with functional groups not found in the 20 common amino acids (including but not limited to, azido, ketone, aldehyde and aminooxy groups) to form stable conjugates. For example, a modified relaxin polypeptide that includes a non-naturally encoded amino acid containing an azido functional group can be reacted with a polymer or PK extender, or, alternatively, a second polypeptide containing an alkyne moiety to form a stable conjugate resulting for the selective reaction of the azide and the alkyne functional groups to form a Huisgen [3+2] cycloaddition product.

The generic structure of an alpha-amino acid is illustrated as follows (Formula IV):

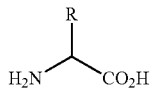

IV

A non-naturally encoded amino acid is typically any structure having the above-listed formula wherein the R group is any substituent other than one used in the twenty natural amino acids, and may be suitable for use in the modified relaxin polypeptides of the present disclosure. Because the non-naturally encoded amino acids of the disclosure typically differ from the natural amino acids only in the structure of the side chain, the non-naturally encoded amino acids form amide bonds with other amino acids, including but not limited to, natural or non-naturally encoded, in the same manner in which they are formed in naturally occurring polypeptides. However, the non-naturally encoded amino acids have side chain groups that distinguish them from the natural amino acids. For example, R optionally comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof.

Exemplary non-naturally encoded amino acids that may be suitable for use in the present disclosure and that are useful for reactions with PK extenders and polymers include, but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine.

Many of the non-naturally encoded amino acids provided herein are commercially available, e.g., from Sigma-Aldrich (St. Louis, Mo., USA), Novabiochem (a division of EMD Biosciences, Darmstadt, Germany), or Peptech (Burlington, Mass., USA). Those that are not commercially available are optionally synthesized as provided herein or using standard methods known to those of ordinary skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). See, also, U.S. Pat. Nos. 7,045,337 and 7,083,970, which are incorporated by reference herein. In addition to unnatural amino acids that contain novel side chains, unnatural amino acids that may be suitable for use in the present disclosure also optionally comprise modified backbone structures, including but not limited to, as illustrated by the structures of Formula V and VI:

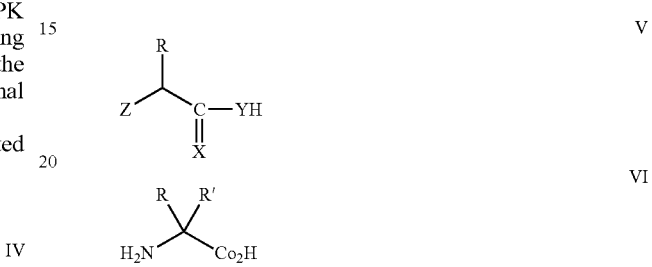

wherein Z typically comprises OH, $NH_2$, SH, NH—R', or S—R'; X and Y, which can be the same or different, typically comprise S or O, and R and R, which are optionally the same or different, are typically selected from the same list of constituents for the R group described above for the unnatural amino acids having Formula I as well as hydrogen. For example, unnatural amino acids of the disclosure optionally comprise substitutions in the amino or carboxyl group as illustrated by Formulas V and VI. Unnatural amino acids of this type include, but are not limited to, α-hydroxy acids, α-thioacids, α-aminothiocarboxylates, including but not limited to, with side chains corresponding to the common twenty natural amino acids or unnatural side chains. In addition, substitutions at the α-carbon optionally include, but are not limited to, L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, β and γ amino acids such as substituted β-alanine and γ-amino butyric acid.

Many unnatural amino acids are based on natural amino acids, such as tyrosine, glutamine, phenylalanine, and the like, and are suitable for use in the present disclosure. Tyrosine analogs include, but are not limited to, para-substituted tyrosines, ortho-substituted tyrosines, and meta substituted tyrosines, where the substituted tyrosine comprises, including but not limited to, a keto group (including but not limited to, an acetyl group), a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, an alkynyl group or the like. In addition, multiply substituted aryl rings are also contemplated. Glutamine analogs that may be suitable for use in the present disclosure include, but are not limited to, α-hydroxy derivatives, γ-substituted derivatives, cyclic derivatives, and amide substituted glutamine derivatives. Example phenylalanine analogs that may be suitable for use in the present disclosure include, but are not limited to, para-substituted phenylalanines, ortho-substituted phenylalanines, and meta-substituted phenylalanines, where the substituent comprises, including but not limited to, a hydroxy group, a methoxy group, a methyl group, an allyl group, an aldehyde, an azido, an iodo, a bromo, a keto group (including but not limited to, an acetyl group), a benzoyl, an alkynyl group, or the like. Specific examples of unnatural amino acids that may be suitable for use in the present disclosure include, but are not limited to, a p-acetyl-L-phenylalanine, an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, and a p-propargyloxy-phenylalanine, and the like.

In one embodiment, compositions of a modified relaxin polypeptide comprising an unnatural amino acid (such as p-acetyl-L-phenylalanine) are provided. Various compositions comprising p-acetyl-L-phenylalanine and, including but not limited to, proteins and/or cells, are also provided. In one aspect, a composition that includes the p-acetyl-L-phenylalanine unnatural amino acid, further includes an orthogonal tRNA. The unnatural amino acid can be bonded (including but not limited to, covalently) to the orthogonal tRNA, including but not limited to, covalently bonded to the orthogonal tRNA though an amino-acyl bond, covalently bonded to a 3'OH or a 2'OH of a terminal ribose sugar of the orthogonal tRNA, etc.

The modified relaxin polypeptide described herein may comprise a non-naturally encoded amino acid described in U.S. Pat. No. 8,735,539, entitled "Relaxin polypeptides comprising non-naturally encoded amino acids," which is incorporated herein by reference in its entirety.

V. Structure and Synthesis of Non-Natural Amino Acids

In some embodiments the present disclosure provides modified relaxin polypeptide linked to a PK extender, e.g., comprising a fatty acid, by an oxime bond or linkage. Many types of non-naturally encoded amino acids are suitable for formation of oxime bonds. These include, but are not limited to, non-naturally encoded amino acids containing a carbonyl, dicarbonyl, carbonyl-like, masked carbonyl, protected carbonyl, or hydroxylamine group. Such amino acids, their structure and synthesis are described in U.S. Pat. Nos. 8,012,931 and 8,735,539, which are incorporated herein by reference in their entirety.

Exemplary structures and synthesis methods of non-naturally encoded amino acids, including hydroxylamine-containing amino acids, are known in the art, for example as disclosed in U.S. Pat. No. 7,332,571, U.S. Patent Publication Nos. 2006/0194256, 2006/0217532, and 2006/0217289 and WO 2006/069246, each of which is hereby incorporated in its entirety.

Chemical Synthesis of Non-Naturally Encoded Amino Acids

Many of the unnatural amino acids suitable for use in the present disclosure are commercially available, e.g., from Sigma (USA) or Aldrich (Milwaukee, Wis., USA). Those that are not commercially available are optionally synthesized as provided herein or as provided in various publications or using standard methods known to those of ordinary skill in the art.

A. Carbonyl Reactive Groups

Amino acids with a carbonyl reactive group allow for a variety of reactions to link molecules (including but not limited to, PEG or other water soluble molecules such as peptide components) via nucleophilic addition or aldol condensation reactions among others.

The synthesis of p-acetyl-(+/−)-phenylalanine and m-acetyl-(+/−)-phenylalanine is described in Zhang, Z., et al., Biochemistry 42: 6735-6746 (2003), which is incorporated by reference herein. Other carbonyl-containing amino acids can be similarly prepared by one of ordinary skill in the art.

In some embodiments, a modified relaxin polypeptide comprising a non-naturally encoded amino acid may be chemically modified to generate a reactive carbonyl functional group. For instance, an aldehyde functionality useful for conjugation reactions can be generated from a functionality having adjacent amino and hydroxyl groups.

In the present disclosure, a non-naturally encoded amino acid bearing adjacent hydroxyl and amino groups can be incorporated into the polypeptide as a "masked" aldehyde functionality. For example, 5-hydroxylysine bears a hydroxyl group adjacent to the epsilon amine. Reaction conditions for generating the aldehyde typically involve addition of molar excess of sodium metaperiodate under mild conditions to avoid oxidation at other sites within the polypeptide. The pH of the oxidation reaction is typically about 7.0. A typical reaction involves the addition of about 1.5 molar excess of sodium meta periodate to a buffered solution of the polypeptide, followed by incubation for about 10 minutes in the dark. See, e.g. U.S. Pat. No. 6,423,685, which is incorporated by reference herein.

The carbonyl functionality can be reacted selectively with a hydrazine-, hydrazide-, hydroxylamine-, or semicarbazide-containing reagent under mild conditions in aqueous solution to form the corresponding hydrazone, oxime, or semicarbazone linkages, respectively, that are stable under physiological conditions. See, e.g., Jencks, W. P., *J. Am. Chem. Soc.* 81, 475-481 (1959); Shao, J. and Tam, J. P., *J. Am. Chem. Soc.* 117:3893-3899 (1995). Moreover, the unique reactivity of the carbonyl group allows for selective modification in the presence of the other amino acid side chains. See, e.g., Cornish, V. W., et al., *J. Am. Chem. Soc.* 118:8150-8151 (1996); Geoghegan, K. F. & Stroh, J. G., *Bioconjug. Chem.* 3:138-146 (1992); Mahal, L. K., et al., *Science* 276:1125-1128 (1997).

B. Hydrazine, Hydrazide or Semicarbazide Reactive Groups

Non-naturally encoded amino acids containing a nucleophilic group, such as a hydrazine, hydrazide or semicarbazide, allow for reaction with a variety of electrophilic groups to form conjugates.

Hydrazide-, hydrazine-, and semicarbazide-containing amino acids are available from commercial sources. For instance, L-glutamate-γ-hydrazide is available from Sigma Chemical (St. Louis, Mo.). Other amino acids not available commercially can be prepared by one of ordinary skill in the art. See, e.g., U.S. Pat. No. 6,281,211, which is incorporated by reference herein.

Modified relaxin polypeptides containing non-naturally encoded amino acids that bear hydrazide, hydrazine or semicarbazide functionalities can be reacted efficiently and selectively with a variety of molecules that contain aldehydes or other functional groups with similar chemical reactivity. See, e.g., Shao, J. and Tam, J., *J. Am. Chem. Soc.* 117:3893-3899 (1995). The unique reactivity of hydrazide, hydrazine and semicarbazide functional groups makes them significantly more reactive toward aldehydes, ketones and other electrophilic groups as compared to the nucleophilic groups present on the 20 common amino acids (including but not limited to, the hydroxyl group of serine or threonine or the amino groups of lysine and the N-terminus).

C. Aminooxy-Containing Amino Acids

Non-naturally encoded amino acids containing an aminooxy (also called a hydroxylamine) group allow for reaction with a variety of electrophilic groups to form conjugates (including but not limited to, with PEG or peptide components). Like hydrazines, hydrazides and semicarbazides, the enhanced nucleophilicity of the aminooxy group permits it to react efficiently and selectively with a variety of molecules that contain aldehydes or other functional groups with similar chemical reactivity. See, e.g., Shao, J. and Tam, J., *J. Am. Chem. Soc.* 117:3893-3899 (1995); H. Hang and C. Bertozzi, *Acc. Chem. Res.* 34: 727-736 (2001). Whereas the result of reaction with a hydrazine group is the corresponding hydrazone, however, an oxime results generally from the reaction of an aminooxy group with a carbonyl-containing group such as a ketone.

Aminooxy-containing amino acids can be prepared from readily available amino acid precursors (homoserine, serine and threonine). See, e.g., M. Carrasco and R. Brown, *J. Org. Chem.* 68: 8853-8858 (2003). Certain aminooxy-containing amino acids, such as L-2-amino-4-(aminooxy)butyric acid), have been isolated from natural sources (Rosenthal, G., *Life Sci.* 60: 1635-1641 (1997). Other aminooxy-containing amino acids can be prepared by one of ordinary skill in the art.

D. Azide and Alkyne Reactive Groups

The unique reactivity of azide and alkyne functional groups makes them useful for the selective modification of polypeptides and other biological molecules. Organic azides, particularly alphatic azides, and alkynes are generally stable toward common reactive chemical conditions. In particular, both the azide and the alkyne functional groups are inert toward the side chains (i.e., R groups) of the 20 common amino acids found in naturally-occurring polypeptides. When brought into close proximity, however, the "spring-loaded" nature of the azide and alkyne groups is revealed and they react selectively and efficiently via Huisgen [3+2] cycloaddition reaction to generate the corresponding triazole. See, e.g., Chin J., et al., *Science* 301:964-7 (2003); Wang, Q., et al., *J. Am. Chem. Soc.* 125, 3192-3193 (2003); Chin, J. W., et al., *J. Am. Chem. Soc.* 124:9026-9027 (2002).

Because the Huisgen cycloaddition reaction involves a selective cycloaddition reaction (see, e.g., Padwa, A., in COMPREHENSIVE ORGANIC SYNTHESIS, Vol. 4, (ed. Trost, B. M., 1991), p. 1069-1109; Huisgen, R. in 1,3-DIPOLAR CYCLOADDITION CHEMISTRY, (ed. Padwa, A., 1984), p. 1-176) rather than a nucleophilic substitution, the incorporation of non-naturally encoded amino acids bearing azide and alkyne-containing side chains permits the resultant polypeptides to be modified selectively at the position of the non-naturally encoded amino acid. Cycloaddition reaction involving azide or alkyne-containing modified relaxin polypeptide can be carried out at room temperature under aqueous conditions by the addition of Cu(II) (including but not limited to, in the form of a catalytic amount of $CuSO_4$) in the presence of a reducing agent for reducing Cu(II) to Cu(I), in situ, in catalytic amount. See, e.g., Wang, Q., et al., *J. Am. Chem. Soc.* 125, 3192-3193 (2003); Tornoe, C. W., et al., *J. Org. Chem.* 67:3057-3064 (2002); Rostovtsev, et al., *Angew. Chem. Int. Ed.* 41:2596-2599 (2002). Exemplary reducing agents include, including but not limited to, ascorbate, metallic copper, quinine, hydroquinone, vitamin K, glutathione, cysteine, $Fe^{2+}$, $Co^{2+}$, and an applied electric potential.

In some cases, where a Huisgen [3+2] cycloaddition reaction between an azide and an alkyne is desired, the modified relaxin polypeptide may comprise a non-naturally encoded amino acid comprising an alkyne moiety and the PK enhancer to be attached to the amino acid may comprise an azide moiety. Alternatively, the converse reaction (i.e., with the azide moiety on the amino acid and the alkyne moiety present on the water soluble polymer) can also be performed.

The azide functional group can also be reacted selectively with a water soluble polymer containing an aryl ester and appropriately functionalized with an aryl phosphine moiety to generate an amide linkage. The aryl phosphine group reduces the azide in situ and the resulting amine then reacts efficiently with a proximal ester linkage to generate the corresponding amide. See, e.g., E. Saxon and C. Bertozzi, *Science* 287, 2007-2010 (2000). The azide-containing amino acid can be either an alkyl azide (including but not limited to, 2-amino-6-azido-1-hexanoic acid) or an aryl azide (p-azido-phenylalanine).

The azide functional group can also be reacted selectively with a water soluble polymer containing a thioester and appropriately functionalized with an aryl phosphine moiety to generate an amide linkage. The aryl phosphine group reduces the azide in situ and the resulting amine then reacts efficiently with the thioester linkage to generate the corresponding amide.

Alkyne-containing amino acids are commercially available. Alternatively, alkyne-containing amino acids can be prepared according to standard methods. For instance, p-propargyloxyphenylalanine can be synthesized, for example, as described in Deiters, A., et al., *J. Am. Chem. Soc.* 125: 11782-11783 (2003), and 4-alkynyl-L-phenylalanine can be synthesized as described in Kayser, B., et al., *Tetrahedron* 53(7): 2475-2484 (1997). Other alkyne-containing amino acids can be prepared by one of ordinary skill in the art.

Azide-containing amino acids are available from commercial sources. For those azide-containing amino acids that are not commercially available, the azide group can be prepared relatively readily using standard methods known to those of ordinary skill in the art, including but not limited to, via displacement of a suitable leaving group (including but not limited to, halide, mesylate, tosylate) or via opening of a suitably protected lactone. See, e.g., *Advanced Organic Chemistry* by March (Third Edition, 1985, Wiley and Sons, New York).

A molecule that can be added to a protein of the disclosure through a [3+2] cycloaddition includes virtually any molecule with an azide or alkynyl derivative. Molecules include, but are not limited to, dyes, fluorophores, crosslinking agents, saccharide derivatives, polymers (including but not limited to, polymers comprising polyethylene glycol), photocrosslinkers, cytotoxic compounds, affinity labels, derivatives of biotin, resins, beads, a peptide, a second protein or polypeptide (or more), polynucleotide(s) (including but not limited to, DNA, RNA, etc.), metal chelators, cofactors, fatty acids, carbohydrates, and the like. These molecules can be added to an unnatural amino acid with an alkynyl group, including but not limited to, p-propargyloxyphenylalanine, or azido group, including but not limited to, p-azido-phenylalanine, respectively.

E. Aminothiol Reactive Groups

The unique reactivity of beta-substituted aminothiol functional groups makes them useful for the selective modification of polypeptides and other biological molecules that contain aldehyde groups via formation of the thiazolidine.

See, e.g., J. Shao and J. Tam, *J. Am. Chem. Soc.* 1995, 117 (14) 3893-3899. In some embodiments, beta-substituted aminothiol amino acids can be incorporated into modified relaxin polypeptides and then reacted with PK enhancer comprising an aldehyde functionality. In some embodiments, a PK enhancer, drug conjugate or other payload can be coupled to a modified relaxin polypeptide comprising a beta-substituted aminothiol amino acid via formation of the thiazolidine.

F. Additional Reactive Groups

Additional reactive groups and non-naturally encoded amino acids that can be incorporated into modified relaxin polypeptides of the disclosure are described in the following patent applications which are all incorporated by reference in their entirety herein: U.S. Patent Publication No. 2006/0194256, U.S. Patent Publication No. 2006/0217532, U.S. Patent Publication No. 2006/0217289, and International Patent Application Pub. No. WO/2007/070659.

VI. In Vivo Generation of Modified Relaxin Polypeptides Comprising Non-Naturally-Encoded Amino Acids The modified relaxin polypeptides of the disclosure can be generated in vivo using modified tRNA and tRNA synthetases to add or substitute amino acids that are not encoded in naturally-occurring systems. Such methods are described in U.S. Pat. No. 8,735,539, which is incorporated herein by reference in its entirety.

Methods for generating tRNAs and tRNA synthetases which use amino acids that are not encoded in naturally-occurring systems are described in, e.g., U.S. Pat. Nos. 7,045,337 and 7,083,970 which are incorporated by reference herein. These methods involve generating a translational machinery that functions independently of the synthetases and tRNAs endogenous to the translation system (and are therefore sometimes referred to as "orthogonal"). Typically, the translation system comprises an orthogonal tRNA (O-tRNA) and an orthogonal aminoacyl tRNA synthetase (O—RS). Typically, the O—RS preferentially aminoacylates the O-tRNA with at least one non-naturally occurring amino acid in the translation system and the O-tRNA recognizes at least one selector codon that is not recognized by other tRNAs in the system. The translation system thus inserts the non-naturally-encoded amino acid into a protein produced in the system, in response to an encoded selector codon, thereby "substituting" an amino acid into a position in the encoded polypeptide.

Use of O-tRNA/aminoacyl-tRNA synthetases involves selection of a specific codon which encodes the non-naturally encoded amino acid. While any codon can be used, it is generally desirable to select a codon that is rarely or never used in the cell in which the O-tRNA/aminoacyl-tRNA synthetase is expressed. For example, exemplary codons include nonsense codon such as stop codons (amber, ochre, and opal), four or more base codons and other natural three-base codons that are rarely or unused.

Specific selector codon(s) can be introduced into appropriate positions in the modified relaxin polynucleotide coding sequence using mutagenesis methods known in the art (including but not limited to, site-specific mutagenesis, cassette mutagenesis, restriction selection mutagenesis, etc.).

VII. Expression in Non-Eukaryotes and Eukaryotes

Expression Systems, Culture, and Isolation

Unmodified or modified relaxin polypeptides may be expressed in any number of suitable expression systems including, for example, yeast, insect cells (e.g., Baculovirus-Infected Insect Cells), mammalian cells, and bacteria. A description of exemplary expression systems is provided below.

Yeast: As used herein, the term "yeast" includes any of the various yeasts capable of expressing a gene encoding a modified relaxin polypeptide, including, but not limited to, *P. pastoris, P. guillerimondii, S. cerevisiae, S. carlsbergensis, S. diastaticus, S. douglasii, S. kluyveri, S. norbensis, S. oviformis, K. lactis, K. fragilis, C. albicans, C. maltosa,* and *H. polymorpha*. WO 2005/091944, which is incorporated by reference, herein describes the expression of relaxin in yeast.

*E. Coli, Pseudomonas* species, and other Prokaryotes:

The term "bacterial host" or "bacterial host cell" refers to a bacterial that can be, or has been, used as a recipient for recombinant vectors or other transfer DNA. The term includes the progeny of the original bacterial host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding an unmodified or modified relaxin polypeptide, are included in the progeny intended by this definition.

In selecting bacterial hosts for expression, suitable hosts may include those shown to have, inter alia, good inclusion body formation capacity, low proteolytic activity, and overall robustness. Industrial/pharmaceutical fermentation generally use bacterial derived from K strains (e.g. W3110) or from bacteria derived from B strains (e.g. BL21). Other examples of suitable *E. coli* hosts include, but are not limited to, strains of BL21, DH10B, or derivatives thereof. In another embodiment of the methods of the present disclosure, the *E. coli* host is a protease minus strain including, but not limited to, OMP- and LON-. The host cell strain may be a species of *Pseudomonas*, including but not limited to, *Pseudomonas fluorescens, Pseudomonas aeruginosa,* and *Pseudomonas putida. Pseudomonas fluorescens* biovar 1, designated strain MB101, is known to be useful for recombinant production and is available for therapeutic protein production processes.

Once a recombinant host cell strain has been established (i.e., the expression construct has been introduced into the host cell and host cells with the proper expression construct are isolated), the recombinant host cell strain is cultured under conditions appropriate for production of modified relaxin polypeptides.

Recombinant host cells may be cultured in batch or continuous formats, with either cell harvesting (in the case where the modified relaxin polypeptide accumulates intracellularly) or harvesting of culture supernatant in either batch or continuous formats.

Modified relaxin polypeptides produced in bacterial host cells may be poorly soluble or insoluble (in the form of inclusion bodies). In one embodiment of the present disclosure, amino acid substitutions may readily be made in the modified relaxin polypeptide that are selected for the purpose of increasing the solubility of the recombinantly produced protein. The modified relaxin polypeptide may be solubilized, for example, with urea or guanidine hydrochloride.

In the case of soluble modified relaxin protein, the relaxin may be secreted into the periplasmic space or into the culture medium. For example, modified relaxin is secreted into the periplasmic space of W3110-B2 cells by using plasmids encoding constructs including eight different leader sequences, including those listed in SEQ ID NOs: 39-44, and transforming these into W3110-B2 cells, the cells were then grown at 37° C. until OD reached about 0.8, at which point the expression is induced with 0.01% arabinose. Five hours later the periplasmic release samples can be prepped from the cultures. In addition, soluble modified relaxin may be present in the cytoplasm of the host cells. It may be desired to concentrate soluble modified relaxin prior to performing purification steps.

When modified relaxin polypeptide is produced as a fusion protein, the fusion sequence may be removed. Removal of a fusion sequence may be accomplished by enzymatic or chemical cleavage. Enzymatic removal of fusion sequences may be accomplished using methods known to those of ordinary skill in the art. The choice of enzyme for removal of the fusion sequence may be determined by the identity of the fusion, and the reaction conditions may be specified by the choice of enzyme as will be apparent to one of ordinary skill in the art. Chemical cleavage may be accomplished using reagents known to those of ordinary skill in the art, including but not limited to, cyanogen bromide, TEV protease, and other reagents. The cleaved modified relaxin polypeptide may be purified from the cleaved fusion sequence by methods known to those of ordinary skill in the art.

In general, it is occasionally desirable to denature and reduce expressed polypeptides and then to cause the polypeptides to re-fold into the preferred conformation. For example, guanidine, urea, DTT, DTE, and/or a chaperonin can be added to a translation product of interest. The proteins can be refolded in a redox buffer containing, including but not limited to, oxidized glutathione and L-arginine. Refolding reagents can be flowed or otherwise moved into contact with the one or more polypeptide or other expression product, or vice-versa.

In the case of prokaryotic production of modified relaxin polypeptide, the modified relaxin polypeptide thus produced may be misfolded and thus lacks or has reduced biological activity. The bioactivity of the protein may be restored by "refolding". In general, misfolded unmodified or modified relaxin polypeptide is refolded by solubilizing (where the modified relaxin polypeptide is also insoluble), unfolding and reducing the polypeptide chain using, for example, one or more chaotropic agents (e.g. urea and/or guanidine) and a reducing agent capable of reducing disulfide bonds (e.g. dithiothreitol, DTT or 2-mercaptoethanol, 2-ME). At a moderate concentration of chaotrope, an oxidizing agent is then added (e.g., oxygen, cystine or cystamine), which allows the reformation of disulfide bonds. Modified relaxin polypeptide may be refolded using standard methods known in the art, such as those described in U.S. Pat. Nos. 4,511,502, 4,511,503, and 4,512,922, which are incorporated by reference herein. The modified relaxin polypeptide may also be cofolded with other proteins to form heterodimers or heteromultimers.

After refolding, the modified relaxin may be further purified. Purification of modified relaxin may be accomplished using a variety of techniques known to those of ordinary skill in the art, including hydrophobic interaction chromatography, size exclusion chromatography, ion exchange chromatography, reverse-phase high performance liquid chromatography, affinity chromatography, and the like or any combination thereof. Additional purification may also include a step of drying or precipitation of the purified protein.

After purification, modified relaxin may be exchanged into different buffers and/or concentrated by any of a variety of methods known to the art, including, but not limited to, diafiltration and dialysis. Modified relaxin that is provided as a single purified protein may be subject to aggregation and precipitation.

The purified modified relaxin may be at least 90% pure (as measured by reverse phase high performance liquid chromatography, RP-HPLC, or sodium dodecyl sulfate-polyacrylamide gel electrophoresis, SDS-PAGE) or at least 95% pure, or at least 98% pure, or at least 99% or greater pure. Regardless of the exact numerical value of the purity of the modified relaxin, the modified relaxin is sufficiently pure for use as a pharmaceutical product or for further processing, such as conjugation with a PK enhancer.

Certain modified relaxin molecules may be used as therapeutic agents in the absence of other active ingredients or proteins (other than excipients, carriers, and stabilizers, serum albumin and the like), or they may be complexed with another protein or a polymer.

In some embodiments of the present disclosure, the yield of modified relaxin after each purification step may be at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99.9%, or at least about 99.99%, of the unmodified or modified relaxin in the starting material for each purification step.

VIII. Expression in Alternate Systems

Modified relaxin polypeptides of the present disclosure may be expressed using a cell-free (e.g., in vitro) translational system. Translation systems may be cellular or cell-free, and may be prokaryotic or eukaryotic. Cellular translation systems include, but are not limited to, whole cell preparations such as permeabilized cells or cell cultures wherein a desired nucleic acid sequence can be transcribed to mRNA and the mRNA translated. Cell-free translation systems are commercially available and many different types and systems are well-known. Examples of cell-free systems include, but are not limited to, prokaryotic lysates such as *Escherichia coli* lysates, and eukaryotic lysates such as wheat germ extracts, insect cell lysates, rabbit reticulocyte lysates, rabbit oocyte lysates and human cell lysates. Membranous extracts, such as the canine pancreatic extracts containing microsomal membranes, are also available which are useful for translating secretory proteins.

IX. Fusion Proteins Containing Modified Relaxin Polypeptides

The disclosure also provides modified relaxin polypeptides, or a fragments thereof, comprising the modified relaxin polypeptide sequence and a fusion partner. The fusion partner may confer a functional property, including but not limited to, half-life extension, facilitating protein purification and/or manufacturing, enhanced biophysical properties such as increase solubility or stability, and reduced immunogenicity or toxicity, or any other purpose. For example, the fusion protein may exhibit extended in vivo half-life, thereby facilitating a less frequent dosing (such as dosing twice per week, once per week, or once every other week, etc.) in a therapeutic regimen. Exemplary fusion proteins comprise a modified relaxin fused to a fusion partner such as an albumin (e.g., human serum albumin), PK extending (PKE) adnectin, XTEN, Fc domain, immunoglobulin constant region, or a fragment of any of the foregoing, or a combination of any of the foregoing. A fusion protein can be produced by expressing a nucleic acid which encodes the modified relaxin polypeptide sequence and a fusion partner sequence in the same reading frame, optionally separated by a sequence encoding a connecting peptide. The fusion protein may comprise the modified relaxin polypeptide and fusion partner in any order, e.g., one or more fusion partners linked to the N-terminus and/or C-terminus of the modified relaxin polypeptide sequence, or one or more fusion partners linked to both the N-terminus and C-terminus.

X. Glycosylation of Modified and Unmodified Relaxin Polypeptides

The present disclosure includes modified relaxin polypeptides comprising one or more non-naturally encoded amino acids bearing saccharide residues. The saccharide residues may be either natural (including but not limited to, N-acetylglucosamine) or non-natural (including but not limited to, 3-fluorogalactose). The saccharides may be linked to the non-naturally encoded amino acids either by an N- or O-linked glycosidic linkage (including but not limited to, N-acetylgalactose-L-serine) or a non-natural linkage (including but not limited to, an oxime or the corresponding C- or S-linked glycoside).

The saccharide (including but not limited to, glycosyl) moieties can be added to modified relaxin polypeptides either in vivo or in vitro. In some embodiments of the present disclosure, a modified relaxin polypeptide comprising a carbonyl-containing non-naturally encoded amino acid may be modified with a saccharide derivatized with an aminooxy group to generate the corresponding glycosylated polypeptide linked via an oxime linkage. Once attached to the non-naturally encoded amino acid, the saccharide may be further elaborated by treatment with glycosyltransferases and other enzymes to generate an oligosaccharide bound to the modified relaxin polypeptide. See, e.g., H. Liu, et al. *J. Am. Chem. Soc.* 125: 1702-1703 (2003).

XI. Administration And Pharmaceutical Compositions

Also provided herein are compositions comprising a therapeutically effective amount of the modified relaxin polypeptide, described herein, and a pharmaceutically acceptable carrier or excipient. Such a carrier or excipient includes, but is not limited to, saline, buffered saline, dextrose, sucrose, histidine, water, glycerol, PS80 (Polysorbate 80), ethanol, and/or combinations thereof. The formulation is made to suit the mode of administration.

For example, a modified relaxin polypeptide described herein may be administered to a patient at a concentration of between about 0.1 and 100 mg/kg of body weight of recipient patient. In an embodiment, a modified relaxin polypeptide described herein may be administered to a patient at a concentration of about 0.5-5 mg/kg of body weight of recipient patient. In another embodiment, a modified relaxin polypeptide described herein may be administered to a recipient patient with a frequency of between once per day and once per two weeks, three weeks, or four weeks, such as about once per week, twice per week, once every two days, once every three days, once every four days, once every five days, or once every six days. In another embodiment, a modified relaxin polypeptide described herein may be administered to a patient once per week.

It is to be understood that the concentration of the modified relaxin polypeptide administered to a given patient may be greater or lower than the exemplary administration concentrations set forth above.

Based upon the information provided in the present disclosure, a person of skill in the art would be able to determine an effective dosage and frequency of administration through routine experimentation, for example guided by the disclosure herein and the teachings in Goodman et al., (2006). Goodman & Gilman's the pharmacological basis of therapeutics. New York: McGraw-Hill; or Howland et al., (2006). Pharmacology. Lippincott's illustrated reviews. Philadelphia: Lippincott Williams & Wilkins.

Average quantities of the modified relaxin may vary and in particular should be based upon the recommendations and prescription of a qualified physician. The exact amount of modified relaxin is a matter of preference subject to such factors as the exact type of condition being treated, the condition of the patient being treated, as well as the other ingredients in the composition. The present disclosure also provides for administration of a therapeutically effective amount of another active agent. The amount to be given may be readily determined by one of ordinary skill in the art.

A "pharmaceutical composition" refers to a chemical or biological composition suitable for administration to a mammal. Such compositions may be specifically formulated for administration via one or more of a number of routes, including but not limited to buccal, epicutaneous, epidural, inhalation, intraarterial, intracardial, intracerebroventricular, intradermal, intramuscular, intranasal, intraocular, intraperitoneal, intraspinal, intrathecal, intravenous, oral, parenteral, rectally via an enema or suppository, subcutaneous, subdermal, sublingual, transdermal, and transmucosal. In addition, administration can occur by means of injection, powder, liquid, gel, drops, or other means of administration.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. In another embodiment, the carrier is suitable for subcutaneous administration. Alternatively, the carrier can be suitable for intravenous, intraperitoneal, intramuscular, or sublingual administration. Pharmaceutically acceptable carriers include sterile aqueous solutions or dispersions and sterile powders for the extemporaneous preparation of sterile injectable solutions or dispersions.

In some embodiments, the pharmaceutical composition may be present in lyophilized form. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol), and suitable mixtures thereof. In some embodiments, the pharmaceutical composition comprises a stabilizer. The proper fluidity can be maintained, for example, by the maintenance of the required particle size in the case of dispersion and by the use of surfactants.

In some embodiments, the pharmaceutical composition comprises a isotonic agent, for example, sugars such as sucrose, polyalcohols such as mannitol, sorbitol, or sodium chloride in the composition. By including an agent such as, monostearate salts and gelatin, the absorption of the injectable compositions can be prolonged. Moreover, the polypeptide can be formulated in a time-release formulation, for example in a composition which includes a slow release polymer. The active compounds can be prepared with carriers that may protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG).

Modified relaxin polypeptides and compositions of the present disclosure may be administered by any conventional route suitable for proteins or peptides, including, but not limited to parenterally, e.g. injections including, but not limited to, subcutaneously or intravenously or any other form of injections or infusions. Polypeptide compositions can be administered by a number of routes including, but not limited to oral, intravenous, intraperitoneal, intramuscular, transdermal, subcutaneous, topical, sublingual, or rectal means. Compositions comprising modified relaxin may also be administered via liposomes. The modified relaxin polypeptide, may be used alone or in combination with other suitable components such as a pharmaceutical carrier. The modified relaxin polypeptide may be used in combination with other agents as described herein.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of modified relaxin can be presented in unit-dose or multi-dose sealed containers, such as ampules and vials.

The dose administered to a patient, in the context of the present disclosure, is sufficient to have a beneficial therapeutic response in the patient over time, or other appropriate activity, depending on the application. The dose is determined by the efficacy of the formulation, and the activity, stability or serum half-life of the modified relaxin polypeptide employed and the condition of the patient, as well as the body weight or surface area of the patient to be treated.

The dose administered, for example, to a 70 kilogram patient, is typically in the range equivalent to dosages of currently-used therapeutic proteins, adjusted for the altered activity or serum half-life of the relevant composition.

For administration, formulations of the present disclosure are administered at a rate determined by the LD-50 or ED-50 of the relevant formulation, and/or observation of any side-effects of the modified relaxin polypeptides at various concentrations, including but not limited to, as applied to the mass and overall health of the patient. Administration can be accomplished via single or divided doses.

Modified relaxin polypeptides of the present disclosure can be administered directly to a mammalian subject. Modified relaxin polypeptides of the present disclosure can be prepared in a mixture in a unit dosage injectable form (including but not limited to, solution, suspension, or emulsion) with a pharmaceutically acceptable carrier. Modified relaxin polypeptides of the present disclosure can also be administered by continuous infusion (using, including but not limited to, minipumps such as osmotic pumps), single bolus or slow-release depot formulations.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. Solutions and suspensions can be prepared from sterile powders, granules, and tablets of the kind previously described.

Pharmaceutically acceptable carriers include but are not limited to, buffers containing succinate, phosphate, borate, HEPES, citrate, histidine, imidazole, acetate, bicarbonate, and other organic acids; antioxidants including but not limited to, ascorbic acid; low molecular weight polypeptides including but not limited to those less than about 10 residues; proteins, including but not limited to, serum albumin, gelatin, or immunoglobulins; hydrophilic polymers including but not limited to, polyvinylpyrrolidone; amino acids including but not limited to, glycine, glutamine, asparagine, arginine, histidine or histidine derivatives, methionine, glutamate, or lysine; monosaccharides, disaccharides, and other carbohydrates, including but not limited to, trehalose, sucrose, glucose, mannose, or dextrins; chelating agents including but not limited to, EDTA and edentate disodium; divalent metal ions including but not limited to, zinc, cobalt, or copper; sugar alcohols including but not limited to, mannitol or sorbitol; salt-forming counter ions including but not limited to, sodium and sodium chloride; and/or nonionic surfactants including but not limited to Tween™ (including but not limited to, Tween 80 (polysorbate 80 or PS80) and Tween 20 (polysorbate 20), Pluronics™ and other pluronic acids, including but not limited to, and other pluronic acids, including but not limited to, pluronic acid F68 (poloxamer 188), or PEG. Suitable surfactants include for example but are not limited to polyethers based upon poly(ethylene oxide)-poly(propylene oxide)-poly(ethylene oxide), i.e., (PEO-PPO-PEO), or poly(propylene oxide)-poly(ethylene oxide)-poly(propylene oxide), i.e., (PPO-PEO-PPO), or a combination thereof. PEO-PPO-PEO and PPO-PEO-PPO are commercially available under the trade names Pluronics™, R-Pluronics™, Tetronics™ and R-Tetronics™ (BASF Wyandotte Corp., Wyandotte, Mich.) and are further described in U.S. Pat. No. 4,820,352 incorporated herein in its entirety by reference. Other ethylene/polypropylene block polymers may be suitable surfactants. A surfactant or a combination of surfactants may be used to stabilize modified relaxin against one or more stresses including but not limited to stress that results from agitation. Some of the above may be referred to as "bulking agents." Some may also be referred to as "tonicity modifiers." Antimicrobial preservatives may also be applied for product stability and antimicrobial effectiveness; suitable preservatives include but are not limited to, benzyl alcohol, benzalkonium chloride, metacresol, methyl/propyl parabene, cresol, and phenol, or a combination thereof. In some embodiments, the pharmaceutical composition may comprise a buffer containing succinate, phosphate, borate, HEPES, citrate, histidine, imidazole, acetate, bicarbonate, and/or other organic acids; a carbohydrate (e.g. monosaccharides, disaccharides, and other carbohydrates), such as trehalose, sucrose, glucose, mannose, or dextrin; and a surfactants such as Tween™ 80 (polysorbate 80 or PS80) or Tween 20 (polysorbate 20). In some embodiments, the pharmaceutical composition may comprise a buffer containing histidine, a carbohydrate such as sucrose; and a surfactants such as PS80.

Modified relaxin polypeptides of the present disclosure, including those linked to a PK enhancer can also be administered by or as part of sustained-release systems. Sustained-release compositions include, including but not limited to, semi-permeable polymer matrices in the form of shaped articles, including but not limited to, films, or microcapsules. Sustained-release matrices include from biocompatible materials such as poly(2-hydroxyethyl methacrylate), ethylene vinyl acetate (or poly-D-(−)-3-hydroxybutyric acid, polylactides (polylactic acid), polyglycolide (polymer of glycolic acid), polylactide co-glycolide (copolymers of lactic acid and glycolic acid) polyanhydrides, copolymers of L-glutamic acid and gamma-ethyl-L-glutamate, poly(ortho) esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Sustained-release compositions also include a liposomally entrapped compound.

The dose administered to a patient in the context of the present disclosure should be sufficient to cause a beneficial response in the subject over time. Generally, the total pharmaceutically effective amount of the modified relaxin polypeptide of the present disclosure administered parenterally (e.g., intravenously or subcutaneously) per dose may be in the range of about 0.01 µg/kg to about 500 mg/kg, about 0.01 µg/kg to about 100 mg/kg, about 0.05 mg/kg to about 50 mg/kg, about 100 µg/kg to about 40 mg/kg, about 0.2 mg/kg to about 20 mg/kg, or about 0.5 mg/kg to about 10 mg/kg, or is about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 12 mg/kg, about 15 mg/kg, about 20 mg/kg, about 30 mg/kg, about 40 mg/kg, about 50 mg/kg, or about 100 mg/kg, of patient body weight, although this is subject to therapeutic discretion. In some embodiments, the modified relaxin polypeptide of the present disclosure administered parenterally (e.g., intravenously or subcutaneously) per dose may be in the range of about 0.2 mg/kg to about 5 mg/kg, 0.5 mg/kg to about 3 mg/kg, or 1 mg/kg to about 3 mg/kg, or is about 0.5 mg/kg, 1 mg/kg, 2 mg/kg, 3 mg/kg, 4 mg/kg, 5 mg/kg, 10 mg/kg, 20 mg/kg, 30 mg/kg, 50 mg/kg, or 80 mg/kg. In some embodiments, the modified relaxin polypeptide of the present disclosure administered parenterally (e.g., intravenously or subcutaneously) per dose may be about 1 mg/kg. In some embodiments, the modified relaxin polypeptide of the present disclosure administered parenterally (e.g., intravenously or subcutaneously) per dose may be a flat dose in the range from about 0.1 mg to about 10,000 mg, from about 1 mg to about 5,000 mg, from about 10 mg to about 2,500 mg, from about 100 mg to about 1,000 mg, from about 200 mg to about 800 mg, from about 400 mg to about 600 mg, from about 1 mg to about 10 mg, from about 10 mg to about 50 mg, from about 50 mg to about 100 mg, from about 100 mg to about 300 mg, from about 300 mg to about 500 mg, from about 500 mg to about 700 mg, from about 700 mg to about 900 mg, from about 900 mg to about 1,200 mg, from about 1,000 mg to about 2,000 mg, from about 2,000 mg to about 3,000 mg, from about 3,000 mg to about 4,000 mg, from about 4,000 mg to about 5,000 mg, from about 5,000 mg to about 6,000 mg, from about 6,000 mg to about 7,000 mg, from about 7,000 mg to about 8,000 mg, from about 8,000 mg to about 9,000 mg, or from about 9,000 mg to about 10,000 mg.

XII. Therapeutic Uses of Modified Relaxin Polypeptides

The present disclosure provides for the use of modified relaxin polypeptides in the treatment of diseases including cardiovascular disease or fibrotic disease, such as heart failure, pancreatitis, inflammation, cancer, scleroderma, pulmonary fibrosis, renal fibrosis, hepatic fibrosis, or cardiac fibrosis.

Said cardiovascular disease may include, but is not limited to, coronary artery disease, heart attack, arrhythmia or abnormal heart rhythms, heart failure, heart valve disease, congenital heart disease, cardiomyopathy (heart muscle disease), pericardial disease, aorta disease, Marfan syndrome, or vascular disease (blood vessel disease).

In some embodiments, said heart failure may comprise one or more of advanced heart failure, cardio-renal syndrome, heart failure with impaired kidney function, chronic heart failure, chronic heart failure with mid-range ejection fraction (HFmEF), acute heart failure, post-acute heart failure such as post-acute decompensated heart failure, compensated heart failure, decompensated heart failure, right heart failure, left heart failure, global heart failure, ischemic cardiomyopathy, dilated cardiomyopathy, heart failure associated with congenital heart defects, heart failure associated with heart valve defects, mitral stenosis, mitral insufficiency, aortic stenosis, aortic insufficiency, tricuspid stenosis, tricuspid insufficiency, pulmonary stenosis, pulmonary valve insufficiency, angina, hypertension, pulmonary hypertension or pulmonary artery hypertension, heart failure associated with combined heart valve defects, myocardial inflammation (myocarditis), chronic myocarditis, acute myocarditis, viral myocarditis, diabetic heart failure, alcoholic cardiomyopathy, heart failure associated with cardiac storage disorders, diastolic heart failure, systolic heart failure, diastolic dysfunction, post myocardial remodeling, chronic heart failure with preserved ejection fraction (HFpEF), or chronic heart failure with reduced ejection fraction (HFrEF).

In some embodiments, said heart failure is selected from chronic heart failure, acute heart failure, post-acute heart failure, chronic heart failure with reduced ejection fraction (HFrEF), chronic heart failure with preserved ejection fraction (HFpEF), chronic heart failure with mid-range ejection fraction (HFmEF), diastolic heart failure, systolic heart failure, post myocardial remodeling, angina, hypertension, pulmonary hypertension and pulmonary artery hypertension. In some embodiments, said heart failure is selected from post-acute heart failure, advanced heart failure, cardio-renal syndrome, and heart failure with impaired kidney function.

Fibrosis is the formation of excess fibrous connective tissue in an organ or tissue. Excess deposition of fibrous tissue is associated with pathological conditions that can lead to impairment of organ or tissue function. Affected organs can include the lungs (lung or pulmonary fibrosis), liver (liver or hepatic fibrosis), kidney (kidney or renal fibrosis), and heart (cardiac fibrosis). Fibrosis can also affect other tissues and organs including joints, skin, intestine, bone marrow, and others. Exemplary fibrotic conditions or diseases include, but are not limited to, nonalcoholic steatohepatitis (NASH), which affects the liver; diabetic kidney disease and diabetic nephropathy, which affect the kidney; and metabolic heart failure, which affects the heart. For example, NASH is characterized by fat, inflammation and damage in the liver in people who consume little or no alcohol and can lead to liver cirrhosis. NASH tends to be diagnosed in overweight or obese middle-aged people who often have elevated blood lipid levels and diabetes or prediabetes.

Biological activity of modified relaxin polypeptides for potential therapeutic use can be determined using standard or known in vitro or in vivo assays. Relaxin polypeptides may be analyzed for biological activity by suitable methods known in the art. Such assays include, but are not limited to, receptor binding assays.

With respect to diseases such as heart failure and fibrotic disease, activity of a modified relaxin may be determined using one or more in vivo assays. Said assays typically involve administration of a relaxin in an animal model of said disease and determining the effect on disease progression, severity, or other indicia of efficacious treatment. Such assays may be used to determine efficacious dosages and treatment regimens in the model system, and based thereon predict a dosing regimen for clinical use, e.g., for human patients. Exemplary HF assays that may be utilized include: 1) the mouse left anterior descending (LAD) coronary ligation model which mimics the cardiac changes of patients suffering a myocardial infarction and progression to HF (Samuel et al., Lab. Investigation 91:675-690, 2011); 2) limited AngII-infusion model in which minimal concentrations AngII are utilized to induce cardiac fibrosis (Xu et al., J. Cardiovasc. Pharmacol. 51:62-70, 2008); 3) Dahl-Salt sensitive rat model which is characterized by hypertension, renal impairment, and blood volume overload (Sakata et al., Circulation 109:2143-2149, 2004); 4) Aged-Spontaneously Hypertensive Rat (SHR) model of cardiac and renal fibrosis which was previously utilized to demonstrate WT-RLX efficacy (Lekgabe et al., Hypertension 46:412-418, 2005); and 5) rat thoracic aortic constriction model of pressure overload (Kuster et al., Circulation 111:420-427, 2005). In addition to these models, activity of modified relaxins may also be determined in a dog model, such as in normal and tachypacing-induced HF dogs. Additionally, these assays may be performed to determine whether a modified relaxin is efficacious when given not only in preventative mode, but also in therapeutic mode. Further, modified relaxins may be tested in models of fibrosis including renal (Yoshida et al., Nephrol. Dialysis Transplant 27: 2190-2197, 2012), lung (Huang et al., Am. J. Pathol. 179:2751-2765, 2011), and liver fibrosis (Williams et al., Gut 49:577-583, 2001). For example, efficacy of a modified relaxin may be compared to efficacy of wild-type relaxin (e.g., wild-type human relaxin).

Administered quantities of relaxin, relaxin polypeptides, and/or relaxin analogues of the present invention may vary and in particular should be based upon the recommendations and prescription of a qualified physician. The exact amount of relaxin, relaxin polypeptides, and/or relaxin analogues of the present invention is a matter of preference subject to such factors as the exact type and/or severity of the condition being treated, the condition of the patient being treated, as well as the other ingredients in the composition. The invention may further comprise administration of a therapeutically effective amount of another active agent. The amount to be given may be readily determined by one of ordinary skill in the art based upon therapy with relaxin, available relaxin therapies, and/or other relaxin analogues.

Compounds of the present disclosure may be used for reducing the area of myocardium affected by an infarction, and for the prophylaxis of secondary infarctions. Further provided is the use of the compounds of the present disclosure for the prophylaxis and/or treatment of thromboembolic disorders, reperfusion damage following ischemia, micro- and macrovascular lesions (vasculitis), arterial and venous thromboses, edemas, ischemias such as myocardial infarction, stroke and transient ischemic attacks, for cardio protection in connection with coronary artery bypass operations (coronary artery bypass graft, CABG), primary percutaneous transluminal coronary angioplasties (PTCAs), PTCAs after thrombolysis, rescue PTCA, heart transplants and open-heart operations, and for organ protection in connection with transplants, bypass operations, catheter examinations and other surgical procedures. Further provided is the use of the compounds of the present disclosure for the prophylaxis and/or treatment of respiratory disorders, such as, for example, chronic obstructive pulmonary disease (chronic bronchitis, COPD), asthma, pulmonary emphysema, bronchiectases, cystic fibrosis (mucoviscidosis) and pulmonary hypertension, in particular pulmonary arterial hypertension.

Exemplary embodiments of the present disclosure provide use of a modified relaxin of the disclosure as a medicament for the prophylaxis and/or treatment of kidney diseases, including but not limited to, acute and chronic kidney diseases and acute and chronic renal insufficiencies, as well as acute and chronic renal failure, including acute and chronic stages of renal failure with and without the requirement of dialysis, as well as the underlying or related kidney diseases such as renal hypoperfusion, dialysis induced hypotension, glomerulopathies, glomerular and tubular proteinuria, renal edema, hematuria, primary, secondary, as well as acute and chronic glomerulonephritis, membranous and membranoproliferative glomerulonephritis, Alport-Syndrome, glomerulosclerosis, interstistial tubular diseases, nephropathic diseases, such as primary and inborn kidney diseases, renal inflammation, immunological renal diseases like renal transplant rejection, immune complex induced renal diseases, as well as intoxication induced nephropathic diseases, diabetic and non-diabetic renal diseases, pyelonephritis, cystic kidneys, nephrosclerosis, hypertensive nephrosclerosis, nephrotic syndrome, that are characterized and diagnostically associated with an abnormal reduction in creatinine clearance and/or water excretion, abnormal increased blood concentrations of urea, nitrogen, potassium and/or creatinine, alteration in the activity of renal enzymes, such as glutamylsynthetase, urine osmolarity and urine volume, increased microalbuminuria, macroalbuminuria, glomerular and arteriolar lesions, tubular dilation, hyperphosphatemia and/or the requirement of dialysis.

In addition, a modified relaxin of the disclosure can be used as a medicament for the prophylaxis and/or treatment of renal carcinomas, after incomplete resection of the kidney, dehydration after overuse of diuretics, uncontrolled blood pressure increase with malignant hypertension, urinary tract obstruction and infection, amyloidosis, as well as systemic diseases associated with glomerular damage, such as Lupus erythematodes, and rheumatic immunological systemic diseases, as well as renal artery stenosis, renal artery thrombosis, renal vein thrombosis, analgetics induced nephropathy and renal tubular acidosis.

In addition, the present disclosure provides the use of a modified relaxin of the disclosure as a medicament for the prophylaxis and/or treatment of contrast medium induced and drug induced acute and chronic interstitial kidney diseases, metabolic syndrome and dyslipemia.

In addition, the present disclosure provides the use of a modified relaxin of the disclosure as a medicament for the prophylaxis, alleviation, and/or treatment of aftereffects or symptoms associated with acute and/or chronic kidney diseases, such as pulmonary edema, heart failure, uremia, anemia, electrolyte disturbances (e.g. hyperkalemia, hyponatremia), as well as bony and carbohydrate metabolism.

In addition, the present disclosure provides the use of a modified relaxin of the disclosure as a medicament for improving, stabilizing or restoring renal function in a patient in need thereof, for example, a patient having a kidney disease as described above.

Further exemplary embodiments provide use of the modified relaxin for the treatment and/or prophylaxis of lung diseases especially of asthmatic disorders, pulmonary arterial hypertension (PAH) and other forms of pulmonary hypertension (PH) including left-heart disease, HIV, sickle cell anemia, thromboembolisms (CTEPH), sarcoidosis, COPD or pulmonary fibrosis-associated pulmonary hypertension, chronic-obstructive pulmonary disease (COPD), acute respiratory distress syndrome (ARDS), acute lung injury (ALI), alpha-1-antitrypsin deficiency (AATD), pulmonary fibrosis, pulmonary emphysema (for example pulmonary emphysema induced by cigarette smoke) and cystic fibrosis (CF).

Further exemplary embodiments provide use of the modified relaxin for the treatment and/or prophylaxis of fibrotic disorders, including fibrotic disorders of the internal organs such as, for example, the lung, the heart, the kidney, the bone marrow and in particular the liver, and also dermatological fibrosis and fibrotic eye disorders.

The present disclosure furthermore provides the use of modified relaxin for preparing a medicament for the treatment and/or prevention of disorders, in particular the disorders mentioned above.

The present disclosure furthermore provides a method for the treatment and/or prevention of disorders, in particular the disorders mentioned above, using an effective amount of at least one modified relaxin of the disclosure.

The present disclosure furthermore provides a modified relaxin for use in a method for the treatment and/or prophylaxis of coronary heart disease, acute coronary syndrome, heart failure (e.g. acute heart failure, chronic heart failure, or advanced heart failure), and myocardial infarction.

Pharmaceutical compositions suitable for use in the methods and compositions of the present disclosure include compositions wherein the active ingredients are contained in an effective amount to achieve the intended purpose, e.g., treating heart failure. The determination of an effective dose is well within the capability of those skilled in the art in view of the present disclosure.

For any compound, the therapeutically effective dose can be estimated initially either in in vitro assays, e.g. RXFP1 receptor activation, ex vivo in isolated perfused rat hearts, or in animal models, usually mice, rats, rabbits, dogs, or pigs. The animal model is also used to achieve a desirable concentration range and route of administration. Such information can then be used to determine useful doses and routes for administration in humans.

A therapeutically effective dose refers to that amount of a modified relaxin that ameliorates the symptoms or condition. Therapeutic efficacy and toxicity of such compounds can be determined by standard pharmaceutical procedures in vitro or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, ED50/LD50. Exemplary pharmaceutical compositions exhibit large therapeutic indices. The data obtained from in vitro assays and animal studies are used in formulating a range of dosage for human use. The dosage of such compounds lies for example within a range of circulating concentrations that include the ED50 with little or no toxicity. The dosage varies within this range depending upon the dosage form employed, sensitivity of the patient, and the route of administration.

Normal dosage amounts may vary from 0.1 to 100,000 milligrams total dose, depending upon the route of administration. Guidance as to particular dosages and methods of delivery is provided in the literature. See U.S. Pat. Nos. 4,657,760; 5,206,344; or 5,225,212.

XIII. Combinations

A modified relaxin of the disclosure can be administered alone or in combination with other active compounds. In this context, the term combination encompasses any means of concurrent or sequential administration, whether or not the modified relaxin and the other agent are contained in the same composition or administered separately, which administration may be through the same or different modes of administration. The present disclosure provides medicaments comprising at least one modified relaxin and one or more further active ingredients, in pharmaceutical compositions where it is mixed with excipient(s) or pharmaceutically acceptable carriers, for the treatment and/or prevention of the disorders mentioned above.

Suitable active ingredients for combination may include, by way of example: active ingredients which modulate lipid metabolism, antidiabetics, hypotensive agents, perfusion-enhancing and/or antithrombotic agents, antioxidants, chemokine receptor antagonists, p38-kinase inhibitors, NPY agonists, orexin agonists, anorectics, PAF-AH inhibitors, antiphlogistics (COX inhibitors, $LTB_4$-receptor antagonists), analgesics for example aspirin, P2Y12 Inhibitors such as Clopidogrel, PCSK9 inhibitors such as evolocumab (REPATHA) or alirocumab (PRALUENT), antidepressants and other psychopharmaceuticals.

The present disclosure further provides combinations of at least one modified relaxin with at least one lipid metabolism-altering active ingredient, antidiabetic, blood pressure reducing active ingredient and/or agent having antithrombotic effects.

The modified relaxin can be combined with one or more lipid metabolism-modulating active ingredients, for example, HMG-CoA reductase inhibitors, inhibitors of HMG-CoA reductase expression, squalene synthesis inhibitors, ACAT inhibitors, LDL receptor inductors, cholesterol absorption inhibitors, polymeric bile acid adsorbers, bile acid reabsorption inhibitors, MTP inhibitors, lipase inhibitors, LpL activators, fibrates, niacin, niacin receptor agonists, CETP inhibitors, PPAR-α, PPAR-γ and/or PPAR-δ agonists, RXR modulators, FXR modulators, LXR modulators, thyroid hormones and/or thyroid mimetics, ATP citrate lyase inhibitors, Lp(a) antagonists, cannabinoid receptor 1 antagonists, leptin receptor agonists, bombesin receptor agonists, PCSK9 inhibitors, histamine receptor agonists and the antioxidants/radical scavengers.

In some embodiments, a modified relaxin is administered in combination with an HMG-CoA reductase inhibitor from the class of the statins, e.g., lovastatin, simvastatin, pravastatin, fluvastatin, atorvastatin, rosuvastatin or pitavastatin. In another embodiment, the modified relaxin is administered in combination with a squalene synthesis inhibitor, e.g., BMS-188494 or TAK-475. In another embodiment, the modified relaxin is administered in combination with an ACAT inhibitor, e.g., avasimibe, melinamide, pactimibe, eflucimibe or SMP-797. In another embodiment, the other modified relaxin is administered in combination with a cholesterol absorption inhibitor, e.g., ezetimibe, tiqueside or pamaqueside. In another embodiment, the modified relaxin is administered in combination with an MTP inhibitor, e.g., implitapide, BMS-201038, R-103757 or JTT-130. In another embodiment, the modified relaxin is administered in combination with a lipase inhibitor, e.g., orlistat. In another embodiment, the modified relaxin is administered in combination with a thyroid hormone and/or thyroid mimetic, e.g., D-thyroxine or 3,5,3'-triiodothyronine (T3). In another embodiment, the modified relaxin is administered in combination with an agonist of the niacin receptor, e.g., niacin, acipimox, acifran or radecol. In another embodiment, the modified relaxin is administered in combination with a CETP inhibitor, e.g., dalcetrapib, BAY 60-5521, anacetrapib or CETP vaccine (CETi-1). In another embodiment, the modified relaxin is administered in combination with a PPAR-γ agonist, for example from the class of the thiazolidinediones, e.g., pioglitazone or rosiglitazone. In another embodiment, the modified relaxin is administered in combination with a PPAR-δ agonist, e.g., GW-501516 or BAY 68-5042. In another embodiment, the modified relaxin is administered in combination with a polymeric bile acid adsorber, e.g., cholestyramine, colestipol, colesolvam, CholestaGel or colestimide. In another embodiment, the modified relaxin is administered in combination with a bile acid reabsorption inhibitor, e.g., ASBT (=IBAT) inhibitors, such as, for example, AZD-7806, S-8921, AK-105, BARI-1741, SC-435 or SC-635. In another embodiment, the modified relaxin is administered in combination with an antioxidant/radical scavenger, e.g., probucol, AGI-1067, BO-653 or AEOL-10150. In another embodiment, the modified relaxin is administered in combination with a cannabinoid receptor 1 antagonist, e.g., rimonabant or SR-147778.

The modified relaxin can be combined with one or more antidiabetics, e.g., insulin and insulin derivatives, sulfonylureas, biguanides, meglitinide derivatives, glucosidase inhibitors, PPAR-gamma agonists, inhibitors of dipeptidylpeptidase IV (DPP-IV inhibitors), oxadiazolidinones, thiazolidinediones, GLP 1 receptor agonists, glucagon antagonists, insulin sensitizers, CCK 1 receptor agonists, leptin receptor agonists, inhibitors of liver enzymes involved in the stimulation of gluconeogenesis and/or glycogenolysis, modulators of glucose uptake and also potassium channel openers.

In some embodiments, the modified relaxin is administered in combination with insulin or an insulin derivative. In another embodiment, the modified relaxin is administered in combination with a sulfonylurea, e.g., tolbutamide, glibenclamide, glimepiride, glipizide or gliclazide. In another embodiment, the modified relaxin is administered in combination with a biguanide, e.g., metformin. In another embodiment, the modified relaxin is administered in combination with a meglitinide derivative, e.g., repaglinide or nateglinide. In another embodiment, the modified relaxin is administered in combination with a glucosidase inhibitor, e.g., miglitol or acarbose. In another embodiment, the modified relaxin is administered in combination with a DPP-IV inhibitor, e.g., sitagliptin and vildagliptin. In another embodiment, the modified relaxin is administered in combination with a PPAR-gamma agonist, for example from the class of the thiazolinediones, e.g., pioglitazone or rosiglitazone.

The modified relaxin can be combined with one or more hypotensive active ingredients, e.g., calcium antagonists, angiotensin II antagonists, ACE inhibitors, refill inhibitors, beta-receptor blockers, alpha-receptor blockers, diuretics, aldosterone antagonists, mineralocorticoid receptor antagonists, ECE inhibitors, ACE/NEP inhibitors and the vasopeptidase inhibitors.

In some embodiments, the modified relaxin is administered in combination with a calcium antagonist, e.g., nifedipine, amlodipine, verapamil or diltiazem. In another embodiment, the modified relaxin is administered in combination with an angiotensin II antagonist, e.g., losartan, valsartan, candesartan, embusartan, olmesartan or telmisartan. In another embodiment, the modified relaxin is administered in combination with an ACE inhibitor, e.g., enalapril, captopril, lisinopril, ramipril, delapril, fosinopril, quinapril, perindopril or trandopril. In another embodiment, the modified relaxin is administered in combination with a beta-receptor blocker, e.g., propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol. In another embodiment, the modified relaxin is administered in combination with an alpha-receptor blocker, e.g., prazosin. In another embodiment, the modified relaxin is administered in combination with a diuretic, e.g., furosemide, bumetanide, torsemide, bendroflumethiazide, chlorothiazide, hydrochlorothiazide, hydroflumethiazide, methyclothiazide, polythiazide, trichloromethiazide, chlorothalidone, indapamide, metolazone, quinethazone, acetazolamide, dichlorophenamide, methazolamide, glycerol, isosorbide, mannitol, amiloride or triamteren. In another embodiment, the modified relaxin is administered in combination with an aldosterone or mineralocorticoid receptor antagonist, e.g., spironolactone or eplerenone. In another embodiment, the modified relaxin is administered in combination with a vasopressin receptor antagonist, e.g., conivaptan, tolvaptan, lixivaptan or SR-121463.

The modified relaxin can be combined with one or more of the following: antithrombotic agents, e.g., platelet aggregation inhibitors or the anticoagulants; diuretics; vasopressin receptor antagonists; organic nitrates and NO donors; compounds with positive inotropic activity; compounds which inhibit the degradation of cyclic guanosine monophosphate (cGMP) and/or cyclic adenosine monophosphate (cAMP), such as, for example, inhibitors of phosphodiesterases (PDE) 1, 2, 3, 4 and/or 5, in particular PDE 5 inhibitors, such as sildenafil, vardenafil and tadalafil, and also PDE 3 inhibitors, such as milrinone; natriuretic peptides, e.g., "atrial natriuretic peptide" (ANP, anaritide), "B-type natriuretic peptide" or "brain natriuretic peptide" (BNP, nesiritide), "C-type natriuretic peptide" (CNP) and also urodilatin; agonists of the prostacyclin receptor (IP receptor), for example, iloprost, beraprost, cicaprost; inhibitors of the If (funny channel) channel, e.g., ivabradine; calcium sensitizers, such as, by way of example, levosimendan; potassium supplements; NO-independent, but heme-dependent stimulators of guanylate cyclase, e.g., the compounds described in WO 00/06568, WO 00/06569, WO 02/42301 and WO 03/095451; NO- and heme-independent activators of guanylate cyclase, e.g., the compounds described in WO 01/19355, WO 01/19776, WO 01/19778, WO 01/19780, WO 02/070462 and WO 02/070510; inhibitors of human neutrophil elastase (HNE), e.g., sivelestat and DX-890 (Reltran); compounds which inhibit the signal transduction cascade, e.g., tyrosine-kinase inhibitors, e.g., sorafenib, imatinib, gefitinib and erlotinib; and/or compounds which modulate the energy metabolism of the heart, e.g., etomoxir, dichloroacetate, ranolazine and trimetazidine.

In some embodiments, the modified relaxin is administered in combination with an organic nitrate or NO donor, e.g., sodium nitroprusside, nitroglycerol, isosorbide mononitrate, isosorbide dinitrate, molsidomin or SIN-1, or in combination with inhalative NO. In another embodiment, the modified relaxin is administered in combination with a positive-inotropic compound, e.g., cardiac glycosides (digoxin), beta-adrenergic and dopaminergic agonists, such as isoproterenol, adrenaline, noradrenaline, dopamine or dobutamine. In another embodiment, the modified relaxin is administered in combination with antisympathotonics, such as reserpine, clonidine or alpha-methyldopa, or in combination with potassium channel agonists, such as minoxidil, diazoxide, dihydralazine or hydralazine, or with substances which release nitrogen oxide, such as glycerol nitrate or sodium nitroprusside. In another embodiment, the modified relaxin is administered in combination with a platelet aggregation inhibitor, e.g., aspirin, clopidogrel, ticlopidine or dipyridamol. In another embodiment, the modified relaxin is administered in combination with a thrombin inhibitor, e.g., ximelagatran, melagatran, dabigatran, bivalirudin or clexane. In another embodiment, the modified relaxin is administered in combination with a GPIIb/IIIa antagonist, e.g., tirofiban or abciximab. In another embodiment, the modified relaxin is administered in combination with a factor Xa inhibitor, e.g., rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428. In another embodiment, the modified relaxin is administered in combination with heparin or a low molecular weight (LMW) heparin derivative. In another embodiment, the modified relaxin is administered in combination with a vitamin K antagonist, such as, by way of example, Coumadin (warfarin).

The present disclosure furthermore provides medicaments comprising at least one modified relaxin, usually together with one or more inert nontoxic pharmaceutically suitable auxiliaries, and also their use for the purposes mentioned above. Optionally said medicament may comprise said modified relaxin and another active ingredient, such as those identified above. For example, said medicament may comprise said modified relaxin and another active ingredient in an amount effective for the treatment or prevention of heart failure and/or a disease associated with fibrosis.

EXAMPLES

Example 1: Ribosomal Incorporate of a Non-Naturally Encoded Amino Acid into PreproRelaxin This example exemplifies cloning and expression of a relaxin polypeptide including a non-naturally encoded amino acid in *E. coli.*

Methods for cloning relaxin are known to those of ordinary skill in the art. Polypeptide and polynucleotide sequences for relaxin and cloning of relaxin into host cells are detailed in U.S. Pat. Nos. 4,758,516; 5,166,191; 5,179,195, 5,945,402; and 5,759,807; all of which patents are herein incorporated by reference.

cDNA encoding relaxin is shown as SEQ ID NO: 12 and the mature polypeptide amino acid sequence is shown as SEQ ID NO: 1. Exemplary relaxin sequences are provided in Table 1.

TABLE 1

Relaxin Sequences

| SEQ ID NO: | Sequence Name | Sequence |
|---|---|---|
| 1 | Relaxin amino acid sequence (A and B chains) | QLYSALANKCCHVGCTKRSLARFC DSWMEEVIKLCGRELVRAQIAICGMSTWS |
| 2 | Relaxin amino acid sequence B1 Ala (A and B chains) | QLYSALANKCCHVGCTKRSLARFC ASWMEEVIKLCGRELVRAQIAICGMSTWS |
| 3 | Exemplary pro-relaxin amino acid sequence | DSWMEEVIKLCGRELVRAQIAICGMSTWSRREAEDLQVGQ VELGGGPGAGSLQPLALEGSLQKRQLYSALANKCCHVGCT KRSLARFC |
| 4 | Relaxin A chain, amino acid sequence | QLYSALANKCCHVGCTKRSLARFC |
| 5 | Relaxin B chain, amino acid sequence | DSWMEEVIKLCGRELVRAQIAICGMSTWS |
| 6 | Relaxin B chain, amino acid sequence with B1 Ala | ASWMEEVIKLCGRELVRAQIAICGMSTWS |
| 7 | Exemplary C peptide (connecting peptide) amino acid sequence | RREAEDLQVGQVELGGGPGAGSLQPLALEGSLQKR |
| 8 | Exemplary Relaxin leader amino acid sequence | MKKNIAFLLKR |
| 9 | Exemplary Insulin leader amino acid sequence | MIEGGR |
| 10 | Exemplary Relaxin A chain, nucleic acid sequence | caactctacagtgcattggctaataaatgttgccatgttggttgtaccaaaagatctcttgctagatt ttgc |
| 11 | Exemplary Relaxin B chain, nucleic acid sequence | gactcatggatggaggaagttattaaattatgggccgcgaattagttcgcgcgcagattgccat ttgcggcatgagcacctggagc |

TABLE 1-continued

Relaxin Sequences

| SEQ ID NO: | Sequence Name | Sequence |
|---|---|---|
| 12 | Exemplary Relaxin, A and B chains, nucleic acid sequence | caactctacagtgcattggctaataaatgttgccatgttggttgtaccaaaagatctcttgctagattttgc gactcatggatggaggaagttattaaattatgcggccgcgaattagttcgcgcgcagattgccat ttgcggcatgagcacctggagc |
| 13 | Exemplary Relaxin leader nucleic acid sequence | atgaaaaagaatatcgcatttatcttaaacgg |
| 14 | Exemplary Insulin leader nucleic acid sequence | atgattgaaggtggtcgt |
| 15 | Example of a relaxin expression construct amino acid sequence | MIEGGRDSWMEEVIKLCGRELVRAQIAICGMSTWSRREAED LQVGQVELGGGPGAGSLQPLALEGSLQKRQLYSALANKCC HVGCTKRSLARFC |
| 35 | Relaxin A chain substituted with para-acetyl-L-phenylalanine at position 1 | (pAcF)LYSALANKCCHVGCTKRSLARFC |
| 36 | Relaxin A chain substituted with asparagine at position 1 | NLYSALANKCCHVGCTKRSLARFC |
| 37 | Relaxin B chain substituted with para-acetyl phenylalanine at position 25 | ASWMEEVIKLCGRELVRAQIAICG(pAcF)STWS |
| 38 | Exemplary prepro-Relaxin expression sequence (X may be, e.g., pAcF) | MIEEGR ASWMEEVIKLCGRELVRAQIAICGMSTWS RREAEDLQVGQVELGGGPGAGSLQPLALEGSLQGR XLYSALANKCCHVGCTKRSLARFC |
| 39 | Exemplary Insulin leader amino acid sequence | MIEEGR |

An introduced translation system that comprises an orthogonal tRNA (O-tRNA) and an orthogonal aminoacyl tRNA synthetase (O—RS) is used to express relaxin or relaxin analogs containing a non-naturally encoded amino acid. The O—RS preferentially aminoacylates the O-tRNA with a non-naturally encoded amino acid. In turn the translation system inserts the non-naturally encoded amino acid into the relaxin or relaxin analog, in response to an encoded selector codon. Suitable O—RS and O-tRNA sequences are described in WO 2006/068802 entitled "Compositions of Aminoacyl-tRNA Synthetase and Uses Thereof" (E9; SEQ ID NO: 16) and WO 2007/021297 entitled "Compositions of tRNA and Uses Thereof" (F13; SEQ ID NO: 17), which are incorporated by reference in their entirety herein. Exemplary sequences that may be utilized are illustrated in Table 2.

TABLE 2

Sequences Utilized in Expression Systems

| | | |
|---|---|---|
| SEQ ID NO: 18 | *M. jannaschii* mtRNA$_{CUA}^{Tyr}$ | tRNA |
| SEQ ID NO: 19 | HLAD03; an optimized amber supressor tRNA | tRNA |
| SEQ ID NO: 20 | HL325A; an optimized AGGA frameshift supressor tRNA | tRNA |
| SEQ ID NO: 21 | Aminoacyl tRNA synthetase for the incorporation of p-azido-L-phenylalanine p-Az-PheRS(6) | RS |
| SEQ ID NO: 22 | Aminoacyl tRNA synthetase for the incorporation of p-benzoyl-L-phenylalanine p-BpaRS(1) | RS |
| SEQ ID NO: 23 | Aminoacyl tRNA synthetase for the incorporation of propargyl-phenylalanine Propargyl-PheRS | RS |
| SEQ ID NO: 24 | Aminoacyl tRNA synthetase for the incorporation of propargyl-phenylalanine Propargyl-PheRS | RS |
| SEQ ID NO: 25 | Aminoacyl tRNA synthetase for the incorporation of propargyl-phenylalanine Propargyl-PheRS | RS |
| SEQ ID NO: 26 | Aminoacyl tRNA synthetase for the incorporation of p-azido-phenylalanine p-Az-PheRS(1) | RS |

TABLE 2-continued

Sequences Utilized in Expression Systems

| | | |
|---|---|---|
| SEQ ID NO: 27 | Aminoacyl tRNA synthetase for the incorporation of p-azido-phenylalanine p-Az-PheRS(3) | RS |
| SEQ ID NO: 28 | Aminoacyl tRNA synthetase for the incorporation of p-azido-phenylalanine p-Az-PheRS(4) | RS |
| SEQ ID NO: 29 | Aminoacyl tRNA synthetase for the incorporation of p-azido-phenylalanine p-Az-PheRS(2) | RS |
| SEQ ID NO: 30 | Aminoacyl tRNA synthetase for the incorporation of p-acetyl-phenylalanine (LW1) | RS |
| SEQ ID NO: 31 | Aminoacyl tRNA synthetase for the incorporation of p-acetyl-phenylalanine (LW5) | RS |
| SEQ ID NO: 32 | Aminoacyl tRNA synthetase for the incorporation of p-acetyl-phenylalanine (LW6) | RS |
| SEQ ID NO: 33 | Aminoacyl tRNA synthetase for the incorporation of p-azido-phenylalanine (AzPheRS-5) | RS |
| SEQ ID NO: 34 | Aminoacyl tRNA synthetase for the incorporation of p-azido-phenylalanine (AzPheRS-6) | RS |

The transformation of *E. coli* with plasmids containing the modified relaxin or relaxin analog gene and the orthogonal aminoacyl tRNA synthetase/tRNA pair (specific for the desired non-naturally encoded amino acid) allows the site-specific incorporation of non-naturally encoded amino acid into the relaxin polypeptide, as described in U.S. Pat. No. 8,735,539, which is incorporated herein in its entirety.

Wild type mature relaxin is amplified by PCR from a cDNA synthesis reaction using standard protocols and cloned into a plasmid vector, such as pET30 (NcoI-BamHI). Relaxin sequence is subcloned into a suppression vector containing an amber suppressor tyrosyl tRNATyr/CUA from *Methanococcus jannaschii* (Mj tRNATyr/CUA) under constitutive control of a synthetic promoter derived from the *E. coli* lipoprotein promoter sequence (Miller, J. H., Gene, 1986), as well as well as the orthogonal tyrosyl-tRNA-synthetase (MjTyrRS) (e.g. E9) under control of the *E. coli* GlnRS promoter. Expression of relaxin is under control of the T7 promoter, which is indirectly induced by L-arabinose. Amber mutations are introduced using standard quick change mutation protocols (Stratagene; La Jolla, Calif.). Constructs are sequence verified.

Suppression with Para-Acetyl-Phenylalanine (pAcF)

Plasmids containing the modified relaxin gene comprising an amber mutation (encoding SEQ ID NO: 38 with pAcF at A chain residue 1, see FIG. 4) and the orthogonal aminoacyl tRNA synthetase/tRNA pair as described above were used to transform into the *Escherichia coli* strain W3110B55 [F-IN (rrnD-rrnE) lambdaaraB::g1 tetA fhuA::dhfr proS W375R::cat] to produce strains of *E. coli* in which expression of the T7 polymerase was under control of an arabinose-inducible promoter. Overnight bacterial cultures are diluted 1:100 into shake flasks containing 2×YT culture media and grown at 37° C. to an $OD_{600}$ of ~0.8. Protein expression is induced by the addition of arabinose (0.2% final), and para-acetyl-phenylalanine (pAcF) to a final concentration of 4 mM. Cultures are incubated at 37° C. for 5 hours. Cells are pelleted and resuspended in B-PER lysis buffer (Pierce) 100 ul/OD/ml+10 ug/ml DNase and incubated at 37° C. for 30 min. Cellular material is removed by centrifugation and the supernatant removed. The pellet is re-suspended in an equal amount of SDS-PAGE protein loading buffer. All samples are loaded on a 4-12% PAGE gel with MES and DTT. Expression of relaxin is confirmed by SDS-PAGE, Western Blot analyses, or electrospray-ionization ion trap mass spectrometry and the like.

The modified relaxin gene sequence may include an N-terminal His tag, e.g., HHHHHHSGG (SEQ ID NO: 55). His-tagged mutant relaxin proteins can be purified using methods known to those of ordinary skill in the art. The ProBond Nickel-Chelating Resin (Invitrogen, Carlsbad, Calif.) may be used via the standard His-tagged protein purification procedures provided by the manufacturer. Functional measurements of the proteins may be done through methods known in the art, methods provided within this application and incorporated references, and alternatively an ELISA on live cells can be developed to assess relaxin polypeptides of the invention.

Example 2: Production and Purification of Mature Relaxin Containing a Non-Naturally Encoded Amino Acid PreproRelaxin (SEQ ID NO: 38 with pAcF at A chain residue 1, see FIG. 4) was produced by fermentation in *E. coli* cells as inclusion bodies. The non-naturally encoded amino acid para-acetyl-phenylalanine was ribosomally incorporated using the general methods provided in Example 1.

*E. coli* cells containing the plasmid expressing modified relaxin polypeptide were grown in a fermentor containing fermentation medium. Kanamycin was added to the fermentor to promote plasmid stability. L-alanine-L-para-acetyl-phenylalanine hydrochloride (L-Ala-pAcF) was added to the fermentor to enable incorporation of p-acetylphenylalanine (pAcF) in the PreproRelaxin amino acid sequence. Finally, L-arabinose was added to induce PreproRelaxin expression. The PreproRelaxin produced inside the cells resulted in the formation of insoluble inclusion bodies (IBs). The fermentation broth was harvested after a post-induction duration. The fermentation titer was approximately 4.5 g of Prepro-Relaxin per L of fermentation.

The inclusion bodies (IBs) were separated from the intact cells by lysing the cells under high shear. The intact IBs were recovered by centrifugation. After recovery, the IB pellets were re-suspended in water and re-centrifuged to remove impurities. The washed IBs were solubilized at pH 8.5 in 5M guanidine/Tris buffer containing 5 mM dithiothreitol (DTT). Refolding of PreproRelaxin was achieved by slowly diluting the solubilized IB solution approximately 4.5 fold into chilled pH 8.5 Tris buffer containing 5 mM DTT and 8.5 mM cystamine. The refold solution was incubated for a minimum of 12 hrs before continuing with processing. After the incubation period was complete the pH was dropped to 3.5-4.0 by addition of acetic acid and hydrochloric acid, to promote precipitation of impurities. Precipitated material was removed by centrifugation followed by depth filtration.

The depth filtered refold solution was diluted approximately 6.5 fold with pH 4 acetate buffer to reduce the conductivity in preparation for loading onto a Tosoh Bioscience SP550C cation exchange column. After loading, the SP550C column was washed and then PreproRelaxin was eluted using a 10%-90% gradient of 50 mM acetate pH 5.5 buffer containing 1M NaCl. The SP550C eluate was diluted with purified water until the PreproRelaxin concentration was 1.5 mg/mL. The pH was adjusted to 8.0 by addition of 2M Tris, pH 8.0 followed by addition of 2 mM CaCl2 in preparation for enzymatic conversion.

Wild type trypsin was modified with succinic anhydride (i.e. succinylation) to facilitate removal from the PreproRelaxin/trypsin reaction mixture at the completion the trypsin treatment step. Concentrated wild type trypsin in 10 mM HCl, 20 mM CaCl2 was diluted to 5 mg/mL with purified water then 1M pH 7.6 borate buffer was added to a final concentration of 0.2M. Solid succinic anyhydride was added to the diluted, pH adjusted trypsin solution in a 100 molar excess over trypsin in three equi-molar additions (3×33.3 molar excess additions) mixing for 10 minutes between each addition.

Succinylated trypsin was added to the PreproRelaxin solution incubated at 22° C. for 4 hours to ensure complete enzymatic removal of the connecting peptide and leader sequence of the PreproRelaxin molecule. The resulting Relaxin-R molecule contains a C-terminal arginine on the B-chain. The trypsin treated material was next processed through a Sartobind STIC® PA anion exchange filter which binds the succinylated trypsin while the Relaxin-R was collected in the flow through. Carboxypeptidase-B (CPB) was added to the STIC® PA filtrate and incubated with stirring for 2 hours to ensure complete enzymatic removal of the B-chain C-terminal arginine residue. The CPB reaction was quenched by dropping the pH of the reaction mixture to 2.8-3.2.

The mature Relaxin was purified using Tosoh Bioscience SP-5PW cation exchange resin. The mature Relaxin was loaded onto the column and then followed by three column washes; 1) 50 mM acetate pH 5.5, 2) 50 mM acetate pH 5.5, 0.1 M NaCl and, 3) 50 mM acetate pH 4.0. Bound relaxin was eluted at pH 4 using a linear gradient from 0% to 100% 2M KCl over 20 column volumes. The eluted Relaxin solution was pH adjusted to 3.0 using 1M HCl before further processing. Alternatively, trypsin was removed from the reaction mixture by precipitation. Relaxin precipitates after increasing the pH of the reaction mixture to 8.0 for 1 hour at room temperature. Precipitated Relaxin was then recovered by centrifugation. The pellet was washed 3 times by resuspending the pellet in pH 8 Tris buffer followed by centrifugation. After the final wash, the pellet was re-solubilized in 20 mM acetic acid. Purified Relaxin did not show any tryptic activity. The final product was mature Relaxin.

Essentially the same synthesis method was used to produce RLX-AQ1 ("AQ1") (FIG. 2) and RLX-BM25/AN1 ("BM25/AN1") (FIG. 3), with the appropriate modification of the PreproRelaxin sequence.

Example 3: Conjugation of Relaxin to PK Enhancer Comprising a Peptide Linked to a Fatty Acid The purified Relaxin was concentrated by ultrafiltration to approximately 10 mg/mL. Aminooxy activated PK enhancer comprising a peptide and a C15 fatty acid (e.g., GGGGS-Glu$^Y$ (SEQ ID NO: 139)-C14-COOH) was added to the reaction mixture at a 1.5 molar excess over Relaxin. A hydrazide additive (i.e. 4 amino-benzoichydrazide) was then added at a 45 molar excess over Relaxin. The solution was adjusted as needed with 1 M HCl to maintain a pH between 3.5 and 4.0 and the temperature was controlled at 30° C. The conjugation reaction formed a stable oxime bond between the peptide linker linked to a C15 fatty acid (e.g., GGGGS-Glu$^Y$ (SEQ ID NO: 139)-C14-COOH), as prepared following the procedure described in Example 4, and the para-acetyl-phenylalanine residue in Relaxin. The reaction was complete within 16 hours.

The conjugation reaction mixture was diluted to <4 mS/cm with 10 mM pH 4.0 acetate buffer then loaded on to a GE Healthcare SP HP cation exchange column. After loading was complete, the column was washed with 20 mM histidine pH 6.0 to remove impurities. The Relaxin-C15 conjugate (comprising, e.g., AQ1-Relaxin-GGGGS-Glu$^Y$ (SEQ ID NO: 139)-C14-COOH) was then eluted with 50 mM ammonium bicarbonate, pH 8.5. The structure of the mature relaxin is illustrated schematically in FIG. 5 and in Formula III:

(Formula III)

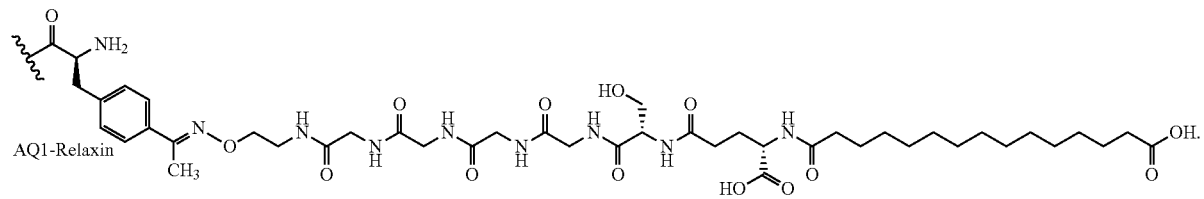

The purified Relaxin-C15 conjugate was concentrated and then diafiltered into an appropriate final formulation buffer. An exemplary composition of the conjugate is 8 mg/mL Relaxin-C15 conjugate in 20 mM histidine, 0.25 M sucrose, 0.05% (w/v) polysorbate-80, pH 5.5. The composition is stored frozen at 5 −60° C.

Other Relaxin-fatty acid conjugates may be prepared using similar processes.

Example 4: Solid Phase Synthesis of PK Enhancers

The PK Enhancers disclosed herein may be prepared using the procedures exemplified below.

The abbreviations used in the present application, including particularly in the illustrative schemes and examples which follow, are known to those skilled in the art. Some of the abbreviations used are as follows: min for minutes; h for hours; rt for room temperature; sat. for saturated; TFA for trifluoroacetic acid; DMF for N,N-dimethylformamide; DCM for dichloromethane; Fmoc for 9-fluorenylmethyloxycarbonyl; HATU=1-[Bis(dimethylamino)methylene]-1H-1,2,3-triazolo[4,5-b]pyridinium 3-oxid hexafluorophosphate; DIEA or DIPEA for diisopropylethylamine; NMP for N-methylpyrrolidone; EDC for I-ethyl-3-(3-dimethylaminopropyl)carbodiimide; DMSO for dimethylsulfoxide; MeOH for methanol; EtOAc for ethyl acetate; $Et_3N$ for triethylamine; MeCN or ACN for acetonitrile.

Analytical Data:

Mass Spectrometry: "ESI-MS(+)" signifies electrospray ionization mass spectrometry performed in positive ion mode; "ESI-MS(−)" signifies electrospray ionization mass spectrometry performed in negative ion mode; "ESI-HRMS (+)" signifies high-resolution electrospray ionization mass spectrometry performed in positive ion mode; "ESI-HRMS (−)" signifies high-resolution electrospray ionization mass spectrometry performed in negative ion mode. The detected masses are reported following the "m/z" unit designation. Compounds with exact masses greater than 1000 were often detected as double-charged, triple-charged ions, and/or quadruple-charged ions. CAD: Charged aerosol detector. ELSD: Evaporative light scattering detector.

Analysis LCMS Condition A:

Column: Waters Acuity UHPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 min, then a 1.0-min hold at 100% B; Flow: 1 mL/min; Detection: mass.

Analysis LCMS Condition B:

Column: Waters Acuity UHPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 1.0-min hold at 100% B; Flow: 1.0 mL/min; Detection: mass.

Analysis UHPLC-CAD Condition A:

Column: Waters BEH Phenyl, 150×2.1 mm, 1.7-μm particles; Mobile phase A: water with 0.05% TFA, Mobile phase B: acetonitrile with 0.05% TFA; Temperature: 35° C.; Gradient Profile: 10% B to 35% B from 0 min to 15 min, 35% B to 95% B from 16 min to 25 min, then a 1.0 min hold at 95% B; Post Run Time: 4 min (under the initial mobile phase conditions); Flow rate: 0.35 mL/min; Injection volume: 3 μL of 2 mg/mL sample in DMSO; Detection: CAD at 100 PA range and 35 psi gas.

Analysis UHPLC-CAD Condition B:

Column: Waters BEH Phenyl, 150×2.1 mm, 1.7-μm particles; Mobile phase A: water with 0.05% TFA, Mobile phase B: acetonitrile with 0.05% TFA; Temperature: 35° C.; Gradient Profile: 10% B to 95% B from 0 min to 25 min, then a 1.0 min hold at 95% B; Post Run Time: 4 min (under the initial mobile phase conditions); Flow rate: 0.35 mL/min; Injection volume: 3 μL of 2 mg/mL sample in DMSO; Detection: CAD at 100 PA range and 34 psi gas.

General Procedures:

All manipulations were performed under automation on a Prelude peptide synthesizer (Protein Technologies). All procedures unless noted were performed in a 40 mL polypropylene reaction vessel fitted with a bottom fit. The vessel connected to the Prelude peptide synthesizer through both the bottom and the top of the vessel. DMF can be added through the top and bottom of the vessel, which washes up and down the sides of the vessel equally. The reagents were added only through the bottom of the vessel and pass up through the frit to contact the resin. All solutions were removed through the bottom of the vessel. "Periodic agitation" describes a brief pulse of $N_2$ gas through the bottom frit; the pulse lasted approximately 5 seconds and occurred every 30 seconds. Amino acid solutions were generally not used beyond two weeks from preparation. HATU solutions were used within two weeks of preparation. DMF=dimethylformamide; HATU=1-[Bis(dimethylamino)methylene]-1H-1,2,3-triazolo[4,5-b]pyridinium 3-oxid hexafluorophosphate; DIPEA=diisopropylethylamine; 2-chlorotrityl chloride resin=2-chlorotriphenylmethyl chloride resin (Chem-Imprex, 100-200 mesh, yellow beads, 1.1 meg/g). Common amino acids used are listed below with side-chain protecting groups indicated inside parenthesis. Fmoc-Ala-OH; Fmoc-Arg(Pbf)-OH; Fmoc-Asn(Trt)-OH; Fmoc-Asp(O$^t$Bu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Hyp($^t$Bu)-OH; Fmoc-Ile-OH; Fmoc-Leu-OH; Fmoc-Lys(Boc)-OH; Fmoc-Nle-OH; Fmoc-Met-OH; Ftnoc-[N-Me]Ala-OH; Fmoc[N-Me]Nle-OH; Frnoc-Phe-OH; Fmoc-Pro-OH; Fmoc-Sar-OH; Fmoc-Ser($^t$Bu)-OH; Fmoc-Thr($^t$Bu)-OH; Fmoc-Trp(Boc)-OH; Fmoc-Tyr($^t$Bu)-OH; Fmoc-Val-OH. The following fatty acid derivatives were used for the very last coupling step, $HO_2C(CH_2)_nCH_3$, n=10–18, and $HO_2C(CH_2)_n(CO_2{}^tBu)$, n=10–18.

The general procedure describes an experiment performed on a 0.4 mmol scale, where the scale was determined by the amount of (9H-fluoren-9-yl)methyl (2-(aminooxy)ethyl)carbamate bound to the resin. This scale corresponds to approximately 364 mg of the resin described above. However, 800 mg of the resin was used based on the assumption of 46% of loading efficiency. The excess of 2-chlorotriphenylmethyl chloride was quenched by methanol at the end of loading reaction. All procedures can be scaled down from 0.400 mmol scale by adjusting the described volumes by the multiple of the scale. Prior to amino acid coupling, all peptide synthesis sequences began with a linker loading procedure and resin-swelling procedure, described below as "Linker Loading Procedure", and "Resin-Swelling Procedure". Then, coupling of amino acids to a primary amine N-terminus used the "Primary Amine-Coupling Procedure" described below. Coupling of amino acids to a secondary amine N-terminus used the "Secondary-Coupling Procedure" described below. Global deprotection and cleavage from resins used the "Global Deprotection Procedure" described below. Finally, the preparation of clear solution containing crude products for LC-MS purification used the "Sample Preparation Procedure" described below.

Linker-Loading Procedure:

The scale 0.4 mmol was used to prepare six reaction vessels (RVs) with a loading of 0.4 mmol of (9H-fluoren-9-yl)methyl (2-(aminooxy)ethyl)carbamate for the resins in each RV. DIEA (2.95 mL, 16.9 mmol) was added to a mixture of (9H-fluoren-9-yl)methyl (2-(aminooxy)ethyl)carbamate hydrochloride (compound 4, 0.803 g, 2.4 mmol) in $CH_2Cl_2$ (72 mL) at 0° C. Immediately after it became homogeneous, 12 mL of this clear solution was added to a 30 mL vial containing 800 mg of 2-chlorotrityl chloride resin. All 6 vials were placed on a shaker for 75 min at 750 rpm. Then, 0.2 mL of MeOH was added to one vial at a time, each shaken for 2 min at 750 rpm. The resins were transferred to a 40 mL RV, washed with $CH_2Cl_2$ (8 mL×3), DMF (8 mL×3), $CH_2Cl_2$ (10 mL×3). This process (MeOH quench and $CH_2Cl_2$/DMF/$CH_2Cl_2$ washes) were applied to the other 5 vials to afford resin bound linker compound 5 in six RVs.

Resin-Swelling Procedure:

The RVs containing the resins from the previous step were connected to the Prelude Peptide Synthesizer, and washed (swelled) three times as follows: to the RV was added DMF (10 mL), after which the mixture was periodically agitated for 10 min before the solvent was drained through the frit.

Primary Amine-Coupling Procedure:

To the RV containing resin from the previous step was added piperidine:DMF (20:80 v/v, 10.0 mL). The mixture was periodically agitated for 5 min and then the solution was drained through the frit. To the RV was again added piperidine:DMF (20:80 v/v, 10.0 mL). The mixture was periodically agitated for 5 min and then the solution was drained through the frit. The resin was bottom-washed once as follows: DMF (10.0 mL) was added through the bottom of the vessel and the resulting mixture was periodically agitated for 2 min before the solution was drained through the frit. The resin was top-washed successively four times as follows: for each wash, DMF (10.0 mL) was added through the top of the vessel and the resulting mixture was periodically agitated for 2 min before the solution was drained through the frit. To the RV was added an amino acid or a fatty acid (0.2 M in DMF, 4.0 mL, 2 eq), HATU (0.2 M in DMF, 4.0 mL, 2 eq), and DIPEA (0.8 M in DMF, 2.0 mL, 4 eq) in that order. The mixture was periodically agitated for 15 min or 30 min, then the reaction mixture solution was drained through the frit (the 15 min reaction time was used only for the very first coupling reaction to form the first amide bond on the Prelude synthesizer; for all other sequences, the 30 min reaction time was applied). The resin was washed successively three times as follows: for each wash, DMF (8.0 mL) was added through the top of the vessel and the resulting mixture was periodically agitated for 2 min before the solution was drained through the frit. To the RV was added DMF (3.3 mL), DIPEA (0.8 M in DMF, 1.5 mL, 3 eq). After the mixture was agitated for 30 seconds, acetic anhydride (1.0 M in DMF, 5.0 mL, 12.5 eq) was added. The mixture was periodically agitated for 10 min, then the solution was drained through the frit. The resin was bottom-washed once as follows: DMF (10.0 mL) was added through the bottom of the vessel and the resulting mixture was periodically agitated for 2 min before the solution was drained through the frit. The resin was top-washed successively four times as follows: for each wash, DMF (10.0 mL) was added through the top of the vessel and the resulting mixture was periodically agitated for 2 min before the solution was drained through the frit. The resulting resin was used directly in the next step.

Secondary Amine-Coupling Procedure:

To the RV containing the resins from the previous step was added piperidine:DMF (20:80 v/v, 10.0 mL). The mixture was periodically agitated for 5 min and then the solution was drained through the frit. To the RV was again added piperidine:DMF (20:80 v/v, 10.0 mL). The mixture was periodically agitated for 5 min and then the solution was drained through the frit. The resin was bottom-washed once as follows: DMF (10.0 mL) was added through the bottom of the vessel and the resulting mixture was periodically agitated for 2 min before the solution was drained through the frit. The resin was top-washed successively four times as follows: for each wash, DMF (10.0 mL) was added through the top of the vessel and the resulting mixture was periodically agitated for 2 min before the solution was drained through the frit. To the reaction vessel was added an amino acid or a fatty acid (0.2 M in DMF, 4.0 mL, 2 eq), HATU (0.2 M in DMF, 4.0 mL, 2 eq), and DIPEA (0.8 M in DMF, 2.0 mL, 4 eq) in this order. The mixture was periodically agitated for 30 min, then the reaction solution was drained through the frit. The resin was top-washed successively three times as follows: for each wash, DMF (8.0 mL) was added through the top of the vessel and the resulting mixture was periodically agitated for 2 min before the solution was drained through the frit. To the reaction vessel was added again an amino acid or a fatty acid (0.2 M in DMF, 4.0 mL, 2 eq), HATU (0.2 M in DMF, 4.0 mL, 2 eq), and DIPEA (0.8 M in DMF, 2.0 mL, 4 eq) in this order. The mixture was periodically agitated for 30 min, then the reaction solution was drained through the frit. The resin was top-washed successively three times as follows: for each wash, DMF (8.0 mL) was added through the top of the vessel and the resulting mixture was periodically agitated for 2 min before the solution was drained through the frit. To the RV was added DMF (3.3 mL), DIPEA (0.8 M in DMF, 1.5 mL, 3 eq). After the mixture was agitated for 30 seconds, acetic anhydride (1.0 M in DMF, 5.0 mL, 12.5 eq) was added. The mixture was periodically agitated for 10 min, then the solution was drained through the frit. The resin was bottom-washed once as follows: DMF (10.0 mL) was added through the bottom of the vessel and the resulting mixture was periodically agitated for 2 min before the solution was drained through the frit. The resin was top-washed successively four times as follows: for each wash, DMF (10.0 mL) was added through the top of the vessel and the resulting mixture was periodically agitated for 2 min before the solution was drained through the frit. The resulting resin was used directly in the next step.

Global Deprotection Procedure:

After the procedure on the Prelude was finished, each RV was washed with $CH_2Cl_2$ (8 mL×6), and allowed to air dry. Once the resin was free flowing, it was transferred into a 30 mL vial, and 8 mL of the cleavage solution (see below) was added. After the vial was agitated in a shaker for 75 min at 750 rpm, the reaction mixture was filtered. The resulting clear tan solution was divided into four 25 mL test tubes, each containing 16 mL of diethyl ether, resulting in the formation of white suspensions. Each was centrifuged, washed twice with diethyl ether to form white solids in each of the test tubes. The cleavage solution (50 mL) was prepared as follows: to a 250 ml Erlenmeyer flask was added 500 mg dithiothreitol, 46 mL TFA, 2.5 mL water, and 1.0 mL triisopropylsilane, with stirring to form a clear solution.

Sample Preparation Procedure:

To each test tube containing crude product obtained from the previous step was added, in order, 0.4 mL DMSO and 0.4 mL MeOH. After stirring for 1 min, a clear solution was formed in many cases. However, if solids were still present in the test tube, more DMSO (0.2 mL) was added, and the mixture was stirred for 2 min. At this point, if solids remained, the clear solution was removed and more DMSO (up to 1.0 mL) was added. The resulting clear solution was subjected to preparative LC-MS at 2.0 mL per injection.

Synthesis of Compound A
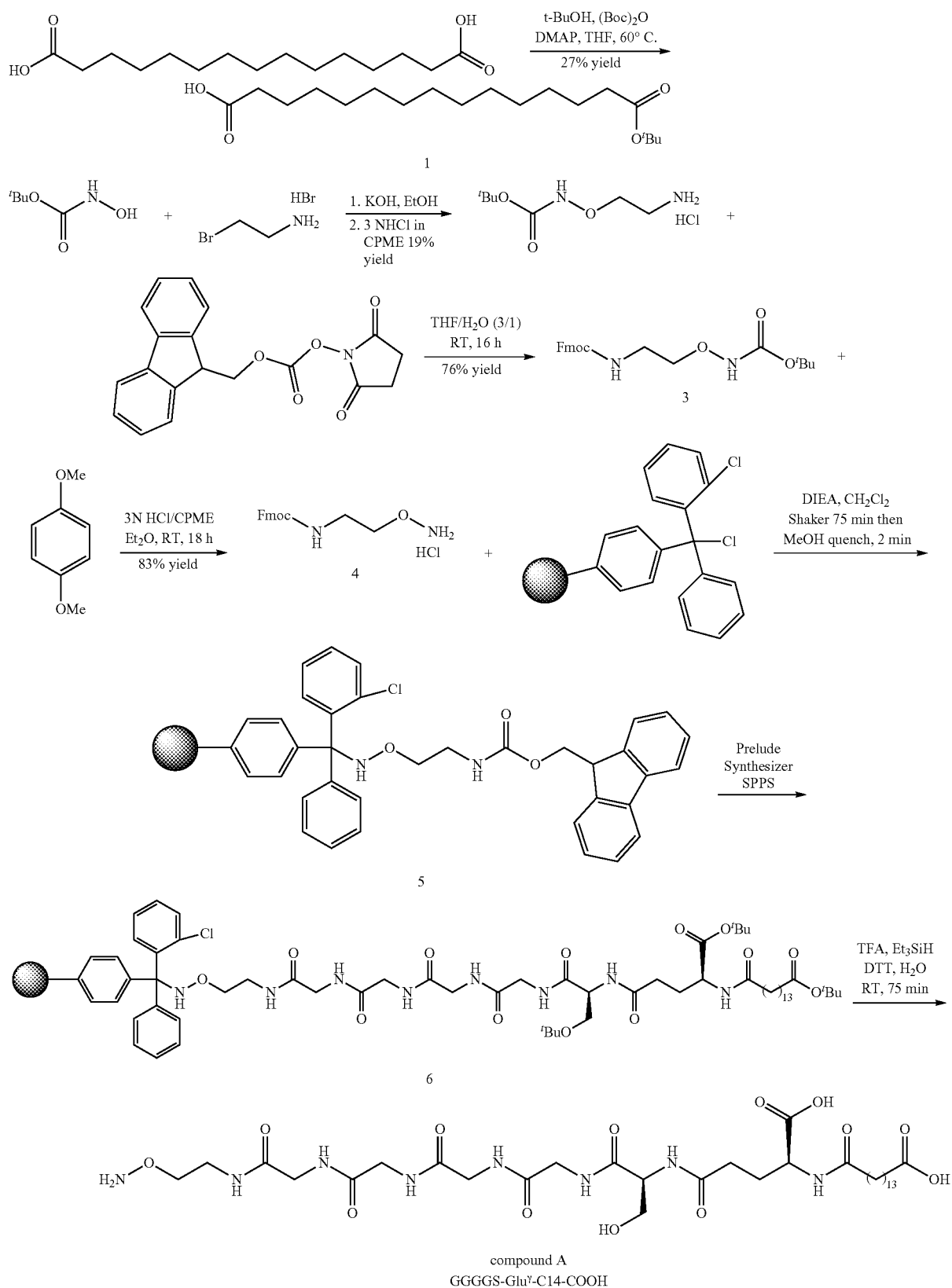
compound A
GGGGS-Glu$^\gamma$-C14-COOH

DMAP (2.80 g, 23.0 mmol) was added to a mixture of pentadecanedioic acid (25.0 g, 92.0 mmol) in 2-Me-THF (250 mL). After stirring at rt for 10 min, tert-butanol (13.2 mL, 138 mmol) was added and stirring was continued at rt for 10 min. After the resulting suspension was heated at 60° C. for 10 min, it became a clear colorless solution. A solution of BOC-anhydride (26.0 g, 119 mmol) in THF (100 mL) was added over 2 h in a pressure-equalized addition funnel to the above reaction mixture at 60° C. Toward the end of addition, the reaction mixture became a light pink clear solution. Stirring was continued at 60° C. for 18 h. After cooling to 0° C., 100 mL of 1.5 N HCl was added over 5 min. Then, the mixture was warmed to rt and stirred for 15 min. After separation, the organic layer was washed with brine (250 mL×2), dried over Na$_2$SO$_4$, filtered, and concentrated. The resulting material was suspended in acetonitrile (250 mL), stirred at rt for 1 h, and filtered to remove unreacted diacid starting material. Then, the filtrate was concentrated to approximately 125 mL. The resulting suspension was stirred at 0° C. for 2 h, becoming cloudier over time. The resulting solid was filtered, washed with cold (0° C.) acetonitrile (2×15 mL), and dried, affording 15-(tert-butoxy)-15-oxo-pentadecanoic acid (compound 1, 8.20 g, 25.0 mmol, 27.2% yield) as an off white solid. NMR (400 MHz, CDCl$_3$, ppm) δ 2.35 (t, J=7.58 Hz, 2H), 2.20 (t, J=7.46 Hz, 2H), 1.68-1.54 (m, 4H), 1.45 (s, 9H), 1.34-1.24 (m, 18H). $^{13}$C NMR (125 MHz, CDCl$_3$, ppm) δ 179.91, 173.44, 79.93, 35.64, 34.08, 29.57, 29.48, 29.46, 29.41, 29.39, 29.29, 29.23, 29.09, 29.06, 28.12, 25.12, 24.70.

The following compounds were prepared according to the above procedure, HO$_2$C(CH$_2$)—CO$_2$$^t$Bu, n=10–18. The separation of desired product—mono ester HO$_2$C(CH$_2$)$_n$CO$_2$$^t$Bu from unreacted diacid HO$_2$C(CH$_2$)$_n$CO$_2$H and overreacted diester $^t$BuO$_2$C(CH$_2$)$_n$CO$_2$$^t$Bu was achieved in each case by utilizing their differing solubilities in acetonitrile.

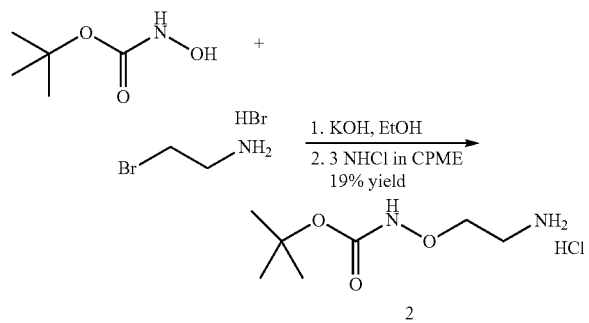

Potassium hydroxide (74.1 g, 1122 mmol) was added in portions over 10 min to a clear solution of tert-butyl N-hydroxycarbamate (50.0 g, 376 mmol) in anhydrous ethanol (500 mL) at 0° C., using a mechanical stirrer. After stirring at 0° C. for 10 min, and then at rt for 20 min, the reaction mixture was cooled to 0° C., and 2-bromoethylamine hydrobromide (100 g, 488 mmol) was added in portions over 15 min. After stirring at 0° C. for 30 min, and then at rt for 5 h, the resulting white suspensions were filtered and the filter cake was washed with EtOH (40 mL×2). The combined filtrates were concentrated to a volume of 100 mL, extracted with t-BuOMe (500 mL) and H$_2$O (250 mL). After separation, the aqueous layer was extracted with t-BuOMe (200 mL). The combined organic layers were washed with brine (2×200 mL), dried over Na$_2$SO$_4$, filtered, concentrated and dried under high vacuum to afford a very viscous liquid (20.0 g). The resulting liquid was dissolved in t-BuOMe (300 mL). HCl (3 M in cyclopentylmethyl ether) (40 mL, 120 mmol) was added dropwise to the above clear solution at rt. A white suspension was formed. After stirring at rt for 4 h, the resulting white solids were filtered, washed with t-BuOMe, and dried under vacuum for 45 min to afford tert-butyl 2-aminoethoxycarbamate hydrochloride (compound 2, 15.5 g, 72.9 mmol, 19.4% yield) as a white solid. $^1$H NMR (400 MHz, DMSO-d$_6$, ppm) δ 10.21 (br s, 1H), 8.27 (br s, 2.6H), 3.92 (t, J=5.26 Hz, 2H), 2.98 (t, J=5.26 Hz, 2H), 1.41 (s, 9H). $^{13}$C NMR (125 MHz, DMSO-d$_6$, ppm) δ 157.10, 80.79, 72.00, 37.46, 28.46.

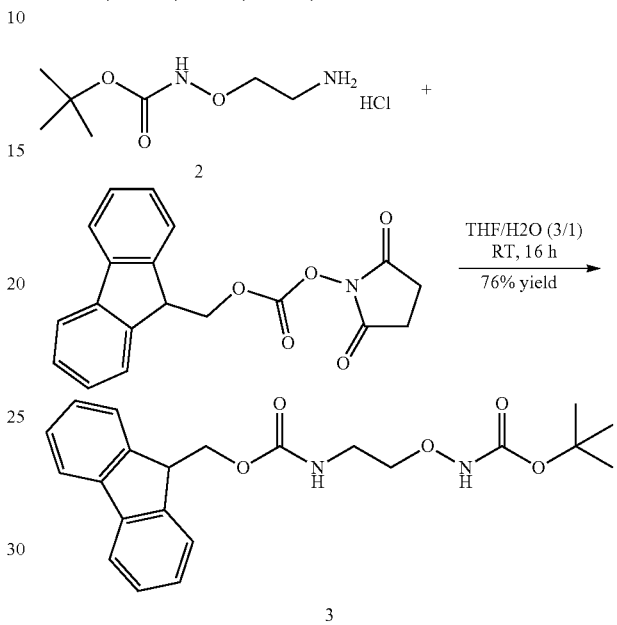

Sodium bicarbonate (8.00 g, 95 mmol) was added to a stirred mixture of tert-butyl 2-aminoethoxycarbamate hydrochloride (compound 2, 13.5 g, 63.5 mmol), Fmoc-OSu (25.7 g, 76.0 mmol) in THF (450 mL) and water (150 mL). After stirred at rt overnight, all volatiles components were removed under vacuum. The residue was extracted with EtOAc (400 mL, 200 mL) after the aqueous layer had been saturated with solid NaCl. The combined organic layers were dried over Na$_2$SO$_4$, filtered, concentrated. The residue was subjected to flash chromatography on silica gel, eluting with EtOAc/hexanes. The purer fractions were combined, concentrated, and the residue was re-purified using the above conditions. Again, the purer fractions were combined and concentrated. The residue was purified a third time using identical conditions. The pure fractions were combined, concentrated, and dried under high vacuum to afford (compound 3, 19.2 g, 48.2 mmol, 76% yield). $^1$H NMR (400 MHz, CDCl$_3$, ppm) δ 7.78 (d, J=7.32 Hz, 2H), 7.65 (d, J=7.32 Hz, 2H), 7.63, (s, 1H), 7.42 (t, J=7.32 Hz, 2H), 7.33 (t, J=7.232 Hz, 2H), 6.00 (br s, 1H), 4.40 (d, 2H), 4.26 (t, J=7.10 Hz, 1H), 3.91 (t, J=4.20 Hz, 2H), 3.49-3.46 (m, 2H), 1.52 (s, 9H). $^{13}$C NMR (125 MHz, CDCl$_3$, ppm) δ 157.54, 156.90, 144.06, 141.32, 127.68, 127.08, 125.23, 119.96, 82.11, 75.66, 66.91, 47.30, 39.23, 28.24.

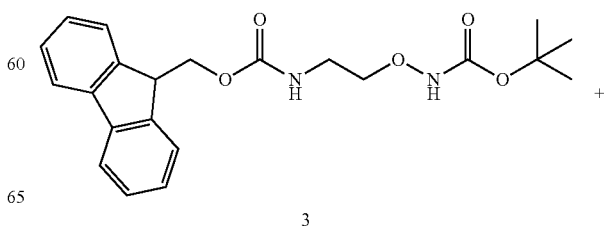

-continued

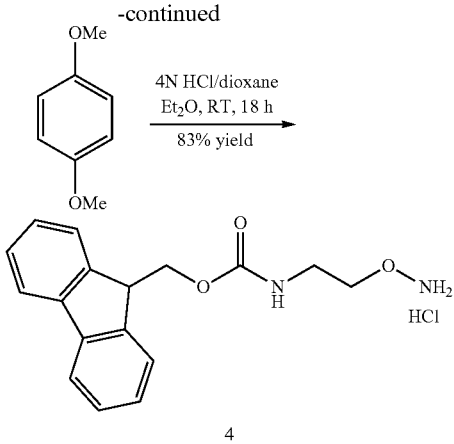

4

HCl (100 mL, 400 mmol, 4 M in dioxane) was added at rt to a stirred solution of compound 3 (8.6 g, 21.6 mmol), 1,4-dimethoxybenzene (7.46 g, 54.0 mmol) in diethyl ether (100 mL). After stirring at rt overnight, the mixture became a thick suspension that could be barely stirred. More ether (400 mL) was added and the resulting suspension was stirred at rt for 30 min. It was then filtered under nitrogen and the solids washed with ether (3×100 mL) to afford compound 4 (6.36 g, 19.0 mmol, 87% yield) as a white solid. $^1$H NMR (400 MHz, DMSO-$d_6$, ppm) δ 11.10 (br, s, 2.60 H), 7.89 (d, J=7.58 Hz, 2H), 7.70 (d, J=7.34 Hz, 2H), 7.54 (br t, J=5.5 Hz, 1H), 7.42 (t, J=7.32 Hz, 2H), 7.34 (t, J=7.32 Hz, 2H), 4.31 (d, J=6.6 Hz, 2H), 4.23 (t, J=6.6 Hz, 1H), 4.06 (t, J=5.38 Hz, 2H), 3.28 (q, J=5.22 Hz). $^{13}$C NMR (125 MHz, DMSO-$d_6$, ppm) δ 156.74, 144.32, 141.22, 128.11, 127.57, 125.64, 120.60, 73.50, 66.08, 47.17, 38.91.

Compound A

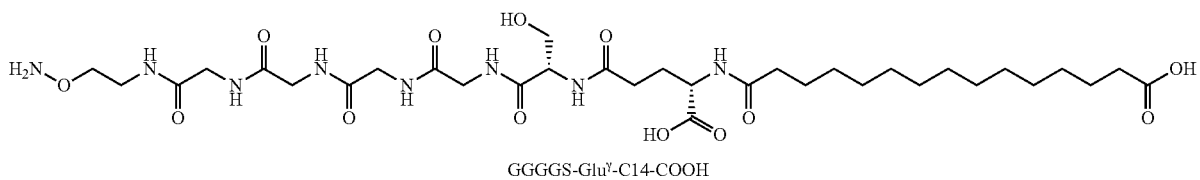

GGGGS-Glu$^\gamma$-C14-COOH

The crude material was purified via preparative LC/MS using the following conditions: Column: XBridge CSH C18, 19×200 mm, 5-μm particles; Mobile Phase A: 5:95 acetonitrile: water with 0.1% triflouroacetic acid; Mobile Phase B: 95:5 acetonitrile: water with 01.% triflouroacetic acid; Gradient: 0-34.9% B over 23 min, then a 2-min hold at 100% B; Flow: 20 mL/min. Fractions containing the desired product were combined and volatile organics were removed using a flow of nitrogen. The resulting aqueous containing the desired product was cooled to −78° C. under a flow of nitrogen and lyophilized to afford the title compound A as a white solid (88 mg, 25.9% yield, LC-CAD purity 98.6%).

Analysis condition A: Retention time=1.24 min; ESI-MS (M+H)$^+$=775.30.

Analysis condition B: Retention time=1.05 min; ESI-MS (M+H)$^+$=775.25.

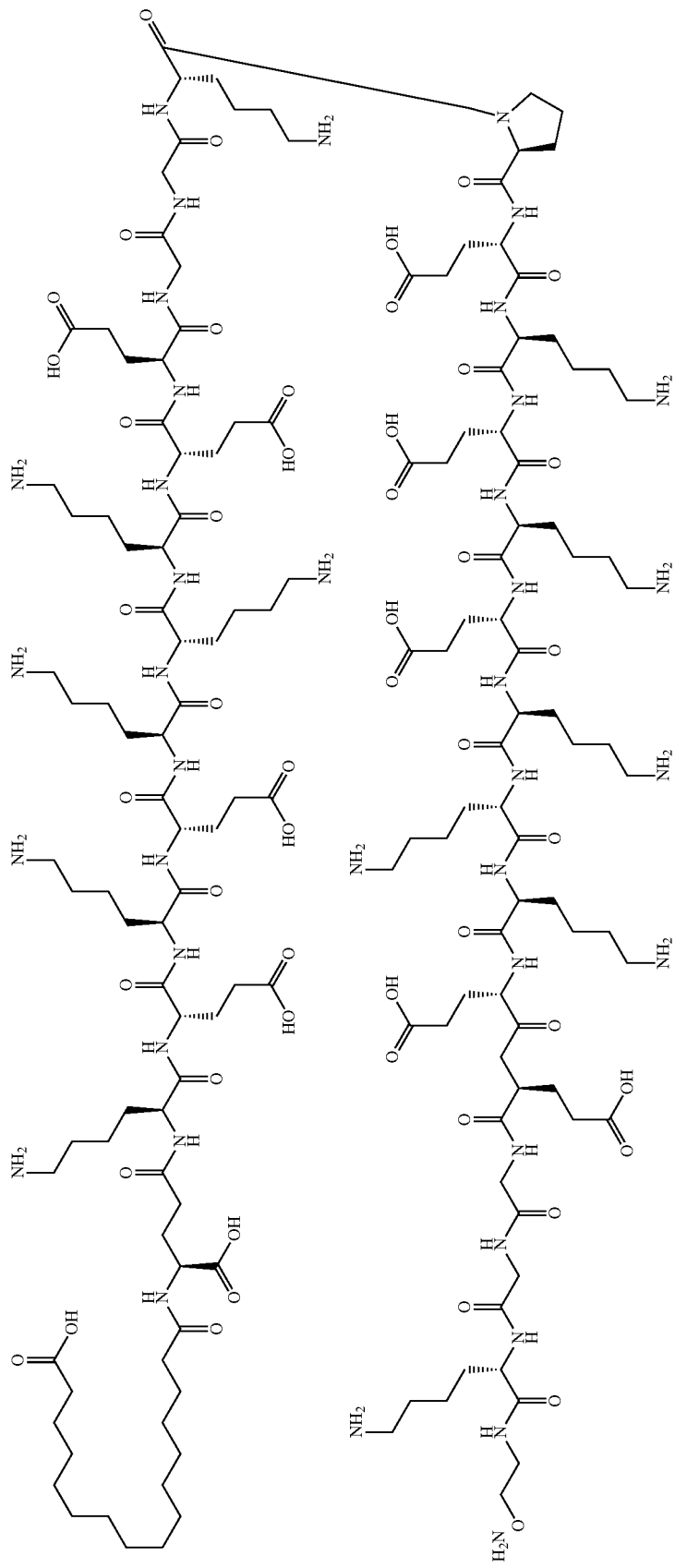

The crude material was purified via preparative LC/MS using the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 20-70% B over 20 min, then a 5-min hold at 100% B; Flow: 20 mL/min. Fractions containing the desired product were combined and volatile organics were removed using a flow of nitrogen. The resulting aqueous containing the desired product was cooled to −78° C. under a flow of nitrogen and lyophilized to afford the title compound as a white solid (47 mg, 3.4% yield, LC-CAD purity 72%).

Analysis condition A: Retention time=1.14 min; ESI-MS $(M+3H)^{+3}$=1166.90, $(M+3H)^{+4}$=875.45.

Analysis condition B: Retention time=0.991 min; ESI-MS $(M+3H)^{+3}$=1166.90, $(M+3H)^{+4}$=875.50.

Example 5: Solution Phase Synthesis of PK Enhancers

The PK enhancers disclosed herein may be prepared using the procedures exemplified below.

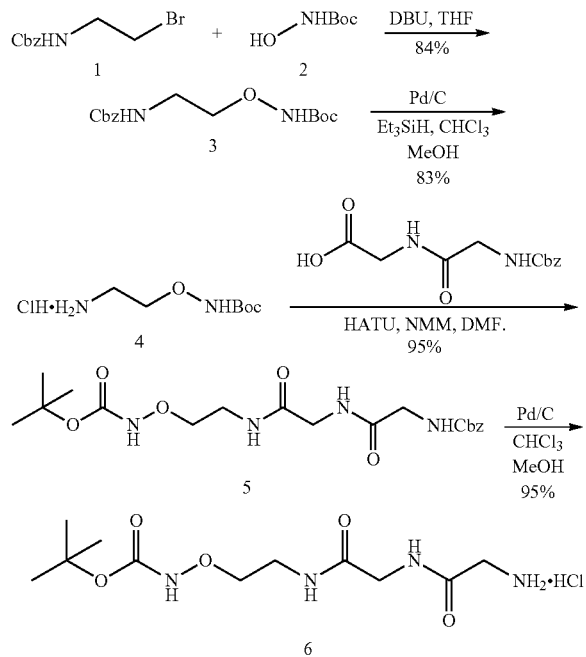

Benzyl (2-(((tert-butoxycarbonyl)amino)oxy)ethyl) carbamate, 3

DBU (26.3 ml, 174 mmol) was added portionwise to a stirring mixture of benzyl (2-bromoethyl)carbamate (30 g, 116 mmol) and tert-butyl hydroxycarbamate (24.76 g, 186 mmol) in THF (75 ml). The reaction mixture was stirred overnight at rt (precipitates was observed). LCMS shows only trace amount of starting material left. The reaction mixture was concentrated, quenched with water, extracted with ethyl acetate. The ethyl acetate phase were combined, washed with water, brine, then dried with $Na_2SO_4$. After concentration, 45 g crude product was obtained and submitted for chromatography separation (0-20% acetone in hexane). After separation, Benzyl (2-(((tert-butoxycarbonyl) amino)oxy)ethyl)carbamate (32.9 g, 106 mmol, 91% yield) was obtained as a very viscous light yellow oil. $^1$H NMR (400 MHz, CHLOROFORM-d) δ 7.43-7.30 (m, 5H), 5.75 (br. s., 1H), 5.32 (s, 1H), 5.14 (s, 2H), 3.94-3.85 (m, 2H), 3.54-3.42 (m, 2H), 1.50 (s, 9H).

tert-butyl (2-aminoethoxy)carbamate hydrochloride, 4

Benzyl (2-(((tert-butoxycarbonyl)amino)oxy)ethyl)carbamate (16.4 g, 52.8 mmol) was dissolved in MeOH (161 ml) and chloroform (5.33 ml, 66.1 mmol) was added. The solution was purged with nitrogen before the careful addition of Pd/C (2.81 g, 2.64 mmol). The solution was then cooled to 0° C. and triethylsilane (76 ml, 476 mmol) added dropwise slowly. $H_2$ evolution was observed during the addition and it was exothermic. After addition, the reaction was then allowed to warm up gradually to rt overnight. The reaction mixture was filtered through a celite pad and washed with additional methanol before evaporating in vacuo. The residue was then triturated with hexane and the resulting solid was filtered, washed with additional hexane and allowed to dry under suction to give tert-butyl 2-aminoethoxycarbamate hydrochloride (10.2 g, 48.0 mmol, 91% yield) as a pinkish solid. $^1$H NMR (400 MHz, CHLOROFORM-d) δ 8.78 (br. s., 1H), 8.31 (br. s., 2H), 4.24 (s., 2H), 3.39 (s., 2H), 1.48 (s, 9H).

tert-butyl ((3,6,9-trioxo-1-phenyl-2-oxa-4,7,10-triazadodecane-12-yl)oxy)carbamate, 5

N-Methylmorpholine (5.17 ml, 47.0 mmol) was added dropwise to a solution of tert-butyl 2-aminoethoxycarbamate hydrochloride (4 g, 18.81 mmol), 242-(((benzyloxy) carbonyl)amino)acetamido)acetic acid (5.01 g, 18.81 mmol) and HATU (7.87 g, 20.69 mmol) in anhydrous DMF (75 ml). The mixture was allowed to stir at rt overnight. The reaction was diluted with ethyl acetate and washed with 1N HCl. The separated aqueous was then extracted with an additional portion of ethyl acetate and the combined organics were then washed with 1N HCl, brine, sat. sodium bicarbonate solution followed by an additional brine wash. The organic layer was then dried ($Na_2SO_4$) and evaporated in vacuo. The crude was then purified by column chromatography using ethyl acetate-hexane as eluant to give 6.25 g (78%) of title compound. $^1$H NMR (400 MHz, CHLOROFORM-d) δ 7.69 (s, 1H), 7.41-7.28 (m, 6H), 7.00-6.87 (m, 1H), 5.81 (br s, 1H), 5.14 (s, 2H), 3.98 (dd, J=16.7, 5.7 Hz, 4H), 3.86 (t, J=4.8 Hz, 2H), 3.55-3.46 (m, 2H), 1.46 (s, 9H). MS m/e 447.0 (M+Na$^+$).

tert-butyl (2-(2-(2-aminoacetamido)acetamido)ethoxy)carbamate hydrochloride, 6

5 (6.25 g, 14.72 mmol) was dissolved in anhydrous methanol (58.9 ml) and chloroform (1.782 ml, 22.09 mmol) added followed by Pd-C (1.567 g, 1.472 mmol). The reaction flask was then purged with hydrogen (balloon) and allowed to stir for 6 hrs before filtering through celite and evaporating to give tert-butyl 2-(2-(2-aminoacetamido)acetamido)ethoxycarbamate hydrochloride (4.87 g, 14.90 mmol, 101% yield). $^1$H NMR (400 MHz, DMSO-$d_6$) δ 10.00 (br s, 1H), 8.71 (br t, J=5.7 Hz, 1H), 8.18-7.99 (m, 4H), 3.77 (d, J=5.7 Hz, 2H), 3.69 (t, J=5.9 Hz, 2H), 3.59 (s, 2H), 3.36-3.23 (m, 3H), 1.41 (s, 9H).

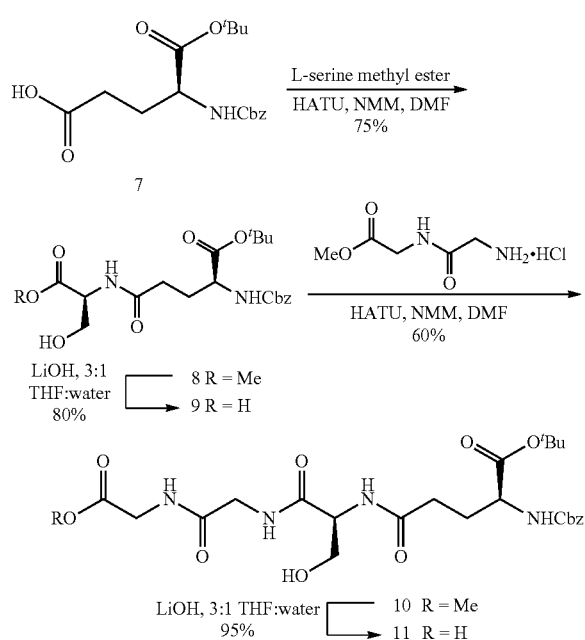

(S)-tert-butyl 2-(((benzyloxy)carbonyl)amino)-5-(((S)-3-hydroxy-1-methoxy-1-oxopropan-2-yl)amino)-5-oxopentanoate, 8

(S)-4-(((benzyloxy)carbonyl)amino)-5-(tert-butoxy)-5-oxopentanoic acid (7., purchased from Chemlmpex) (15 g, 44.5 mmol) and (S)-methyl 2-amino-3-hydroxypropanoate hydrochloride (6.92 g, 44.5 mmol) was dissolved in DMF (148 ml) and the solution was cooled to 0° C. HATU (18.60 g, 48.9 mmol) was added followed by N-methylmorpholine (12.22 ml, 111 mmol). The reaction was allowed to stir at 0° C. under $N_2$ for 12 hrs. The reaction mixture was diluted with EtOAc, quenched with 1N HCl, then washed with sat. $NaHCO_3$, and brine. The organic phase was dried over anhydrous $Na_2SO_4$ and concentrated in vacuo. The crude product was purified by chromatographic purification (0-40% acetone/Hexane) to give (S)-tert-butyl 2-(((benzyloxy)carbonyl)amino)-5-(((S)-3-hydroxy-1-methoxy-1-oxopropan-2-yl)amino)-5-oxopentanoate (16.31 g, 36.5 mmol, 82% yield) as an offwhite solid. $^1$H-NMR (CDCl$_3$, 400 MHz) δ 7.37 (m, 5H), 6.5 (bs, 1H), 5.53 (m, 1H); 5.1 (s, 2H), 4.7 (m, 1H), 4.28 (m, 1H), 4.1 (bs, 1H), 3.95 (m, 1H), 3.8 (s, 3H), 2.4 (m, 2H), 2.3 (M, 1H), 1.7 (m, 1H), 1.5 (s, 9H); MS m/e 439.2 (M+H$^+$).

(S)-2-((S)-4-(((benzyloxy)carbonyl)amino)-5-(tert-butoxy)-5-oxopentanamido)-3-hydroxypropanoic Acid, 9

(S)-tert-butyl 2-(((benzyloxy)carbonyl)amino)-5-(((S)-3-hydroxy-1-methoxy-1-oxopropan-2-yl)amino)-5-oxopentanoate (14 g, 31.9 mmol) was dissolved in THF (106 ml) and Water (53.2 ml) and was cooled to 0° C. After stirring for 30 minutes, LiOH (0.688 g, 28.7 mmol) was added. The reaction mixture was stirred at this temperature under $N_2$. After the reaction was completed, the pH of the reaction mixture was adjusted to ~4 at 0° C. The reaction mixture was extracted with EtOAc (3×150 ml). The combined organic phase was dried over anhydrous $Na_2SO_4$ and was concentrated under rot vap to give (S)-2-((S)-4-(((benzyloxy)carbonyl)amino)-5-(tert-butoxy)-5-oxopentanamido)-3-hydroxypropanoic acid (13.01 g, 30.7 mmol, 96% yield) as an off white solid. MS m/e 425.0 (M+H$^+$).

(5S,10S)-methyl 5-(tert-butoxycarbonyl)-10-(hydroxymethyl)-3,8,11,14-tetraoxo-1-phenyl-2-oxa-4,9,12,15-tetraazaheptadecan-17-oate, 10. Methyl 2-(2-aminoacetamido)acetate hydrochloride (5 g, 27.4 mmol) was dissolved in DMF (116 ml) and was charged (S)-2-((S)-4-(((benzyloxy)carbonyl)amino)-5-(tert-butoxy)-5-oxopentanamido)-3-hydroxypropanoic acid (11.62 g, 27.4 mmol). To this reaction mixture was added HATU (11.45 g, 30.1 mmol) and N-methylmorpholine (7.53 ml, 68.5 mmol). The reaction mixture was stirred at rt under $N_2$ for 12 hrs. LC/MS and HPLC indicated the completion of the reaction. The reaction mixture was diluted with EtOAc (150 mL) and was quenched with 1N HCl. The organic layer was separated and was washed with brine (50 mL), aq. $NaHCO_3$ (50 mL) and finally brine (3×50 mL). The organic layer was dried over anhydrous $Na_2SO_4$ and evaporated in vacua to give the desired product as a thick oil, which was for chromatographic purification (0-10% MeOH/DCM) to give the desired product (5S,10S)-methyl 5-(tert-butoxycarbonyl)-10-(hydroxymethyl)-3,8,11,14-tetraoxo-1-phenyl-2-oxa-4,9,12,15-tetraazaheptadecan-17-oate (14 g, 25.3 mmol, 93% yield) as a thick oil. $^1$H-NMR (CDCl$_3$, 400 MHz) δ 7.38 (m, 5H), 5.1 (m, 2H), 4.0 (m, 6H), 3.7 (s, 3H), 2.4 (m, 2H), 2.2 (M, 1H), 1.9 (m, 1H), 1.45 (s, 9H); MS m/e 553.2 (M+H$^+$).

(5S,10S)-5-(tert-butoxycarbonyl)-10-(hydroxymethyl)-3,8,11,14-tetraoxo-1-phenyl-2-oxa-4,9,12,15-tetraazaheptadecan-17-oic acid, 11. (55,10S)-methyl (5S,10S)-methyl 5-(tert-butoxycarbonyl)-10-(hydroxymethyl)-3,8,11,14-tetraoxo-1-phenyl-2-oxa-4,9,12,15-tetraazaheptadecan-17-oate (20 g, 36.2 mmol) was dissolved in THF (193 ml) and Water (97 ml) and was cooled to 0° C. After stirring for 30 minutes, LiOH (0.780 g, 32.6 mmol) was added. The reaction mixture was stirred at 0c under N2 for 5 hrs. Progress of the reaction was monitored by LC/MS and HPLC. After the reaction was completed, it was diluted with EtOAC (150 mL) and was neutralized by 1N HCl. The organic phase was separated, and the aqueous phase was extracted with EtOAc (3×50 mL), dried over anhydrous $Na_2SO_4$, concentrated under vacuo and dried under high vac for 12 hrs to give the desired product as an offwhite solid (18 g, 96% yield). MS m/e 539.1 (M+H$^+$).

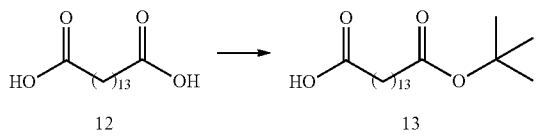

15-(tert-butoxy)-15-oxopentadecanoic Acid, 13

A suspension of pentadecanedioic acid (20.2 g, 70.5 mmol) in acetic anhydride (70 ml) was heated to 128° C. under Ar. The resulting solution was stirred at this temperature for 6.0 h and then cooled to room temperature. The solution was diluted with toluene (100 mL) and evaporated. The residue was stripped with toluene (4×80 mL) and dried under vacuum for 6.5 h to give 27.53 g of an off-white solid. To a mixture of the above solid (27.53 g) and t-butanol (235 ml), at room temperature and under Ar, was added 4-dimethylaminopyridine (34.8 g, 282 mmol) in three portions over a period of 15 min. The mixture was heated to 50° C. and the resulting solution was stirred at this temperature for 34.0 h. After cooling to room temperature, the mixture was diluted with toluene (50 mL) and evaporated. The residue was stripped with toluene (2×100 mL) and then taken up in 9/1 Ether/CH$_2$Cl$_2$ (600 mL). The solution was washed with 1M HCl (400 mL), 0.5M HCl (400 mL), water (300 mL) and brine (300 mL). The organic layer was dried (Na$_2$SO$_4$) and evaporated. The crude was taken up in CH$_2$Cl$_2$ (50 mL) and sonicated. The resulting suspension was filtered through a medium fritted funnel and the solid in the funnel was rinsed with two small portions of CH$_2$Cl$_2$. The filtrate and rinses were combined and evaporated. The concentrate was chromatographed (120 g flash column cartridge, CH$_2$Cl$_2$ to 9/1 CH$_2$Cl$_2$/i-PrOH) to give, in order of elution:
- a ~5/1 mixture (7.19 g, colorless oil) of di-tert-butyl pentadecanedioate and 15-(tert-butoxy)-15-oxopentadecanoic acid.
- 15-(tert-butoxy)-15-oxopentadecanoic acid (4.38 g, 19% yield) as a white solid: LC/MS [M–H]$^{-1}$=327; $^1$H NMR (400 MHz, CDCl$_3$) δ 2.37 (t, J=7.4 Hz, 2H), 2.22 (t, J=7.5 Hz, 2H), 1.63 (m, 4H), 1.47 (s, 9H), 1.28 (m, 18H).
- a ~4/1 mixture (4.42 g, off-white solid) of 15-(tert-butoxy)-15-oxopentadecanoic acid and pentadecanedioic acid.

The mixture of di- and mono tert-butyl esters (7.19 g) was separated by chromatography (120 g flash column cartridge, CH$_2$Cl$_2$ to 9/1 CH$_2$Cl$_2$/i-PrOH) to afford an additional amount 15-(tert-butoxy)-15-oxopentadecanoic acid (0.8 g, 4% yield) as a white solid.

The mixture of mono tert-butyl ester and diacid (4.42 g) was separated by chromatography (330 g flash column cartridge, Hex to 4/1 Hex/acetone) to afford an additional amount of 15-(tert-butoxy)-15-oxopentadecanoic acid (2.92 g, 13% yield) as a white solid.

The total isolated amount of 15-(tert-butoxy)-15-oxopentadecanoic acid was 8.1 g (36% yield).

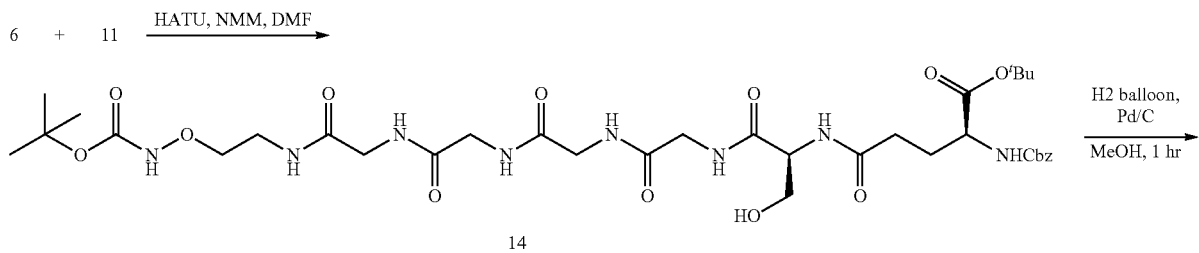

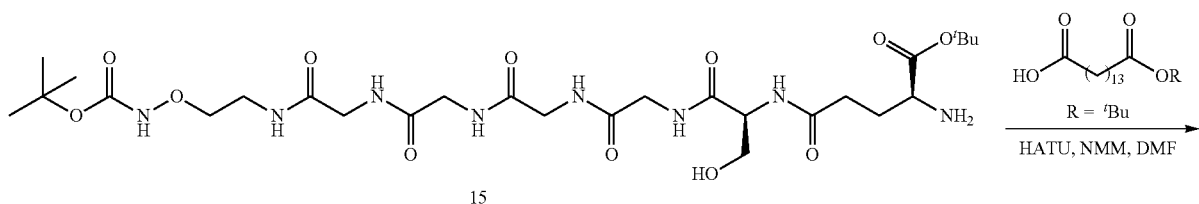

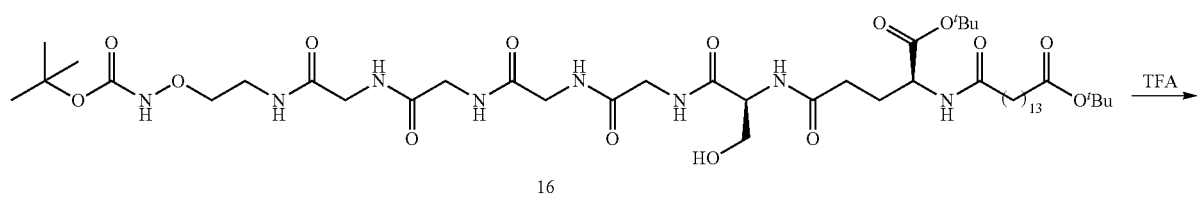

compound A tert-butyl N2-((benzyloxy)carbonyl)-N5-((S)-1-((2-((2-((2-((2,2-dimethyl-4,10-dioxo-3,6-dioxa-5,9-diazaundecan-11-yl)amino)-2-oxoethyl)amino)-2-oxoethyl)amino)-2-oxoethyl)amino)-3-hydroxy-1-oxopropan-2-yl)-L-glutaminate, 14 tert-butyl 2-(2-(2-aminoacetamido)acetamido)ethoxycarbamate hydrochloride (3.73 g, 11.41 mmol) and (5S,10S)-5-(tert-butoxycarbonyl)-10-(hydroxymethyl)-3,8,11,14-tetraoxo-1-phenyl-2-oxa-4,9,12,15-tetraazaheptadecan-17-oic acid (5.85 g, 10.87 mmol) were dissolved in DMF (36.2 ml) at rt under a nitrogen atmosphere. The solution was cooled to 0° C. before adding HATU (4.55 g, 11.96 mmol) followed by the dropwise addition of N-methyl morpholine (2.99 ml, 27.2 mmol). The reaction was allowed to warm to rt overnight. The reaction was cooled to 0° C. before quenching with ice water and stirring vigorously as the ice melted. When all of the ice had melted surrounding the flask, a ppte had formed which was then filtered with suction overnight (slow). The resulting waxy solid was dissolved in methanol (200 mL) before evaporating. Treatment with methanol (ca 20 mL) followed by the addition of diethyl ether then ppted the product which was collected by suction to give (23S, 28S)-tert-butyl 28-(((benzyloxy)carbonyl)amino)-23-(hydroxymethyl)-2,2-dimethyl-4,10,13,16,19,22,25-heptaoxo-3,6-dioxa-5,9,12,15,18,21,24-heptaazanonacosan-29-oate 6.4 g (73% yield). $^1$H NMR (400 MHz, DMSO-d$_6$) δ 9.96 (br s, 1H), 8.24-8.01 (m, 5H), 7.87 (br t, J=5.6 Hz, 1H), 7.62 (br d, J=7.8 Hz, 1H), 7.40-7.30 (m, 5H), 5.10-4.96 (m, 3H), 4.30-4.24 (m, 1H), 4.10 (q, J=5.3 Hz, 3H), 3.93-3.84 (m, 1H), 3.80-3.53 (m, 13H), 3.31-3.23 (m, 2H), 3.17 (d, J=5.3 Hz, 7H), 2.90 (s, 1H), 2.75-2.67 (m, 1H), 2.35-2.20 (m, 2H), 1.98-1.86 (m, 1H), 1.82-1.71 (m, 1H), 1.42-1.24 (m, 20H). MS m/e 811.4 (M+H$^+$).

tert-butyl N5-((S)-1-((2-((2-((2-((2,2-dimethyl-4,10-dioxo-3,6-dioxa-5,9-diazaundecan-11-yl)amino)-2-oxoethyl)amino)-2-oxoethyl)amino)-2-oxoethyl)amino)-3-hydroxy-1-oxopropan-2-yl)-L-glutaminate, 15

Methanol (158 ml) was added in one portion to (23S, 28S)-tert-butyl 28-(((benzyloxy)carbonyl)amino)-23-(hydroxymethyl)-2,2-dimethyl-4,10,13,16,19,22,25-heptaoxo-3,6-dioxa-5,9,12,15,18,21,24-heptaazanonacosan-29-oate (6.4 g, 7.89 mmol) and the solid was allowed to stir under a nitrogen atmosphere until the amine had dissolved (ca. 3 hrs). Pd/C (0.840 g, 0.789 mmol) was then added and an atmosphere of hydrogen was then introduced via a balloon. The reaction was allowed to stir at rt before filtering through glass filter paper and evaporating the filtrate to give (23S, 28S)-tert-butyl 28-amino-23-(hydroxymethyl)-2,2-dimethyl-4,10,13,16,19,22,25-heptaoxo-3,6-dioxa-5,9,12,15,18,21,24-heptaazanonacosan-29-oate 4.8 g (90% yield) as an off-white crispy solid.

$^1$H NMR (400 MHz, DMSO-d$_6$) δ 9.96 (br s, 1H), 8.29-8.19 (m, 1H), 8.17-7.96 (m, 3H), 7.87 (br t, J=5.7 Hz, 1H), 5.00 (br s, 1H), 4.28-4.08 (m, 1H), 3.78-3.56 (m, 10H), 3.30-3.14 (m, 3H), 2.90 (s, 1H), 2.75-2.67 (m, 1H), 2.34-2.06 (m, 3H), 1.87-1.74 (m, 1H), 1.68-1.50 (m, 1H), 1.41 (d, J=4.3 Hz, 15H), 1.10 (s, 1H).

tert-butyl (23S,28S)-28-(tert-butoxycarbonyl)-23-(hydroxymethyl)-2,2-dimethyl-4,10,13,16,19,22,25,30-octaoxo-3,6-dioxa-5,9,12,15,18,21,24,29-octaazatetratracontan-44-oate, 16

N-Methyl morpholine (1.950 ml, 17.73 mmol) was added dropwise to a partial solution of (23S,28S)-tert-butyl 28-amino-23-(hydroxymethyl)-2,2-dimethyl-4,10,13,16,19, 22,25-heptaoxo-3,6-dioxa-5,9,12,15,18,21,24-heptaazanonacosan-29-oate (4.8 g, 7.09 mmol), 15-(tert-butoxy)-15-oxopentadecanoic acid (2.446 g, 7.45 mmol) and HATU (2.97 g, 7.80 mmol) at 0° C. under a nitrogen atmosphere. An additional 20 mL DMF added was added to solubilize the reaction mixture which was then allowed to warm slowly to rt overnight. The reaction was then cooled in an ice batch before quenching with ice and allowing to melt whilst vigorously stirring the mixture. The solid was then filtered to give a gum-like solid (6.1 g) that was transferred to SFC for purification. SFC purification yielded (23S,28S)-tert-butyl 28-(tert-butoxycarbonyl)-23-(hydroxymethyl)-2,2-dimethyl-4,10,13,16,19,22,25,30-octaoxo-3,6-dioxa-5,9,12,15,18,21,24,29-octaazatetratracontan-44-oate (2.5 g, 2.53 mmol, 35.7% yield) as a white solid that was used in the next step. $^1$H NMR (400 MHz, DMSO-d$_6$) δ 9.96 (br s, 1H), 8.23-8.02 (m, 1H), 7.97 (br d, J=7.5 Hz, 1H), 7.84 (t, J-5.8 Hz, 1H), 4.96 (t, J=5.6 Hz, 1H), 4.32-4.21 (m, 1H), 4.17-4.03 (m, 1H), 3.85 (d, J=6.0 Hz, 1H), 3.76 (br d, J=5.1 Hz, 1H), 3.72-3.55 (m, 1H), 3.30-3.24 (m, 1H), 2.27-2.07 (m, 1H), 2.01-1.86 (m, 1H), 1.80-1.65 (m, 1H), 1.49-1.38 (m, 5H), 1.35 (br s, 1H), 1.29-1.16 (m, 4H). MS m/e 987.7 (M+H$^+$).

(17S,22S)-1-(aminooxy)-22-carboxy-17-(hydroxymethyl)-4,7,10,13,16,19,24-heptaoxo-3,6,9,12,15,18,23-heptaazaoctatriacontan-38-oic Acid, Compound A (23S,28S)-tert-butyl 28-(tert-butoxycarbonyl)-23-(hydroxymethyl)-2,2-dimethyl-4,10,13,16,19,22,25,30-octaoxo-3,6-dioxa-5,9,12,15,18,21,24,29-octaazatetratracontan-44-oate (2.5 g, 2.53 mmol) was dissolved in 25 mL+10 mL washing mixture of cooled 92:8 TFA:TIPS. The solution was added directly to the white solid and allowed to stir at rt for 3 hrs. The solution was cooled to 0° C. and 320 mL Heptane: 40 mL MTBE added before transferring to the refrigerator overnight. A clear oil had separated and was visible at the bottom of the flask. The supernatant was removed and cold diethyl ether (1 L) was added. The resulting white solid was stirred for 2 hrs before quickly filtering and drying in a buchner funnel to give (17S,22S)-1-(aminooxy)-22-carboxy-17-(hydroxymethyl)-4,7,10,13, 16,19,24-heptaoxo-3,6,9,12,15,18,23-heptaazaoctatriacontan-38-oic acid 2.1 g (95% yield). $^1$H NMR (400 MHz, DMSO-d$_6$) δ 8.42-8.34 (m, 1H), 8.20-7.95 (m, 3H), 4.81-4.74 (m, 1H), 4.61 (dd, J=10.9, 4.6 Hz, 1H), 4.48 (dd, J=10.8, 7.5 Hz, 1H), 4.30-4.03 (m, 1H), 3.93-3.30 (m, 10H), 2.47-2.39 (m, 1H), 2.33 (dt, J=3.7, 1.9 Hz, 1H), 2.27-2.08 (m, 3H), 2.05-1.91 (m, 1H), 1.82-1.69 (m, 1H), 1.52-1.43 (m, 2H), 1.24 (s, 9H), 1.21-1.00 (m, 1H). HPLC analysis with CAD detection indicated 81% purity, Agilent 1100 LC/UV/CAD, ACE C18-300 300×4.6 mm ID, 5 µm, A: Water 0.05% TFA; B: ACN 0.05% TFA.

Example 6: Solution Phase Syntheses of Additional PK Enhancers

Analysis LCMS Condition A:
Column: Waters Acuity UHPLC BEH C18, 2.1×50 mm, 1.7-µm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 min, then a 1.0-min hold at 100% B; Flow: 1 mL/min; Detection: mass.

Analysis LCMS Condition B:

Column: Waters Acuity UHPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 1.0-min hold at 100% B; Flow: 1.0 mL/min; Detection: mass.

Analysis UHPLC-ELSD Condition A: HPLC Conditions:

Column: Waters BEH C18, 150×2.1 mm, 1.7-µm particles; Mobile phase A: water with 0.05% TFA, Mobile phase B: acetonitrile with 0.05% TFA; Temperature: 35° C.; Gradient Profile: 10% B to 50% B from 0 min to 15 min, 50% B to 60% B from 16 min to 20 min, 60% B to 95% B from 21 min to 26 min then a 4.0 min hold at 95% B; Post Run Time: 4 min (under the initial mobile phase conditions); Flow rate: 0.35 mL/min; Injection volume: 5 µL of 1 mg/mL sample in 50/50 MeCN/water; MS Conditions: Mass range m/z 120-2000. Ionization and mode: Electrospray ionization, positive ion mode. ELSD Conditions: Gain: 20. Drift tube temperature: 60° C. Gas flow rate: 40 psi.

Analysis UHPLC-ELSD Condition B: HPLC Conditions:

Column: Waters BEH CSH C18, 150×2.1 mm, 1.7-µm particles; Mobile phase A: water with 0.05% TFA, Mobile phase B: acetonitrile with 0.05% TFA; Temperature: 35° C.; Gradient Profile: 10% B to 95% B from 0 min to 24 min, then a 3.0 min hold at 95% B; Post Run Time: 4 min (under the initial mobile phase conditions); Flow rate: 0.35 mL/min; Injection volume: 2 µL of 1 mg/mL sample in 50/50 MeCN/water; MS Conditions: Mass range m/z 120-2000. Ionization and mode: Electrospray ionization, positive ion mode. ELSD Conditions: Gain: 50. Drift tube temperature: 60° C. Gas flow rate: 40 psi Analysis UHPLC-CAD Condition C: HPLC Conditions:

Column: Waters BEH Phenyl, 150×2.1 mm, 1.7-µm particles; Mobile phase A: water with 0.05% TFA, Mobile phase B: acetonitrile with 0.05% TFA; Temperature: 35° C.; Gradient Profile: 10% B to 95% B from 0 min to 25 min, then a 2.0 min hold at 95% B; Post Run Time: 4 min (under the initial mobile phase conditions); Flow rate: 0.35 mL/min; Injection volume: 5 µL of 1 mg/mL sample in MeOH; MS Conditions: Mass range m/z 120-2000. Ionization and mode: Electrospray ionization, positive ion mode. CAD Conditions: Range: 100 PA. Gas flow rate: 35 psi.

Analysis UHPLC-CAD Condition D: HPLC Conditions:

Column: Waters BEH Phenyl, 150×2.1 mm, 1.7-µm particles; Mobile phase A: water with 0.05% TFA, Mobile phase B: acetonitrile with 0.05% TFA; Temperature: 35° C.; Gradient Profile: 10% B to 35% B from 0 min to 15 min, 35% B to 95% B from 16 min to 25 min, then a 2.0 min hold at 95% B; Post Run Time: 3 min (under the initial mobile phase conditions); Flow rate: 0.35 mL/min; Injection volume: 2 µL of 1 mg/mL sample in 50/50 MeOH/water; MS Conditions: Mass range m/z 120-2000. Ionization and mode: Electrospray ionization, positive ion mode. CAD Conditions: Range: 100 PA. Gas flow rate: 35 psi Synthesis of $PEG_{36}$-$Glu^{\gamma}$-$C_{13}$—$CH_3$ (8).

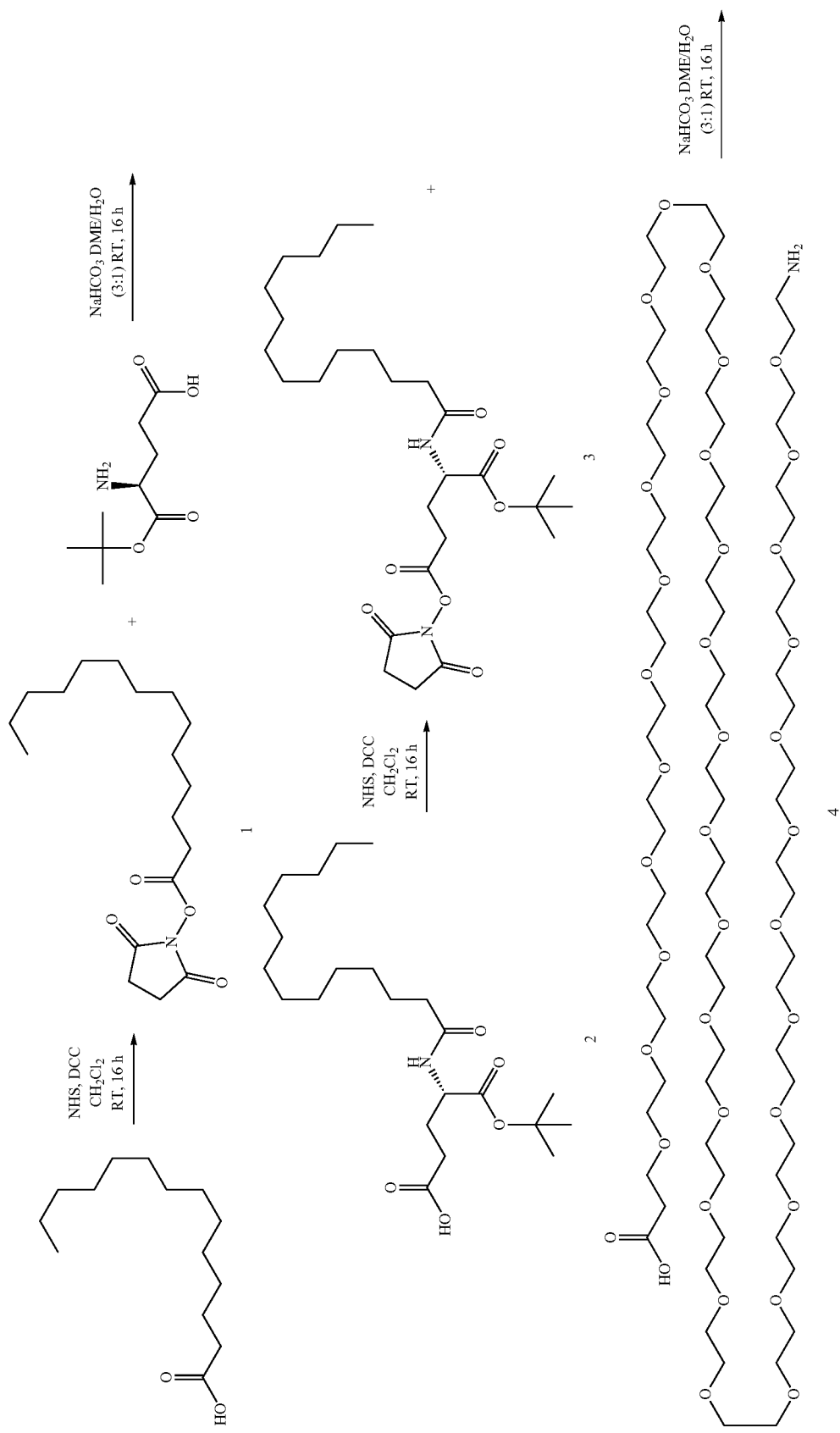

-continued
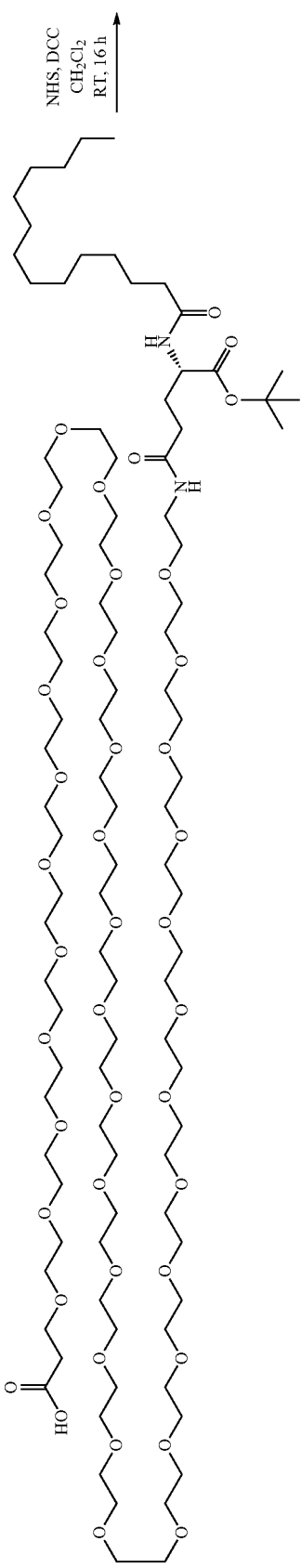
5
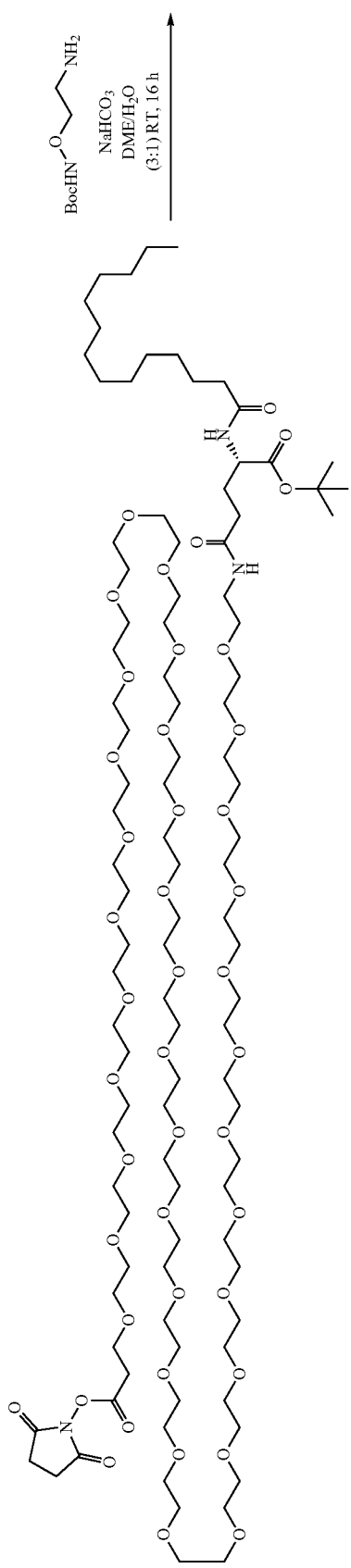
6
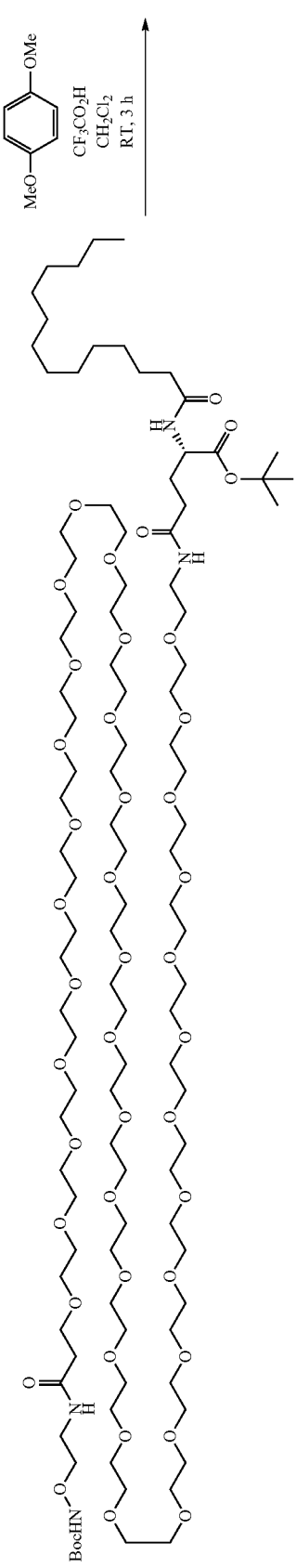
7

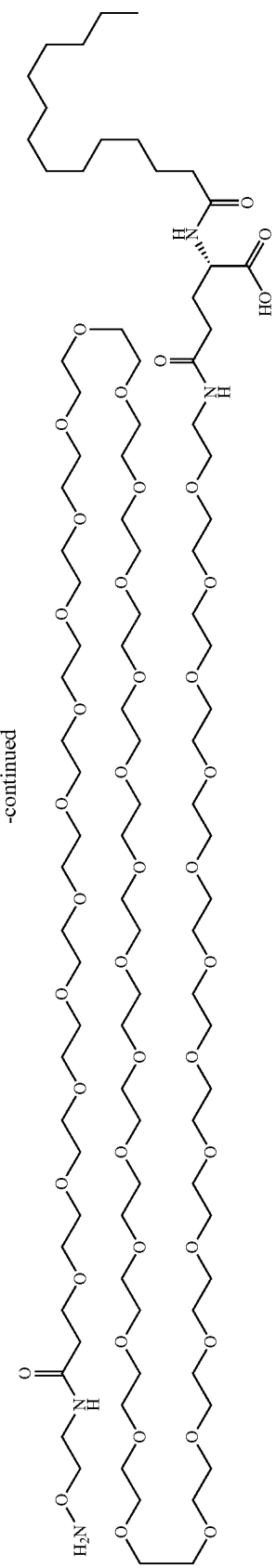

2,5-Dioxopyrrolidin-1-yl Tetradecanoate (1)

DCC in $CH_2Cl_2$ (1M, 99 mL, 99 mmol) was added to a stirred solution of tetradecanoic acid (20.55 g, 90 mmol) in DMF (100 mL). The mixture was stirred at RT overnight, filtered, concentrated and dried under high vacuum. The resulting solids were suspended in ether/hexanes (1:3, 80 mL) for 45 min, collected by filtration and dried to afford 2,5-dioxopyrrolidin-1-yl tetradecanoate (1) (16.96 g, 52.1 mmol, 58% yield) as a white solid, which was used directly in the next step without further purification.

(S)-5-(tert-Butoxy)-5-oxo-4-tetradecanamidopentanoic Acid (2)

Water (150 ml) was added to a stirred mixture of (S)-4-amino-5-(tert-butoxy)-5-oxopentanoic acid (10.5 g, 51.7 mmol), 2,5-dioxopyrrolidin-1-yl tetradecanoate (1) (16.81 g, 51.7 mmol), and $NaHCO_3$ (5.21 g, 62.0 mmol) in DME (450 mL). The resulting clear solution was stirred at RT for 4 h. DME was removed under vacuum, and then aqueous HCl (1 M, 67.2 ml, 67.2 mmol) was added to adjust the pH to 2-3. The resulting suspension was stirred at 0° C. for 30 min, and then filtered. The resulting white solid was azeotropically dried with DME (2×), then suspended in ether/hexanes 1:3 (160 mL) at RT for 1 h. The resulting white solid was collected by filtration and dried under high vacuum to afford (S)-5-(tert-butoxy)-5-oxo-4-tetradecanamidopentanoic acid (2) (8.5 g, 21 mmol, 40% yield), which was used directly in the next step without further purification.

(S)-1-tert-Butyl 5-(2,5-dioxopyrrolidin-1-yl) 2-tetradecanamidopentanedioate (3)

DCC in $CH_2Cl_2$ (1M, 26.6 mL, 26.6 mmol) was added to a stirred mixture of (S)-5-(tert-butoxy)-5-oxo-4-tetradecanamidopentanoic acid (2) (10.0 g, 24.2 mmol), and 1-hydroxypyrrolidine-2,5-dione (3.06 g, 26.6 mmol) in DMF (30 mL) at RT. The reaction mixture was stirred at RT overnight, filtered, and concentrated. The residue was dissolved in $CH_2Cl_2$ and purified by flash chromatography on silica gel, eluting with EtOAc/hexanes (1:2) to afford (S)-1-tert-butyl 5-(2,5-dioxopyrrolidin-1-yl) 2-tetradecanamidopentanedioate (3) (8.95 g, 17.5 mmol, 73% yield) as a white solid. $^1$H-NMR (CDCl$_3$, 400 MHz) δ 6.29 (d, J=8.0 Hz, 1H), 4.58 (m, 1H), 2.82 (s, 4H), 2.70 (m, 1H), 2.63 (m, 1H), 2.29 (m, 1H), 2.20 (t, J=7.5 Hz, 2H), 2.06 (m, 1H), 1.60 (m, 2H), 1.46 (s, 9H), 1.25 (m, 20H), 0.86 (t, J=6.3 Hz, 3H). $^{13}$C-NMR (CDCl$_3$, 100 MHz) δ ppm 173.0, 170.3, 168.7, 167.6, 82.4, 51.2, 36.0, 31.5, 29.29, 29.27, 29.25, 29.11, 28.97, 28.92, 27.6, 27.15, 27.10, 25.21, 25.11, 22.3, 13.7.

Compound 5.

Water (4.5 mL) was added at RT to a stirred mixture of compound 4 (750 mg, 0.448 mmol), (S)-1-tert-butyl 5-(2,5-dioxopyrrolidin-1-yl) 2-tetradecanamidopentanedioate 3 (297 mg, 0.582 mmol), and $NaHCO_3$ (75 mg, 0.90 mmol) in DME (13.5 mL). After the resulting clear solution was stirred at RT overnight, aqueous HCl (1M, 0.896 mL, 0.896 mmol) was added, and the mixture was concentrated under vacuum. The residue was purified by medium pressure reverse phase chromatography on a C-18 column, eluting with MeCN/aq.$NH_4$OAc (monitored by ELSD-MS). Fractions containing the desired product were combined and volatile organics were removed using a flow of nitrogen. The resulting aqueous solution containing the desired product was lyophilized to afford the title compound 5 (610 mg, 66% yield) as a white solid. $(M+2H)^{2+}$1036, $(M+3H)^{3+}$691.

Compound 6.

DCC in $CH_2Cl_2$ (1 M, 0.32 mL, 0.32 mmol) was added to a stirred mixture of compound 5 (550 mg, 0.266 mmol), and 1-hydroxypyrrolidine-2,5-dione (36.7 mg, 0.319 mmol) in $CH_2Cl_2$ (12 mL). The mixture was stirred at RT overnight, filtered, and concentrated under vacuum to afford compound 6 as a white solid, which was used directly in the next step without further purification.

Compound 7.

Water (2.5 mL) was added to a stirred mixture of compound 6 (577 mg, 0.266 mmol), tert-butyl 2-aminoethoxycarbamate (Miao, Z.; Liu, J.; Norman, T.; Driver, R. WO 2006/069246) (70.3 mg, 0.399 mmol), and $NaHCO_3$ (33.5 mg, 0.40 mmol) in DME (7.5 mL) at RT. The mixture was stirred at RT overnight and concentrated. The residue was purified by medium pressure reverse phase chromatography on a C-18 column, eluting with MeCN/aq.$NH_4$Cl (monitored by ELSD-MS). Fractions containing the desired product were combined and volatile organics were removed using a flow of nitrogen. The resulting aqueous solution containing the desired product was lyophilized to afford the title compound 7 (360 mg, 61% yield) as a white solid. $(M+2H)^{2+}$ 1115, $(M+3H)^{3+}$743.

Compound 8.

TFA (2 mL) was added to a stirred mixture of compound 7 (274 mg, 0.123 mmol), 1,4-dimethoxybenzene (155 mg, 1.12 mmol) in $CH_2Cl_2$ (2 mL) at RT. The mixture was stirred at RT for 4 h, and then concentrated. The residue was purified by medium pressure reverse phase chromatography on a C-18 column, eluting with MeCN/aq.$NH_4$Cl (monitored by ELSD-MS). Fractions containing the desired product were combined and volatile organics were removed using a flow of nitrogen. The resulting aqueous solution containing the desired product was lyophilized to afford the title compound 8 (228 mg, 84% yield) as a white solid. Its UHPLC-ELSD purity was determined to be 93.3% using Analysis UHPLC-ELSD Condition A. $(M+2H)^{2+}$ 1037, $(M+3H)^{3+}$ 691.

Synthesis of $PEG_{36}$-Glu$^\gamma$-$C_{13}$—$CO_2H$ (16).

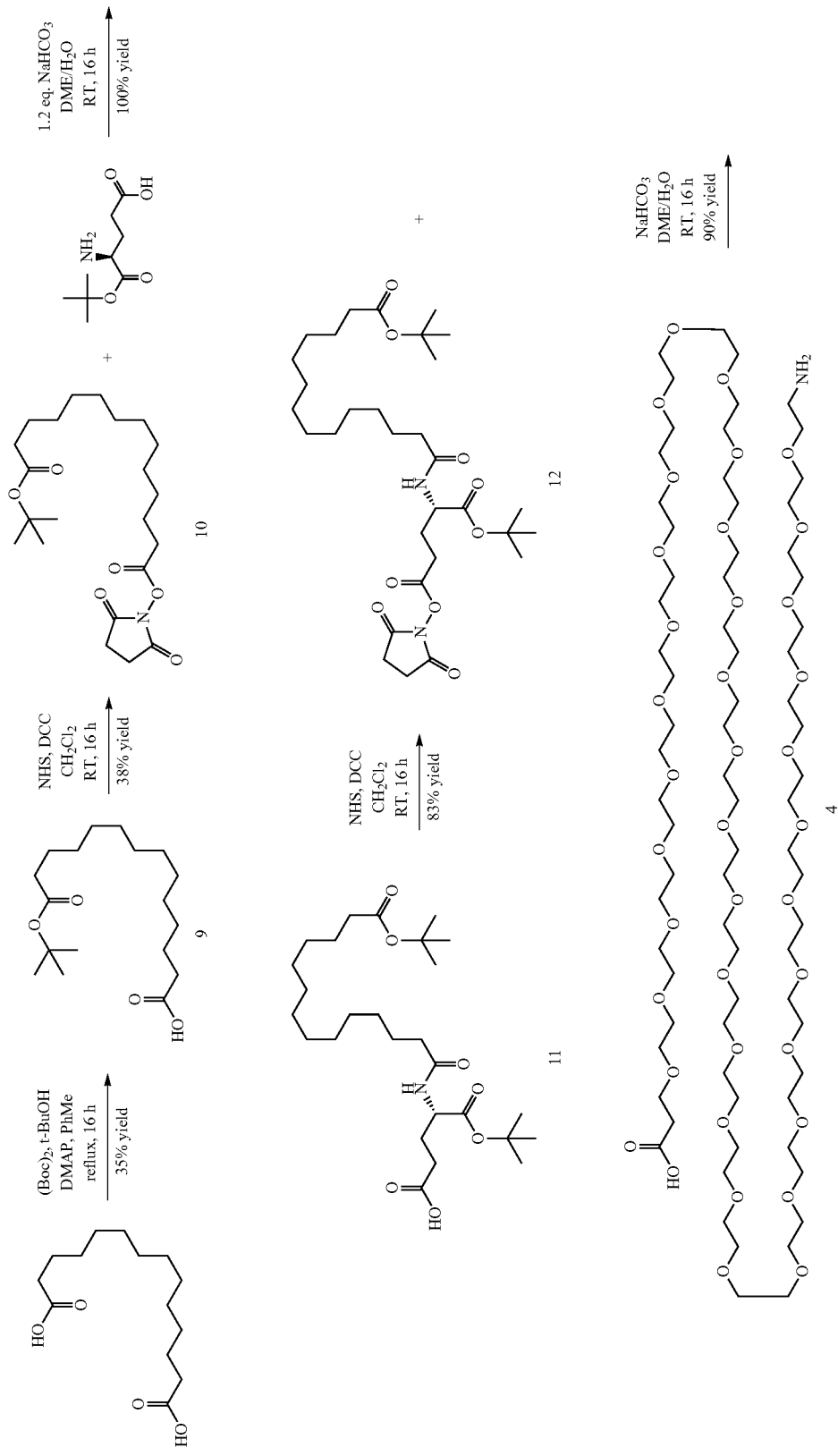

-continued
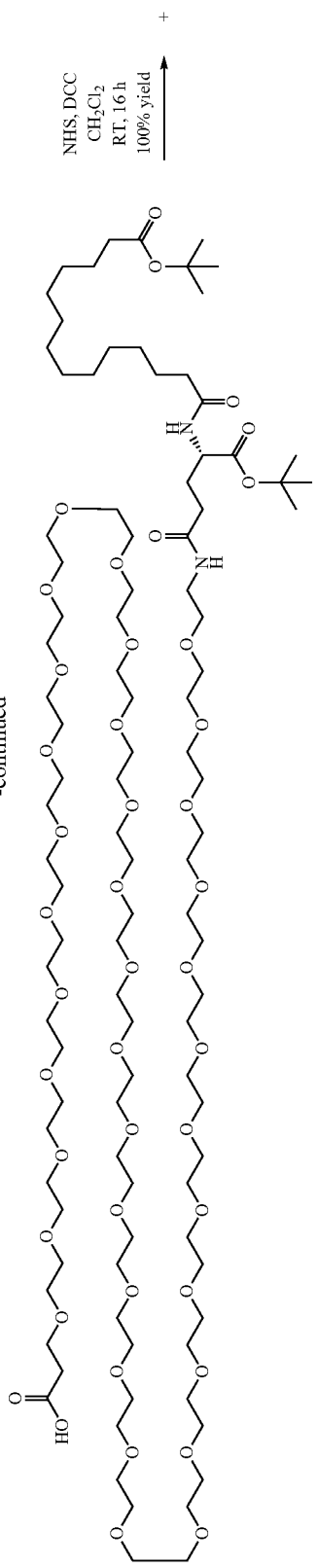
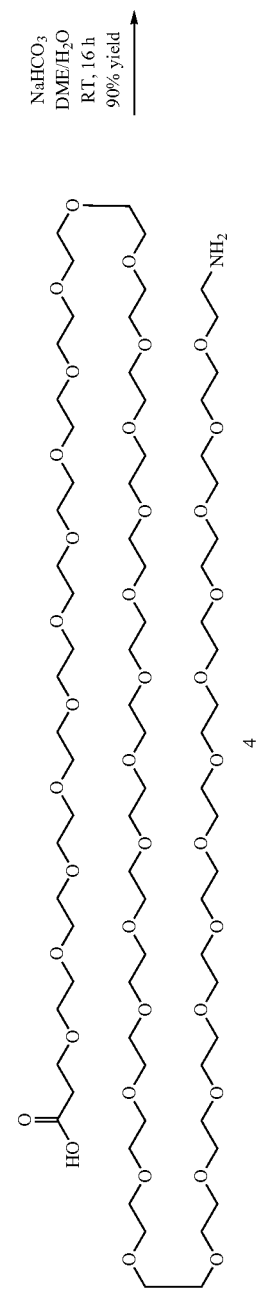
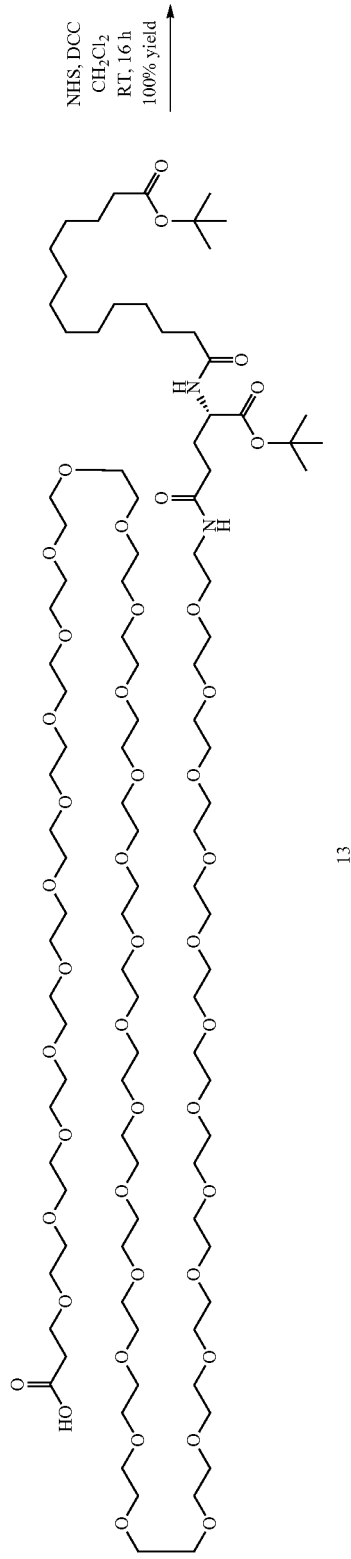

-continued
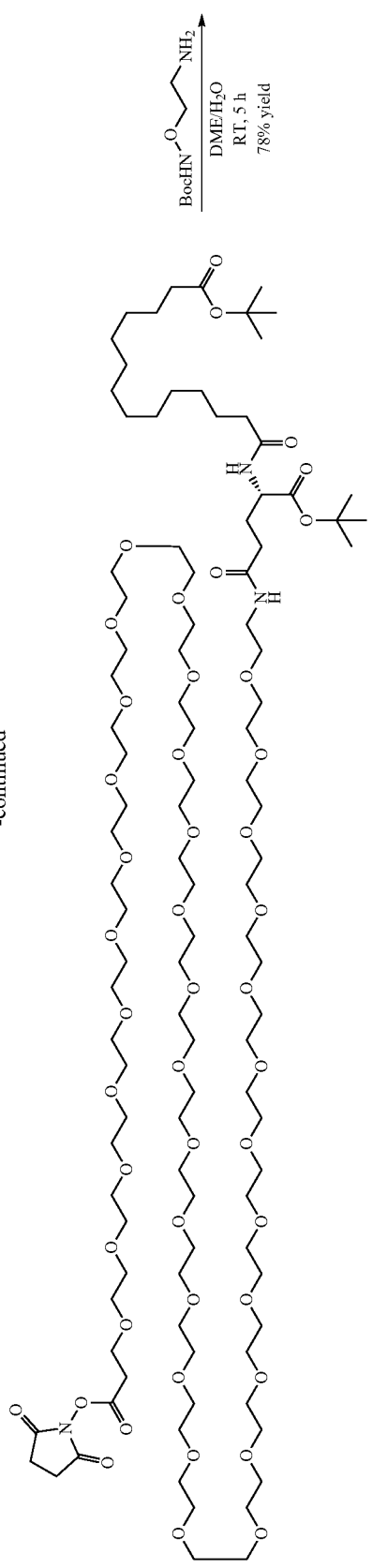
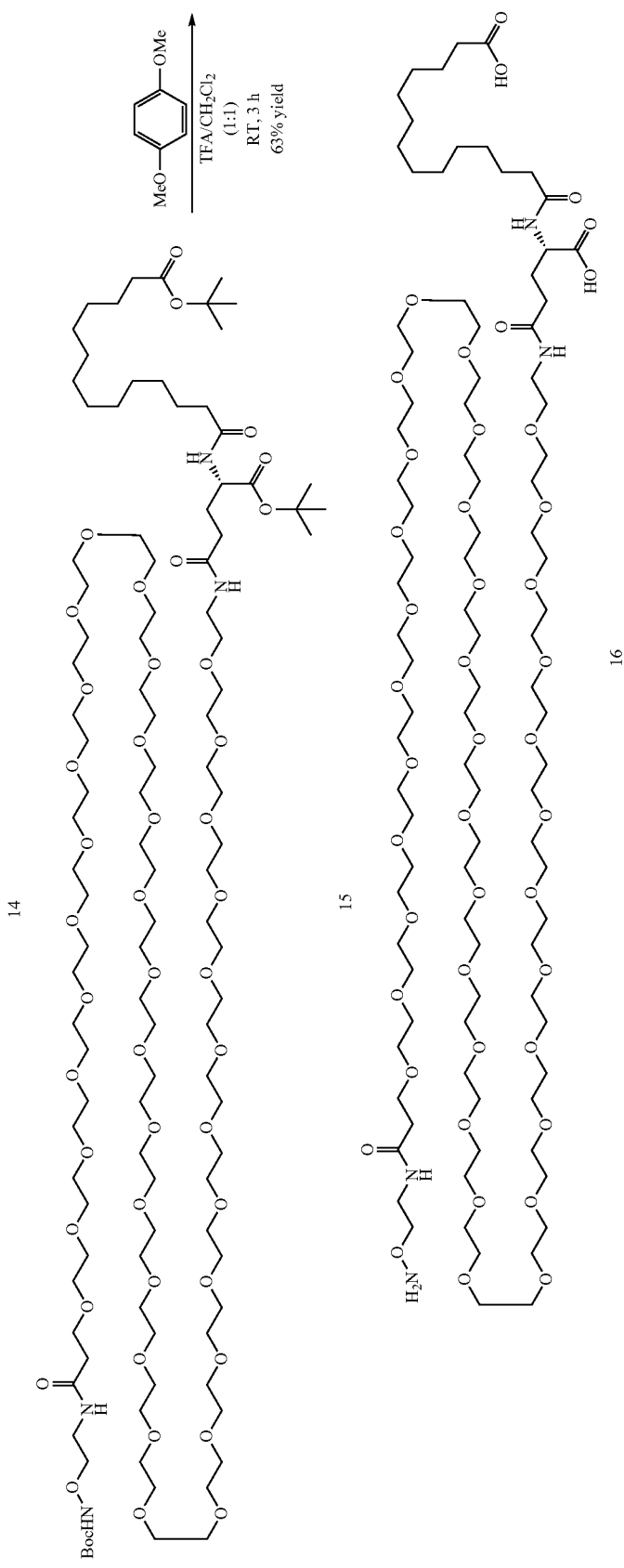

14-(tert-Butoxy)-14-oxotetradecanoic Acid (9)

A 1 L flame dried round bottom flask was charged with tetradecanedioic acid (21 g, 81 mmol), DMAP (9.93 g, 81 mmol) and toluene (300 mL). After the mixture was stirred at RT for 15 min, 2-methylpropan-2-ol (11.7 mL, 122 mmol) and di-tert-butyl dicarbonate (26.6 g, 122 mmol) were added. The resulting mixture was stirred at RT for 30 min, and then heated at 116° C. for 15 h. The mixture was concentrated, and the residue was subjected to flash chromatography on silica gel, eluting with EtOAc/hexanes (1:2) containing 1% HOAc, to afford 14-(tert-butoxy)-14-oxotetradecanoic acid (9) (9.0 g, 29 mmol, 35% yield). The material was approximately 80% pure by $^1$H-NMR (the major impurity was the di-tert-butyl ester), and it was used directly in the next step without further purification.

1-tert-Butyl 14-(2,5-dioxopyrrolidin-1-yl) tetradecanedioate (10)

DCC in $CH_2Cl_2$ (1M, 59.6 mL, 59.6 mmol) was added to a stirred solution of 14-(tert-butoxy)-14-oxotetradecanoic acid (9) (12.5 g, 39.8 mmol), and 1-hydroxypyrrolidine-2,5-dione (6.86 g, 59.6 mmol) in $CH_2Cl_2$ (200 mL). The mixture was stirred at RT overnight, filtered, and concentrated. The residue was purified by flash chromatography on silica gel, eluting with $CH_2Cl_2$ to afford 1-tert-butyl 14-(2,5-dioxopyrrolidin-1-yl) tetradecanedioate (10) (6.2 g, 15 mmol, 38% yield) as a white solid. $^1$H-NMR (CDCl$_3$, 400 MHz) δ 2.84 (br s, 4H), 2.60 (t, J=7.2 Hz, 2H), 2.20 (t, J=7.5 Hz, 2H), 1.74 (m, 2H), 1.57 (m, 2H), 1.44 (s, 9H), 1.40 (m, 2H), 1.26 (m, 14H). $^{13}$C-NMR (CDCl$_3$, 100 MHz) δ 173.4, 169.2, 168.7, 79.9, 35.6, 31.0, 29.54, 29.51, 29.47, 29.34, 29.31, 29.09, 28.8, 28.1, 25.6, 25.1.

(S)-5-(tert-Butoxy)-4-(14-(tert-butoxy)-14-oxotetradecanamido)-5-oxopentanoic Acid (11)

Water (40 ml) was added to a stirred mixture of (S)-4-amino-5-(tert-butoxy)-5-oxopentanoic acid (1.600 g, 7.87 mmol), 1-tert-butyl 14-(2,5-dioxopyrrolidin-1-yl) tetradecanedioate (10) (3.6 g, 7.87 mmol), and NaHCO$_3$ (0.794 g, 9.45 mmol) in DME (120 mL). The resulting clear solution was stirred at RT overnight. DME was removed under vacuum, and aqueous HCl (1 M, 9.45 ml, 9.45 mmol) was added to adjust the pH to 2-3. The mixture was extracted with $CH_2Cl_2$ (1×250 mL, 2×50 mL) while the aqueous layer was saturated with solid NaCl. The combined organic layers were dried over Na$_2$SO$_4$, filtered, concentrated and dried under high vacuum to afford (S)-5-(tert-butoxy)-4-(14-(tert-butoxy)-14-oxotetradecanamido)-5-oxopentanoic acid (11) (5.14 g, 10.3 mmol) as a white solid which was used directly in the next step without further purification.

(S)-1-tert-Butyl 5-(2,5-dioxopyrrolidin-1-yl) 2-(14-(tert-butoxy)-14-oxotetradecanamido)pentanedioate (12)

DCC in $CH_2Cl_2$ (1 M, 11.8 mL, 11.8 mmol) was added to a stirred solution of (S)-5-(tert-butoxy)-4-(14-(tert-butoxy)-14-oxotetradecanamido)-5-oxopentanoic acid (11) (3.93 g, 7.87 mmol), and 1-hydroxypyrrolidine-2,5-dione (1.359 g, 11.81 mmol) in $CH_2Cl_2$ (100 mL). The mixture was stirred at RT for 20 h, and then filtered. The filtrate was concentrated under vacuum, and the residue purified by flash chromatography on silica gel, eluting with EtOAc/$CH_2Cl_2$ (1:19) to afford ((S)-1-tert-butyl 5-(2,5-dioxopyrrolidin-1-yl) 2-(14-(tert-butoxy)-14-oxotetradecanamido)pentanedioate (12) (3.2 g, 68% yield). $^1$H-NMR (CDCl$_3$, 400 MHz) δ 6.27 (d, J=7.8 Hz, 1H), 4.59 (m, 1H), 2.84 (s, 4H), 2.71 (m, 1H), 2.63 (m, 1H), 2.31 (m, 1H), 2.22 (d, J=8.2 Hz, 2H), 2.18 (d, J=7.8 Hz, 2H), 2.08 (m, 1H), 1.58 (m 4H), 1.47 (s, 9H), 1.43 (s, 9H), 1.25 (m, 16H). $^{13}$C-NMR (CDCl$_3$, 100 MHz) δ 173.41, 173.37, 170.7, 169.1, 168.0, 82.8, 79.9, 51.6, 36.4, 35.6, 29.58, 29.47, 29.35, 29.30, 29.10, 28.12, 27.99, 27.55, 27.50, 25.59, 25.48, 25.13.

Compound 13.

Water (4 mL) was added to a stirred mixture of compound 4 (750 mg, 0.448 mmol) (purchased from Quanta BioDesign, Powell, Ohio), (S)-1-tert-butyl 5-(2,5-dioxopyrrolidin-1-yl) 2-(14-(tert-butoxy)-14-oxotetradecanamido)pentanedioate (12) (401 mg, 0.672 mmol), and NaHCO$_3$ (45.1 mg, 0.537 mmol) in DME (12 mL). After the mixture was stirred at RT overnight, aqueous HCl (1M, 0.537 mL, 0.537 mmol) was added. The mixture was concentrated under vacuum, and the residue purified by medium pressure reverse phase chromatography on a C-18 column, eluting with MeCN/aq.NH$_4$Cl (monitored by ELSD-MS). Fractions containing the desired product were combined and volatile organics were removed using a flow of nitrogen. The resulting aqueous solution containing the desired product was lyophilized to afford the title compound 13 (870 mg, 90% yield) as a white solid. $(M+2H)^{2+}$1079, $(M+3H)^{3+}$719.

Compound 14.

DCC in $CH_2Cl_2$ (1 M, 0.605 mL, 0.605 mmol) was added to a stirred mixture of compound 13 (870 mg, 0.403 mmol), and 1-hydroxypyrrolidine-2,5-dione (69.6 mg, 0.605 mmol) in $CH_2Cl_2$ (10 mL) at RT. The mixture was stirred at RT overnight, filtered, concentrated and dried under high vacuum to afford compound 14 as a white solid which was used directly in the next step without further purification.

Compound 15.

Water (4 mL) was added to a stirred mixture of compound 14 (908 mg, 0.403 mmol), and tert-butyl 2-aminoethoxycarbamate (2) (142 mg, 0.806 mmol) in DME (12 mL) at RT. The mixture was stirred at RT overnight, concentrated, and the residue purified by medium pressure reverse phase chromatography on a C-18 column, eluting with MeCN/aq.NH$_4$Cl (Column: Teledyne Isco C18 Redi SepRf High performance Gold; Detector: ELSD; Rate: 60 mL/min; Solvent A: 95% H$_2$O, 5% MeCN 10 mM NH$_4$OAc; Solvent B: 5% H$_2$O, 95% MeCN, 10 mM NH$_4$OAc). Fractions containing the desired product were combined and volatile organics were removed using a flow of nitrogen. The resulting aqueous solution containing the desired product was lyophilized to afford the title compound 15 (730 mg, 78% yield) as a white solid. $(M+2H)^{2+}$1158, $(M+3H)^{3+}$772.

Compound 16.

TFA (8 mL, 104 mmol) was added to a stirred mixture of compound 15 (420 mg, 0.181 mmol), and 1,4-dimethoxybenzene (201 mg, 1.451 mmol) in $CH_2Cl_2$ (8 mL) at RT. The mixture was stirred at RT for 3 h, concentrated, and the residue purified by medium pressure reverse phase chromatography on a C-18 column, eluting with MeCN/aq.NH$_4$Cl (monitored by ELSD-MS). Fractions containing the desired product were combined and volatile organics were removed using a flow of nitrogen. The resulting aqueous solution containing the desired product was lyophilized to afford the title compound 16 (240 mg, 63% yield) as a white solid. Its UHPLC-ELSD purity was determined to be 75.2% using Analysis UHPLC-ELSD Condition B. $(M+2H)^{2+}$1052, $(M+3H)^{3+}$701.

Synthesis of Spermine-Glu$^\gamma$-C$_{14}$—CO$_2$H (27)

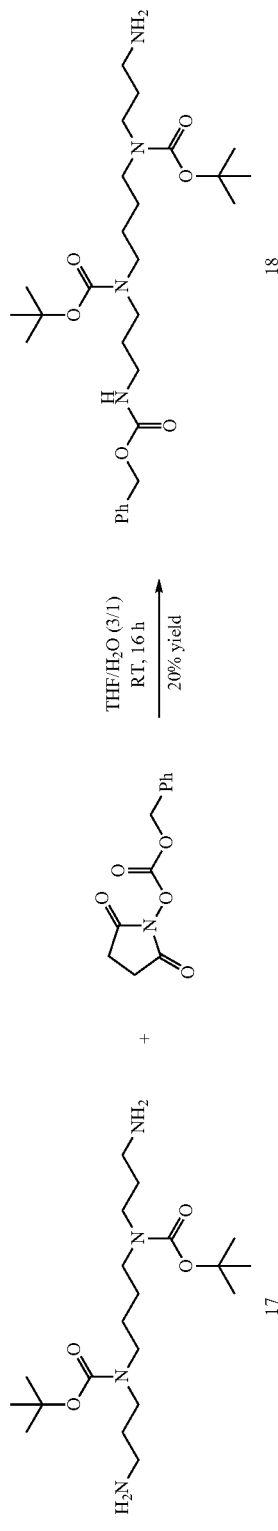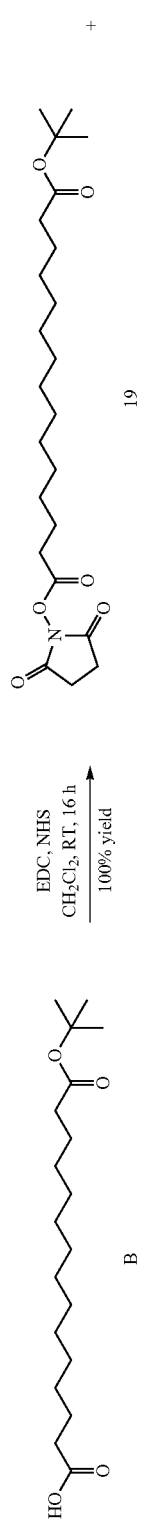

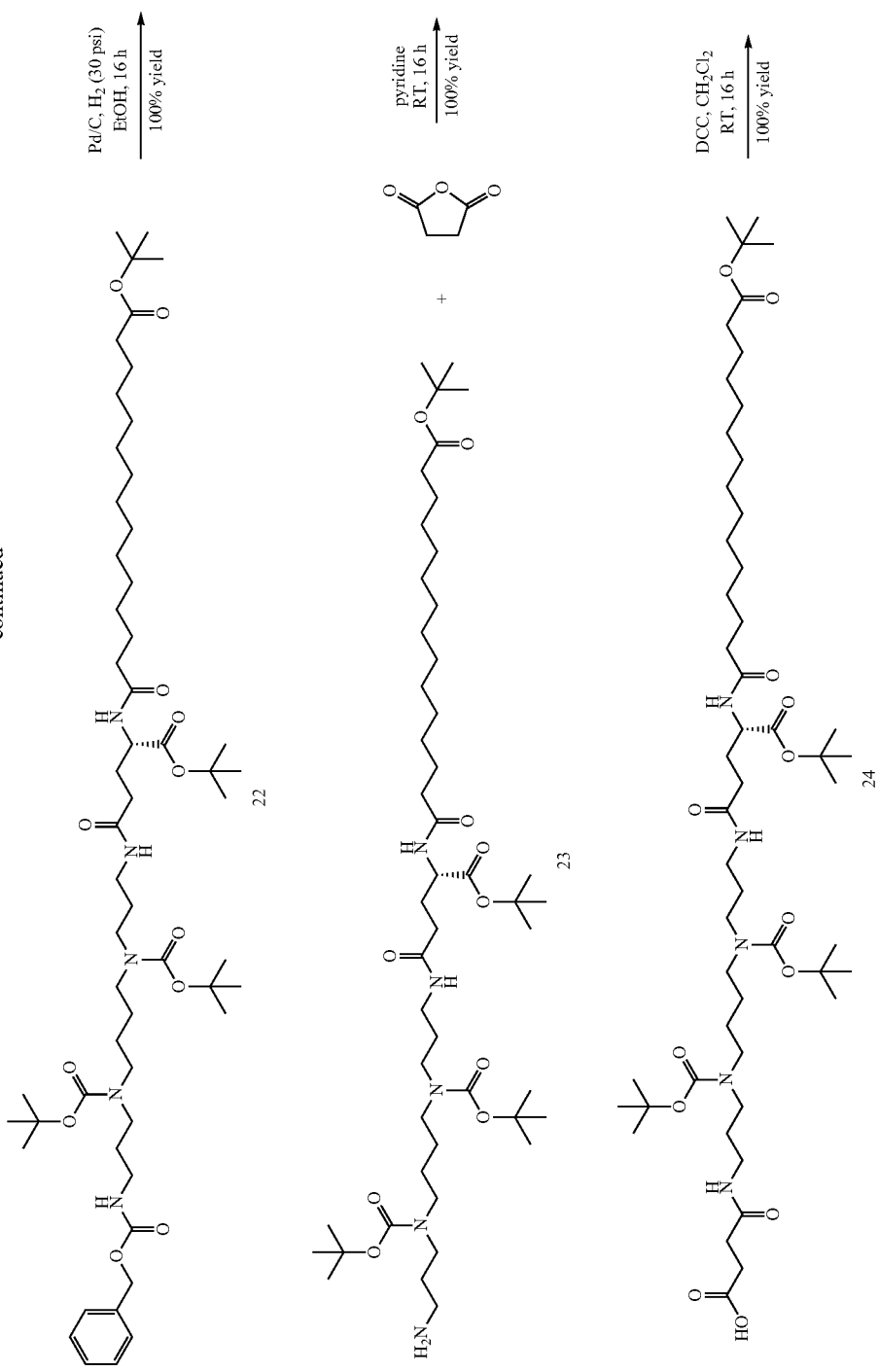

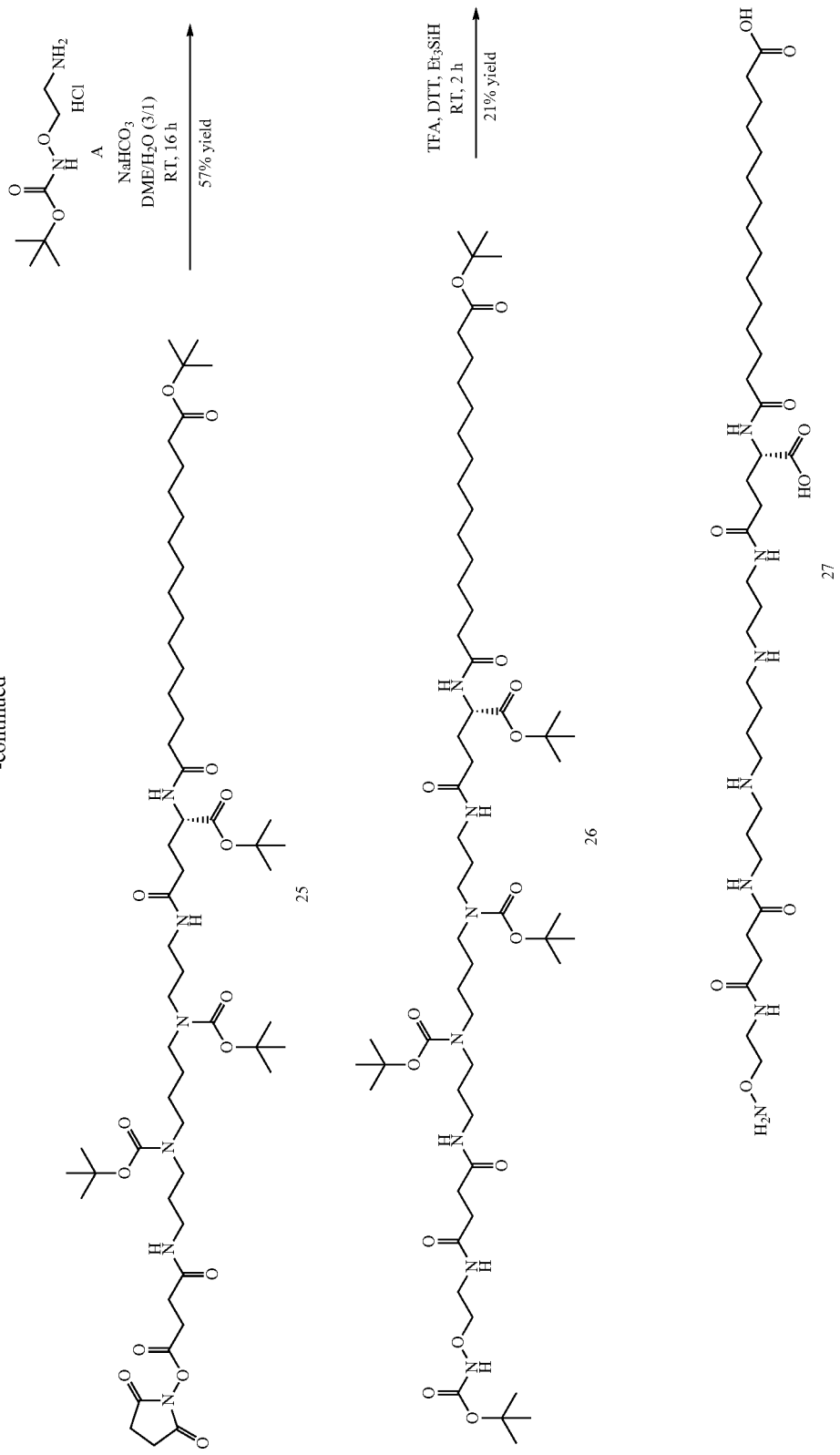

tert-butyl (4-((3-aminopropyl)(tert-butoxycarbonyl) amino)butyl)(3-(((benzyloxy)carbonyl)amino)propyl)carbamate (18)

Water (100 mL) was added to a mixture of N-(benzyloxycarbonyloxy)succinimide (16.6 g, 66.4 mmol), di-tert-butyl butane-1,4-diylbis((3-aminopropyl)carbamate) (17) (Strømgaard, K; Bjørnsdottir, I; Andersen, K; Brierley, M. J.; Rizoli, S.; Eldursi, N; Mellor, I, R.; 4 Peter N. R. Usherwood, P. N. R.; Hansen, S. H.; Krogsgaard-Larsen, P.; Jaroszewski, J. W. Chirality, 2000, 12, 93) (19.1 g, 47.4 mmol) in THF (300 mL). After it was stirred at RT overnight, all THF was removed under vacuum and the mixture was extracted with $CH_2Cl_2$ (350 ml, 100 ml×2) while the aqueous layer was saturated with solid NaCl. The combined organic layers were dried over $Na_2SO_4$, filtered, concentrated under vacuum, and purified by flash chromatography eluting with 2M $NH_3$-MeOH/$CH_2Cl_2$ (from 1:19 to 1:9) to afford tert-butyl (4-((3-aminopropyl)(tert-butoxycarbonyl) amino)butyl)(3-(((benzyloxy)carbonyl)amino)propyl)carbamate (18) (5.19 g, 9.67 mmol, 20.4% yield). $^1$H-NMR (400 MHz, $CDCl_3$) δ ppm 7.22-7.40 (m, 5H), 5.01-5.12 (m, 2H), 3.34-3.48 (m, 4H), 3.01-3.31 (m, 5H), 2.65 (br t, J=6.60 Hz, 2H), 1.86-2.19 (m, 4H), 1.55-1.75 (m, 4H), 1.43-1.50 (m, 4H), 1.43 (s, 9H), 1.42 (s, 9H). The $^{13}$C-NMR spectra was very complex due to the presence of rotamers.

1-(tert-butyl) 15-(2,5-dioxopyrrolidin-1-yl) pentadecanedioate (19)

A mixture of 15-(tert-butoxy)-15-oxopentadecanoic acid (Compound 1 in Example 4) (3.28 g, 10.0 mmol), 1-hydroxypyrrolidine-2,5-dione (1.73 g, 15.0 mmol), and EDC (2.88 g, 15.0 mmol) in $CH_2Cl_2$ (100 mL) was stirred at RT for 16 h. It was then diluted with $CH_2Cl_2$ (200 mL), and washed with brine/water (1:1) twice, dried over $Na_2SO_4$, filtered, concentrated, and dried under high vacuum to afford 1-tert-butyl 15-(2,5-dioxopyrrolidin-1-yl) pentadecanedioate (19) (4.26 g, 10.0 mmol, 100% yield), which was used directly in the next step.

(S)-5-(tert-butoxy)-4-(15-(tert-butoxy)-15-oxopentadecanamido)-5-oxopentanoic acid (20)

A solution of $NaHCO_3$ (1.01 g, 12.0 mmol) in water (30 mL) was added to a mixture of (S)-4-amino-5-(tert-butoxy)-5-oxopentanoic acid (2.44 g, 12.0 mmol), and 1-tert-butyl 15-(2,5-dioxopyrrolidin-1-yl) pentadecanedioate (19) (4.26 g, 10.0 mmol) in DME (90 mL). After the mixture was stirred at RT for 16 h, all DME removed under vacuum, the pH was adjusted to 2-3, and the mixture was extracted with $CH_2Cl_2$ (350 mL, 150 mL). The combined organic layers were dried over $Na_2SO_4$, filtered, concentrated and dried under high vacuum to afford (S)-5-(tert-butoxy)-4-(15-(tert-butoxy)-15-oxopentadecanamido)-5-oxopentanoic acid (20) (5.14 g, 10.0 mmol, 100% yield), which was used directly for the next step.

1-(tert-butyl) 5-(2,5-dioxopyrrolidin-1-yl) (15-(tert-butoxy)-15-oxopentadecanoyl)-L-glutamate (21)

A mixture of (S)-5-(tert-butoxy)-4-(15-(tert-butoxy)-15-oxopentadecanamido)-5-oxopentanoic acid (20) (5.14 g, 10.0 mmol), 1-hydroxypyrrolidine-2,5-dione (1.73 g, 15.0 mmol), EDC (2.88 g, 15.0 mmol) in $CH_2Cl_2$ (100 mL) was stirred at RT for 16 h. It was then diluted with $CH_2Cl_2$ (200 mL), and washed with brine/water (1:1) twice. The organic layer was dried over $Na_2SO_4$, filtered, concentrated under vacuum, and the residue subjected to flash chromatography eluting with EtOAc/$CH_2Cl_2$ to afford (S)-1-tert-butyl 5-(2,5-dioxopyrrolidin-1-yl) 2-(15-(tert-butoxy)-15-oxopentadecanamido)pentanedioate (21) (3.41 g, 5.58 mmol, 55.8% yield) (55.8% yield for 3 steps) as a white solid. $^1$H-NMR (400 MHz, $CDCl_3$) δ ppm 6.20 (br d, J=7.82 Hz, 1H), 4.62 (td, J=7.95, 4.89 Hz, 1H), 2.80-2.91 (m, 4H), 2.56-2.79 (m, 2H), 2.29-2.42 (m, 1H), 2.17-2.28 (m, 4H), 2.02-2.16 (m, 1H), 1.54-1.69 (m, 4H), 1.48-1.53 (m, 9H), 1.44-1.48 (m, 9H), 1.21-1.39 (m, 18H). $^{13}$C-NMR (101 MHz, $CDCl_3$) δ ppm 173.35, 173.33, 170.66, 168.95, 168.01, 82.82, 79.85, 51.66, 36.46, 35.66, 29.61, 29.49, 29.35, 29.31, 29.12, 28.15, 28.00, 27.62, 27.54, 25.60, 25.48, 25.15.

tert-butyl (S)-8,13,21-tris(tert-butoxycarbonyl)-3,18,23-trioxo-1-phenyl-2-oxa-4,8,13,17,22-pentaazaheptatriacontan-37-oate (22)

Water (20 mL) was added to a mixture of tert-butyl (4-((3-aminopropyl)(tert-butoxycarbonyl)amino)butyl)(3-(((benzyloxy)carbonyl)amino)propyl)carbamate (18) (1.42 g, 2.65 mmol), (S)-1-tert-butyl 5-(2,5-dioxopyrrolidin-1-yl) 2-(15-(tert-butoxy)-15-oxopentadecanamido)pentanedioate (21) (1.62 g, 2.65 mmol) in DME (60 mL). After the mixture was stirred at RT overnight, all volatile components (including water) were removed under high vacuum, and the residue was azeotropically dried with MeOH (2×). The residue was dissolved in MeOH/$CH_2Cl_2$ (1:9, <10 mL) and subjected to flash chromatography, eluting with MeOH/$CH_2Cl_2$ to afford (S)-tert-butyl 8,13,21-tris(tert-butoxycarbonyl)-3,18,23-trioxo-1-phenyl-2-oxa-4,8,13,17,22-pentaazaheptatriacontan-37-oate (22) (2.74 g, 2.65 mmol, 100% yield) as a viscous liquid. $^1$H-NMR (400 MHz, $CDCl_3$) δ ppm 7.29-7.39 (m, 5H), 7.12-7.25 (m, 1H), 6.69-6.89 (m, 1H), 5.67-5.95 (m, 1H), 5.03-5.15 (m, 2H), 4.30-4.47 (m, 1H), 3.38-3.54 (m, 8H), 3.05-3.32 (m, 8H), 2.12-2.35 (m, 6H), 1.86-2.05 (m, 1H), 1.51-1.76 (m, 7H), 1.45 (s, 9H), 1.44 (s, 27H), 1.17-1.33 (m, 20H). The $^{13}$C-NMR spectra was very complex due to the presence of rotamers.

tert-butyl (S)-5-(3-aminopropyl)-10,18-bis(tert-butoxycarbonyl)-2,2-dimethyl-4,15,20-trioxo-3-oxa-5,10,14,19-tetraazatetratriacontan-34-oate (23)

A mixture of (S)-tert-butyl 8,13,21-tris(tert-butoxycarbonyl)-3,18,23-trioxo-1-phenyl-2-oxa-4,8,13,17,22-pentaazaheptatriacontan-37-oate (22) (1.36 g, 1.32 mmol), and Pd-C (0.140 g, 10% by weight) in ethanol (100 mL) was hydrogenated in a Parr shaker ($H_2$, 30 psi) for 18 h at RT. The mixture was filtered, washed with EtOH, concentrated and dried under high vacuum to afford (S)-tert-butyl 5-(3-aminopropyl)-10,18-bis(tert-butoxycarbonyl)-2,2-dimethyl-4,15,20-trioxo-3-oxa-5,10,14,19-tetraazatetratriacontan-34-oate (23) (1.19 g, 1.32 mmol, 100% yield), which was used directly for the next step. $^1$H-NMR (400 MHz, $CDCl_3$) δ ppm 6.91-7.09 (m, 1H), 6.46-6.73 (m, 1H), 4.34-4.54 (m, 1H), 3.66-3.81 (m, 1H), 3.10-3.36 (m, 10H), 2.82-2.93 (m, 2H), 2.58-2.67 (m, 3H), 2.13-2.36 (m, 6H), 1.55-1.72 (m, 6H), 1.49-1.53 (m, 4H), 1.48 (s, 9H), 1.47 (d, J=3.18 Hz, 27H), 1.22-1.37 (m, 20H). The $^{13}$C-NMR spectra was very complex due to the presence of rotamers.

(S)-20,28,33-tris(tert-butoxycarbonyl)-2,2-dimethyl-4,18,23,38-tetraoxo-3-oxa-19,24,28,33,37-pentaazahentetracontan-41-oic acid (24)

Pyridine (13 mL) was added to a mixture of (S)-tert-butyl 5-(3-aminopropyl)-10,18-bis(tert-butoxycarbonyl)-2,2-dimethyl-4,15,20-trioxo-3-oxa-5,10,14,19-tetraazatetratriacontan-34-oate (23) (1.19 g, 1.32 mmol), and dihydrofuran-2,5-dione (0.66 g, 6.6 mmol). After the mixture was stirred at RT for 16 h, all volatile components were removed under vacuum, and the residue subjected to flash chromatography eluting with MeOH/CH$_2$Cl$_2$ containing 0.5% AcOH to afford (S)-20,28,33-tris(tert-butoxycarbonyl)-2,2-dimethyl-4,18,23,38-tetraoxo-3-oxa-19,24,28,33,37-pentaazahentetracontan-41-oic acid (24) (1.32 g, 1.32 mmol, 100% yield) as a viscous liquid. $^1$H-NMR (400 MHz, CHLOROFORM-d) δ ppm 4.38-4.50 (m, 1H), 3.47-3.58 (m, 1H), 3.09-3.32 (m, 9H), 2.75 (s, 4H), 2.64-2.73 (m, 2H), 2.46-2.59 (m, 2H), 2.27-2.35 (m, 2H), 2.17-2.27 (m, 4H), 2.07-2.14 (m, 4H), 1.83-2.04 (m, 1H), 1.67-1.80 (m, 3H), 1.55-1.66 (m, 4H), 1.41-1.54 (m, 38H), 1.19-1.37 (m, 20H).

21,36-di-tert-butyl 1-(2,5-dioxopyrrolidin-1-yl) (S)-8,13-bis(tert-butoxycarbonyl)-3,18,23-trioxo-4,8,13,17,22-pentaazahexatriacontane-1,21,36-tricarboxylate (25)

DCC in CH$_2$Cl$_2$ (1.0 M, 2.0 mL, 2.0 mmol) was added to a mixture of (S)-20,28,33-tris(tert-butoxycarbonyl)-2,2-dimethyl-4,18,23,38-tetraoxo-3-oxa-19,24,28,33,37-pentaazahentetracontan-41-oic acid (24) (1.32 g, 1.32 mmol), 1-hydroxypyrrolidine-2,5-dione (0.23 g, 2.0 mmol) in CH$_2$Cl$_2$ (20 mL). After the mixture was stirred at RT for 16 h, it was filtered, concentrated, and dried under high vacuum to afford 21,36-di-tert-butyl 1-(2,5-dioxopyrrolidin-1-yl) (S)-8,13-bis(tert-butoxycarbonyl)-3,18,23-trioxo-4,8,13,17,22-pentaazahexatriacontane-1,21,36-tricarboxylate (25) (1.45 g, 1.32 mmol, 100% yield), which was used directly for the next step.

tert-butyl (S)-18,23,31-tris(tert-butoxyearbonyl)-2,2-dimethyl-4,10,13,28,33-pentaoxo-3,6-dioxa-5,9,14,18,23,27,32-heptaazaheptatetracontan-47-oate (26)

A solution of NaHCO$_3$ (0.233 g, 2.77 mmol) in water (4 mL) was added to a mixture of (S)-21,36-di-tert-butyl 1-(2,5-dioxopyrrolidin-1-yl) 8,13-bis(tert-butoxycarbonyl)-3,18,23-trioxo-4,8,13,17,22-pentaazahexatriacontane-1,21,36-tricarboxylate (25) (1.45 g, 1.32 mmol), and tert-butyl 2-aminoethoxycarbamate hydrochloride (0.561 g, 2.64 mmol) in DME (12 mL) at RT. After the mixture was stirred at RT for 6 h, all volatile components, including water, were removed under vacuum, and the residue was azeotropilcaaly dried with THF. The residue was subjected to flash chromatography eluting with MeOH/CH$_2$Cl$_2$ to afford tert-butyl (S)-18,23,31-tris(tert-butoxycarbonyl)-2,2-dimethyl-4,10,13,28,33-pentaoxo-3,6-dioxa-5,9,14,18,23,27,32-heptaazaheptatetracontan-47-oate (26) (0.87 g, 0.75 mmol, 57% yield) as a viscous liquid. $^1$H-NMR (400 MHz, CDCl$_3$) δ ppm 4.33-4.48 (m, 1H), 3.80-3.94 (m, 4H), 3.42-3.55 (m, 14H), 3.08-3.32 (m, 7H), 2.68-2.77 (m, 4H), 2.50-2.63 (m, 4H), 2.13-2.34 (m, 4H), 1.54-1.74 (m, 6H), 1.43-1.53 (m, 45H), 1.22-1.35 (m, 20H). The $^{13}$C-NMR spectra was very complex due to the presence of rotamers.

(S)-1-(aminooxy)-25-carboxy-4,7,22,27-tetraoxo-3,8,12,17,21,26-hexaazahentetracontan-41-oic acid (27)

To a mixture of (S)-tert-butyl 18,23,31-tris(tert-butoxycarbonyl)-2,2-dimethyl-4,10,13,28,33-pentaoxo-3,6-dioxa-5,9,14,18,23,27,32-heptaazaheptatetracontan-47-oate (26) (0.50 g, 0.43 mmol), and DTT (0.067 g, 0.43 mmol) in TFA (1.5 ml), was added triethylsilane (0.10 ml, 0.63 mmol) and water (0.10 mL, 5.6 mmol). The resulting mixture was stirred at RT for 2 h, and then all volatile components were removed using a flow of N$_2$ overnight. The residue was subjected to purification by preparative LC/MS using the following conditions: Column: Waters CSH C18, 19×200 mm, 5-µm particles; Mobile Phase A: 5:95 acetonitrile: water with 0.1% trifluoroacetic acid; Mobile Phase B: 95:5 acetonitrile: water with 0.1% trifluoroacetic acid; Gradient: 0-35% B over 25 minutes, then a 5-minute hold at 100% B; Flow: 20 mL/min. Fractions containing the desired product were combined and volatile organic components were removed using a flow of nitrogen. The resulting aqueous solution containing the desired product was cooled to −78° C. under a flow of nitrogen and lyophilized to afford the title compound (27) as a white solid (72 mg, 21% yield). Its LC-CAD purity was determined to be 94.9% using Analysis UHPLC-CAD Condition C. [MH]$^+$ 745.09.

Analysis condition A: Retention time=1.27 min; ESI-MS (MH)$^+$=744.55.

Analysis condition B: Retention time=1.20 min; ESI-MS (MH)$^+$=744.40.

Synthesis of Compound 39:

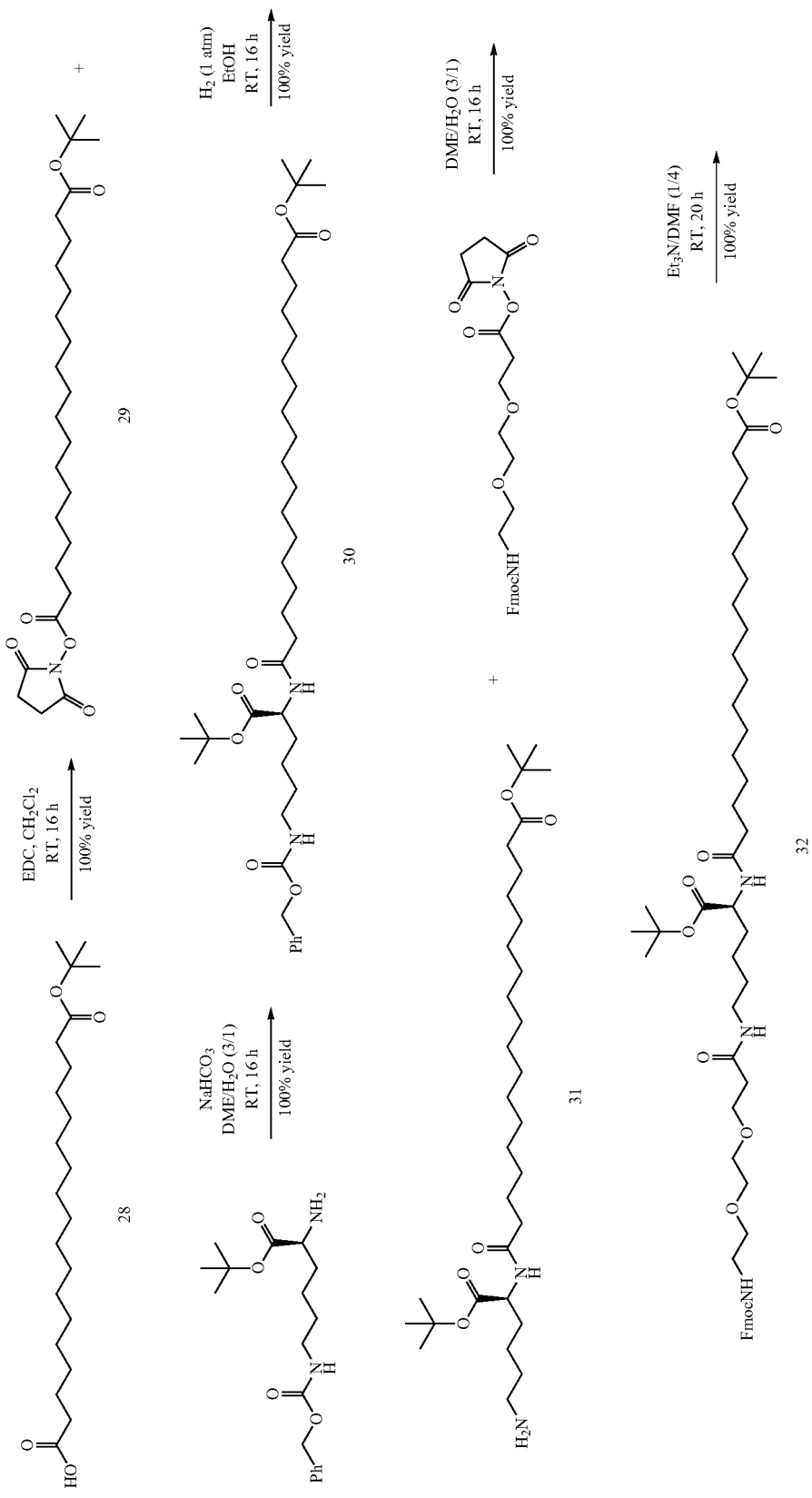

-continued
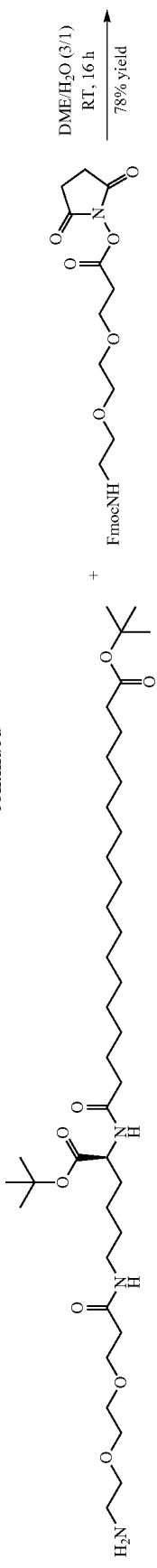
33
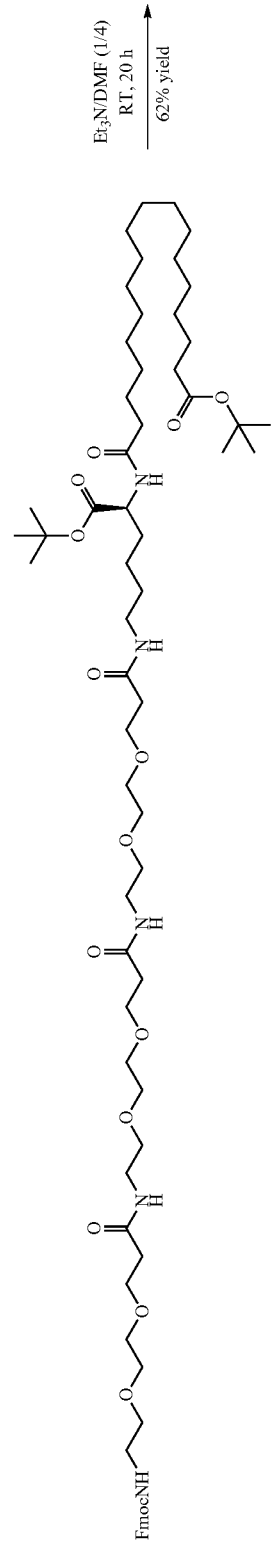
34
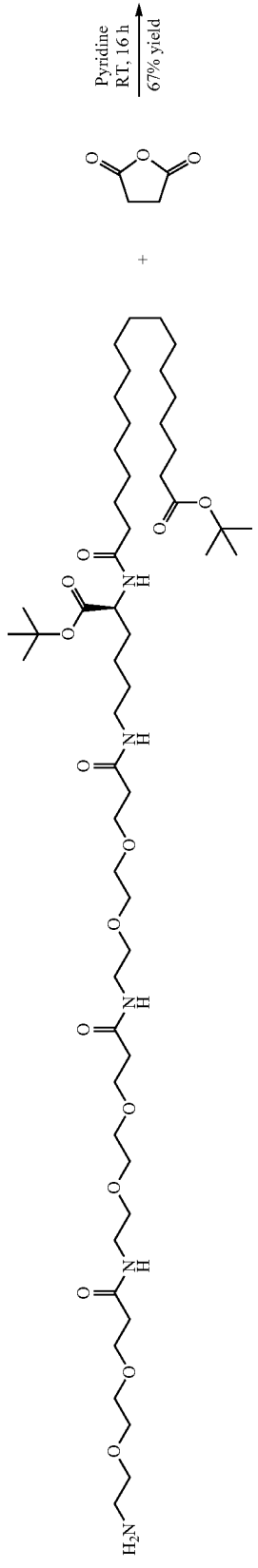
35

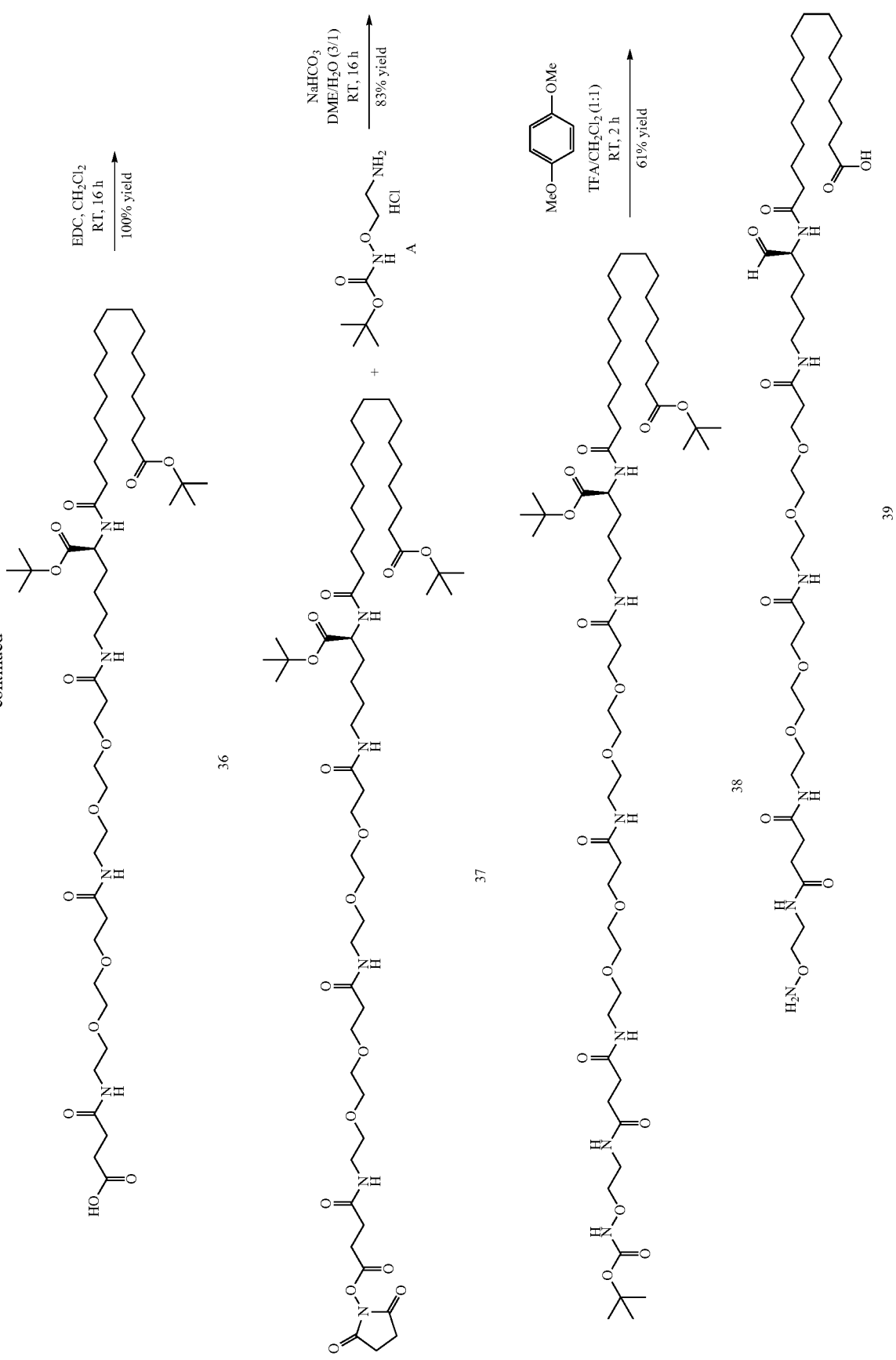

1-(tert-butyl) 18-(2,5-dioxopyrrolidin-1-yl) octadecanedioate (29)

EDC (1.406 g, 7.33 mmol) was added to a mixture of 18-(tert-butoxy)-18-oxooctadecanoic acid (28) (prepared by method similar to that used to prepare Compound 1 in Example 4) (2.09 g, 5.64 mmol), and 1-hydroxypyrrolidine-2,5-dione (0.844 g, 7.33 mmol) in $CH_2Cl_2$ (40 mL). The mixture was stirred at RT overnight, diluted with $CH_2Cl_2$ (100 mL) and washed with $NaHCO_3$. After separation, the aqueous layer was extracted with $CH_2Cl_2$ (80 mL×2). The combined organic layers were washed with brine, dried over $Na_2SO_4$, filtered, and concentrated under vacuum. The residue was subjected to flash chromatography eluting with $CH_2Cl_2$ to afford 1-tert-butyl 18-(2,5-dioxopyrrolidin-1-yl) octadecanedioate (29) (2.13 g, 4.55 mmol, 81% yield) as a white solid. $^1$H-NMR (400 MHz, $CDCl_3$) δ 2.85 (br s, 4H), 2.62 (t, J=7.5 Hz, 2H), 2.22 (t, J=7.6 Hz, 2H), 1.77 (quin, J=7.5 Hz, 2H), 1.67-1.54 (m, 3H), 1.50-1.37 (m, 10H), 1.37-1.21 (m, 22H). $^{13}$C-NMR (101 MHz, $CDCl_3$) δ ppm 173.33, 169.12, 168.67, 79.85, 35.67, 30.98, 29.65 (br s), 29.62 (br s), 25.61, 29.55, 29.50, 29.36, 29.31, 29.12, 29.09, 28.81, 28.15, 25.15, 24.60.

tert-butyl (S)-18-((6-(((benzyloxy)carbonyl)amino)-1-(tert-butoxy)-1-oxohexan-2-yl)amino)-18-oxoetadecanoate (30)

$NaHCO_3$ (0.41 g, 4.83 mmol) was added to a mixture of 1-tert-butyl 18-(2,5-dioxopyrrolidin-1-yl) octadecanedioate (29) (1.13 g, 2.416 mmol), and Lys($N^\epsilon$—CBZ)-O$^t$Bu hydrochloride (1.17 g, 3.14 mmol) in DME (60 mL) and water (20 mL). The resulting light suspension was stirred at RT overnight. DME was removed under vacuum, and then aqueous HCl (1 M, 4.83 mL, 4.83 mmol) was added to adjust the pH to 2-3. The mixture was extracted with EtOAc (200 mL, 100 mL×2). The combined organic layers were washed with brine, dried over $Na_2SO_4$, filtered, concentrated under vacuum and subjected to flash chromatography eluting with EtOAc/$CH_2Cl_2$ to afford (S)-tert-butyl 18-((6-(((benzyloxy)carbonyl)amino)-1-(tert-butoxy)-1-oxohexan-2-yl)amino)-18-oxooctadecanoate (30) (1.66 g, 2.42 mmol, 100% yield) as a colorless, viscous liquid. $^1$H-NMR (400 MHz, $CDCl_3$) δ ppm 7.29-7.38 (m, 5H), 6.08 (br d, J=7.34 Hz, 1H), 5.06-5.19 (m, 2H), 4.84-5.02 (m, 1H), 4.48 (td, J=7.70, 5.14 Hz, 1H), 3.07-3.27 (m, 2H), 2.15-2.24 (m, 4H), 1.75-1.88 (m, 1H), 1.49-1.70 (m, 7H), 1.46 (s, 9H), 1.44 (s, 9H), 1.20-1.34 (m, 26H). $^{13}$C-NMR (101 MHz, $CDCl_3$) δ ppm 173.30, 172.87, 171.81, 171.05, 156.49, 136.67, 128.47, 128.03, 82.03, 79.82, 66.55, 60.35, 52.24, 40.66, 36.65, 35.64, 32.35, 29.67, 29.64, 29.61, 29.50, 29.48, 29.44, 29.33, 29.29, 29.10, 28.13, 28.00, 25.63, 25.13, 22.25, 21.00, 14.19. [MH]$^+$ 689.62.

tert-butyl (S)-18-((6-amino-1-(tert-butoxy)-1-oxohexan-2-yl)amino)-18-oxooctadecanoate (31)

A mixture of (S)-tert-butyl 18-((6-(((benzyloxy)carbonyl)amino)-1-(tert-butoxy)-1-oxohexan-2-yl)amino)-18-oxooctadecanoate (30) (1.060 g, 1.2 mmol), and Pd-C (0.128 g, 1.200 mmol) in EtOH (50 mL) was hydrogenated (balloon) overnight at RT. After several cycles of vacuum purging with nitrogen, the reaction mixture was carefully filtered, and washed with EtOH. The filtrate was concentrated and dried under high vacuum to afford (31) (S)-tert-butyl 18-((6-amino-1-(tert-butoxy)-1-oxohexan-2-yl)amino)-18-oxooctadecanoate (0.67 g, 1.2 mmol, 100% yield) as a colorless liquid, which was used directly in the next step. $^1$H-NMR (400 MHz, $CDCl_3$) δ ppm 6.40-6.59 (m, 1H), 4.30-4.50 (m, 1H), 3.16-3.37 (m, 2H), 2.65-2.81 (m, 2H), 2.10-2.25 (m, 4H), 1.72-1.84 (m, 1H), 1.47-1.67 (m, 7H), 1.43 (s, 9H), 1.41 (s, 9H), 1.22-1.36 (m, 26H). $^{13}$C-NMR ($CDCl_3$) δ ppm 173.53, 173.48, 171.90, 82.10, 79.95, 52.47, 50.19, 40.80, 36.50, 35.62, 32.11, 30.66, 29.63, 29.60, 29.56, 29.48, 29.44, 29.33, 29.25, 29.05, 28.07, 27.94, 25.66, 25.09, 22.41. [MH]$^+$ 555.63.

tert-butyl (S)-19-(tert-butoxycarbonyl)-1-(9H-fluoren-9-yl)-3,13,21-trioxo-2,7,10-trioxa-4,14,20-triazaoctatriacontan-38-oate (32)

$NaHCO_3$ (0.202 g, 2.40 mmol) was added to a mixture of 2,5-dioxopyrrolidin-1-yl 1-(9H-fluoren-9-yl)-3-oxo-2,7,10-trioxa-4-azatridecan-13-oate (0.715 g, 1.44 mmol), (S)-tert-butyl 18-((6-amino-1-(tert-butoxy)-1-oxohexan-2-yl)amino)-18-oxooctadecanoate (31) (0.67 g, 1.2 mmol) in DME (15 mL) and water (5). After stirring at RT overnight, all volatile components were removed under vacuum, and the residue was subjected to flash chromatography, eluting EtOAc/$CH_2Cl_2$ to afford (S)-tert-butyl 19-(tert-butoxycarbonyl)-1-(9H-fluoren-9-yl)-3,13,21-trioxo-2,7,10-trioxa-4,14,20-triazaoctatriacontan-38-oate (32) (1.12 g, 1.20 mmol, 100% yield) as a colorless, viscous liquid. $^1$H-NMR (400 MHz, $CDCl_3$) δ ppm 7.78 (d, J=7.58 Hz, 2H), 7.63 (d, J=7.34 Hz, 2H), 7.37-7.47 (m, 2H), 7.30-7.36 (m, 2H), 6.21-6.37 (m, 1H), 6.00-6.17 (m, 1H), 5.43-5.63 (m, 1H), 4.40-4.54 (m, 3H), 4.19-4.33 (m, 1H), 3.75 (t, J=5.87 Hz, 2H), 3.53-3.68 (m, 6H), 3.42 (br d, J=4.89 Hz, 2H), 3.22 (q, J=6.28 Hz, 2H), 2.44 (br t, J=5.38 Hz, 2H), 2.22 (t, J=7.58 Hz, 4H), 1.75-1.89 (m, 1H), 1.55-1.69 (m, 7H), 1.47 (s, 9H), 1.46 (s, 9H), 1.20-1.35 (m, 26H). $^{13}$C-NMR (101 MHz, $CDCl_3$) δ ppm 173.34, 173.01, 171.82, 171.38, 156.56, 143.99, 141.34, 127.70, 127.05, 125.06, 119.98, 82.07, 79.87, 70.25, 70.12, 70.05, 67.29, 66.63, 52.27, 47.33, 40.86, 38.99, 37.03, 36.67, 35.67, 32.45, 29.70, 29.67, 29.64, 29.63, 29.53, 29.51, 29.38, 29.33, 29.13, 29.03, 28.15, 28.04, 25.68, 25.16, 22.47. [MH]$^+$ 936.80.

tert-butyl (S)-1-amino-15-(tert-butoxycarbonyl)-9,17-dioxo-3,6-dioxa-10,16-diazatetratriacontan-34-oate (33)

$Et_3N$ (2.5 mL, 18 mmol) was added to a mixture of (S)-tert-butyl 19-(tert-butoxycarbonyl)-1-(9H-fluoren-9-yl)-3,13,21-trioxo-2,7,10-trioxa-4,14,20-triazaoctatriacontan-38-oate (32) (1.12 g, 1.20 mmol) in DMF (10 mL). After the mixture was stirred at RT overnight, more $Et_3N$ (1.0 mL, 7.2 mmol) was added. The mixture was stirred at RT for another 7 h. All volatile components were removed under vacuum, and the residue was dried under high vacuum to afford (S)-tert-butyl 1-amino-15-(tert-butoxycarbonyl)-9,17-dioxo-3,6-dioxa-10,16-diazatetratriacontan-34-oate (33) (0.857 g, 1.20 mmol, 100% yield) as a colorless liquid, which was used directly in the next step. [MH]$^+$ 714.70.

tert-butyl (S)-39-(tert-butoxycarbonyl)-1-(9H-fluoren-9-yl)-3,13,23,33,41-pentaoxo-2,7,10,17,20,27,30-heptaoxa-4,14,24,34,40-pentaazaoctapentacontan-58-oate (34)

$NaHCO_3$ (0.20 g, 2.4 mmol) was added to a mixture of 2,5-dioxopyrrolidin-1-yl 1-(9H-fluoren-9-yl)-3-oxo-2,7,10-trioxa-4-azatridecan-13-oate (0.715 g, 1.44 mmol), (S)-tert-butyl 1-amino-15-(tert-butoxycarbonyl)-9,17-dioxo-3,6-dioxa-10,16-diazatetratriacontan-34-oate (33) (0.857 g, 1.20 mmol) in DME (15 mL) and water (5 mL). After the mixture was stirred at RT overnight, all volatile components were removed under vacuum, and aqueous HCl (1 M, 2.4 mL, 2.4 mmol) was added to adjust the pH to 2-3. The resulting mixture was extracted with EtOAc (200 mL, 100 mL×2). The combined organic layers were washed with brine, dried over $Na_2SO_4$, filtered, and concentrated under vacuum. The residue was subjected to flash chromatography (silica gel) eluting with MeOH/$CH_2Cl_2$ to afford (S)-tert-butyl 29-(tert-butoxycarbonyl)-1-(9H-fluoren-9-yl)-3,13,23,31-tetraoxo-2,7,10,17,20-pentaoxa-4,14,24,30-tetraazaoctatetracontan-48-oate (34) (1.03 g, 0.940 mmol, 78% yield) as a colorless, viscous liquid. $^1$H-NMR (400 MHz, $CDCl_3$) δ ppm 7.78 (d, J=7.58 Hz, 2H), 7.63 (br d, J=7.34 Hz, 2H), 7.39-7.46 (m, 2H), 7.30-7.36 (m, 2H), 6.74 (br s, 1H), 6.27-6.39 (m, 1H), 6.05-6.24 (m, 1H), 5.60-5.78 (m, 1H), 5.19-5.40 (m, 3H), 4.38-4.55 (m, 3H), 4.17-4.32 (m, 1H), 3.74-3.79 (m, 2H), 3.72 (t, J=5.99 Hz, 2H), 3.61-3.67 (m, 4H), 3.54-3.61 (m, 8H), 3.48-3.54 (m, 6H), 3.37-3.47 (m, 4H), 3.17-3.29 (m, 2H), 2.49 (br t, J=5.87 Hz, 2H), 2.43 (t, J=5.87 Hz, 2H), 2.18-2.26 (m, 4H), 1.76-1.90 (m, 1H), 1.51-1.73 (m, 7H), 1.48 (s, 9H), 1.46 (s, 9H), 1.18-1.37 (m, 26H). $^{13}$C-NMR (101 MHz, $CDCl_3$) δ ppm 173.34, 173.04, 171.80, 171.43, 171.34, 156.62, 144.00, 141.35, 127.69, 127.05, 125.04, 119.97, 82.05, 79.87, 77.55, 70.22, 70.18, 70.16, 70.07, 69.92, 67.23, 66.51, 53.40, 52.29, 50.86, 47.34, 40.99, 39.18, 39.04, 37.04, 36.95, 36.67, 35.67, 32.42, 29.70 (br s), 29.68 (br s), 29.65 (br s), 29.63 (br s), 29.54, 29.51, 29.38, 29.34, 29.32, 29.12, 29.01, 28.15, 28.0, 25.68, 25.16, 22.51. [MH]$^+$ 1254.90.

tert-butyl (S)-1-amino-25-(tert-butoxycarbonyl)-9,19,27-trioxo-3,6,13,16-tetraoxa-10,20,26-triazatetratetracontan-44-oate (35)

$Et_3N$ (1.2 mL, 8.61 mmol) was added to a mixture of (S)-tert-butyl 29-(tert-butoxycarbonyl)-1-(9H-fluoren-9-yl)-3,13,23,31-tetraoxo-2,7,10,17,20-pentaoxa-4,14,24,30-tetraazaoctatetracontan-48-oate (34) (330 mg, 0.301 mmol) in DMF (3 mL). After the mixture was stirred at RT for 20 h, all volatile components were removed under high vacuum. The residue subjected to flash chromatography, eluting with 2M $NH_3$-MeOH/$CH_2Cl_2$ (1:9), to afford (S)-tert-butyl 1-amino-25-(tert-butoxycarbonyl)-9,19,27-trioxo-3,6,13,16-tetraoxa-10,20,26-triazatetratetracontan-44-oate (35) (164 mg, 0.188 mmol, 62.3% yield) as a colorless liquid. $^1$H-NMR (400 MHz, $CDCl_3$) δ ppm 6.78-6.92 (m, 1H), 6.48-6.62 (m, 1H), 6.15-6.35 (m, 1H), 4.35-4.53 (m, 1H), 3.75 (q, J=6.11 Hz, 4H), 3.59-3.68 (m, 8H), 3.54-3.59 (m, 2H), 3.49-3.54 (m, 2H), 3.40-3.48 (m, 3H), 3.16-3.29 (m, 2H), 2.80-2.92 (m, 2H), 2.38-2.57 (m, 4H), 2.12-2.32 (m, 4H), 1.75-1.87 (m, 1H), 1.49-1.75 (m, 8H), 1.47 (s, 9H), 1.45 (s, 9H), 1.20-1.38 (m, 26H). $^{13}$C-NMR (101 MHz, $CDCl_3$) δ ppm 173.32, 173.04, 171.80, 171.47, 171.37, 81.99, 79.85, 74.86, 73.34, 70.30, 70.23, 70.12, 70.08, 69.88, 67.30, 52.31, 50.60, 41.74, 39.18, 39.00, 37.05, 37.00, 36.64, 35.65, 32.35, 29.67, 29.66, 29.61, 29.52, 29.48, 29.33, 29.31, 29.31, 29.11, 29.04, 28.13, 28.03, 25.68, 25.13, 22.51. [MH]$^+$ 873.75.

(S)-23-(tert-butoxycarbonyl)-2,2-dimethyl-4,21,29,39,49-pentaoxo-3,32,35,42,45-pentaoxa-22,28,38,48-tetraazadopentacontan-52-oic acid (36)

Pyridine (5.0 mL) was added to a mixture of (S)-tert-butyl 1-amino-25-(tert-butoxycarbonyl)-9,19,27-trioxo-3,6,13, 16-tetraoxa-10,20,26-triazatetratetracontan-44-oate (35) (164 mg, 0.188 mmol), and dihydrofuran-2,5-dione (94 mg, 0.939 mmol) at RT. After the mixture was stirred at RT overnight, all volatile components were removed under high vacuum. The residue was purified by medium pressure reverse phase chromatography on a C-18 column, eluting with MeCN/aq. TFA (monitored by ELSD-MS). Fractions containing the desired product were combined and volatile organic components were removed using a flow of nitrogen. The resulting aqueous solution containing the desired product was lyophilized to afford the title compound (S)-23-(tert-butoxycarbonyl)-2,2-dimethyl-4,21,29,39,49-pentaoxo-3,32,35,42,45-pentaoxa-22,28,38,48-tetraazadopentacontan-52-oic acid (36) (123 mg, 0.126 mmol, 67.3% yield) as a colorless liquid. [MH]$^+$ 973.81.

29,47-di-tert-butyl 1-(2,5-dioxopyrrolidin-1-yl) (S)-3,13,23,31-tetraoxo-7,10,17,20-tetraoxa-4,14,24,30-tetraazaheptatetracontane-1,29,47-tricarboxylate (37)

To a mixture of (S)-23-(tert-butoxycarbonyl)-2,2-dimethyl-4,21,29,39,49-pentaoxo-3,32,35,42,45-pentaoxa-22, 28,38,48-tetraazadopentacontan-52-oic acid (36) (123 mg, 0.126 mmol), 1-hydroxypyrrolidine-2,5-dione (21.8 mg, 0.190 mmol), and EDC (31.5 mg, 0.164 mmol), was added $CH_2Cl_2$ (5 mL). After the resulting clear solution was stirred at RT overnight, LC/ELSD-MS showed approximately 70% conversion. More 1-hydroxypyrrolidine-2,5-dione (21.8 mg, 0.190 mmol), and EDC (31.5 mg, 0.164 mmol) were added, and the mixture was stirred at RT for 3.5 h. LC/ELSD-MS showed complete conversion. The mixture was diluted with $CH_2Cl_2$ (150 mL) and washed with water/brine (2:1), dried over $Na_2SO_4$, filtered, concentrated under high vacuum to afford (S)-29,47-di-tert-butyl 1-(2,5-dioxopyrrolidin-1-yl) 3,13,23,31-tetraoxo-7,10,17,20-tetraoxa-4,14,24,30-tetraazaheptatetracontane-1,29,47-tricarboxylate (37) (135 mg, 0.126 mmol, 100% yield) as a colorless liquid, which was used directly in the next step. [MH]$^+$ 1070.93.

tert-butyl (S)-39-(tert-butoxycarbonyl)-2,2-dimethyl-4,10,13,23,33,41-hexaoxo-3,6,17,20,27,30-hexaoxa-5,9,14,24,34,40-hexaazaoctapentacontan-58-oate (38)

$NaHCO_3$ (21.2 mg, 0.252 mmol) was added to a mixture of (S)-29,47-di-tert-butyl dioxopyrrolidin-1-yl) 3,13,23,31-tetraoxo-7,10,17,20-tetraoxa-4,14,24,30-tetraazaheptatetracontane-1,29,47-tricarboxylate (37) (135 mg, 0.126 mmol), and tert-butyl 2-aminoethoxycarbamate hydrochloride (53.6 mg, 0.252 mmol) in DME (4.5 mL) and water (1.5 mL). The resulting clear solution was stirred at RT overnight. All volatile components were removed under vacuum, and the residue was purified by medium pressure reverse phase chromatography on a C-18 column, eluting with MeCN/aq.TFA (monitored by ELSD-MS). Fractions containing the desired product were combined and volatile organic components were removed using a flow of nitrogen. The resulting aqueous solution containing the desired product was lyophilized to afford the title compound (S)-tert-butyl 39-(tert-butoxycarbonyl)-2,2-dimethyl-4,10,13,23,33,41-hexaoxo-3,6,17,20,27,30-hexaoxa-5,9,14,24,34,40-hexaazaoctapentacontan-58-oate (38) (118 mg, 0.104 mmol, 83.0% yield). [MH]$^+$ 1131.99.

(S)-1-(aminooxy)-33-carboxy-4,7,17,27,35-pentaoxo-11,14,21,24-tetraoxa-3,8,18,28,34-pentaazadopentacontan-52-oic Acid (39)

TFA (2 mL) was added at 0° C. to a mixture of (S)-tert-butyl 39-(tert-butoxycarbonyl)-2,2-dimethyl-4,10,13,23,33, 41-hexaoxo-3,6,17,20,27,30-hexaoxa-5,9,14,24,34,40-hexaazaoctapentacontan-58-oate (38) (118 mg, 0.104 mmol), and 1,4-dimethoxybenzene (144 mg, 1.043 mmol) in $CH_2Cl_2$ (2 mL). The mixture was stirred at 0° C. for 5 min, and then RT for 2 h. The mixture was concentrated, and then dried under high vacuum for 30 min. The residue was purified by medium pressure reverse phase chromatography on a C-18 column, eluting with MeCN/aq. TFA (monitored by ELSD-MS). Fractions containing the desired product were combined and volatile organic components were removed using a flow of nitrogen. The resulting aqueous solution containing the desired product was cooled to −78° C. under a flow of nitrogen and lyophilized to afford (S)-1-(aminooxy)-33-carboxy-4,7,17,27,35-pentaoxo-11,14,21,24-tetraoxa-3,8,18,28,34-pentaazadopentacontan-52-oic acid (39) (60.0 mg, 0.064 mmol, 61.3% yield) as a white solid. Its LC-CAD purity was determined to be 98.0% using Analysis UHPLC-CAD Condition D. $[MH]^+$ 919.88, $[M+21-1]^+/2$ 460.69.

Example 7: Intracellular cAMP Accumulation Assay

Effects of H2 relaxin are mediated via its cognate G protein coupled-receptor, Relaxin Family Peptide Receptor (RXFP1), leading to stimulation of a combination of cell signalling pathways that are cell type dependent and can includes adenylate cyclase, protein kinase A, protein kinase C, phosphatidylinositol 3-kinase, and extracellular signaling regulated kinase (Erk1/2). Bathgate, et al., 2006. *Pharmacol. Rev.* 58, 7-31. The intracellular cAMP accumulation assay described herein was used to assess relaxin bioactivity and potency. The test compounds were based on WT-RLX (FIG. 1), AQ1 (FIG. 2), and BM25/AN1 (FIG. 3). PK extenders as shown were conjugated to the para-acetyl-phenylalanine contained in AQ1 and BM25/AN1 via an oxime linkage as described in Example 3.

CHO-K1 cells (ATCC; Cat. # CRL-9618) stably expressing the human RXFP1 receptor (locus number L0059350) (10,000/well) were plated into 96-well plates and cultured overnight at 37° C. and 5% $CO_2$. On the following day, the medium was removed from the wells and the cells were stimulated with the addition of ligand (relaxin polypeptide) in 50 uL buffer (1×HBSS, 5 mM HEPES (7.2), 0.5 mM IBMX, 0.1% BSA); incubation was for 10 min at 37° C. Unstimulated cells were utilized as reference controls. Reactions were terminated and cellular cAMP levels were measured using the Homogeneous Time Resolved Fluorescence (HTRF) Dynamic 2 cAMP kit (CisBio, #62AM4PEC) according to the manufacturer's protocol. Plates were analyzed using an EnVision 2104 Multilablel Reader (PerkinElmer). Signal was expressed in terms of the ratio of fluorescence intensity @ 665 nm/fluorescence intensity @ 620 nm×10,000. The concentration of cAMP in the sample was determined by comparison with standard curves generated from known concentrations of cAMP. The potency of each relaxin was determined using a ten-point concentration response curves which was performed in duplicate. The data were analyzed using Microsoft Excel, Version 2013 Xlfit software. Effective concentration 50 (EC50) values, the point at which the response was one-half maximal, were calculated using a four-parameter logistic equation that allowed for a variable-slope (Table 3).

Table 3. Intracellular cAMP accumulation assay results. Abbreviations used in this table: dK: D-lysine; Sar: sarcosine (N-methylglycine); dGlu: D-glutamic acid; 20 kDa PEG: poly(ethylene glycol), 20 kDa molecular weight; PEGn (e.g., n is 2, 12, 24, or 36): —(O—$CH_2$—$CH_2$)$_n$—O—; —C13-: —(C=O)—$(CH_2)_{12}$—; —C14-: —(C=O)—$(CH_2)_{13}$—; —C15-: —(C=O)—$(CH_2)_{14}$— (these abbreviations are illustrative of, but do not limit, the —Cn- of Formula I or uses of these terms outside of this table). In $Glu^\gamma$-C13-, $Glu^\gamma$-C14-, $Glu^\gamma$-C15-, and $Glu^\gamma$-C17- in Table 3, the first carbonyl carbon of the fatty acid is bonded to the (gamma) Glu residue via an amide bond.

| Relaxin Conjugate Name | hRXFP1/CHO-K1 cAMP EC50 (nM, avg) | Peptide component SEQ ID NO: |
|---|---|---|
| WT-RLX | 0.12 | |
| BM25/AN1 | 0.09 | |
| BM25/AN1-C13—CH3 | 1.85 | |
| AQ1 | 0.11 | |
| AQ1-20 kDa PEG | 3.22 | |
| AQ1-Glu-C13—CH3 | 0.95 | |
| AQ1-Glu-C13—COOH | 0.18 | |
| AQ1-PEG36-Glu-C13—CH3 | 0.15 | |
| AQ1-PEG36-Glu-C13—COOH | 0.25 | |
| AQ1-GGGGS-Glu$^\gamma$-C13—COOH | 0.14 | 101 |
| AQ1-DRDDRD-C13—COOH | 0.32 | 102 |
| AQ1-KKKKKK-Glu$^\gamma$-C13—COOH | 0.08 | 103 |
| AQ1-RGGEEKKKEKEK-Glu$^\gamma$-C13—COOH | 0.29 | 104 |
| AQ1-GGGEEE-Glu$^\gamma$-C13—COOH | 0.22 | 105 |
| AQ1-EEEGGG-Glu$^\gamma$-C13—COOH | 0.31 | 106 |
| AQ1-KKKGGG-Glu$^\gamma$-C13—COOH | 0.09 | 107 |
| AQ1-GETGSSGEGT-Glu$^\gamma$-C13—COOH | 0.65 | 108 |
| AQ1-GGGKKK-Glu$^\gamma$-C13—COOH | 0.19 | 109 |
| AQ1-GSHHHHHGS-Glu$^\gamma$-C13—COOH | 0.28 | 110 |
| AQ1-Sar-Sar-Sar-Sar-Sar-Ser-Sar-Sar-Sar-Sar-Glu$^\gamma$-C13—COOH | 0.39 | 111 |
| AQ1-Sar-Sar-Sar-Sar-Ser-Glu$^\gamma$-C13—COOH | 0.32 | 112 |
| AQ1-Sar-Sar-Sar-Glu-Glu-Glu$^\gamma$-C13—COOH | 0.59 | 113 |
| AQ1-KKSGGSGG-Glu$^\gamma$-C13—COOH | 0.34 | 114 |
| AQ1-KKSGGSGG-Glu$^\alpha$-C13—COOH | 0.27 | 115 |
| AQ1-KKSAGSAG-Glu$^\gamma$-C13—COOH | 0.27 | 116 |
| AQ1-KSGGSGG-Glu$^\gamma$-C13—COOH | 0.24 | 117 |
| AQ1-KKKSGGSGG-Glu$^\gamma$-C13—COOH | 0.14 | 118 |
| AQ1-KKSGGSGGEE-Glu$^\gamma$-C13—COOH | 0.16 | 119 |
| AQ1-dKdKdKdKdK-Glu$^\gamma$-C13—COOH | 0.10 | 120 |

-continued

| Relaxin Conjugate Name | hRXFP1/CHO-K1 cAMP EC50 (nM, avg) | Peptide component SEQ ID NO: |
|---|---|---|
| AQ1-EESGGSGG-Glu$^\gamma$-C13—COOH | 0.83 | 121 |
| AQ1-GGGGS-Glu$^\gamma$-C15—COOH | 1.55 | 122 |
| AQ1-GSGSGSGS-Glu$^\gamma$-C15—COOH | 2.79 | 123 |
| AQ1-EEEGGG-Glu$^\gamma$-C15—COOH | 5.26 | 124 |
| AQ1-EEEGGG-Glu$^\gamma$-C17—COOH | 10.52 | 125 |
| AQ1-EEEGGG-Glu$^\gamma$-C13—CH3 | 0.38 | 126 |
| AQ1-EEEGGG-Glu$^\gamma$-C15—CH3 | 0.46 | 127 |
| AQ1-EEEGGG-dGlu$^\gamma$-C13—COOH | 1.91 | 128 |
| AQ1-EEEGGG-Glu$^\gamma$-C14—COOH | 1.88 | 129 |
| AQ1-EGGGGSK-Glu$^\gamma$-C13—COOH | 0.31 | 130 |
| AQ1-EEEEEE-Glu$^\gamma$-C15—COOH | 11.06 | 131 |
| AQ1-Compound 39 | 2.23 | |
| AQ1-EEEEPEEEEPEEEEPEEEE-Glu$^\gamma$-C14—CH3 | 0.33 | 133 |
| AQ1-EEEEPEEEEPEEEEPEEEE-Glu$^\gamma$-C15—CH3 | 0.34 | 134 |
| AQ1-EEEEPEEEEPEEEEPEEGGG-C14—CH3 | 0.16 | 135 |
| AQ1-EEEEGEEEEGEEEEGEEEE-Glu$\gamma$-C14—CH3 | 0.67 | 136 |
| AQ1-KGGEEKKKEKEKEPKGGEEKKKKEKEK-Glu$^\gamma$-C15—COOH | 1.81 | 137 |
| AQ1-EAQKAQAEAQKAQAEAQKAQA-Glu$^\gamma$-C15—COOH | 4.96 | 138 |
| AQ1-GGGGS-Glu$^\gamma$-C14—COOH$^a$ | 0.28 | 139 |
| AQ1-KK-Glu$^\gamma$-C13—COOH | 0.10 | 140 |
| AQ1-KK-Glu$^\gamma$-C14—COOH | 0.34 | 141 |
| AQ1-KK-Glu$^\gamma$-C15—COOH | 0.40 | 142 |
| AQ1-EEEEEE-Glu$^\gamma$-C14—CH3 | 0.38 | 143 |
| AQ1-KK-Glu$^\gamma$-C14—CH3 | 0.35 | 144 |
| AQ1-KGP-Glu$^\gamma$-C14—COOH | 0.27 | 145 |
| AQ1-KGPKGP-Glu$^\gamma$-C14—COOH | 0.23 | 146 |
| AQ1-SGGGS-Glu$^\gamma$-C14—COOH | 0.32 | 147 |
| AQ1-KGGGS-Glu$^\gamma$-C14—COOH | 0.34 | 148 |
| AQ1-KGGGSE-Glu$^\gamma$-C14—COOH | 0.37 | 149 |
| AQ1-GSPGSP-Glu$^\gamma$-C14—COOH | 0.29 | 150 |
| AQ1-GGGGP-Glu$^\gamma$-C14—COOH | 0.39 | 151 |
| AQ1-EGGS-Glu$^\gamma$-C14—COOH | 0.33 | 152 |
| AQ1-EGGGP-Glu$^\gamma$-C14—COOH | 0.44 | 153 |
| AQ1-KGPGSE-Glu$^\gamma$-C14—COOH | 0.60 | 154 |
| AQ1-Spermine-Glu$^\gamma$-C14—COOH | 0.39 | |
| AQ1-KKGGS-Glu$^\gamma$-C15—COOH | 1.36 | 156 |

$^a$Relaxin Conjugate AQ1-GGGGS-Glu$^\gamma$ (SEQ ID NO: 139)-C14—COOH comprises a relaxin A chain polypeptide of SEQ ID NO: 35 and a relaxin B chain polypeptide of SEQ ID NO: 6, wherein the modified para-acetyl-L-phenylalanine located at the N-terminus of said relaxin A chain polypeptide is linked to the PK enhancer comprising GGGGS-Glu$^\gamma$ (SEQ ID NO: 139)-C14—COOH, as depicted in Formula III AQ1-Relaxin

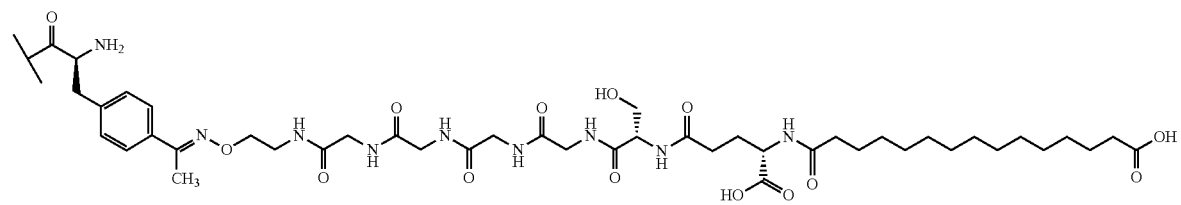 [SMILES: C/C(=N\OCCNC(=O)CNC(=O)CNC(=O)CNC(=O)CNC(=O)[C@H](CO)NC(=O)CC[C@H](NC(=O)CCCCCCCCCCCCCC(=O)O)C(=O)O)c1ccc(C[C@H](N)C(=O)C(C)C)cc1]

(Formula III).

Example 8: In Vivo Pharmacokinetic (PK) Studies

Male Sprague-Dawley rats (n=3) received a single intravenous (IV) or subcutaneous (SC) dose (1 mg/kg) of relaxin constructs (as described in Example 7, above) formulated in a suitable buffer (e.g. 20 mM Histidine, 750 mM NaCl, pH 6.0). Blood samples were collected via jugular vein at different time points out to 72 hours. Blood samples were allowed to coagulate at room temperature (30-60 min) and then centrifuged (1500-2000) at 4° C. to obtain serum. After centrifugation serum samples were transferred to 96 well plates and stored at −80° C. until bioanalysis. Relaxin concentrations were measured from serum by ELISA.

Relaxin concentration-time profiles from individual animals were used for analysis. Pharmacokinetic parameters were calculated by non-compartmental methods using Phoenix WinNonlin (version 6.4) or Kinetica (version 5). Mean pharmacokinetic parameters $C_{max}$, $AUC_{inf}$, $C_{24}$ and half-life were reported (Table 4).

TABLE 4

In vivo PK data (abbreviations as in Table 3).

| Relaxin Conjugate Name | Rat PK SC Dose (mg/kg) | Rat PK AUC Total h*nmol/L | Rat PK C24 (nM) | SEQ ID NO: of peptide component |
|---|---|---|---|---|
| AQ1-20kDa PEG | 1.0[a] | 1475 | 39 | |
| AQ1-PEG36-Glu-C13-COOH | 1.0 | 1003 | 9.7 | |
| AQ1-GGGGS-Glu$^\gamma$-C13-COOH | 0.8 | 1096 | 1.52 | 101 |
| AQ1-DRDDRD-C13-COOH | 1.0 | 1008 | 0.38 | 102 |
| AQ1-KKKKKK-Glu$^\gamma$-C13-COOH | 1.0 | 38 | 0.05 | 103 |
| AQ1-RGGEEKKKEKEK-Glu$^\gamma$-C13-COOH | 1.0 | 987 | 0.10 | 104 |
| AQ1-GGGEEE-Glu$^\gamma$-C13-COOH | 1.0 | 866 | 0.18 | 105 |
| AQ1-EEEGGG-Glu$^\gamma$-C13-COOH | 1.0 | 1381 | 0.29 | 106 |
| AQ1-KKKGGG-Glu$^\gamma$-C13-COOH | 1.0 | 258 | 0.24 | 107 |
| AQ1-GETGSSGEGT-Glu$^\gamma$-C13-COOH | 1.0 | 1112 | 0.28 | 108 |
| AQ1-GGGKKK-GlU$^\gamma$-C13-COOH | 1.0 | 231 | 0.10 | 109 |
| AQ1-GSHHHHHGS-Glu$^\gamma$-C13-COOH | 1.0 | 582.0 | 0.46 | 110 |
| AQ1-KSGGSGG-Glu$^\gamma$-C13-COOH | 1.0 | 814 | 0.73 | 117 |
| AQ1-KKKSGGSGG-Glu$^\gamma$-C13-COOH | 1.0 | 264 | 0.21 | 118 |
| AQ1-KKSGGSGGEE-Glu$^\gamma$-C13-COOH | 1.0 | 676 | 0.09 | 119 |
| AQ1-dKdKdKdKdKdK-Glu$^\gamma$-C13-COOH | 1.0 | 31.2 | 0.06 | 120 |
| AQ1-GGGGS-Glu$^\gamma$-C15-COOH | 1.0[b] | 5526 | 44 | 122 |
| AQ1-EEEGGG-Glu$^\gamma$-C15-COOH | 1.0 | 3553 | 22 | 124 |
| AQ1-EEEGGG-Glu$^\gamma$-C13-CH3 | 1.0 | 274 | 0.4 | 126 |
| AQ1-EEEGGG-Glu$^\gamma$-C15-CH3 | 1.0 | 370 | 0.89 | 127 |
| AQ1-EEEGGG-Glu$^\gamma$-C14-COOH | 1.0[c] | 2137 | 5.2 | 129 |
| AQ1-GGGGS-Glu$^\gamma$-C14-COOH | 1.0 | 2308 | 17 | 139 |
| AQ1-KK-Glu$^\gamma$-C14-COOH | 1.0 | 451 | 1.5 | 141 |
| AQ1-KK-Glu$^\gamma$-C15-COOH | 1.0 | 820 | 8.8 | 142 |
| AQ1-GSPGSP-Glu$^\gamma$-C14-COOH | 1.0 | 1979 | 5 | 150 |
| AQ1-GGGGP-Glu$^\gamma$-C14-COOH | 1.0 | 2179 | 3.9 | 151 |

[a]Adjusted from 0.2 mpk
[b]Adjusted from 0.3 mpk
[c]Adjusted from 0.5 mpk

Example 9: Rat Renal Blood Flow Studies

Male Sprague Dawley rats (~250-300 g) were anesthetized with sodium pentobarbital (50 mg/kg), the trachea was cannulated with PE-205 tubing to maintain airway patency, and temperature was maintained at 37° C. with a heated surgical plate. A 1.4 F pressure catheter (Millar Inc., Houston, Tex.) was advanced into the right carotid artery to measure aortic blood pressure. The right jugular vein was cannulated with PE-50 tubing for administration of test articles. The left kidney was exposed by a retroperitoneal incision, and a Doppler flow probe (Model 0.5 VB, Transonic System Inc., Ithaca, N.Y.) was attached to the left renal artery to monitor blood flow. Sodium pentobarbital (15 mg/kg, intraperitoneal) was supplemented after completion of these surgical procedures. Following a 10-15 min equilibration, the relaxin was administered at 1 mg/kg intravenously in a dosing volume of 0.15 to 1.82 mL/kg over 30 seconds via an infusion pump (Harvard Apparatus, Holliston, Mass.). Blood pressure, heart rate and renal blood flow were continuously recorded for 45 min after relaxin administration using a Millar MPVS Ultra Signal Conditioning unit connected to a desktop computer running LabChart 7-Pro data acquisition software (ADInstruments, Dunedin, New Zealand) (Table 5).

The results tabulated above illustrate the complex relationship among the conjugate structure and position and the resulting renal blood flow. WT-RLX alone elicited approximately a 25% increase in renal blood flow over baseline, which was expected given the known vascular activity of relaxin. It was expected that the various test compounds, being relaxin agonists (see Example 7), should likewise

TABLE 5

Rat renal blood flow changes (abbreviations as in Table 3).

| Relaxin Conjugate | % change in RBF over baseline | SEQ ID NO: OF PEPTIDE COMPONENT |
|---|---|---|
| WT-RLX | +25 | |
| AQ1-201kDa PEG | +21 | |
| BM25/AN1 | -20 | |
| BM25/AN1-C13-CH3 | -100[a] | |
| BM25/AN1-PEG36-C13-CH3 | -90 | |
| BM25/AN1-PEG36-Glu-C13-CH3 | -25 | |
| AQ1 | -17 | |
| AQ1-Glu-C13-CH3 | -27[b] | |
| AQ1-Glu-C13-COOH | +14[b] | |
| AQ1-PEG36-Glu-C13-CH3 | +20[b] | |
| AQ1-PEG36-C13-COOH | +22 | |
| AQ1-PEG36-Glu-C13-COOH | +24 | |
| AQ1-PEG36-Glu-C15-COOH | +30 | |
| AQ1-PEG24-Glu-C13-COOH | +15 | |
| AQ1-PEG12-Glu-C13-COOH | +5 | |
| AQ1-GGGGS-Glu$^\gamma$-C13-COOH | +2 | 101 |
| AQ1-DRDDRD-C13-COOH | +11 | 102 |
| AQ1-KKKKKK-Glu$^\gamma$-C13-COOH | +12 | 103 |
| AQ1-RGGEEKKKEKEK-Glu$^\gamma$-C13-COOH | +19 | 104 |
| AQ1-GGGEEE-Glu$^\gamma$-C13-COOH | +11 | 105 |
| AQ1-EEEGGG-Glu$^\gamma$-C13-COOH | +7[b] | 106 |
| AQ1-KKKGGG-Glu$^\gamma$-C13-COOH | +10[b] | 107 |
| AQ1-GGGKKK-Glu$^\gamma$-C13-COOH | +9 | 109 |
| AQ1-GSHHHHHGS-Glu$^\gamma$-C13-COOH | +16 | 110 |
| AQ1-Sar-Sar-Sar-Sar-Ser-Glu$^\gamma$-C13-COOH | +6 | 157 |
| AQ1-Sar-Sar-Sar-Glu-Glu-Glu$^\gamma$-C13-COOH | +5 | 158 |
| AQ1-KSGGSGG-Glu$^\gamma$-C13-COOH | +17 | 117 |
| AQ1-EEEGGG-Glu$^\gamma$-C13-CH3 | +1 | 126 |
| AQ1-EEEGGG-Glu$^\gamma$-C15-CH3 | +18 | 127 |
| AQ1-GGGGS-Glu$^\gamma$-C14-COOH | +10 | 139 |

[a]Animals died shortly after compound administration. Necropsy showed pale coloration of the kidneys, indicating complete loss of blood flow.
[b]The compound was observed to be poorly soluble.

elicit an increase in renal blood flow. Surprisingly, however, it was observed that some of the compounds elicited decreases in renal blood flow. Such impairment of renal blood flow could be a clinically significant contraindication, especially in heart failure, in which renal impairment is often observed. The compounds BM25/AN1, BM25/AN1-C13-CH3, BM25/AN1-PEG36-C13-CH3, BM25/AN1-PEG36-Glu-C13-CH3, AQ1, and AQ1-Glu-C13-CH3 all resulted in impaired renal blood flow (Table 5, above).

These results were unexpected and unpredictable. Structurally related compounds exhibited divergent effects on renal blood flow. LEVEMIR®, an FDA-approved, marketed long-acting form of insulin for treating diabetes, is an insulin-C13-CH3 conjugate that has demonstrated safety (NDA 21-878 by Novo Nordisk A/S, page 1). In contrast, administration of BM25/AN1-C13-CH3, which is structurally similar to LEVEMIR®, was fatal in the rats, and necropsy showed pale kidneys indicating that renal blood flow was blocked. In addition, AQ1 relaxin, which contains a single amino acid substitution with para-acetyl-phenylalanine at position 1 of the A chain, decreased renal blood flow, while the AQ1-20 kDa PEG compound, which contains the same non-natural amino acid substitution but is conjugated to a 20 kDa PEG, increased renal blood flow. Further, BM25/AN1-PEG36-Glu-C13-CH3 decreased renal blood flow, but AQ1-PEG36-Glu-C13-CH3 increased renal blood flow. Several of the aforementioned compounds causing decreased renal blood flow contained a PK enhancer ending with a methyl group, e.g. BM25/AN1-C13-CH3, BM25/AN1-PEG36-C13-CH3, and AQ1-Glu-C13-CH3. However, animals treated with AQ1-EEEGGG-Glu$^\gamma$-C15-CH3 and AQ1-PEG36-Glu-C13-CH3 exhibited good renal blood flow, indicating that the methyl group did not invariably cause poor renal blood flow. In contrast, AQ1-GGGGS-Glu$^\gamma$ (SEQ ID NO: 139)-C14-COOH, and other tested AQ1 relaxin molecules conjugated to a PK enhancer comprising a peptide component and a —C13-COOH, —C14-COOH or —C15-COOH fatty acid, generally showed improved renal blood flow (Table 5, above).

Example 10: Rat Toxicity Studies

Figure 7B:
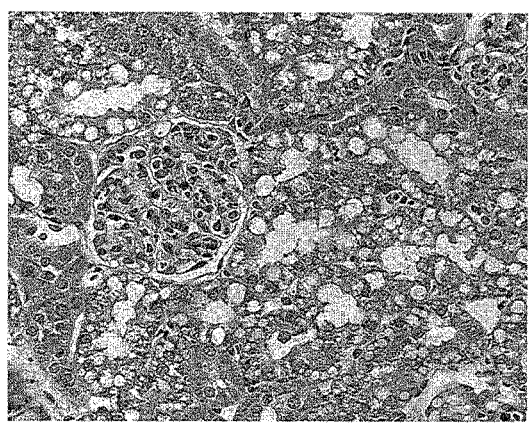
Figure 7C:
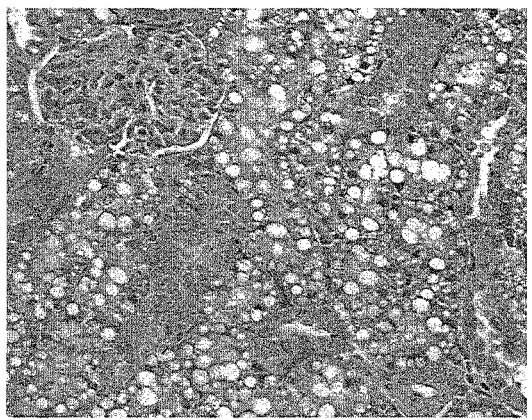

AQ1-20 kDa-PEG was given to rats by subcutaneous administration at doses of 1, 5, and 15 mg/kg/day for 10 days. Following the final dose animals were euthanized, dissected, and kidney histopathology was performed. Vacuoles were observed in renal tubular epithelial cells at all doses (FIG. 7C). In contrast, vacuoles were not observed in renal tubular epithelial cells of rats dosed with Vehicle (150 mM Arg in 10 mM citrate buffer pH 5.5) subcutaneously for 10 days (FIG. 7A).

AQ1-PEG36-Glu-C13-COOH was given to rats by subcutaneous administration at doses of 10 and 40 mg/kg/day for 7 days. Following the final dose animals were euthanized, dissected, and kidney histopathology was performed. Vacuoles were observed in renal tubular epithelial cells at all doses (FIG. 7B).

Figure 7D:
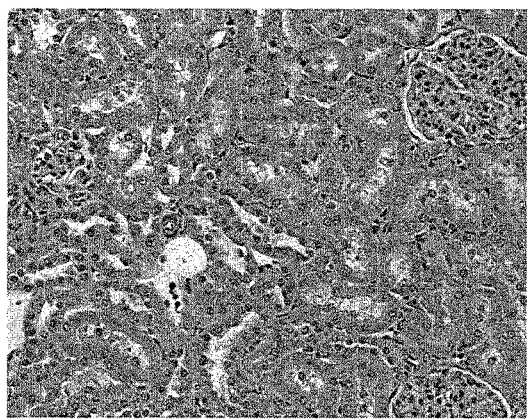

AQ1-GGGGS-Glu$^\gamma$ (SEQ ID NO: 139)-C14-COOH was given to rats by subcutaneous administration at doses of 5, 20, and 40 mg/kg/day for 7 days. Following the final dose animals were euthanized, dissected, and kidney histopathology was performed. At all doses, renal tubular epithelial cells appeared normal with no evidence of test-article related vacuoles (FIG. 7D).

The compound AQ1-GGGGS-Glu$^\gamma$ (SEQ ID NO: 139)-C14-COOH also showed good renal blood flow results (Example 9), favorable solubility profile (data not shown), and significantly lower viscosity than AQ1-20 kDa PEG.

Example 11: Effect of Relaxin on Human Primary Cardiac Fibroblasts

Primary Human Cardiac Fibroblasts (NHCF-V) were purchased from Lonza, Fairlawn, N.J. (Cat.#: CC-2904). NHCF-V cells were isolated from the ventricle of normal, adult heart tissue. Cells stained positive for smooth muscle α-actin and expressed ≥90% collagen I and ≤10% Von Willibrand factor VIII. Cells at passages 3 through 6 were used for the real-time quantitative reverse transcription-polymerase chain reaction (qRT-PCR) studies. Cells were cultured in FGM™-3 BulletKit™ (Cat. #: CC-4526, Lonza) containing 10% FBS complete medium. At confluence, cells were split and cultured in 6-well plates at a density of 150,000/well for 24 hr in complete medium. Cells were subsequently changed to serum-free medium (Cat. #: CC-3131, Fibroblast Basal Medium, Lonza) for 24 hr, then treated with human H2 relaxin (Cat. #: 3596-RN, R&D Systems) or AQ1-GGGGS-Glu$^\gamma$ (SEQ ID NO: 139)-C14-COOH in the presence of 0.5 ng/mL of TGF-β (Cat. #: 240-B, R&D Systems) for another 24 hours. Selection of TGF-β concentrations for profiling and duration of treatment were based on previous reports. Cells in 6-well plates were harvested for total RNA extraction and qRT-PCR analysis.

Total RNA was extracted using the RNeasy Mini Kit (Cat. #: 74106, Qiagen) according to the manufacturer's protocols including the on-column removal of genomic cDNA. Real-time qRT-PCR was performed in a two-step manner; cDNA synthesis and real-time detection were carried out in a PTC-100 Thermal Cycler (MJ Research) and an ABI Prism 7700 Sequence Detection System (Applied Biosystems), respectively. TaqMan Universal PCR Master Mix (Applied Biosystems) was used in subsequent PCR reactions according to the manufacturer's protocols. All qRT-PCR reactions were performed in duplicate. Sequence-specific primers for smooth muscle alpha-actin (Sense: 5'-AAATACTCTGTCTGGATCGGTGGCTCC-3' (SEQ ID NO:51); Antisense: 5'-CACATAGGTAACGAGTCAGAGCTTTGGCTA-3' (SEQ ID NO:52)) and housekeeping gene L30 (Sense: 5'-GCTGGAGTCGATCAACTCTAGG-3' (SEQ ID NO:53); Antisense: 5'-CCAATTTCGCTTTGCCTTGTC-3' (SEQ ID NO:54)) were designed using Primer Express Version 2 software (Applied Biosystems) based on published sequences (www.ncbi.nlm.nih.gov). Expression levels of smooth muscle alpha actin were normalized to expression levels of housekeeping gene L30. Human cardiac fibroblasts treated with AQ1-GGGGS-Glu$^\gamma$ (SEQ ID NO: 139)-C14-COOH were analyzed for significance differences from vehicle-treated cells using a Student's T-test (Microsoft Excel, Version 2013) with a P value of <0.05 deemed as significant.

AQ1-GGGGS-Glu$^\gamma$ (SEQ ID NO: 139)-C14-COOH was demonstrated to reduce the expression of pro-fibrotic gene, smooth muscle alpha-actin, in TGF-beta treated (0.5 ng/mL; 24 hr) primary human cardiac fibroblasts. As shown in FIGS. 6A-6B, decreases in gene expression were concentration dependent and equally robust for both human H2 relaxin and AQ1-GGGGS-Glu$^\gamma$ (SEQ ID NO: 139)-C14-COOH. AQ1-GGGGS-Glu$^\gamma$ (SEQ ID NO: 139)-C14-COOH may be used as an antifibrotic agent for treating fibrotic diseases, for example, cardiac fibrosis.

Example 12: Additional Examples of PK Enhancers

PK enhancers as shown in Tables 6 below are produced, generally in accord with the methods described in Examples 4, 5, and 6, above. These PK enhancers are conjugated to modified relaxin polypeptides comprising a non-naturally encoded amino acid (e.g., at A chain position 1, such as RLX-AQ1) using the methods described in Example 3 and are characterized, including testing for biological activity, pharmacokinetic properties, effects on renal blood flow, vacuole formation, and effects on cardiac fibroblasts as described in Examples 7-11.

TABLE 6

Exemplary PK enhancers (abbreviations as in Table 3, and as indicated below).

| PK Enhancer Structure | Peptide component SEQ ID NO: |
|---|---|
| AAAAAS-X-FA | 159 |
| AAAAS-X-FA | 160 |
| AAAS-X-FA | 161 |
| AASAASAASAA-X-FA | 162 |
| AASAASAAS-X-FA | 163 |
| AASAAS-X-FA | 164 |
| AASSA-X-FA | 165 |
| AAS-X-FA | 166 |
| AGAGS-X-FA | 167 |
| AGAGS-X-FA | 168 |
| AGAS-X-FA | 169 |
| AGAS-X-FA | 170 |
| AGGAS-X-FA | 171 |
| AGGAS-X-FA | 172 |
| AGGGS-X-FA | 173 |
| AGGGS-X-FA | 174 |
| AS-X-FA | 175 |
| $A^\beta A^\beta A^\beta A^\beta S$-X-FA | 176 |
| $A^\beta A^\beta A^\beta S$-X-FA | 177 |
| $A^\beta A^\beta S$-X-FA | 178 |
| $A^\beta S$-X-FA | 179 |
| EGGEGG-Z-FA | 180 |
| EGGEGP-Z-FA | 181 |
| EGPEGP-Z-FA | 182 |
| GGAAS-X-FA | 183 |
| GGAAS-X-FA | 184 |
| GGAS-X-FA | 185 |
| GGAS-X-FA | 186 |
| GGGAS-X-FA | 187 |
| GGGAS-X-FA | 188 |
| GGGGGGS-X-FA | 189 |
| GGGGGS-X-FA | 190 |

TABLE 6-continued

Exemplary PK enhancers (abbreviations as in Table 3, and as indicated below).

| PK Enhancer Structure | Peptide component SEQ ID NO: |
|---|---|
| GGGGS-FA | 191 |
| GGGGS-PEG2-PEG2-X-FA | 192 |
| GGGGS-X-C14-COOH | 193 |
| GGGGS-X-FA-malonic acid tail | 194 |
| GGGGS-X-FA-succinic acid tail | 195 |
| GGGGS-Z-FA | 196 |
| GGGGS-Z-FA | 197 |
| GGGGT-FA | 198 |
| GGGSG-X-FA | 199 |
| GGGSSS-X-FA | 200 |
| GGGSS-X-FA | 201 |
| GGGSS-X-FA | 202 |
| GGGS-X-FA | 203 |
| GGGTTTT-X-FA | 204 |
| GGSGGGGG-X-FA | 205 |
| GGSGGSGGSGG-X-FA | 206 |
| GGSGGSGGS-X-FA | 207 |
| GGSGGS-X-FA | 208 |
| GGSGG-X-FA | 209 |
| GGSGS-X-FA | 210 |
| GGSSG-X-FA | 211 |
| GGSSSS-X-FA | 212 |
| GGSSS-X-FA | 213 |
| GGSS-X-FA | 214 |
| GGSS-X-FA | 215 |
| GGSS-X-FA | 216 |
| GGS-Z-FA | 217 |
| GGTTTT-X-FA | 218 |
| GGTTT-X-FA | 219 |
| GGTT-X-FA | 220 |
| GSGGG-X-FA | 221 |
| GSGGS-X-FA | 222 |
| GSGSGSGSGS-X-FA | 223 |
| GSGSGSGS-X-FA | 224 |
| GSGSGS-X-FA | 225 |
| GSGSG-X-FA | 226 |
| GSGS-X-FA | 227 |

TABLE 6-continued

Exemplary PK enhancers (abbreviations as in Table 3, and as indicated below).

| PK Enhancer Structure | Peptide component SEQ ID NO: |
|---|---|
| GSP-Z-FA | 228 |
| GSSSS-X-FA | 229 |
| GSSS-X-FA | 230 |
| GSS-X-FA | 231 |
| GS-Z-FA | 232 |
| GTTT-X-FA | 233 |
| GTT-X-FA | 234 |
| KGGGS-Z-FA | 235 |
| KGGKGG-Z-FA | 236 |
| KK-PEG2-PEG2-X-FA | 237 |
| KKS-FA | 238 |
| KKS-Z-FA | 239 |
| KKT-FA | 240 |
| KKT-Z-FA | 241 |
| KK-X-malonic acid tail | 242 |
| KK-X-succinic acid tail | 243 |
| KK-Z-FA | 244 |
| KPKS-Z-FA | 245 |
| KSGGGSK-Z-FA | 246 |
| KSGKSG-Z-FA | 247 |
| SGGGGG-X-FA | 248 |
| SGGGG-X-FA | 249 |
| SGGGG-X-FA | 250 |
| SGGGS-X-FA | 251 |
| SGGG-X-FA | 252 |
| SGG-X-FA | 253 |
| SG-X-FA | 254 |

X = $Glu^\gamma$, (D)-$Glu^\gamma$, $Asp^\alpha$, $Asp^\beta$, (D)-$Asp^\alpha$, or (D)-$Asp^\beta$
Z = (D)-$Glu^\gamma$, $Asp^\alpha$, $Asp^\beta$, (D)-$Asp^\alpha$, or (D)-$Asp^\beta$
FA = Fatty Acid = e.g., C13-COOH, C14-COOH, or C15-COOH; unless indicated otherwise The PK enhancers shown in Table 7 below were synthesized, generally in accord with the methods described in Examples 3-5 herein. These PK enhancers are conjugated to modified relaxin polypeptides comprising a non-naturally encoded amino acid (e.g., at A chain position 1, such as in RLX-AQ1) using the methods described in Example 3 and are characterized, including testing for biological activity, pharmacokinetic properties, effects on renal blood flow, vacuole formation, and effects on cardiac fibroblasts as described in Examples 7-11.

TABLE 7

Exemplary PK enhancers (abbreviations: N-MeK: 6-N-methyllysine; Dap: 2,3-diaminopropionic acid; others as in Table 3).

| PK Enhancer Structure | Peptide component SEQ ID NO: |
|---|---|
| GS-$Glu^\gamma$-C14-COOH | 255 |
| GGS-$Glu^\gamma$-C14-COOH | 256 |
| GSP-$Glu^\gamma$-C14-COOH | 257 |
| EGGEGG-$Glu^\gamma$-C14-COOH | 258 |
| $Glu^\gamma$GGGGS-$Glu^\gamma$-C14-COOH | 259 |
| EGGEGP-$Glu^\gamma$-C14-COOH | 260 |
| EGPEGP-$Glu^\gamma$-C14-COOH | 261 |
| Spermine-$Glu^\gamma$-C13-COOH | |
| KGGGS-$Glu^\gamma$-C15-COOH | 262 |
| KSGGGSK-$Glu^\gamma$-C15-COOH | 263 |
| KSGKSG-$Glu^\gamma$-C15-COOH | 264 |
| KGGKGG-$Glu^\gamma$-C15-COOH | 265 |
| KPKS-$Glu^\gamma$-C15-COOH | 266 |
| dKdKdKdKdK-$Glu^\gamma$-C13-COOH | 267 |
| DapDapDapDapDapDap-$Glu^\gamma$-C13-COOH | 268 |
| N-MeK-N-MeK-N-MeK-N-MeK-N-MeK-N-MeK-$Glu^\gamma$-C13-COOH | 269 |
| dKdKdKGGG-$Glu^\gamma$-C13-COOH | 270 |
| OGGEEE-$Glu^\gamma$-C15-COOH | 271 |
| GGGEEE-$Glu^\gamma$-C17-COOH | 272 |
| KKKKP-$Glu^\gamma$-C13-COOH | 273 |
| KKKKKK-C13-COOH | 274 |
| KAQKAQA-$Glu^\gamma$-C13-COOH | 275 |
| KKKKPKKKK-$Glu^\gamma$-C13-COOH | 276 |
| KKKKKKGGG-$Glu^\gamma$-C13-COOH | 277 |
| EEEGGG-d$Glu^\gamma$-C13-CH3 | 278 |
| GGGGS-$Glu^\gamma$-C13-CH3 | 279 |

It is understood that the examples and embodiments described herein are for illustrative purposes only and that various modifications or changes in light thereof will be suggested to those of ordinary skill in the art and are to be included within the spirit and purview of this application and scope of the appended claims. It is also to be understood that the terminology used herein is for the purpose of describing exemplary embodiments only, and is not intended to limit the scope of the present disclosure, which are limited only by the appended claims. All publications, patents, patent applications, and/or other documents cited in this application are incorporated by reference in their entirety for all purposes to the same extent as if each individual publication, patent, patent application, and/or other document are individually indicated to be incorporated by reference for all purposes.

What is claimed is:

1. A modified relaxin polypeptide comprising a non-naturally encoded amino acid, wherein:
   (a) the modified relaxin polypeptide comprises the relaxin A chain polypeptide of SEQ ID NO: 4 and the relaxin B chain polypeptide of SEQ ID NO: 5 or SEQ ID NO: 6, substituted with a non-naturally encoded amino acid at A chain residue 1, and having zero, one, or two additional amino acid changes in said relaxin A chain and having zero, one, or two additional amino acid changes in said relaxin B chain, wherein each of said amino acid changes is independently a substitution, insertion or deletion;
   (b) said non-naturally encoded amino acid has the structure:

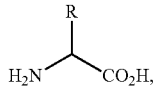

wherein the R group is any substituent other than the side chain found in alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine; and
   (c) said non-naturally encoded amino acid is linked to a pharmacokinetic enhancer comprising a peptide component having between 4 and 8 amino acids and a half-life extending moiety comprising a fatty acid of Formula I:

$$—C_n—COOH \qquad \text{(Formula I)}$$

wherein n is between 12 and 16, wherein said peptide component comprises $Glu^\gamma$.

2. The modified relaxin polypeptide of claim 1, wherein said non-naturally encoded amino acid comprises a carbonyl group, an aminooxy group, a hydrazide group, a hydrazine group, a semicarbazide group, an azide group, or an alkyne group.

3. The modified relaxin polypeptide of claim 1, wherein said non-naturally encoded amino acid comprises a phenylalanine derivative.

4. The modified relaxin polypeptide of claim 1, wherein said non-naturally encoded amino acid is directly linked to said peptide component.

5. The modified relaxin polypeptide of claim 1, wherein said non-naturally encoded amino acid is linked to said pharmacokinetic enhancer through an oxime linkage or triazole linkage.

6. The modified relaxin polypeptide of claim 1, wherein said relaxin A chain polypeptide comprises SEQ ID NO: 35, and said relaxin B chain polypeptide comprises SEQ ID NO: 5 or SEQ ID NO: 6.

7. The modified relaxin polypeptide of claim 1, wherein said peptide component comprises Glu, GGGGS-$Glu^\gamma$ (SEQ ID NO: 139), DRDDRD (SEQ ID NO: 102), KKKKKK-$Glu^\gamma$ (SEQ ID NO: 103), GGGEEE-$Glu^\gamma$ (SEQ ID NO: 105), EEEGGG-$Glu^\gamma$ (SEQ ID NO: 106), KKKGGG-$Glu^\gamma$ (SEQ ID NO: 107), GGGKKK-$Glu^\gamma$ (SEQ ID NO: 109), Sar-Sar-Sar-Sar-Ser-$Glu^\gamma$ (SEQ ID NO: 112), Sar-Sar-Sar-Glu-Glu-$Glu^\gamma$ (SEQ ID NO: 113), KSGGSGG-$Glu^\gamma$ (SEQ ID NO: 117), dKdKdKdKdKdK-$Glu^\gamma$ (SEQ ID NO: 120), EEEGGG-$dGlu^\gamma$ (SEQ ID NO: 128), EGGGGSK-$Glu^\gamma$ (SEQ ID NO: 130), EEEEEE-$Glu^\gamma$ (SEQ ID NO: 131), KK-$Glu^\gamma$ (SEQ ID NO: 140), KGPKGP-$Glu^\gamma$ (SEQ ID NO: 146), SGGGS-$Glu^\gamma$ (SEQ ID NO: 147), KGGGS-$Glu^\gamma$ (SEQ ID NO: 148), KGGGSE-$Glu^\gamma$ (SEQ ID NO: 149), GSPGSP-$Glu^\gamma$ (SEQ ID NO: 150), GGGGP-$Glu^\gamma$ (SEQ ID NO: 151), EGGS-$Glu^\gamma$ (SEQ ID NO: 152), EGGGP-$Glu^\gamma$ (SEQ ID NO: 153), KGPGSE-$Glu^\gamma$ (SEQ ID NO: 154), Spermine-$Glu^\gamma$, or KKGGS-$Glu^\gamma$ (SEQ ID NO: 156).

8. The modified relaxin polypeptide of claim 1, wherein the relaxin polypeptide comprises the relaxin A chain polypeptide of SEQ ID NO: 4 and the relaxin B chain polypeptide of SEQ ID NO: 5 or SEQ ID NO: 6, substituted with a non-naturally encoded amino acid at A chain residue 1, wherein said non-naturally encoded amino acid is linked to said pharmacokinetic enhancer and said pharmacokinetic enhancer comprises the peptide component GGGGS-$Glu^\gamma$ (SEQ ID NO: 139).

9. The modified relaxin polypeptide of claim 1, wherein said half-life extending moiety comprises a fatty acid or derivative thereof, wherein the fatty acid or derivative thereof is covalently linked to the peptide component.

10. The modified relaxin polypeptide of claim 1, wherein said half-life extending moiety comprises —C14-COOH.

11. The modified relaxin polypeptide of claim 1, wherein said half-life extending moiety comprises a fatty acid of Formula I:

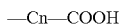 (Formula I)

wherein n is between 12 and 14.

12. The modified relaxin polypeptide of claim 1, wherein said pharmacokinetic enhancer comprises:

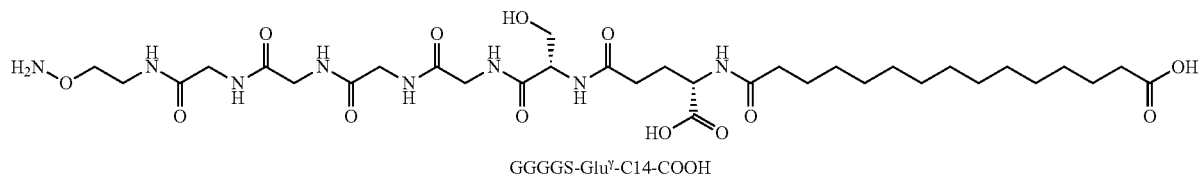

GGGGS-Glu$^\gamma$-C14-COOH wherein the aminooxy group is linked to the non-natural amino acid in said modified relaxin polypeptide.

13. The modified relaxin polypeptide of claim 1, wherein said half-life extending moiety is conjugated to said peptide component through an amide bond.

14. The modified relaxin polypeptide of claim 1, wherein the relaxin polypeptide comprises the relaxin A chain polypeptide of SEQ ID NO: 4 and the relaxin B chain polypeptide of SEQ ID NO: 5 or SEQ ID NO: 6, substituted with a non-naturally encoded amino acid at A chain residue 1;

wherein said non-naturally encoded amino acid comprises para-acetyl-L-phenylalanine linked to said pharmacokinetic enhancer which comprises a peptide component comprising GGGGS-Glu$^\gamma$ (SEQ ID NO: 139); and a half-life extending moiety comprising —C14-COOH.

15. The modified relaxin polypeptide of claim 1, wherein said modified relaxin polypeptide exhibits an increased in vivo half-life by at least 2-fold compared to the wild-type relaxin polypeptide consisting of the relaxin A chain of SEQ ID NO: 4 linked to the relaxin B chain of SEQ ID NO: 5.

16. A pharmaceutical composition comprising the modified relaxin polypeptide of claim 1 and a pharmaceutically acceptable carrier.

17. A method of manufacturing a modified relaxin polypeptide according to claim 1, comprising:

(a) providing a polypeptide comprising said relaxin A chain and said relaxin B chain, wherein said polypeptide comprises said non-naturally encoded amino acid; and (b) linking said non-naturally encoded amino acid to said pharmacokinetic enhancer.

18. The modified relaxin polypeptide of claim 1, wherein said modified relaxin polypeptide exhibits an increased in vivo half-life by at least 5-fold compared to the wild-type relaxin polypeptide consisting of the relaxin A chain of SEQ ID NO: 4 linked to the relaxin B chain of SEQ ID NO: 5.

19. The modified relaxin polypeptide of claim 1, wherein said modified relaxin polypeptide exhibits an increased in vivo half-life by at least 10-fold compared to the wild-type relaxin polypeptide consisting of the relaxin A chain of SEQ ID NO: 4 linked to the relaxin B chain of SEQ ID NO: 5.

20. A modified relaxin polypeptide comprising:

(Formula III)

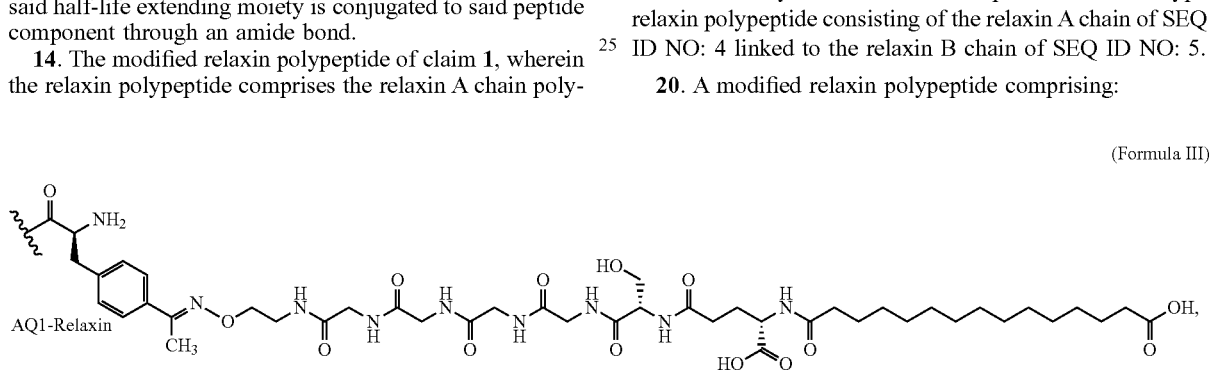

wherein said AQ1-Relaxin comprises a relaxin A chain polypeptide having the amino acid sequence of SEQ ID NO: 35 and a relaxin B chain polypeptide having at least 90% the amino sequence identity to of SEQ ID NO: 5 or SEQ ID NO: 6, and having zero, one, or two amino acid changes in said relaxin A chain and having zero, one, or two amino acid changes in said relaxin B chain, wherein the modified para-acetyl-phenylalanine depicted in Formula III is located at the N-terminus of said relaxin A chain polypeptide.

21. The modified relaxin polypeptide of claim 20, wherein AQ1-Relaxin comprises a relaxin A chain polypeptide of SEQ ID NO: 35 and a relaxin B chain polypeptide of SEQ ID NO: 5 or SEQ ID NO: 6.

22. A pharmaceutical composition comprising the modified relaxin polypeptide of claim 20 and a pharmaceutically acceptable carrier.

23. A modified relaxin polypeptide comprising AQ1-GGGGS-Glu$^\gamma$ (SEQ ID NO: 139)-C14-COOH, which comprises the structure shown in FIG. 9, or which comprises a relaxin A chain polypeptide of SEQ ID NO: 35 and a relaxin B chain polypeptide of SEQ ID NO: 6, wherein the modified para-acetyl-phenylalanine located at the N-terminus of said relaxin A chain polypeptide is linked to the pharmacokinetic enhancer depicted in Formula III:

(Formula III)

24. The modified relaxin polypeptide of claim 23, which comprises the structure shown in FIG. 9.

25. The modified relaxin polypeptide of claim 24, which consists of the structure shown in FIG. 9.

26. The modified relaxin polypeptide of claim 25, wherein said modified relaxin polypeptide exhibits an increased in vivo half-life by at least 2-fold compared to the wild-type relaxin polypeptide consisting of the relaxin A chain of SEQ ID NO: 4 linked to the relaxin B chain of SEQ ID NO: 5.

27. A pharmaceutical composition comprising the modified relaxin polypeptide of claim 25 and a pharmaceutically acceptable carrier.

28. The modified relaxin polypeptide of claim 24, wherein said modified relaxin polypeptide exhibits an increased in vivo half-life by at least 2-fold compared to the wild-type relaxin polypeptide consisting of the relaxin A chain of SEQ ID NO: 4 linked to the relaxin B chain of SEQ ID NO: 5.

29. A pharmaceutical composition comprising the modified relaxin polypeptide of claim 24 and a pharmaceutically acceptable carrier.

30. A pharmaceutical composition comprising the modified relaxin polypeptide of claim 23 and a pharmaceutically acceptable carrier.

\* \* \* \* \*